(12) United States Patent
Donovan et al.

(10) Patent No.: US 12,006,359 B2
(45) Date of Patent: *Jun. 11, 2024

(54) METHODS FOR ALTERING BODY COMPOSITION BY ADMINISTERING ANTI-PRO/LATENT MYOSTATIN ANTIBODIES

(71) Applicant: Scholar Rock, Inc., Cambridge, MA (US)

(72) Inventors: Adriana Donovan, West Roxbury, MA (US); Michelle Straub, Yarmouth, ME (US); Stefan Wawersik, Westborough, MA (US)

(73) Assignee: Scholar Rock, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/083,917

(22) Filed: Oct. 29, 2020

(65) Prior Publication Data
US 2021/0332117 A1 Oct. 28, 2021

Related U.S. Application Data

(63) Continuation of application No. 16/360,142, filed on Mar. 21, 2019, now Pat. No. 10,882,904, which is a continuation of application No. 15/400,825, filed on Jan. 6, 2017, now Pat. No. 10,287,345, which is a continuation of application No. PCT/US2016/052014, filed on Sep. 15, 2016.

(60) Provisional application No. 62/413,278, filed on Oct. 26, 2016, provisional application No. 62/333,810, filed on May 9, 2016, provisional application No. 62/333,816, filed on May 9, 2016, provisional application No. 62/328,597, filed on Apr. 27, 2016, provisional application No. 62/276,698, filed on Jan. 8, 2016.

(51) Int. Cl.
| | |
|---|---|
| *A61K 39/395* | (2006.01) |
| *A61P 3/00* | (2006.01) |
| *A61P 3/04* | (2006.01) |
| *A61P 21/00* | (2006.01) |
| *A61P 21/04* | (2006.01) |
| *A61P 21/06* | (2006.01) |
| *C07K 16/22* | (2006.01) |
| *A61K 39/00* | (2006.01) |
| *A61K 45/06* | (2006.01) |
| *C07K 14/475* | (2006.01) |

(52) U.S. Cl.
CPC .......... *C07K 16/22* (2013.01); *A61K 39/3955* (2013.01); *A61P 3/00* (2018.01); *A61P 3/04* (2018.01); *A61P 21/00* (2018.01); *A61P 21/04* (2018.01); *A61P 21/06* (2018.01); *A61K 2039/505* (2013.01); *A61K 45/06* (2013.01); *C07K 14/475* (2013.01); *C07K 2317/21* (2013.01); *C07K 2317/33* (2013.01); *C07K 2317/51* (2013.01); *C07K 2317/515* (2013.01); *C07K 2317/52* (2013.01); *C07K 2317/524* (2013.01); *C07K 2317/565* (2013.01); *C07K 2317/622* (2013.01); *C07K 2317/71* (2013.01); *C07K 2317/76* (2013.01); *C07K 2317/92* (2013.01)

(58) Field of Classification Search
CPC ....... A61K 39/3955; C07K 16/22; A61P 3/00; A61P 21/00; A61P 21/06
See application file for complete search history.

(56) References Cited

U.S. PATENT DOCUMENTS

| | | |
|---|---|---|
| 6,096,506 A | 8/2000 | Lee et al. |
| 6,656,475 B1 | 12/2003 | Lee et al. |
| 6,858,208 B2 | 2/2005 | Lee et al. |
| 7,138,501 B2 | 11/2006 | Ruben et al. |
| 7,566,768 B1 | 7/2009 | Lee et al. |
| 10,287,345 B2 | 5/2019 | Donovan et al. |
| 10,307,480 B2 | 6/2019 | Straub et al. |
| 10,751,413 B2 | 8/2020 | Carven et al. |
| 10,882,904 B2 | 1/2021 | Donovan et al. |
| 10,946,036 B2 | 3/2021 | Long et al. |
| 11,135,291 B2 | 10/2021 | Straub et al. |
| 11,155,611 B2 | 10/2021 | Donovan et al. |
| 11,439,704 B2 | 9/2022 | Carven et al. |
| 2002/0157126 A1 | 10/2002 | Lee et al. |
| 2003/0167492 A1 | 9/2003 | Lee et al. |
| 2005/0049402 A1 | 3/2005 | Babcook et al. |
| 2005/0143306 A1 | 6/2005 | Junker et al. |
| 2006/0025340 A1 | 2/2006 | Knopf et al. |
| 2006/0216279 A1 | 9/2006 | Glass et al. |
| 2006/0263354 A1 | 11/2006 | Chin et al. |
| 2007/0087000 A1 | 4/2007 | Walsh et al. |

(Continued)

FOREIGN PATENT DOCUMENTS

| | | |
|---|---|---|
| AU | 2011244851 A1 | 11/2011 |
| CN | 103097415 A | 5/2013 |

(Continued)

OTHER PUBLICATIONS

Benjamini et al., 1991. Immunology: A Short Course, 2nd edition, p. 40 only.*

(Continued)

*Primary Examiner* — Zachary C Howard

(74) *Attorney, Agent, or Firm* — Finnegan, Henderson Farabow, Garrett & Dunner, LLP

(57) ABSTRACT

The present invention relates to antibodies that specifically bind pro-myostatin and/or latent myostatin, and methods and uses thereof.

8 Claims, 62 Drawing Sheets

Specification includes a Sequence Listing.

(56) References Cited

U.S. PATENT DOCUMENTS

| | | |
|---|---|---|
| 2007/0178095 A1 | 8/2007 | Smith et al. |
| 2007/0218067 A1 | 9/2007 | Buttner et al. |
| 2008/0119426 A1 | 5/2008 | Dale |
| 2008/0213251 A1 | 9/2008 | Sexton et al. |
| 2008/0299126 A1 | 12/2008 | Han et al. |
| 2009/0131638 A1 | 5/2009 | Davies et al. |
| 2009/0148436 A1 | 6/2009 | LaVallie et al. |
| 2009/0324590 A1 | 12/2009 | Kambadur et al. |
| 2010/0080811 A1 | 4/2010 | Davies et al. |
| 2010/0087631 A1 | 4/2010 | Han et al. |
| 2010/0166764 A1 | 7/2010 | Sayers et al. |
| 2010/0183616 A1 | 7/2010 | Green et al. |
| 2010/0221777 A1 | 9/2010 | Choe et al. |
| 2010/0331252 A1 | 12/2010 | Hamrick |
| 2011/0165175 A1 | 7/2011 | Linhard et al. |
| 2011/0239317 A1 | 9/2011 | Lee et al. |
| 2011/0256132 A1 | 10/2011 | Ashman et al. |
| 2011/0293630 A1 | 12/2011 | Stitt et al. |
| 2013/0065820 A1 | 3/2013 | Bower et al. |
| 2013/0209498 A1 | 8/2013 | Han et al. |
| 2013/0216548 A1 | 8/2013 | Neijssen et al. |
| 2013/0230515 A1 | 9/2013 | Han et al. |
| 2013/0336982 A1 | 12/2013 | Mader et al. |
| 2014/0017262 A1 | 1/2014 | Sanicola-Nadel |
| 2014/0023638 A1 | 1/2014 | LaVallie et al. |
| 2016/0199458 A1 | 7/2016 | Knopf et al. |
| 2017/0198032 A1 | 7/2017 | Donovan et al. |
| 2017/0333558 A1 | 11/2017 | Straub et al. |
| 2021/0046180 A1 | 2/2021 | Carven et al. |
| 2021/0283166 A1 | 9/2021 | Long et al. |

FOREIGN PATENT DOCUMENTS

| | | |
|---|---|---|
| EP | 2853898 A1 | 4/2015 |
| EP | 3922645 | 12/2021 |
| JP | 2003-520839 | 7/2003 |
| JP | 2004-504826 | 2/2004 |
| JP | 2009-545313 | 12/2009 |
| JP | 2010-502633 | 1/2010 |
| JP | 2017536354 | 12/2017 |
| WO | WO 1996/01845 A2 | 1/1996 |
| WO | WO 2002/009641 A2 | 2/2002 |
| WO | WO 2002/085306 A2 | 10/2002 |
| WO | WO 2003/027248 A2 | 4/2003 |
| WO | WO 2004/009776 A2 | 1/2004 |
| WO | WO 2004/024890 A2 | 3/2004 |
| WO | WO 2004/037861 A2 | 5/2004 |
| WO | WO 2005/066204 A2 | 7/2005 |
| WO | WO 2005/084699 A1 | 9/2005 |
| WO | WO 2005/103081 A2 | 11/2005 |
| WO | WO 2005/115439 A2 | 12/2005 |
| WO | WO 2006/116269 A2 | 11/2006 |
| WO | WO 2007/024535 A2 | 3/2007 |
| WO | WO 2007/044411 A2 | 4/2007 |
| WO | WO 2007/044411 A3 | 4/2007 |
| WO | WO 2007/047112 A2 | 4/2007 |
| WO | WO 2007/061995 A2 | 5/2007 |
| WO | WO 2008/067480 A2 | 6/2008 |
| WO | WO 2008/119426 A1 | 10/2008 |
| WO | WO 2009/038760 A2 | 3/2009 |
| WO | WO 2010/070094 A1 | 6/2010 |
| WO | WO 2010/125003 A1 | 11/2010 |
| WO | WO 2010/144452 A1 | 12/2010 |
| WO | WO 2011/122011 A2 | 10/2011 |
| WO | WO 2011/150008 A1 | 12/2011 |
| WO | WO 2012/024242 A1 | 2/2012 |
| WO | WO 2013/071056 A2 | 5/2013 |
| WO | WO 2013/072902 A1 | 5/2013 |
| WO | WO 2013/074557 A1 | 5/2013 |
| WO | WO 2013/148284 A1 | 10/2013 |
| WO | WO 2013/165972 A2 | 11/2013 |
| WO | WO 2013/186719 A1 | 12/2013 |
| WO | WO 2014/074532 A2 | 5/2014 |
| WO | WO 2014/182676 A2 | 11/2014 |
| WO | WO 2015/070158 A1 | 5/2015 |
| WO | WO 2015/195094 A1 | 12/2015 |
| WO | WO 2016/073853 A1 | 5/2016 |
| WO | WO 2016/073879 A2 | 5/2016 |
| WO | WO 2016/073906 A2 | 5/2016 |
| WO | WO 2016/098357 A1 | 6/2016 |
| WO | WO 2016/168613 A1 | 10/2016 |
| WO | WO 2017/049011 A1 | 3/2017 |
| WO | WO 2017/120523 A2 | 7/2017 |
| WO | WO 2017/218592 A1 | 12/2017 |
| WO | WO 2018/116201 A1 | 6/2018 |

OTHER PUBLICATIONS

Ferrara et al (2015. mAbs. 7(1): 32-41).*
Abdiche et al (2014). PLoS One. 9(3): e92451.*
Abdiche et al (2017). PLoS One. 12(1): e0169535.*
Markovitz et al (2013). Blood. 121(14): 2785-95.*
Anonymous (2017) SC 2. Anterolateral Systems—Deficits. Retrieved from: http://www.neuroanatomy.wisc.edu/sc97/text/p2/deficits.htm; on Jul. 11, 2017 (1 page).
Anonymous (2019) "GDF-11/BMP-11 Mouse anti-Human, Clone: 743833, R&D Systems(TM)" [online]. Retrieved from: http://www.fishersci.co.uk/shop/products/gdf-11bpm-11-mouse-anti-human-clone-743833-r-d-systems/15724724; on Feb. 28, 2019 (4 pages).
Australian Application No. 202010134, filed Jul. 27, 2020, for Scholar Rock, Inc.: Examination Report No. 1, issued Oct. 15, 2020.
Baranello et al., (2020) "Evaluation of body composition as a potential biomarker in spinal muscular atrophy", Muscle & Nerve, 61(4):530-534.
Benatar (2007) "Lost in translation: Treatment trials in the SOD1 mouse and in human ALS", Neurobiology of Disease, 26:1-13.
Bräuninger et al., (2003) "Epstein-Barr virus (EBV)-positive lymphoproliferations in post-transplant patients show immunoglobulin V gene mutation patterns suggesting interference of EBV with normal B cell differentiation processes", Eur J Immunol., 33(6): 1593-1602.
Breitbart et al., (2013) "Highly specific detection of myostatin prodomain by an immunoradiometric sandwich assay in serum of healthy individuals and patients", PLoS One, 8(11):e80454 (10 pages).
Brown et al., (1996) "Tolerance of single, but not multiple, amino acid replacements in antibody VH CDR 2: a means of minimizing B cell wastage from somatic hypermutation?", J Immunol., 156(9):3285-3291.
Burch et al., (2017) "Reduced serum myostatin concentrations associated with genetic muscle disease progression", Journal of Neurology, 264(3):541-553.
Ciciliot et al., (2013) "Muscle type and fiber type specificity in muscle wasting", Int J Biochem Cell Biol., 45(10):2191-2199.
Cohen et al., (2015) "Muscle wasting in disease: molecular mechanisms and promising therapies", Nat Rev Drug Discov., 14(1):58-74.
Dalbo et al., (2017) "Testosterone and trenbolone enanthate increase mature myostatin protein expression despite increasing skeletal muscle hypertrophy and satellite cell number in rodent muscle", Andrologia, 49(3):1-11.
Dibernardo et al., (2006) "Translating preclinical insights into effective human trials in ALS", Biochimica et Biophysica Acta, 1762:1139-1149.
D'Ydewalle et al., (2015) "Spinal muscular atrophy therapeutics: where do we stand?", Neurotherapeutics 12(2):303-316.
Egerman et al., (2015) "GDF11 Increases with Age and Inhibits Skeletal Muscle Regeneration", Cell Metabolism, 22(1):164-174.
European Patent Application No. 16828657.3, by Scholar Rock, Inc.: Supplementary European Search Report and Opinion, dated Mar. 20, 2019.
Feng et al., (2016) "Pharmacologically induced mouse model of adult spinal muscular atrophy to evaluate effectiveness of therapeutics after disease onset", Human Molecular Genetics, 25(5):964-975.
Ferrara et al., (2015) "Recombinant renewable polyclonal antibodies", mAbs, 7(1):32-41.

(56) References Cited

OTHER PUBLICATIONS

Ge et al., (2005) "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858.
Giangregorio et al., (2006) "Bone Loss and Muscle Atrophy in Spinal Cord Injury Epidemiology, Fracture Prediction, and Rehabilitation Strategies", J Spinal Cord Med., 29(5)489-500.
Gogliotti et al., (2011) "Characterization of a commonly used mouse model of SMA reveals increased seizures susceptibility and heightened fear response in FVB/N mice", Neurobiol Dis. 43(1):142-151.
Gonzalez et al., (2005) "BMP-1/Tolloid-like Metalloproteases Process Endorepellin, the Angiostatic C-terminal Fragment of Perlecan", The Journal of Biological Chemistry, 280(8):7080-7087.
Graham et al., (2015) "A Soluble Myostatin Inhibitor Does Not Prevent Sublesional Muscle Atrophy 56 Days After Spinal Cord Injury in Mice", Medicine & Science in Sports & Exercise, Abstract No. 2219:587.
Guo et al., (2009) "Myostatin Inhibition in Muscle, but Not Adipose Tissue, Decreases Fat Mass and Improves Insulin Sensitivity", PLoS One, 4(3):e4937 (11 pages).
Holzbaur et al., (2006) "Myostatin inhibition slows muscle atrophy in rodent models of amyotrophic lateral sclerosis", Neurobiol Dis., 23(3):697-707.
International Application No. PCT/US2016/043712, by Scholar Rock, Inc., International Search Report and Written Opinion, mailed Jan. 13, 2017.
International Application No. PCT/US2017/012606, by Scholar Rock, Inc., International Search Report and Written Opinion, mailed Jul. 24, 2017.
International Application No. PCT/US2017/012606, by Scholar Rock, Inc., Written Opinion mailed Jan. 3, 2018 (18 pages).
International Application No. PCT/US2017/037332, by Scholar Rock, Inc., International Search Report and Written Opinion, mailed Nov. 14, 2017.
International Application No. PCT/US2018/012686, by Scholar Rock, Inc., International Search Report and Written Opinion, mailed Apr. 3, 2018.
International Preliminary Report on Patentability for Application No. PCT/US2015/059468, dated May 9, 2017 (12 pages).
International Preliminary Report on Patentability for Application No. PCT/US2016/052014, dated Mar. 29, 2018 (11 pages).
International Search Report and Written Opinion for Application No. PCT/US2016/052014, dated Jan. 9, 2017 (17 pages).
International Search Report for Application No. PCT/US2015/059468, dated Apr. 4, 2016 (6 pages).
International Search Report for Application No. PCT/US2015/059515, dated Mar. 25, 2016 (8 pages).
Jiang et al., (2019) "Genomic analysis of a spinal muscular atrophy (SMA) discordant family identifies a novel mutation in TLL2, an activator of growth differentiation factor 8 (myostatin): a case report", BMC Medical Genetics, 20(1):204.
Kariya et al., (2014) "Requirement of enhanced Survival Motoneuron protein imposed during neuromuscular junction maturation", The Journal of Clinical Investigation, 124(2):785-800.
Latres et al., (2015) "Myostatin blockade with a fully human monoclonal antibody induces muscle hypertrophy and reverses muscle atrophy in young and aged mice", Skeletal Muscle, 5:34.
Latres et al., (2017) "Activin A more prominently regulates muscle mass in primates than does GDF8", Nature Communications, 8:15153.
Liu et al., (2014) "The Smn-Independent Beneficial Effect of Trichostatin A on an Intermediate Mouse Model of Spinal Muscular Atrophy", Plos One, 9(7):e101225. (9 pages).
Loffredo et al., (2013) "Growth differentiation factor 11 is a circulating factor that reverses age-related cardiac hypertrophy", Cell, 153(4):828-839.
Long et al., (2019) "Specific inhibition of myostatin activation is beneficial in mouse models of SMA therapy", Human Molecular Genetics, 28(7):1076-1089.

Mariot et al., (2017) "Downregulation of myostatin pathway in neuromuscular diseases may explain challenges of anti-myostatin therapeutic approaches", Nature Communications, 8(1):1859.
McPherron et al., (2010) "Metabolic Functions of Myostatin and GDF11", Immunol Endocr Metab Agents Med Chem., 10(4):217-231.
Morrison et al., (2009) "A soluble activin type IIB receptor improves function in a mouse model of amyotrophic lateral sclerosis", Exp Neurol, 217(2):258-268.
Mosler et al., (2012) "The anabolic steroid methandienone targets the hypothalamic-pituitary-testicular axis and myostatin signaling in a rat training model", Archives of Toxicology, 86(1):109-119.
Pandya et al., (2013) "Therapeutic neuroprotective agents for amyotrophic lateral sclerosis", Cell Mol Life Sci., 70(24):4729-4745.
Pirruccello-Straub et al., (2018) "Blocking extracellular activation of myostatin as a strategy for treating muscle wasting", Scientific Reports, 8(1):2292.
Pistilli et al., (2011) "Targeting Activin Type IIB Receptor to Improve Muscle Mass and Function in the mdx Mouse Model of Duchenne Muscular Dystrophy", Am J Pathol., 178(3):1287-1297.
Pubchem Substance No. CID 310264710 (trevogrumab); Create Date Feb. 5, 2016 [online]. Retrieved from: http://pubchem.ncbi.nlm.nih.gov/substance/310264710; on Feb. 5, 2020 (6 pages).
Sgoutas et al., (1992) "Effect of Lyophilization on Determinations of Lipoprotein(a) in Serum", Clin Chem, 38(7):1355-1360.
Singapore Patent Application No. 11201805709R, filed Jan. 6, 2017, by Scholar Rock, Inc.: International Search Report and Written Opinion, mailed Oct. 11, 2019 (12 pages).
Smith et al., (2013) "Myostatin inhibitors as therapies for muscle wasting associated with cancer and other disorders", Curr Opin Support Palliat Care, 7(4):352-360.
Smith et al., (2015) "Myostatin Neutralization Results in Preservation of Muscle Mass and Strength in Preclinical Models of Tumor-Induced Muscle Wasting", Mol Cancer Ther., 14(7):1661-1670.
Sumner et al., (2009) "Inhibition of myostatin does not ameliorate disease features of severe spinal muscular atrophy mice", Human Molecular Genetics, 18(17):3145-3152.
Suragani et al., (2014) "Transforming growth factor-β superfamily ligand trap ACE-536 corrects anemia by promoting late-stage erythropoiesis", Nature Medicine, 20(4):408-414.
Szlama et al., (2013) "Latent myostatin has significant activity and this activity is controlled more efficiently by WFIKKN1 than by WFIKKN2", FEBS Journal, 280(16):3822-3839.
Unknown (2000) American Spinal Injury Association (ASIA) Impairment Scale, Standard Neurological Classification of Spinal Cord Injury (2 pages).
Unknown (2013) "Myostatin Propeptide Human, Chicken Polyclonal Antibody", BioVendor, Research and Diagnostic Products, Data Sheet (2 pages).
Wang (2000) "Lyophilization and development of solid protein pharmaceuticals", International Journal of Pharmaceutics, 203(1-2):1-60.
Whittemore et al., (2003) "Inhibition of myostatin in adult mice increases skeletal muscle mass and strength", Biochem Biophys Res Commun, 300(4):965-971.
Wintgens et al., (2012) "Plasma myostatin measured by a competitive ELISA using a highly specific antiserum", Clin Chim Acta., 413(15-16):1288-1294.
Wolfman et al., (2003) "Activation of latent myostatin by the BMP-1/tolloid family of metalloproteinases", Proc Natl Acad Sci U.S.A., 100(26):15842-15846.
Zhao et al., (2016) "Pharmacokinetics, pharmacodynamics, and efficacy of a small molecule SMN2 splicing modifier in mouse models of spinal muscular atrophy", Human Molecular Genetics, 25(10):1885-1899.
Bernardo et al. (2010) "Postnatal PPARdelta activation and myostatin inhibition exert distinct yet complimentary effects on the metabolic profile of obese insulin-resistant mice," PLoS One. 25;5(6):e11307.
Extended European Search Report in EP Application No. 21170667.6 dated Nov. 11, 2021.
Igawa et al. (2013) "Engineered Monoclonal Antibody with Novel AntigenSweeping Activity In Vivo". PLoS One 8(5):e63236.

(56) References Cited

OTHER PUBLICATIONS

Schoch et al., (2015) "Charge-mediated influence of the antibody variable domain on FcRn-dependent pharmacokinetics", Proceedings of the National Academy of Sciences, vol. 112, No. 19, pp. 5997-6002.

Anderson et al., (2008) "Identification of a novel pool of extracellular pro myostatin in skeletal muscle", The Journal of Biological Chemistry, 283(11):7027-7035.

Anonymous (2005) "Human Myostatin ELISA—Prodomain specific", BioVendor Laboratory Medicine, Inc., XP055100354, Retrieved from the Internet: URL:http://deltaclon.es/pdf/RD193058100.pdf (10 pgs.).

Biovendor, Research and Diagnostics Products. Myostatin Propeptide Human, Chicken Polyclonal Antibody. Product Data Sheet 2 pgs. Apr. 11, 2013.

Chen et al., "Considerations for Developing Combination Therapies in SMA", Cure SMA Researcher Meeting, Jun. 16, 2016.

Cully (2014) "Beefing up the right splice variant to treat spinal muscular atrophy". Nat Rev Drug Discov 13, 725. https://doi.org/10.1038/nrd4445 (1 pg.).

Dagbay et al., (2020) "Structural basis of specific inhibition of extracellular activation of pro- or latent myostatin by the monoclonal antibody SRK-015", J. Biol. Chem., 295(16):5404-5418.

Day et al., (2021) "Onasemnogene abeparvovec gene therapy for symptomatic infantile-onset spinal muscular atrophy in patients with two copies of SMN2 (STR1VE): an open-label, single-arm, multicentre, phase 3 trial", Lancet Neurol, 20:284-293.

European Patent Application No. 20179533.3, by Scholar Rock, Inc.: Partial European Search Report, dated Mar. 31, 2021 (12 pgs.).

European Patent Application No. 20193425.4, by Scholar Rock, Inc.: European Search Report, dated Apr. 1, 2021 (9 pgs.).

Farrar et al. (2017) "Emerging therapies and challenges in spinal muscular atrophy" Ann Neural 81(3): 355-368. Published online Feb. 17, 2017. doi: 10.1002/ana.24864. Publication details included.

Fidler, (2016) "Scholar Rock Rolls Up $36M To Move Muscle Drug To Clinical Trials" https://xconomy.com/boston/2016/01/04/scholar-rock-rolls-up-36m-to-move-muscle-drug-to-clinical-trials/.

Heymsfield et al., (2021) "Effect of Bimagrumab vs Placebo on Body Fat Mass Among Adults With Type 2 Diabetes and Obesity: A Phase 2 Randomized Clinical Trial", 4(1):e2033457. doi: 10.1001/jamanetworkopen.2020.33457.

International Search Report for Application No. PCT/US2015/059557, dated May 19, 2016 (5 pgs.).

International Preliminary Report on Patentability for Application No. PCT/US2015/059468, dated May 9, 2017 (12 pgs.).

International Preliminary Report on Patentability for Application No. PCT/US2015/059515, dated May 9, 2017 (12 pgs.).

Japanese Patent Application No. 2019-517209, filed Jun. 13, 2017, by Scholar Rock, Inc., Decision to Grant a Patent, mailed Dec. 8, 2020 (7 pgs.).

Jarolim et al., (2013) "2013 AACC Annual Meeting Abstracts B-175 Determination of Cardiac Troponin with a Single-Molecule High-Sensitivity Assay and Outcomes in Patients with Stable Coronary Artery Disease: Analysis from Prove It-TIMI 22", XP055100559, Retrieved from the Internet: URL:http://www.aacc.org/events/Annual_Meeting/abstracts/Documents/AACC_13_AM_B175-B239.pdf (22 pgs.).

Liu et al., (2016) Activin Receptor Type 11B Inhibition Improves Muscle Phenotype and Function in a Mouse Model of Spinal Muscular Atrophy, PLoS One 11 (11): e0166803, published Nov. 21, 2016.

Muramatsu et al., (2021) "Novel myostatin-specific antibody enhances muscle strength in muscle disease models", Sci Rep, 11:2160, https://doi.org/10.1038/s41598-021-81669-8 (16 pgs.).

Naryshkin et al., (2014) "SMN2 splicing modifiers improve motor function and longevity in mice with spinal muscular atrophy" Science, vol. 345, Issue 6197, pp. 688-693, DOI: 10.1126/science.1250127.

Ojala et al., (2021) "In Search of a Cure: The Development of Therapeutics to Alter the Progression of Spinal Muscular Atrophy", Brain Sci., 11:194 (39 pgs.).

Opposition filed in EP Patent No. 3368069 on Apr. 28, 2021 (37 pgs.).

Opposition filed in EP Patent No. 3368069 on May 4, 2021 (89 pgs.).

Reply to Examination Report dated Feb. 13, 2016 in EP Application No. 17732001.7, on May 31, 2019.

Request for early entry and processing of EP Application No. 17732001.7, on Jun. 1, 2018.

Response to Communication dated Jul. 31, 2018 in EP Application No. 17732001.7, on Dec. 10, 2018.

Rodino-Klapac et al., (2009) "Inhibition of myostatin with emphasis on follistatin as a therapy for muscle disease" Muscle Nerve 39(3):283-96. doi: 10.1002/mus.21244.

Roth et al., (2004) "Myostatin: a therapeutic target for skeletal muscle wasting" Curr Opin Clin Nutr Metab Care 7(3):259-63. doi: 10.1097/00075197-200405000-00004.

ScholarRock Announcement (2015) "Scholar Rock Presents First Data for Niche Modulator Inhibiting Myostatin Activation and Announces SRK-015 as Lead Drug Program" (1 pg.).

Rose et al., (2009) "Delivery of recombinant follistatin lessens disease severity in a mouse model of spinal muscular atrophy" Hum Mol Genet. Mar. 15, 2009; 18(6): 997-1005, Published online Dec. 12, 2008. doi: 10.1093/hmg/ddn426.

ScholarRock.com (2016) "Scholar Rock discovered SRK-015, a selective and local inhibitor or latent myostatin activation for the treatment of primary myopathies" (1 pg.).

Shorrock et al., (2016) "Development and Translation of Therapies for Spinal Muscular Atrophy" EMJ Neurol. 4[1]:64-73.

SMA Annual Conference "The 2016 Annual SMA Conference is here", https://www.curesma.org/the-2016-annual-sma-conference-is-here/ (3 pgs.).

SMA Researcher Meeting Summary: The Changing Landscape of SMA 2016 (5 pgs.).

Spinraza (Nusinersen) FDA label, Dec. 2016 (13 pgs.).

Sumner et al. (2016) "Spinal Muscular Atrophy, Disease Mechanisms and Therapy", Academic Press, pp. 6, 15-19 and 351-356. Publication details included (22 pgs).

Sumner et al., (2016) "Spinal Muscular Atrophy, Disease Mechanisms and Therapy", First edition, Academic Press, Chapters 15, 16, 21, and 23. Publication details included (91 pgs.).

Wagner, (2020) "The elusive promise of myostatin inhibition for muscular dystrophy", Current Opinion in Neurology, 33(5):621-628.

Walker et al., Biochemistry and Biology of GDF11 and Myostatin: similarities, differences and questions for future investigation, Cir. Res. 118(7): 1125-1142, published Apr. 1, 2016.

Walter et al., (2021) "Improving Care and Empowering Adults Living with SMA: A Call to Action in the New Treatment Era", Journal of Neuromuscular Diseases, DOI 10.3233/JND-200611 (9 pgs.).

Amthor et al. "Lack of myostatin results in excessive muscle growth but impaired force generation," Proc Natl Acad Sci U S A. Feb. 6, 2007;104(6):1835-40.

Chen Declaration filed in opposition of EP Patent No. 3368069 on Apr. 27, 2022 ( 2pgs.).

Cure SMA Presentation filed in opposition of EP Patent No. 3368069 on Apr. 27, 2022 (86 pgs.).

Deguise et al. (2017) "New insights into SMA pathogenesis: immune dysfunction and neuroinflammation," Ann Clin Transl Neurol. 4(7):522-53.

Hori et al. (2022) "Elimination of plasma soluble antigen in cynomolgus monkeys by combining pH-dependent antigen binding and novel Fc engineering" MAbs. 14(1):2068213. doi: 10.1080/19420862.2022.2068213.

Jablonka et al.(2022) "Therapy development for spinal muscular atrophy: perspectives for muscular dystrophies and neurodegenerative disorders," Neurol Res Pract. 4(7):522-530.

Jarecki Declaration filed in opposition of EP Patent No. 3368069 on Apr. 27, 2022 (2 pgs.).

(56) References Cited

OTHER PUBLICATIONS

Jobling et al. (2006) "Isoform-specific activation of latent transforming growth factor beta (LTGF-beta) by reactive oxygen species", Radiat Res. 166(6):839-48.
Ling et al. (2012) "Severe neuromuscular denervation of clinically relevant muscles in a mouse model of spinal muscular atrophy" Human Molecular Genetics, vol. 21, No. 1, pp. 185-195.
Opposition Pre-summons Response filed in EP Patent No. 3368069 on Apr. 27, 2022 (33 pgs.).
Rindt et al. (2012) "Transgenic inactivation of murine myostatin does not decrease the severity of disease in a model of Spinal Muscular Atrophy," Neuromuscul Disord. 22(3):277-85.
Suh et al. (2020) "GDF11 promotes osteogenesis as opposed to MSTN, and follistatin, a MSTN/GDF11 inhibitor, increases muscle mass but weakens bone," Proc Natl Acad Sci U S A. 3;117(9):4910-4920.
Anonymous, "History of Changes for Study: NCT03921528", Jan. 13, 2020. URL:https://clinicaltrials.gov/ct2/history/NCT03921528?V_13=View#StudyPageTop (6 pgs.).
Anonymous, "Scholar Rock Announces Positive Proof-of-Concept Data from TOPAZ Phase 2 Trial Interim Analysis of SRK-015 in Patients with Type 2 and Type 3 Spinal Muscular Atrophy" Business Wire, Oct. 27, 2020. (7pgs.).
Barrett et al. "A Randomized Phase 1 Safety, Pharmacokinetic and Pharmacodynamic Study of the Novel Myostatin Inhibitor Apitegromab (SRK-015): A Potential Treatment for Spinal Muscular Atrophy," May 8, 2021 vol. 38, No. 6, p. 3203-3222.
Cambridge Mass et al., "Scholar Rock Announces Positive Interim Results from Phase 1 Trial of SRK-015 in Healthy Volunteers and Updates on Future Development Plans", Feb. 19, 2019. (3pgs.).
Castellana et al. "Resurrection of a clinical antibody: template proteogenomic de novo proteomic sequencing and reverse engineering of an anti-lymphotoxin-α antibody", Proteomics. Feb. 2011; 11(3):395-405.
Crawford et al. "Relationship of pharmacokinetics and pharmacodynamics to apitegromab efficacy in patients with later-onset spinal muscular atrophy (Types 2 and 3 SMA): Results from the TOPAZ study," Oct. 1, 2021, vol. 429.
Extended European Search Report in EP23158609.0, mailed Aug. 8, 2023, 27 pages.
International Search Report and Written Opinion of the International Searching Authority received in PCT/US2021/056517, mailed Mar. 2, 2022 (23 pgs.).
Place A et al. "SMA—THERAPY P.253 Clinical Development of SRK-015, a Fully Human Anti-proMyostatin Monoclonal Antibody, for the Treatment of Later-Onset Spinal Muscular Atrophy," Neuromuscular Disorders, Elsevier Ltd., GB, vol. 30, Oct. 1, 2020. (2 pgs.).
Place et al. "SRK-015: A fully human antibody that blocks cleavage of the Myostatin prodomain A Phase 2 Study to Evaluate the Efficacy and Safety of SRK-015 in Patients with Later-Onset Spinal Muscular Atrophy (TOPAZ): An Introduction Study Design (Continued) Demographics* Disease History* Functional Motor Skills," May 26, 2020. URL:https://scholarrock.com/wp-content/uploads/2020/09/MDA-2020-TOPAZ-SMA-Introduction.pdf [retrieved from internet on Dec. 20, 2021].
Place et al. "TOPAZ: Phase 2 study evaluating efficacy and safety of apitegromab in later-onset spinal muscular atrophy", EMBASE2021, Database accession No. EMB-635747941, Retrieved from the Internet: URL: Elsevier Science Publishers, Amsterdam, NL 1-24 abstract; & Place et al. "TOPAZ: Phase 2 study evaluating efficacy and safety of apitegromab in later-onset spinal muscular atrophy", Journal Of Neuromuscular Diseases 2021 IOS Press NLD, vol. 8, No. Suppl 1, 2021, p. S9 Conf 20210528 to 20210529 Virtual-16th Inte.

* cited by examiner

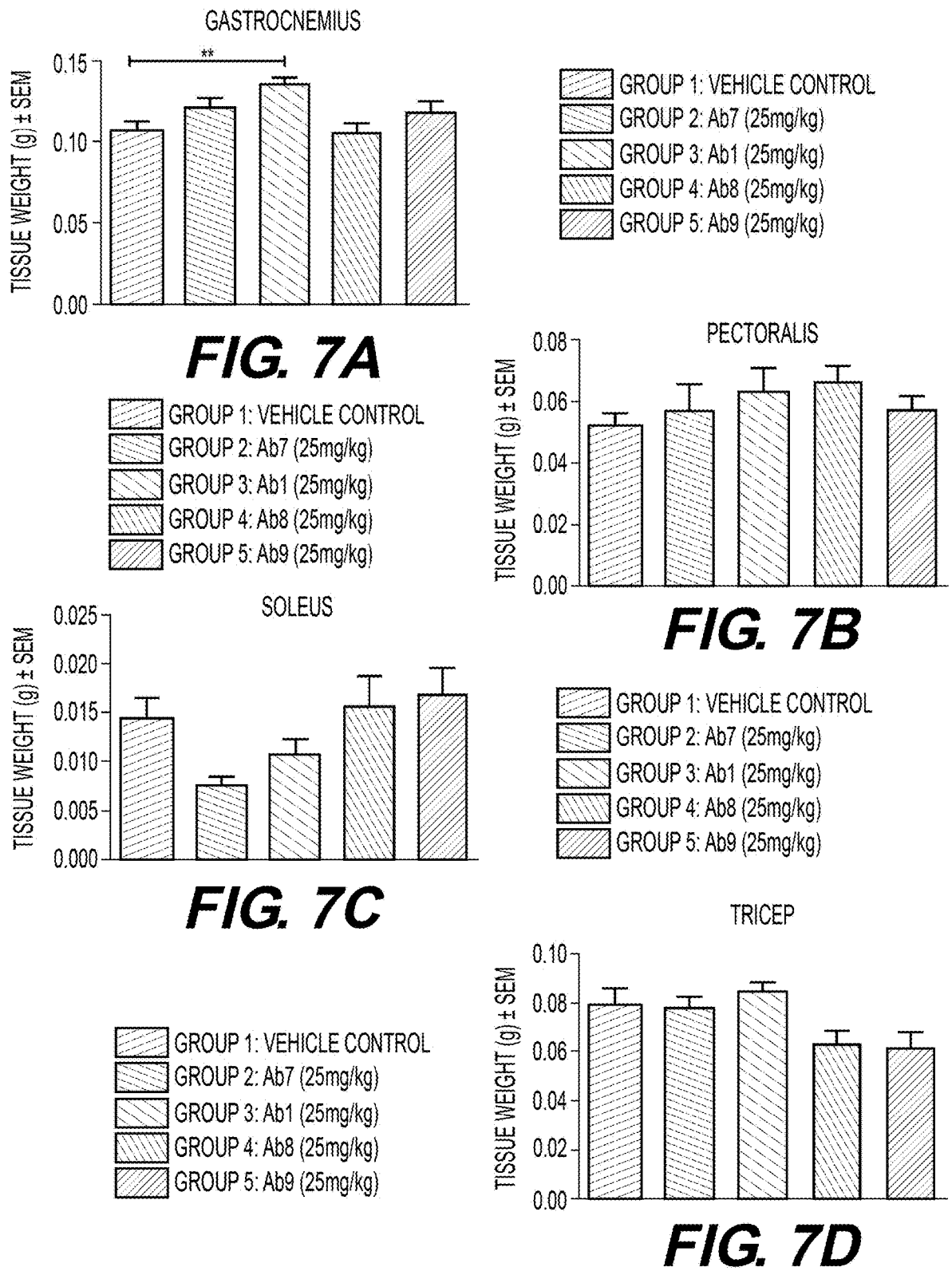

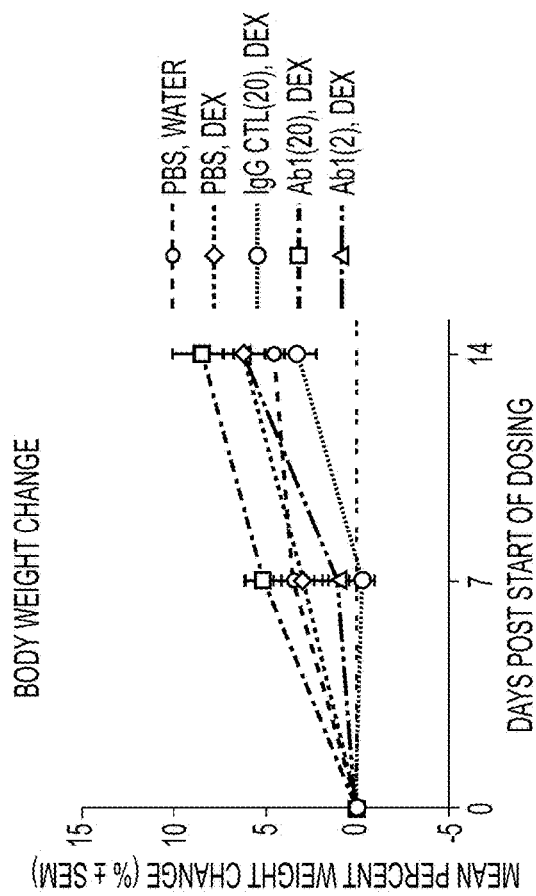
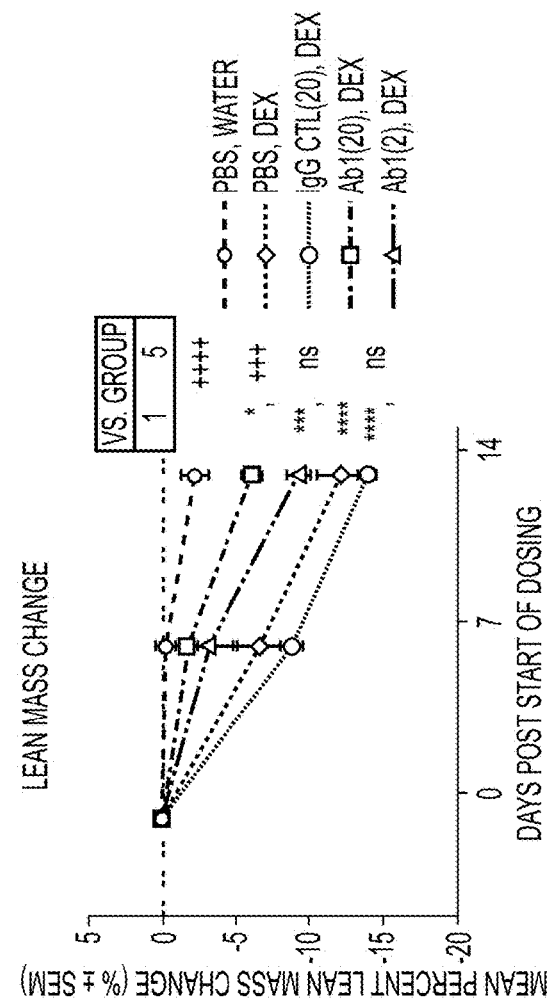
FIG. 11A
FIG. 11B

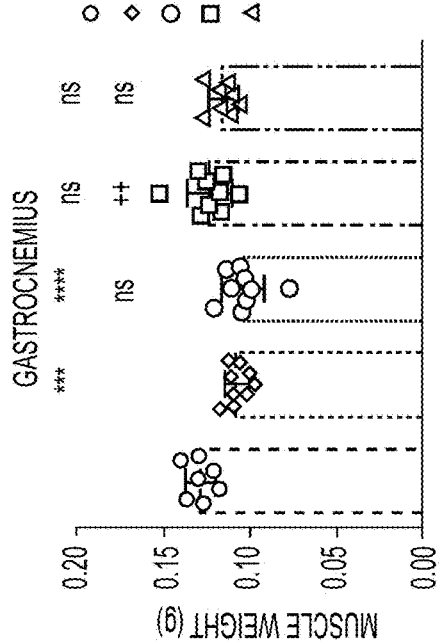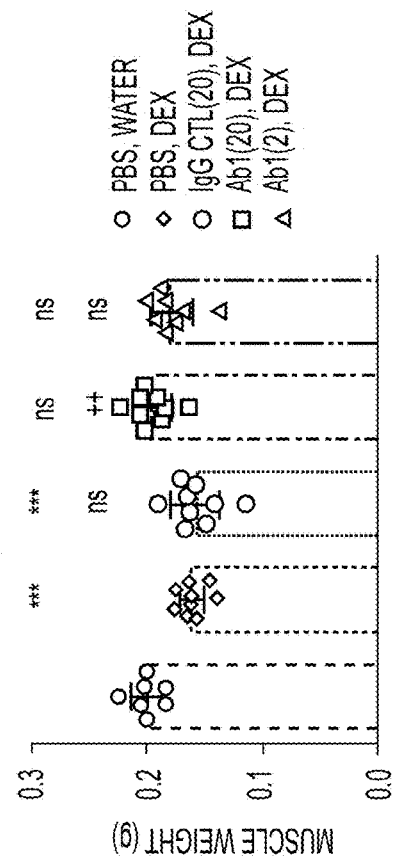

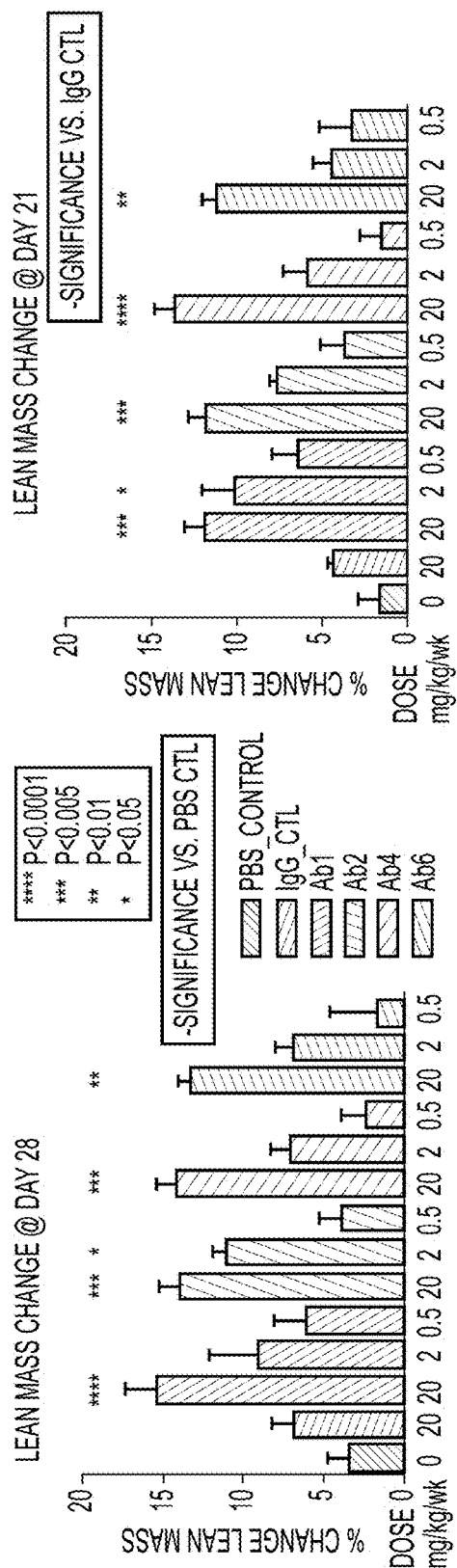
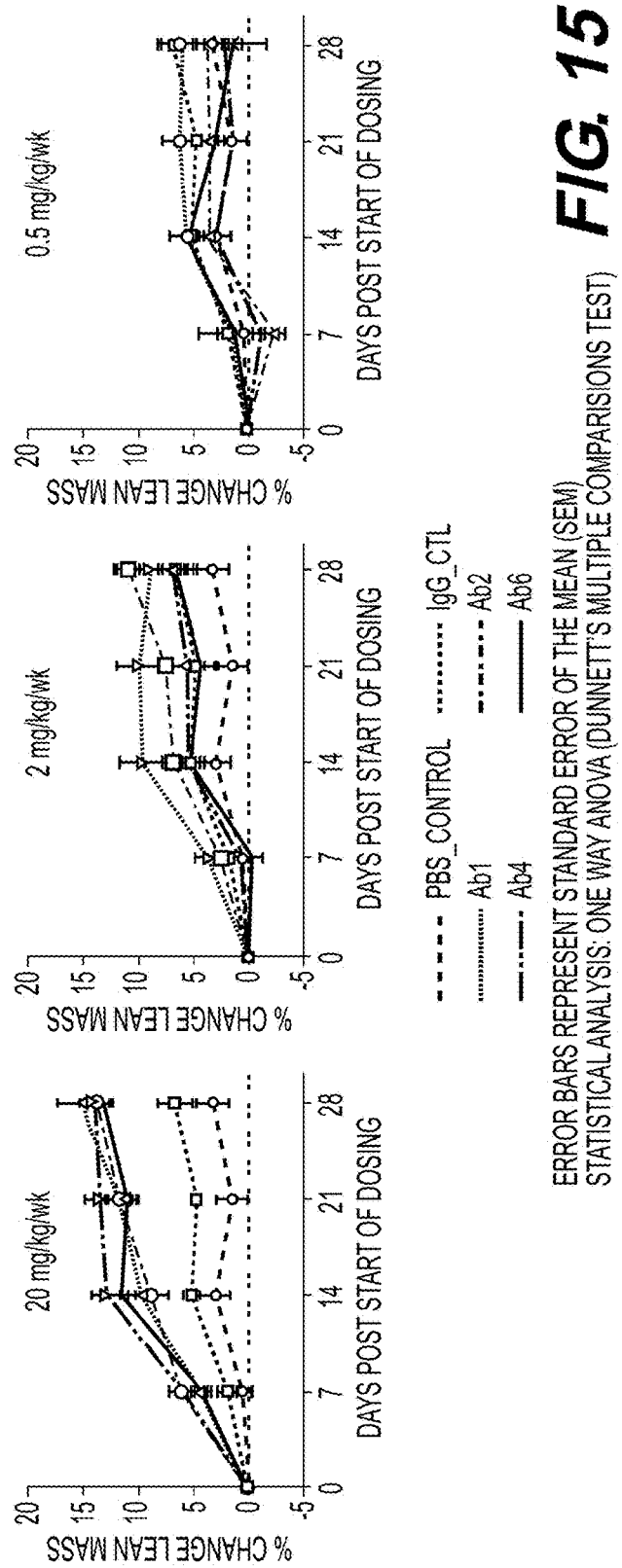
FIG. 15

```
  1 QVQLVESGGGVVQPGRSLRLSCAASGFTFSSYGMHWVRQAPGKGLEWVAVISYDGSNKYY   60
 61 ADSVKGRFTISRDNSKNTLYLQMNSLRAEDTAVYYCARDLLVRFLEWSHYYGMDVWGQGT  120
121 TVTVSSASTKGPSVFPLAPCSRSTSESTAALGCLVKDYFPEPVTVSWNSGALTSGVHTFP  180
181 AVLQSSGLYSLSSVVTVPSSSLGTKTYTCNVDHKPSNTKVDKRVESKYGPPCPPCPAPEF  240
241 LGGPSVFLFPPKPKDTLMISRTPEVTCVVVDVSQEDPEVQFNWYVDGVEVHNAKTKPREE  300
301 QFNSTYRVVSVLTVLHQDWLNGKEYKCKVSNKGLPSSIEKTISKAKGQPREPQVYTLPPS  360
361 QEEMTKNQVSLTCLVKGFYPSDIAVEWESNGQPENNYKTTPPVLDSDGSFFLYSRLTVDK  420
421 SRWQEGNVFSCSVMHEALHNHYTQKSLSLSLG                              452
```

FIG. 21A

```
  1 QSVLTQPPSASGTPGQRVTISCSGSSSNIGSNTVHWYQQLPGTAPKLLIYSDNQRPSGVP   60
 61 DRFSGSKSGTSASLAISGLQSEDEADYYCAAWDDSLNGVFGGGTKLTVLGQPKAAPSVTL  120
121 FPPSSEELQANKATLVCLISDFYPGAVTVAWKADSSPVKAGVETTTPSKQSNNKYAASSY  180
181 LSLTPEQWKSHRSYSCQVTHEGSTVEKTVAPTECS                            215
```

FIG. 21B

```
            FRAMEWORK 1            CDR1        FRAMEWORK 2
Ab1   QIQLVQSGGGVVQPGRSLRLSCAASGFTFSSYGMHWVRQAPGKGLEWVA
Ab3   QIQLVQSGGGVVQPGRSLRLSCAASGFAFSSYGMHWVRQAPGKGLEWVA
Ab5   QIQLVQSGGGVVQPGRSLRLSCAASGFAFSSYGMHWVRQAPGKGLEWVA

CDR2                    FRAMEWORK 3
Ab1   VISYDGSNKYYADSVKGRFTISRDNSKNTLYLQMNSLRAEDTAVYYCAR
Ab3   VISYDGSXKYYADSVKGRFTISRDNSKNTLYLQMNSLRAEDTAVYYCAR
Ab5   VISYDGXNKYYADSVKGRFTISRDNSKNTLYLQMNSLRAEDTAVYYCAR

CDR3              FRAMEWORK 4
Ab1   DLLVRFLEWSHYYGMDVWGQGTTVTVSS
Ab3   DLLVRFLEWSHXYGMDVWGQGTTVTVSS
Ab5   DLLVRFLEWSHXYGMDVWGQGTTVTVSS
```

FIG. 24A

```
            FRAMEWORK 1            CDR1       FRW2
Ab1   QPVLTQPPSASGTPGQRVTISCSGSSSNIGSNTVHWYQQLPGTAPKLLIY
Ab3   QPVLTQPPSASGTPGQRVTISCSGSXSNIGSNTVHWYQQLPGTAPKLLIY
Ab5   QPVLTQPPSASGTPGQRVTISCSGSSSNIGXNTVHWYQQLPGTAPKLLIY

CDR2            FRAMEWORK 3
Ab1   SDNQRPSGVPDRFSGSKSGTSASLVISGLQSDDEADYYC
Ab3   SDXQRPSGVPDRFSGSKSGTSASLVISGLQSDDEADYYC
Ab5   SDXQRPSGVPDRFSGSKSGTSASLVISGLQSDDEADYYC

CDR3         FRAMEWORK 4
Ab1   AAWDDSLNGVFGGGTKLTVL
Ab3   AAWDXSLNGVFGGGTKLTVL
Ab5   AAWDXSLNGVFGGGTKLTVL
```

FIG. 24B

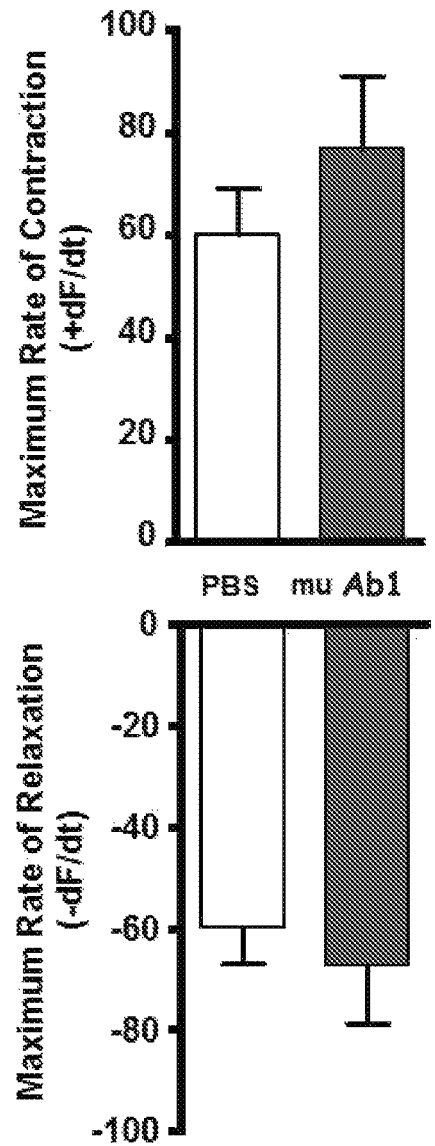
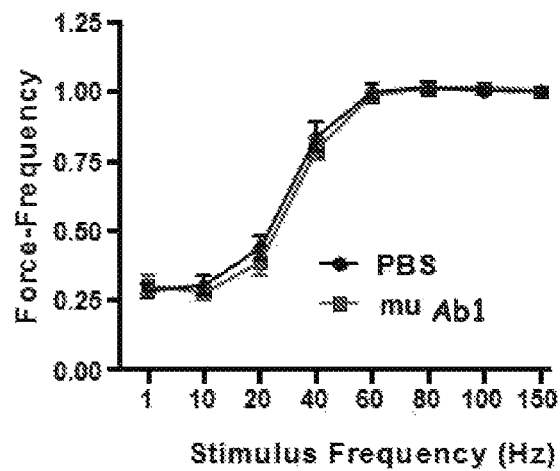
FIG. 38B
FIG. 38A

Supracellular localization of Myostatin precursors

α pro/latent Myostatin

FIG. 40A

α pro/latent Myostatin + 10x proGDF8

FIG. 40B

α pro/latent Myostatin + 10x proGDF11

FIG. 40C

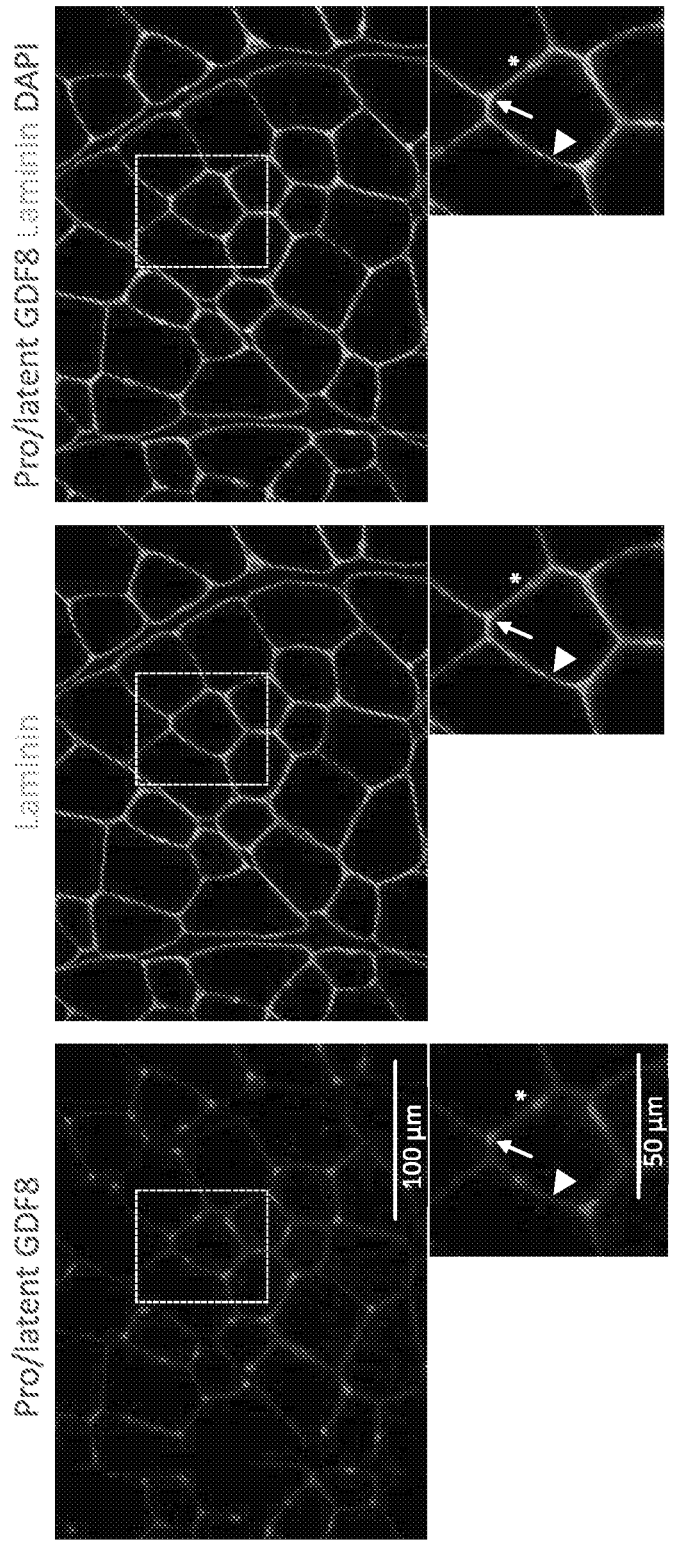

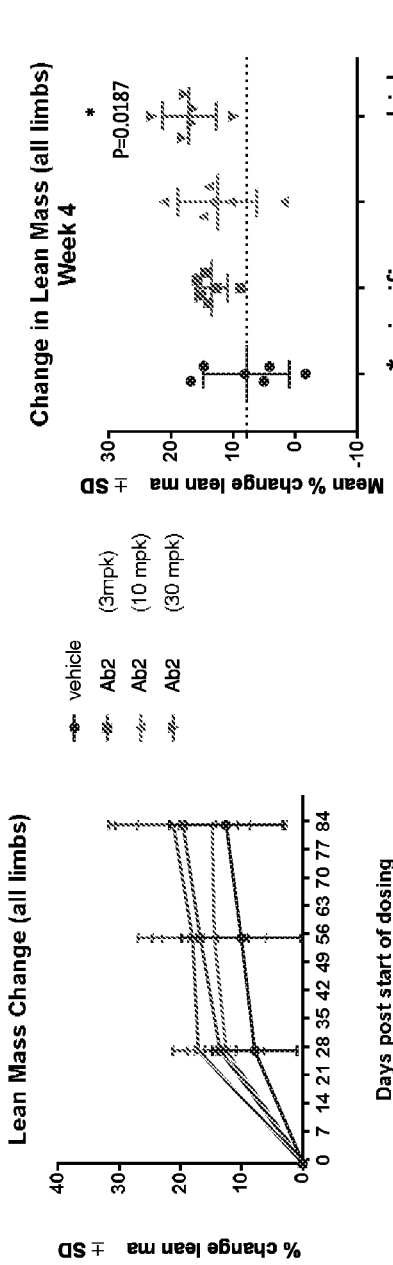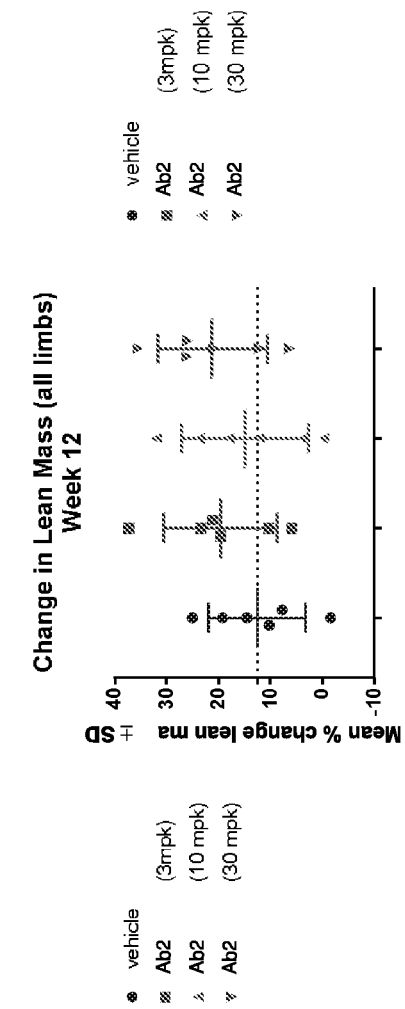
FIG. 43A
FIG. 43B
*, significance vs. vehicle
FIG. 43C
FIG. 43D

| Lean tissue | vehicle | Ab2 (3mpk) | Ab2 (10mpk) | Ab2 (30mpk) |
|---|---|---|---|---|
| Mean % change in lean mass @ 4 weeks | 7.8 | 13.5 | 12.6 | 17.0 |
| Mean % change in lean mass @ 8 weeks | 10.0 | 16.8 | 14.5 | 17.9 |
| Mean % change in lean mass @ 12 weeks | 12.5 | 19.6 | 14.8 | 21.2 |
| % difference in biceps weight vs. vehicle group | 0.0 | 18.0 | 13.0 | 25.5 |
| % difference in gastroc weight vs. vehicle group | 0.0 | 21.7 | 16.0 | 22.9 |

FIG. 45

SEQUENCE LISTING

```
<160> NUMBER OF SEQ ID NOS: 118

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

Ser Ser Tyr Gly Met His
1               5
```

<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 2

Gly Phe Thr Phe Ser Ser Tyr Gly Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

Gly Phe Ala Phe Ser Ser Tyr Gly Met His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 4

Val Ile Ser Tyr Asp Gly Ser Asn Lys Tyr Tyr Ala Asp Ser Val Lys
1               5                   10                  15

Gly

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Ile Ser Tyr Asp Gly Ser Asn
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Val Ile Ser Tyr Asp Gly Ser Ile Lys Tyr Tyr Ala Asp Ser Val Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

```
Ile Ser Tyr Asp Gly Ser Ile
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 8

Val Ile Ser Tyr Asp Gly Asn Asn Lys Tyr Tyr Ala Asp Ser Val Lys
1               5                   10                  15

Gly

<210> SEQ ID NO 9
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 9

Ile Ser Tyr Asp Gly Asn Asn
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Asp Leu Leu Val Arg Phe Leu Glu Trp Ser His Tyr Tyr Gly Met Asp
1               5                   10                  15

Val

<210> SEQ ID NO 11
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 11

Asp Leu Leu Val Arg Phe Leu Glu Trp Ser His Lys Tyr Gly Met Asp
1               5                   10                  15

Val

<210> SEQ ID NO 12
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 12

Ser Gly Ser Ser Ser Asn Ile Gly Ser Asn Thr Val His
1               5                   10

<210> SEQ ID NO 13
<211> LENGTH: 8
<212> TYPE: PRT
```

```
<213> ORGANISM: Artificial Sequence
<220> FEATURE:
<223> OTHER INFORMATION: Synthetic Polypeptide

<400> SEQUENCE: 13

Ser Ser Asn Ile Gly Ser Asn Thr
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 14

Ser Gly Ser Thr Ser Asn Ile Gly Ser Asn Thr Val His
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Thr Ser Asn Ile Gly Ser Asn Thr
1               5

<210> SEQ ID NO 16
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 16

Ser Gly Ser Ser Ser Asn Ile Gly Gly Asn Thr Val His
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 17

Ser Ser Asn Ile Gly Gly Asn Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 18

Ser Asp Asn Gln Arg Pro Ser
1               5

<210> SEQ ID NO 19
<211> LENGTH: 3
<212> TYPE: PRT
<213> ORGANISM: Artificial Sequence
```

```
<220> FEATURE:
<223> OTHER INFORMATION: Synthetic Polypeptide

<400> SEQUENCE: 19

Ser Asp Asn
1

<210> SEQ ID NO 20
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 20

Ser Asp Asp Gln Arg Pro Ser
1               5

<210> SEQ ID NO 21
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 21

Ser Asp Asp
1

<210> SEQ ID NO 22
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 22

Ala Ala Trp Asp Asp Ser Leu Asn Gly Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 23

Ala Ala Trp Asp Glu Ser Leu Asn Gly Val
1               5                   10

<210> SEQ ID NO 24
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 24

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

```
Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asp Leu Leu Val Arg Phe Leu Glu Trp Ser His Tyr Tyr Gly
                100                 105                 110

Met Asp Val Trp Gly Gln Gly Thr Thr Val Thr Val Ser Ser
                115                 120                 125
```

<210> SEQ ID NO 25
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 25

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asp Leu Leu Val Arg Phe Leu Glu Trp Ser His Tyr Tyr Gly
                100                 105                 110

Met Asp Val Trp Gly Gln Gly Thr Thr Val Thr Val Ser Ser
                115                 120                 125
```

<210> SEQ ID NO 26
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 26

```
Gln Ile Gln Leu Val Gln Ser Gly Gly Gly Val Val Gln Pro Gly Arg
  1               5                  10                  15

Ser Leu Arg Leu Ser Cys Ala Ala Ser Gly Phe Ala Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Ile Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Arg Asp Leu Leu Val Arg Phe Leu Glu Trp Ser His Lys Tyr Gly
                100                 105                 110
```

```
Met Asp Val Trp Gly Gln Gly Thr Thr Val Thr Val Ser Ser
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 28

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Synthetic Polypeptide
```

<400> SEQUENCE: 29

Gln Val Gln Leu Val Glu Ser Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Lys Tyr Gly
            100                 105                 110

Met Asp Val Trp Gly Gln Gly Thr Thr Val Thr Val Ser Ser
        115                 120                 125

<210> SEQ ID NO 30
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 30

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu
            100                 105

<210> SEQ ID NO 31
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu
            100                 105

<210> SEQ ID NO 32
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 32

Gln Pro Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 33
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 33

Gln Ser Val Leu Thr Gln Pro Pro Ser Ala Ser Gly Thr Pro Gly Gln
1               5                   10                  15

Arg Val Thr Ile Ser Cys Ser Gly Ser Thr Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 34
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 34

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 35
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val His Trp Tyr Gln Gln Leu Pro Gly Thr Ala Pro Lys Leu Leu
        35                  40                  45

Ile Tyr Ser Asp Asp Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Glu Ser Leu
                85                  90                  95

Asn Gly Val Phe Gly Gly Gly Thr Lys Leu Thr Val Leu
            100                 105

<210> SEQ ID NO 36
<211> LENGTH: 98
<212> TYPE: PRT
<213> ORGANISM: Artificial Sequence
<220> FEATURE:
<223> OTHER INFORMATION: Synthetic Polypeptide

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg

<210> SEQ ID NO 37
<211> LENGTH: 98
<212> TYPE: PRT
<213> ORGANISM: Artificial Sequence
<220> FEATURE:
<223> OTHER INFORMATION: Synthetic Polypeptide

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 38
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 38
cagatccagc tggtgcagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcactac tacggtatgg acgtctgggg ccaagggacc   360
acggtcaccg tctcctca                                                 378

<210> SEQ ID NO 39
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 39
caggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agccgaggac acggctgtgt attactgtgc gagagatctc   300
```
ctggtgcgat ttttggagtg gtcgcactac tacggtatgg acgtctgggg ccaagggacc    360
acggtcaccg tctcctca                                                  378

<210> SEQ ID NO 40
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 40
cagatccagc tggtgcagtc tggggaggc gtggtccagc ctgggaggtc cctgagactc      60
tcctgtgcag cgtctggatt cgccttcagt agctatggca tgcactgggt ccgccaggct   120
ccaggcaagg ggctggagtg gtggcagtt atatcatatg atggaagtat caaatactat    180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378

<210> SEQ ID NO 41
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 41
caggtgcagc tggtggagtc tggggaggc gtggtccagc ctgggaggtc cctgagactc      60
tcctgtgcag cgtctggatt cgccttcagt agctatggca tgcactgggt ccgccaggct   120
ccaggcaagg ggctggagtg gtggcagtt atatcatatg atggaagtat caaatactat    180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378

<210> SEQ ID NO 42
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 42
cagatccagc tggtgcagtc tggggaggc gtggtccagc ctgggaggtc cctgagactc      60
tcctgtgcag cgtctggatt cgccttcagt agctatggca tgcactgggt ccgccaggct   120
ccaggcaagg ggctggagtg gtggcagtt atatcatatg atggaaataa taaatactat    180
gcagactccg tgaagggccg attcaccatc tccagagaca attccaagaa cacgctgtat   240
ctgcaaatga acagcctgag agccgaggac acggctgtgt attactgtgc gagagatctc   300
ctggtgcgat ttttggagtg gtcgcacaag tacggtatgg acgtctgggg ccaagggacc   360
acggtcaccg tctcctca                                                  378

<210> SEQ ID NO 43

-continued

```
<211> LENGTH: 378
<212> TYPE: DNA
<213> ORGANISM: Artificial Sequence
<220> FEATURE:
<223> OTHER INFORMATION: Synthetic Polynucleotide

<400> SEQUENCE: 43
caggtgcagc tggtggagtc tgggggaggc gtggtccagc ctggaggtc cctgagactc      60 tcctgtgcag cgtctggatt cgccttcagt agctatggca tgcactgggt ccgccaggct    120
ccaggcaagg ggctggagtg ggtggcagtt atatcatatg atggaaataa taaatactat    180
gcagactccg tgaagggccg attcaccatc tccagagaca attccaagaa cacgctgtat    240
ctgcaaatga acagcctgag agccgaggac acggctgtgt attactgtgc gagagatctc    300
ctggtgcgat ttttggagtg gtcgcacaag tacggtatgg acgtctgggg ccaagggacc    360
acggtcaccg tctcctca                                                  378

<210> SEQ ID NO 44
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 44
cagcctgtgc tgactcagcc accctcagcg tctgggaccc ccgggcagag ggtcaccatc     60
tcttgttctg gaagcagctc caacatcgga agtaatactg tccactggta ccagcaactc    120
ccaggaacgg cccccaaact cctcatctat agtgataatc agcgcccctc agggtccct    180 gaccgattct ctggctccaa gtctggcacc tcagcctccc tggtcatcag tgggctccag    240
tctgacgatg aggctgatta ttactgtgca gcatgggatg acagcctgaa tggggtgttc    300
ggcggaggga ccaagctgac cgtccta                                        327

<210> SEQ ID NO 45
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 45
cagtctgtgc tgactcagcc accctcagcg tctgggaccc ccgggcagag ggtcaccatc     60
tcttgttctg gaagcagctc caacatcgga agtaatactg tccactggta ccagcaactc    120
ccaggaacgg cccccaaact cctcatctat agtgataatc agcgcccctc agggtccct    180 gaccgattct ctggctccaa gtctggcacc tcagcctccc tggccatcag tgggctccag    240
tctgaggatg aggctgatta ttactgtgca gcatgggatg acagcctgaa tggggtgttc    300
ggcggaggga ccaagctgac cgtccta                                        327

<210> SEQ ID NO 46
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 46
cagcctgtgc tgactcagcc accctcagcg tctgggaccc ccgggcagag ggtcaccatc     60
tcttgttctg gaagcacctc caacatcgga agtaatactg tccactggta ccagcaactc    120
```

```
ccaggaacgg cccccaaact cctcatctat agtgatgatc agcgcccctc agggtccct    180 gaccgattct ctggctccaa gtctggcacc tcagcctccc tggtcatcag tgggctccag    240
tctgacgatg aggctgatta ttactgtgca gcatgggatg agagcctgaa tggggtgttc    300
ggcggaggga ccaagctgac cgtccta                                        327
```

<210> SEQ ID NO 47
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 47

```
cagtctgtgc tgactcagcc accctcagcg tctgggaccc ccgggcagag ggtcaccatc     60
tcttgttctg gaagcacctc caacatcgga agtaatactg tccactggta ccagcaactc    120
ccaggaacgg cccccaaact cctcatctat agtgatgatc agcgcccctc agggtccct    180 gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327
```

<210> SEQ ID NO 48
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 48

```
cagcctgtgc tgactcagcc accctcagcg tctgggaccc ccgggcagag ggtcaccatc     60
tcttgttctg gaagcagctc caacatcgga ggaaatactg tccactggta ccagcaactc    120
ccaggaacgg cccccaaact cctcatctat agtgatgatc agcgcccctc agggtccct    180 gaccgattct ctggctccaa gtctggcacc tcagcctccc tggtcatcag tgggctccag    240
tctgacgatg aggctgatta ttactgtgca gcatgggatg agagcctgaa tggggtgttc    300
ggcggaggga ccaagctgac cgtccta                                        327
```

<210> SEQ ID NO 49
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 49

```
cagtctgtgc tgactcagcc accctcagcg tctgggaccc ccgggcagag ggtcaccatc     60
tcttgttctg gaagcagctc caacatcgga ggaaatactg tccactggta ccagcaactc    120
ccaggaacgg cccccaaact cctcatctat agtgatgatc agcgcccctc agggtccct    180 gaccgattct ctggctccaa gtctggcacc tcagcctccc tggccatcag tgggctccag    240
tctgaggatg aggctgatta ttactgtgca gcatgggatg agagcctgaa tggggtgttc    300
ggcggaggga ccaagctgac cgtccta                                        327
```

<210> SEQ ID NO 50
<211> LENGTH: 452
<212> TYPE: PRT

<213> ORGANISM: Artificial Sequence
<220> FEATURE:
<223> OTHER INFORMATION: Synthetic Polypeptide

<400> SEQUENCE: 50

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
385                 390                 395                 400
Pro Pro Val Leu Asp Ser Asp Gly Ser Phe Phe Leu Tyr Ser Arg Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly
    450

<210> SEQ ID NO 51
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Leu Leu
            35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
            195                 200                 205

Val Ala Pro Thr Glu Cys Ser
    210                 215

<210> SEQ ID NO 52
<211> LENGTH: 352
<212> TYPE: PRT
<213> ORGANISM: Homo sapiens

<400> SEQUENCE: 52

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30
```

Ile Lys Ile Gln Ile Leu Ser Lys Leu Arg Leu Glu Thr Ala Pro Asn
              35                  40                  45

Ile Ser Lys Asp Val Ile Arg Gln Leu Leu Pro Lys Ala Pro Pro Leu
 50                  55                  60

Arg Glu Leu Ile Asp Gln Tyr Asp Val Gln Arg Asp Asp Ser Ser Asp
 65                  70                  75                  80

Gly Ser Leu Glu Asp Asp Tyr His Ala Thr Thr Glu Thr Ile Ile
                 85                  90                  95

Thr Met Pro Thr Glu Ser Asp Phe Leu Met Gln Val Asp Gly Lys Pro
                100                 105                 110

Lys Cys Cys Phe Phe Lys Phe Ser Ser Lys Ile Gln Tyr Asn Lys Val
                115                 120                 125

Val Lys Ala Gln Leu Trp Ile Tyr Leu Arg Pro Val Glu Thr Pro Thr
130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
                180                 185                 190

Leu Lys Gln Pro Glu Ser Asn Leu Gly Ile Glu Ile Lys Ala Leu Asp
                195                 200                 205

Glu Asn Gly His Asp Leu Ala Val Thr Phe Pro Gly Pro Gly Glu Asp
210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
                260                 265                 270

Asp Trp Ile Ile Ala Pro Lys Arg Tyr Lys Ala Asn Tyr Cys Ser Gly
                275                 280                 285

Glu Cys Glu Phe Val Phe Leu Gln Lys Tyr Pro His Thr His Leu Val
                290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
                340                 345                 350

<210> SEQ ID NO 53
<211> LENGTH: 352
<212> TYPE: PRT
<213> ORGANISM: Rattus rattus

<400> SEQUENCE: 53

Asn Glu Asp Ser Glu Arg Glu Ala Asn Val Glu Lys Glu Gly Leu Cys
1               5                   10                  15

Asn Ala Cys Ala Trp Arg Gln Asn Thr Arg Tyr Ser Arg Ile Glu Ala
                20                  25                  30

Ile Lys Ile Gln Ile Leu Ser Lys Leu Arg Leu Glu Thr Ala Pro Asn
              35                  40                  45

Ile Ser Lys Asp Ala Ile Arg Gln Leu Leu Pro Arg Ala Pro Pro Leu

```
            50                  55                  60
Arg Glu Leu Ile Asp Gln Tyr Asp Val Gln Arg Asp Ser Ser Asp
 65                  70                  75                  80

Gly Ser Leu Glu Asp Asp Tyr His Ala Thr Thr Glu Thr Ile Ile
                     85                  90                  95

Thr Met Pro Thr Glu Ser Asp Phe Leu Met Gln Ala Asp Gly Lys Pro
                100                 105                 110

Lys Cys Cys Phe Phe Lys Phe Ser Ser Lys Ile Gln Tyr Asn Lys Val
                115                 120                 125

Val Lys Ala Gln Leu Trp Ile Tyr Leu Arg Ala Val Lys Thr Pro Thr
                130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Ser Pro Gly
                    165                 170                 175

Thr Gly Ile Trp Gln Ser Ile Asp Val Lys Thr Val Leu Gln Asn Trp
                180                 185                 190

Leu Lys Gln Pro Glu Ser Asn Leu Gly Ile Glu Ile Lys Ala Leu Asp
                195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                    245                 250                 255

Arg Cys Cys Arg Tyr Pro Leu Thr Val Asp Phe Glu Ala Phe Gly Trp
                260                 265                 270

Asp Trp Ile Ile Ala Pro Lys Arg Tyr Lys Ala Asn Tyr Cys Ser Gly
                275                 280                 285

Glu Cys Glu Phe Val Phe Leu Gln Lys Tyr Pro His Thr His Leu Val
                290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                    325                 330                 335

Ile Tyr Gly Lys Ile Pro Ala Met Val Val Asp Arg Cys Gly Cys Ser
                340                 345                 350

<210> SEQ ID NO 54
<211> LENGTH: 352
<212> TYPE: PRT
<213> ORGANISM: Mus musculus

<400> SEQUENCE: 54

Asn Glu Gly Ser Glu Arg Glu Glu Asn Val Glu Lys Glu Gly Leu Cys
 1               5                  10                  15

Asn Ala Cys Ala Trp Arg Gln Asn Thr Arg Tyr Ser Arg Ile Glu Ala
                 20                  25                  30

Ile Lys Ile Gln Ile Leu Ser Lys Leu Arg Leu Glu Thr Ala Pro Asn
                 35                  40                  45

Ile Ser Lys Asp Ala Ile Arg Gln Leu Leu Pro Arg Ala Pro Pro Leu
     50                  55                  60

Arg Glu Leu Ile Asp Gln Tyr Asp Val Gln Arg Asp Ser Ser Asp
 65                  70                  75                  80
```

```
Gly Ser Leu Glu Asp Asp Asp Tyr His Ala Thr Thr Glu Thr Ile Ile
             85                  90                  95

Thr Met Pro Thr Glu Ser Asp Phe Leu Met Gln Ala Asp Gly Lys Pro
           100                 105                 110

Lys Cys Cys Phe Phe Lys Phe Ser Ser Lys Ile Gln Tyr Asn Lys Val
           115                 120                 125

Val Lys Ala Gln Leu Trp Ile Tyr Leu Arg Pro Val Lys Thr Pro Thr
130             135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Ser Pro Gly
               165                 170                 175

Thr Gly Ile Trp Gln Ser Ile Asp Val Lys Thr Val Leu Gln Asn Trp
           180                 185                 190

Leu Lys Gln Pro Glu Ser Asn Leu Gly Ile Glu Ile Lys Ala Leu Asp
       195                 200                 205

Glu Asn Gly His Asp Leu Ala Val Thr Phe Pro Gly Pro Gly Glu Asp
   210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
               245                 250                 255

Arg Cys Cys Arg Tyr Pro Leu Thr Val Asp Phe Glu Ala Phe Gly Trp
           260                 265                 270

Asp Trp Ile Ile Ala Pro Lys Arg Tyr Lys Ala Asn Tyr Cys Ser Gly
       275                 280                 285

Glu Cys Glu Phe Val Phe Leu Gln Lys Tyr Pro His Thr His Leu Val
   290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
               325                 330                 335

Ile Tyr Gly Lys Ile Pro Ala Met Val Val Asp Arg Cys Gly Cys Ser
           340                 345                 350

<210> SEQ ID NO 55
<211> LENGTH: 277
<212> TYPE: PRT
<213> ORGANISM: Macaca fascicularis

<400> SEQUENCE: 55

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
               20                  25                  30

Ile Lys Ile Gln Ile Leu Ser Lys Leu Arg Leu Glu Thr Ala Pro Asn
           35                  40                  45

Ile Ser Lys Asp Ala Ile Arg Gln Leu Leu Pro Lys Ala Pro Pro Leu
       50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
               85                  90                  95

Thr Met Pro Thr Glu Ser Asp Phe Leu Met Gln Val Asp Gly Lys Pro
           100                 105                 110
```

```
Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
            165                 170                 175

Thr Gly Ile Trp Gln Ser Ile Asp Val Lys Thr Val Leu Gln Asn Trp
                180                 185                 190

Leu Lys Gln Pro Glu Ser Asn Leu Gly Ile Glu Ile Lys Ala Leu Asp
            195                 200                 205

Glu Asn Gly His Asp Leu Ala Val Thr Phe Pro Gly Pro Gly Glu Asp
210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala
        275
```

<210> SEQ ID NO 56
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 56

Arg Ser Arg Arg
1

<210> SEQ ID NO 57
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 57

Arg Val Arg Arg
1

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Cys Pro Pro Cys Pro
1               5

<210> SEQ ID NO 59
<211> LENGTH: 17
<212> TYPE: PRT
<213> ORGANISM: Artificial Sequence
<220> FEATURE:

<223> OTHER INFORMATION: Synthetic Polypeptide

<400> SEQUENCE: 59

His Tyr Tyr Gly Met Asp Val Trp Gly Gln Gly Thr Thr Val Thr Val
1               5                   10                  15

Ser

<210> SEQ ID NO 60
<211> LENGTH: 89
<212> TYPE: PRT
<213> ORGANISM: Artificial Sequence
<220> FEATURE:
<223> OTHER INFORMATION: Synthetic Polypeptide

<400> SEQUENCE: 60

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys
                85

<210> SEQ ID NO 61
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 61

Val Phe Gly Gly Gly Thr Lys Leu Thr Val Leu
1               5                   10

<210> SEQ ID NO 62
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 62

Pro Lys Ala Pro Pro Leu Arg Glu Leu Ile Asp Gln Tyr Asp Val Gln
1               5                   10                  15

Arg Asp Asp Ser Ser Asp Gly Ser Leu Glu Asp Asp Tyr His Ala
            20                  25                  30

Thr

<210> SEQ ID NO 63
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 63

Gly Leu Asn Pro Phe Leu Glu Val Lys Val Thr Asp Thr Pro Lys Arg

```
1               5                   10                  15
Ser Arg Arg Asp Phe Gly Leu Asp Cys Asp Glu His Ser Thr Glu Ser
                20                  25                  30

Arg Cys
```

<210> SEQ ID NO 64
<211> LENGTH: 80
<212> TYPE: PRT
<213> ORGANISM: Artificial Sequence
<220> FEATURE:
<223> OTHER INFORMATION: Synthetic Polypeptide

<400> SEQUENCE: 64

```
Val Asp Leu Asn Glu Asn Ser Glu Gln Lys Glu Asn Val Glu Lys Glu
1               5                   10                  15

Gly Leu Cys Asn Ala Cys Thr Trp Arg Gln Asn Thr Lys Ser Ser Arg
                20                  25                  30

Ile Glu Ala Ile Lys Ile Gln Ile Leu Ser Lys Leu Arg Leu Glu Thr
            35                  40                  45

Ala Pro Asn Ile Ser Lys Asp Val Ile Arg Gln Leu Leu Pro Lys Ala
        50                  55                  60

Pro Pro Leu Arg Glu Leu Ile Asp Gln Tyr Asp Val Gln Arg Asp Asp
65                  70                  75                  80
```

<210> SEQ ID NO 65
<211> LENGTH: 418
<212> TYPE: PRT
<213> ORGANISM: Artificial Sequence
<220> FEATURE:
<223> OTHER INFORMATION: Synthetic Polypeptide

<400> SEQUENCE: 65

```
Met Asp Met Arg Val Pro Ala Gln Leu Leu Gly Leu Leu Leu Leu Trp
1               5                   10                  15

Phe Ser Gly Val Leu Gly Asp Tyr Lys Asp Asp Asp Lys His His
                20                  25                  30

His His His His Leu Glu Val Leu Phe Gln Gly Pro Ala Glu Gly Pro
            35                  40                  45

Ala Ala Ala Ala Ala Ala Ala Ala Ala Ala Ala Ala Gly Val Gly
        50                  55                  60

Gly Glu Arg Ser Ser Arg Pro Ala Pro Ser Val Ala Pro Glu Pro Asp
65                  70                  75                  80

Gly Cys Pro Val Cys Val Trp Arg Gln His Ser Arg Glu Leu Arg Leu
                85                  90                  95

Glu Ser Ile Lys Ser Gln Ile Leu Ser Lys Leu Arg Leu Lys Glu Ala
            100                 105                 110

Pro Asn Ile Ser Arg Glu Val Val Lys Gln Leu Leu Pro Lys Ala Pro
        115                 120                 125

Pro Leu Arg Glu Leu Ile Asp Gln Tyr Asp Val Gln Arg Asp Asp Ser
    130                 135                 140

Ser Asp Gly Ser Leu Glu Asp Asp Tyr His Ala Thr Thr Glu Thr
145                 150                 155                 160

Ile Ile Thr Met Pro Thr Glu Ser Asp Phe Leu Met Gln Val Asp Gly
                165                 170                 175

Lys Pro Lys Cys Cys Phe Phe Lys Phe Ser Ser Lys Ile Gln Tyr Asn
            180                 185                 190

Lys Val Val Lys Ala Gln Leu Trp Ile Tyr Leu Arg Pro Val Glu Thr
```

```
                195                 200                 205
Pro Thr Thr Val Phe Val Gln Ile Leu Arg Leu Ile Lys Pro Met Lys
    210                 215                 220

Asp Gly Thr Arg Tyr Thr Gly Ile Arg Ser Leu Lys Leu Asp Met Asn
225                 230                 235                 240

Pro Gly Thr Gly Ile Trp Gln Ser Ile Asp Val Lys Thr Val Leu Gln
                245                 250                 255

Asn Trp Leu Lys Gln Pro Glu Ser Asn Leu Gly Ile Glu Ile Lys Ala
            260                 265                 270

Leu Asp Glu Asn Gly His Asp Leu Ala Val Thr Phe Pro Gly Pro Gly
        275                 280                 285

Glu Asp Gly Leu Asn Pro Phe Leu Glu Val Lys Val Thr Asp Thr Pro
    290                 295                 300

Lys Arg Ser Arg Arg Asn Leu Gly Leu Asp Cys Asp Glu His Ser Ser
305                 310                 315                 320

Glu Ser Arg Cys Cys Arg Tyr Pro Leu Thr Val Asp Phe Glu Ala Phe
                325                 330                 335

Gly Trp Asp Trp Ile Ile Ala Pro Lys Arg Tyr Lys Ala Asn Tyr Cys
            340                 345                 350

Ser Gly Gln Cys Glu Tyr Met Phe Met Gln Lys Tyr Pro His Thr His
        355                 360                 365

Leu Val Gln Gln Ala Asn Pro Arg Gly Ser Ala Gly Pro Cys Cys Thr
    370                 375                 380

Pro Thr Lys Met Ser Pro Ile Asn Met Leu Tyr Phe Asn Asp Lys Gln
385                 390                 395                 400

Gln Ile Ile Tyr Gly Lys Ile Pro Gly Met Val Val Asp Arg Cys Gly
                405                 410                 415

Cys Ser

<210> SEQ ID NO 66
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 66

Asp Leu Leu Val Arg Phe Leu Glu Trp Ser His Tyr Tyr Gly Met Asp
1               5                   10                  15

Val

<210> SEQ ID NO 67
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 67

Ala Ala Trp Asp Asp Ser Leu Asn Gly Val
1               5                   10

<210> SEQ ID NO 68
<211> LENGTH: 128
<212> TYPE: PRT
<213> ORGANISM: Artificial Sequence
<220> FEATURE:
<223> OTHER INFORMATION: Synthetic Polypeptide
```

<400> SEQUENCE: 68

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Val Arg Phe Leu Glu Trp Ser His Tyr Tyr Gly
            100                 105                 110

Met Asp Val Trp Gly Gln Gly Thr Thr Val Thr Val Ser Ser Gly Ser
        115                 120                 125

<210> SEQ ID NO 69
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 69

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Asp Asp Glu Ala Asp Tyr Tyr Cys Ala Ala Trp Asp Asp Ser Leu
                85                  90                  95

Asn Gly Val Phe Gly Gly Gly Thr Lys Leu Thr Val Leu Gly Gln Pro
            100                 105                 110

Lys Ala Ala Pro Ser Val Thr Leu Phe Ser Pro Ser Ser
        115                 120                 125

<210> SEQ ID NO 70
<211> LENGTH: 272
<212> TYPE: PRT
<213> ORGANISM: Artificial Sequence
<220> FEATURE:
<223> OTHER INFORMATION: Synthetic Polypeptide

<400> SEQUENCE: 70

Gln Ile Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Leu Val Arg Phe Leu Glu Trp Ser His Tyr Tyr Gly
                100                 105                 110

Met Asp Val Trp Gly Gln Gly Thr Val Thr Val Ser Ser Gly Ser
                115                 120                 125

Ala Ser Ala Pro Thr Leu Gly Gly Gly Ser Gly Gly Gly Ser
        130                 135                 140

Ala Ala Ala Gln Pro Val Leu Thr Gln Pro Ser Ala Ser Gly Thr
145                 150                 155                 160

Pro Gly Gln Arg Val Thr Ile Ser Cys Ser Gly Ser Ser Asn Ile
                165                 170                 175

Gly Ser Asn Thr Val His Trp Tyr Gln Gln Leu Pro Gly Thr Ala Pro
                180                 185                 190

Lys Leu Leu Ile Tyr Ser Asp Asn Gln Arg Pro Ser Gly Val Pro Asp
                195                 200                 205

Arg Phe Ser Gly Ser Lys Ser Gly Thr Ser Ala Ser Leu Val Ile Ser
        210                 215                 220

Gly Leu Gln Ser Asp Asp Glu Ala Asp Tyr Tyr Cys Ala Ala Trp Asp
225                 230                 235                 240

Asp Ser Leu Asn Gly Val Phe Gly Gly Gly Thr Lys Leu Thr Val Leu
                245                 250                 255

Gly Gln Pro Lys Ala Ala Pro Ser Val Thr Leu Phe Ser Pro Ser Ser
                260                 265                 270

<210> SEQ ID NO 71
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 71

Glu Ser Leu Ile Arg Phe Leu Glu Asp Pro Gln Gln Gly Gly Met Asp
 1               5                  10                  15

Val

<210> SEQ ID NO 72
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 72

Asn Ser Trp Thr Arg Ser Asn Asn Tyr Ile
 1               5                  10

<210> SEQ ID NO 73
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 73
```

```
Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Leu Ile Arg Phe Leu Glu Asp Pro Gln Gln Gly Gly
                100                 105                 110

Met Asp Val Trp Gly Gln Gly Thr Thr Val Thr Val Ser Ser Gly Ser
            115                 120                 125

<210> SEQ ID NO 74
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 74

Gln Ser Ala Leu Thr Gln Pro Ala Ser Val Ser Gly Ser Pro Gly Gln
1               5                   10                  15

Ser Leu Thr Ile Ser Cys Thr Gly Thr Ser Ser Asp Ile Gly Gly Tyr
                20                  25                  30

Asn Tyr Val Ser Trp Tyr Gln Gln His Pro Gly Lys Ala Pro Lys Leu
            35                  40                  45

Ile Ile Tyr Asp Val Thr Asp Arg Pro Ser Gly Val Ser Gly Arg Phe
        50                  55                  60

Ser Gly Ser Lys Ser Gly Asn Thr Ala Ser Leu Thr Ile Ser Gly Leu
65                  70                  75                  80

Gln Thr Glu Asp Glu Ala Glu Tyr Phe Cys Asn Ser Trp Thr Arg Ser
                85                  90                  95

Asn Asn Tyr Ile Phe Gly Gly Gly Thr Lys Leu Thr Val Leu Gly Gln
                100                 105                 110

Pro Lys Ala Ala Pro Ser Val Thr Leu Phe Pro Pro Ser Ser
            115                 120                 125

<210> SEQ ID NO 75
<211> LENGTH: 273
<212> TYPE: PRT
<213> ORGANISM: Artificial Sequence
<220> FEATURE:
<223> OTHER INFORMATION: Synthetic Polypeptide

<400> SEQUENCE: 75

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
```

```
                50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ser Leu Ile Arg Phe Leu Glu Asp Pro Gln Gln Gly Gly
                100                 105                 110

Met Asp Val Trp Gly Gln Gly Thr Thr Val Thr Val Ser Ser Gly Ser
                115                 120                 125

Ala Ser Ala Pro Thr Leu Gly Gly Gly Ser Gly Gly Gly Gly Ser
                130                 135                 140

Ala Ala Ala Gln Ser Ala Leu Thr Gln Pro Ala Ser Val Ser Gly Ser
145                 150                 155                 160

Pro Gly Gln Ser Leu Thr Ile Ser Cys Thr Gly Thr Ser Ser Asp Ile
                165                 170                 175

Gly Gly Tyr Asn Tyr Val Ser Trp Tyr Gln Gln His Pro Gly Lys Ala
                180                 185                 190

Pro Lys Leu Ile Ile Tyr Asp Val Thr Asp Arg Pro Ser Gly Val Ser
                195                 200                 205

Gly Arg Phe Ser Gly Ser Lys Ser Gly Asn Thr Ala Ser Leu Thr Ile
                210                 215                 220

Ser Gly Leu Gln Thr Glu Asp Glu Ala Glu Tyr Phe Cys Asn Ser Trp
225                 230                 235                 240

Thr Arg Ser Asn Asn Tyr Ile Phe Gly Gly Gly Thr Lys Leu Thr Val
                245                 250                 255

Leu Gly Gln Pro Lys Ala Ala Pro Ser Val Thr Leu Phe Pro Pro Ser
                260                 265                 270
Ser

<210> SEQ ID NO 76
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 76

Asp Arg Tyr Ser Ser Trp Gly Gly Gly Phe Asp Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 77

Gln Ser Tyr Asp Ala Ser Ser Leu Trp Val
1               5                   10

<210> SEQ ID NO 78
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 78
```

Glu Val Gln Leu Val Gln Ser Gly Gly Val Val Gln Ser Gly Arg
1               5                   10                  15

Ser Leu Arg Leu Ser Cys Val Ala Ser Gly Phe Ser Phe Ser Asn Tyr
            20                  25                  30

Gly Met His Trp Val Arg Gln Ala Pro Gly Lys Gly Leu Glu Trp Leu
            35                  40                  45

Ala Phe Ile Trp Tyr Asp Gly Ser Asn Lys Tyr Ala Asp Ser Val
50                      55                  60

Lys Gly Arg Phe Thr Ile Ser Arg Asp Asn Lys Asn Ala Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Tyr Ser Ser Ser Trp Gly Gly Phe Asp Tyr Trp
            100                 105                 110

Gly Gln Gly Thr Val Leu Thr Val Ser Ser Gly Ser
            115                 120

<210> SEQ ID NO 79
<211> LENGTH: 132
<212> TYPE: PRT
<213> ORGANISM: Artificial Sequence
<220> FEATURE:
<223> OTHER INFORMATION: Synthetic Polypeptide

<400> SEQUENCE: 79

Asn Phe Met Leu Thr Gln Pro His Ser Val Ser Glu Ser Pro Gly Arg
1               5                   10                  15

Thr Val Thr Ile Pro Cys Ser Gly Arg Gly Gly Ser Ile Ala Ser Asp
            20                  25                  30

Ser Val Gln Trp Tyr Gln Gln Arg Pro Gly Ser Ala Pro Thr Thr Ile
            35                  40                  45

Ile Tyr Glu Asp Asn Gln Arg Pro Ser Gly Val Pro Asp Arg Phe Ser
50                      55                  60

Gly Ser Val Asp Ser Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Ala
            85                  90                  95

Ser Ser Leu Trp Val Phe Gly Gly Lys Thr Lys Leu Thr Val Leu Gly
            100                 105                 110

Gln Pro Lys Ala Ala Pro Ser Val Thr Leu Phe Pro Pro Ser Ser Lys
            115                 120                 125

Ala Ser Gly Ala
    130

<210> SEQ ID NO 80
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 80

Glu Val Gln Leu Val Gln Ser Gly Gly Gly Val Val Gln Ser Gly Arg
1               5                   10                  15

Ser Leu Arg Leu Ser Cys Val Ala Ser Gly Phe Ser Phe Ser Asn Tyr
            20                  25                  30

Gly Met His Trp Val Arg Gln Ala Pro Gly Lys Gly Leu Glu Trp Leu
            35                  40                  45

```
Ala Phe Ile Trp Tyr Asp Gly Ser Asn Lys Trp Tyr Ala Asp Ser Val
         50                  55                  60
Lys Gly Arg Phe Thr Ile Ser Arg Asp Asn Ser Lys Asn Ala Leu Tyr
 65                  70                  75                  80
Leu Gln Met Asn Ser Leu Arg Ala Glu Asp Thr Ala Val Tyr Tyr Cys
                 85                  90                  95
Ala Arg Asp Arg Tyr Ser Ser Ser Trp Gly Gly Phe Asp Tyr Trp
                100                 105                 110
Gly Gln Gly Thr Val Leu Thr Val Ser Ser Gly Ser Ala Ser Ala Pro
            115                 120                 125
Thr Leu Gly Gly Gly Ser Gly Gly Gly Ser Ala Ala Ala Asn
        130                 135                 140
Phe Met Leu Thr Gln Pro His Ser Val Ser Glu Ser Pro Gly Arg Thr
145                 150                 155                 160
Val Thr Ile Pro Cys Ser Gly Arg Gly Gly Ser Ile Ala Ser Asp Ser
                165                 170                 175
Val Gln Trp Tyr Gln Gln Arg Pro Gly Ser Ala Pro Thr Thr Ile Ile
            180                 185                 190
Tyr Glu Asp Asn Gln Arg Pro Ser Gly Val Pro Asp Arg Phe Ser Gly
        195                 200                 205
Ser Val Asp Ser Ser Ser Asn Ser Ala Ser Leu Thr Ile Ser Gly Leu
    210                 215                 220
Arg Thr Glu Asp Glu Ala Asp Tyr Tyr Cys Gln Ser Tyr Asp Ala Ser
225                 230                 235                 240
Ser Leu Trp Val Phe Gly Gly Lys Thr Lys Leu Thr Val Leu Gly Gln
                245                 250                 255
Pro Lys Ala Ala Pro Ser Val Thr Leu Phe Pro Pro Ser Ser Lys Ala
            260                 265                 270
Ser Gly Ala
    275

<210> SEQ ID NO 81
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 81

Asp Arg His Ser Leu Gly Asp Phe Asp Tyr
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 82

Gln Ala Trp Asp Ser Thr Thr Val Val
1               5

<210> SEQ ID NO 83
<211> LENGTH: 121
<212> TYPE: PRT
<213> ORGANISM: Artificial Sequence
<220> FEATURE:
<223> OTHER INFORMATION: Synthetic Polypeptide
```

<400> SEQUENCE: 83

Gln Leu Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Arg His Ser Leu Gly Asp Phe Asp Tyr Trp Gly Gln Gly
            100                 105                 110

Thr Leu Val Thr Val Ser Ser Gly Ser
        115                 120

<210> SEQ ID NO 84
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 84

Ser Ser Glu Leu Thr Gln Pro Ser Val Ser Val Ser Pro Gly Gln Thr
1               5                   10                  15

Ala Thr Ile Thr Cys Ser Gly Asp Lys Leu Gly Asp Lys Tyr Ala Ser
            20                  25                  30

Trp Tyr Gln Gln Lys Pro Gly Gln Ser Pro Val Leu Val Ile Tyr Gln
        35                  40                  45

Asp Thr Lys Arg Pro Ser Gly Ile Pro Ala Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Ala Tyr Tyr Cys Gln Ala Trp Asp Ser Thr Thr Val Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser
        115                 120

<210> SEQ ID NO 85
<211> LENGTH: 201
<212> TYPE: PRT
<213> ORGANISM: Artificial Sequence
<220> FEATURE:
<223> OTHER INFORMATION: Synthetic Polypeptide

<400> SEQUENCE: 85

Gln Leu Gln Leu Gln Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

```
Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Asp Arg His Ser Leu Gly Asp Phe Asp Tyr Trp Gly Gln Gly
                100                 105                 110

Thr Leu Val Thr Val Ser Ser Gly Ser Ala Ser Ala Pro Thr Leu Gly
            115                 120                 125

Gly Gly Gly Ser Gly Gly Gly Ser Ala Ala Ala Ser Ser Glu Leu
        130                 135                 140

Thr Gln Pro Pro Ser Val Ser Val Ser Pro Gly Gln Thr Ala Thr Ile
145                 150                 155                 160

Thr Cys Ser Gly Asp Lys Leu Gly Asp Lys Tyr Ala Ser Trp Tyr Gln
                165                 170                 175

Gln Lys Pro Gly Gln Ser Pro Val Leu Val Ile Tyr Gln Asp Thr Lys
                180                 185                 190

Arg Pro Ser Gly Ile Pro Ala Arg Phe
            195                 200

<210> SEQ ID NO 86
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 86

His Gly Leu Met Asp Asp Ser Ser Gly Tyr Tyr Leu Ser Asn Ala Phe
 1               5                  10                  15

Asp Ile

<210> SEQ ID NO 87
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 87

Ala Thr Trp Asp Asp Ser Leu Thr Gly Val Val
 1               5                  10

<210> SEQ ID NO 88
<211> LENGTH: 129
<212> TYPE: PRT
<213> ORGANISM: Artificial Sequence
<220> FEATURE:
<223> OTHER INFORMATION: Synthetic Polypeptide

<400> SEQUENCE: 88

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn His Gly Leu Met Asp Asp Ser Ser Gly Tyr Tyr Leu Ser Asn
            100                 105                 110

Ala Phe Asp Ile Trp Gly Gln Gly Thr Met Val Thr Val Ser Ser Gly
            115                 120                 125

Ser

<210> SEQ ID NO 89
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 89

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Glu Trp Tyr Gln Gln Leu Pro Gly Thr Ala Pro Lys Leu Leu
            35                  40                  45

Ile His Ser Asn Asn Gln Arg Pro Ser Gly Val Pro Asp Arg Phe Ser
        50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Phe Cys Ala Thr Trp Asp Asp Ser Leu
                85                  90                  95

Thr Gly Val Val Phe Gly Gly Gly Thr Thr Leu Thr Val Leu Gly Gln
            100                 105                 110

Pro Lys Ala Ala Pro Ser Val Thr Leu Phe Pro Pro Ser Ser
        115                 120                 125

<210> SEQ ID NO 90
<211> LENGTH: 274
<212> TYPE: PRT
<213> ORGANISM: Artificial Sequence
<220> FEATURE:
<223> OTHER INFORMATION: Synthetic Polypeptide

<400> SEQUENCE: 90

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn His Gly Leu Met Asp Asp Ser Ser Gly Tyr Tyr Leu Ser Asn

```
                100               105               110
Ala Phe Asp Ile Trp Gly Gln Gly Thr Met Val Thr Val Ser Ser Gly
            115               120               125

Ser Ala Ser Ala Pro Thr Leu Gly Gly Gly Ser Gly Gly Gly Gly
130             135               140

Ser Ala Ala Gln Pro Val Leu Thr Gln Pro Ser Ala Ser Gly
145             150               155               160

Thr Pro Gly Gln Arg Val Thr Ile Ser Cys Ser Gly Ser Ser Asn
                165               170               175

Ile Gly Ser Asn Thr Val Glu Trp Tyr Gln Gln Leu Pro Gly Thr Ala
            180               185               190

Pro Lys Leu Leu Ile His Ser Asn Asn Gln Arg Pro Ser Gly Val Pro
            195               200               205

Asp Arg Phe Ser Gly Ser Arg Ser Gly Thr Ser Ala Ser Leu Ala Ile
            210               215               220

Ser Gly Leu Gln Ser Glu Asp Glu Ala Asp Tyr Phe Cys Ala Thr Trp
225             230               235               240

Asp Asp Ser Leu Thr Gly Val Val Phe Gly Gly Thr Thr Leu Thr
                245               250               255

Val Leu Gly Gln Pro Lys Ala Ala Pro Ser Val Thr Leu Phe Pro Pro
            260               265               270

Ser Ser

<210> SEQ ID NO 91
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 91

Val Gly Thr Ala Ala Gly Asp Ala Phe Asp Ile
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 92

Ala Ala Trp Asp Asp Ser Leu Ser Gly Trp Val
1               5                   10

<210> SEQ ID NO 93
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 93

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Tyr
            20                  25                  30

Ser Met Asn Trp Val Arg Gln Ala Pro Gly Lys Gly Leu Glu Trp Val
        35                  40                  45
```

```
Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Val Gly Thr Ala Ala Gly Asp Ala Phe Asp Ile Trp Gly
            100                 105                 110

Gln Gly Thr Met Val Thr Val Ser Ser Gly Ser
            115                 120
```

<210> SEQ ID NO 94
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 94

```
Gln Pro Val Leu Thr Gln Pro Ser Ala Ser Gly Thr Pro Gly Gln
 1               5                  10                  15

Arg Val Thr Ile Ser Cys Phe Gly Ser Ser Asn Ile Gly Ser Asn
                20                  25                  30

Tyr Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser
            115                 120                 125
```

<210> SEQ ID NO 95
<211> LENGTH: 268
<212> TYPE: PRT
<213> ORGANISM: Artificial Sequence
<220> FEATURE:
<223> OTHER INFORMATION: Synthetic Polypeptide

<400> SEQUENCE: 95

```
Gln Val Gln Leu Val Gln Ser Gly Gly Gly Leu Ile Gln Pro Gly Gly
 1               5                  10                  15

Ser Leu Arg Leu Ser Cys Ala Ala Ser Gly Phe Thr Val Ser Ser Tyr
                20                  25                  30

Ser Met Asn Trp Val Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Val Gly Thr Ala Ala Gly Asp Ala Phe Asp Ile Trp Gly
            100                 105                 110
```

-continued

```
Gln Gly Thr Met Val Thr Val Ser Ser Gly Ser Ala Ser Ala Pro Thr
        115                 120                 125
Leu Gly Gly Gly Ser Gly Gly Gly Ser Ala Ala Gln Pro
    130             135             140
Val Leu Thr Gln Pro Pro Ser Ala Ser Gly Thr Pro Gly Gln Arg Val
145                 150                 155                 160
Thr Ile Ser Cys Phe Gly Ser Ser Asn Ile Gly Ser Asn Tyr Val
                165                 170                 175
Tyr Trp Tyr Gln Gln Leu Pro Gly Thr Ala Pro Lys Leu Leu Ile Tyr
            180                 185                 190
Arg Asn Asn Gln Arg Pro Ser Gly Val Pro Asp Arg Phe Ser Gly Ser
                195                 200                 205
Lys Ser Gly Thr Ser Ala Ser Leu Ala Ile Ser Gly Leu Arg Ser Glu
        210                 215                 220
Asp Glu Ala Asp Tyr Tyr Cys Ala Ala Trp Asp Ser Leu Ser Gly
225                 230                 235                 240
Trp Val Phe Gly Gly Gly Thr Lys Leu Thr Val Leu Gly Gln Pro Lys
                245                 250                 255
Ala Ala Pro Ser Val Thr Leu Phe Pro Pro Ser Ser
            260                 265
```

<210> SEQ ID NO 96
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 96

```
Val Gly Phe Tyr Asp Tyr Val Trp Gly Ser Tyr Pro Tyr Asp Ala Phe
1               5                   10                  15
Asp Ile
```

<210> SEQ ID NO 97
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 97

```
Gln Gln Tyr Gly Thr Ser Pro Leu Thr
1               5
```

<210> SEQ ID NO 98
<211> LENGTH: 129
<212> TYPE: PRT
<213> ORGANISM: Artificial Sequence
<220> FEATURE:
<223> OTHER INFORMATION: Synthetic Polypeptide

<400> SEQUENCE: 98

```
Gln Ile Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
```

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Phe Tyr Asp Tyr Val Trp Gly Ser Tyr Pro Tyr Asp
            100                 105                 110

Ala Phe Asp Ile Trp Gly Gln Gly Thr Met Val Thr Val Ser Ser Gly
            115                 120                 125

Ser

<210> SEQ ID NO 99
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 99

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Leu Tyr Tyr Cys Gln Gln Tyr Gly Thr Ser Pro
                85                  90                  95

Leu Thr Phe Gly Gly Gly Thr Lys Leu Glu Ile Lys Arg Thr Val Ala
            100                 105                 110

Ala Pro Ser Val Phe
        115

<210> SEQ ID NO 100
<211> LENGTH: 265
<212> TYPE: PRT
<213> ORGANISM: Artificial Sequence
<220> FEATURE:
<223> OTHER INFORMATION: Synthetic Polypeptide

<400> SEQUENCE: 100

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Phe Tyr Asp Tyr Val Trp Gly Ser Tyr Pro Tyr Asp

```
              100                 105                 110
Ala Phe Asp Ile Trp Gly Gln Gly Thr Met Val Thr Val Ser Ser Gly
        115                 120                 125

Ser Ala Ser Ala Pro Thr Leu Gly Gly Gly Ser Gly Gly Gly Gly
    130                 135                 140

Ser Ala Ala Ala Glu Ile Val Met Thr Gln Ser Pro Gly Thr Leu Ser
145                 150                 155                 160

Leu Ser Pro Gly Glu Arg Ala Thr Leu Ser Cys Arg Ala Ser Gln Ser
                165                 170                 175

Val Ser Ser Asn Tyr Leu Ala Trp Tyr Gln Gln Lys Pro Gly Gln Ala
            180                 185                 190

Pro Arg Leu Leu Ile Tyr Asp Ala Ser Asn Arg Ala Thr Gly Ile Pro
        195                 200                 205

Ala Arg Phe Ser Gly Ser Gly Ser Gly Thr Asp Phe Thr Leu Thr Ile
    210                 215                 220

Ser Ser Leu Glu Pro Glu Asp Phe Ala Leu Tyr Tyr Cys Gln Gln Tyr
225                 230                 235                 240

Gly Thr Ser Pro Leu Thr Phe Gly Gly Gly Thr Lys Leu Glu Ile Lys
                245                 250                 255

Arg Thr Val Ala Ala Pro Ser Val Phe
            260                 265
```

<210> SEQ ID NO 101
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 101

```
Asp Thr Ser Asn Gly Gly Tyr Ser Ser Ser Ser Phe Asp Tyr
1               5                   10
```

<210> SEQ ID NO 102
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 102

```
Ser Ser Tyr Thr Ser Ser Ser Thr Leu Val
1               5                   10
```

<210> SEQ ID NO 103
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 103

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Thr Ser Asn Gly Gly Tyr Ser Ser Ser Phe Asp Tyr
            100                 105                 110

Trp Gly Gln Gly Thr Leu Val Thr Val Ser Ser Gly Ser
        115                 120                 125

<210> SEQ ID NO 104
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 104

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Thr Ala Pro Lys Leu
            35                  40                  45

Met Ile Tyr Asp Val Ser Tyr Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Thr Gly Thr Lys Val Thr Val Leu Gly Gln
            100                 105                 110

Pro Lys Ala Asn Pro Thr Val Thr Leu Phe Pro Pro Ser Ser
        115                 120                 125

<210> SEQ ID NO 105
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 105

Glu Val Gln Leu Val Gln Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Thr Ser Asn Gly Gly Tyr Ser Ser Ser Phe Asp Tyr
            100                 105                 110

Trp Gly Gln Gly Thr Leu Val Thr Val Ser Ser Gly Ser Ala Ser Ala
```

```
              115                 120                 125
Pro Thr Leu Gly Gly Gly Ser Gly Gly Gly Ser Ala Ala Ala
        130                 135                 140

Gln Ser Ala Leu Thr Gln Pro Ala Ser Val Ser Gly Ser Pro Gly Gln
145                 150                 155                 160

Ser Ile Thr Ile Ser Cys Thr Gly Thr Ser Ser Asp Val Gly Gly Tyr
                165                 170                 175

Asn Tyr Val Ser Trp Tyr Gln Gln His Pro Gly Thr Ala Pro Lys Leu
            180                 185                 190

Met Ile Tyr Asp Val Ser Tyr Arg Pro Ser Gly Val Ser Asn Arg Phe
        195                 200                 205

Ser Gly Ser Lys Ser Gly Asn Thr Ala Ser Leu Thr Ile Ser Gly Leu
    210                 215                 220

Gln Ala Glu Asp Glu Ala Asp Tyr Tyr Cys Ser Ser Tyr Thr Ser Ser
225                 230                 235                 240

Ser Thr Leu Val Phe Gly Thr Gly Thr Lys Val Thr Val Leu Gly Gln
                245                 250                 255

Pro Lys Ala Asn Pro Thr Val Thr Leu Phe Pro Pro Ser Ser
            260                 265                 270

<210> SEQ ID NO 106
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 106

Leu Val Tyr Gly Gly Tyr Asp Glu Pro Gly Tyr Tyr Phe Asp Tyr
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 107

Ala Ala Trp Asp Asp Ser Leu Asn Gly Trp Val
1               5                   10

<210> SEQ ID NO 108
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 108

Glu Val Gln Leu Leu Glu Ser Arg Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Pro Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Leu Val Tyr Gly Gly Tyr Asp Glu Pro Gly Tyr Tyr Phe Asp
            100                 105                 110

Tyr Trp Gly Gln Gly Thr Leu Val Thr Val Ser Ser Gly Ser
        115                 120                 125
```

<210> SEQ ID NO 109
<211> LENGTH: 131
<212> TYPE: PRT
<213> ORGANISM: Artificial Sequence
<220> FEATURE:
<223> OTHER INFORMATION: Synthetic Polypeptide

<400> SEQUENCE: 109

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Arg Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Lys Ala
            115                 120                 125

Ser Gly Ala
    130
```

<210> SEQ ID NO 110
<211> LENGTH: 276
<212> TYPE: PRT
<213> ORGANISM: Artificial Sequence
<220> FEATURE:
<223> OTHER INFORMATION: Synthetic Polypeptide

<400> SEQUENCE: 110

```
Glu Val Gln Leu Leu Glu Ser Arg Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Pro Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Val Tyr Gly Gly Tyr Asp Glu Pro Gly Tyr Tyr Phe Asp
            100                 105                 110

Tyr Trp Gly Gln Gly Thr Leu Val Thr Val Ser Ser Gly Ser Ala Ser
```

```
              115                 120                 125
Ala Pro Thr Leu Gly Gly Gly Ser Gly Gly Gly Ser Ala Ala
        130                 135                 140

Ala Gln Ser Val Leu Thr Gln Pro Ser Ala Ser Gly Thr Pro Gly
145                 150                 155                 160

Gln Arg Val Thr Ile Ser Cys Ser Gly Ser Ser Asn Ile Arg Ser
                165                 170                 175

Asn Thr Val Asn Trp Tyr Gln Gln Leu Pro Gly Thr Ala Pro Lys Leu
            180                 185                 190

Leu Ile Tyr Ser Asn Asn Gln Arg Pro Ser Gly Val Pro Asp Arg Phe
        195                 200                 205

Ser Gly Ser Lys Ser Gly Thr Ser Ala Ser Leu Ala Ile Ser Gly Leu
    210                 215                 220

Gln Ser Glu Asp Glu Ala Asp Tyr Tyr Cys Ala Ala Trp Asp Ser
225                 230                 235                 240

Leu Asn Gly Trp Val Phe Gly Gly Thr Lys Leu Thr Val Leu Gly
                245                 250                 255

Gln Pro Lys Ala Ala Pro Ser Val Thr Leu Phe Pro Pro Ser Ser Lys
            260                 265                 270

Ala Ser Gly Ala
        275

<210> SEQ ID NO 111
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 111

Val Asp Gly Leu Glu Tyr Ser Ser Gly His Asn Phe Asp Tyr
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 112

Ser Ser Tyr Ala Gly Ser Tyr Thr Trp Val
1               5                   10

<210> SEQ ID NO 113
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 113

Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Leu Glu Tyr Ser Ser Gly His Asn Phe Asp Tyr
            100                 105                 110

Trp Gly Gln Gly Thr Leu Val Thr Val Ser Ser Gly Ser
        115                 120                 125
```

<210> SEQ ID NO 114
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 114

```
Gln Ser Ala Leu Thr Gln Pro Pro Ser Val Ser Gly Ser Pro Gly Gln
1               5                   10                  15

Ser Val Thr Ile Ser Cys Thr Gly Ser Ser Ser Asp Val Gly Tyr Tyr
                20                  25                  30

Asp His Val Ser Trp Tyr Gln His Pro Gly Arg Ala Pro Lys Val
            35                  40                  45

Ile Ile Tyr Asp Val Thr Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Glu Leu Thr Val Leu Gly Gln
            100                 105                 110

Pro Lys Ala Ala Pro Ser Val Thr Leu Phe Pro Pro Ser Ser
        115                 120                 125
```

<210> SEQ ID NO 115
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 115

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Asp Gly Leu Glu Tyr Ser Ser Gly His Asn Phe Asp Tyr
            100                 105                 110

Trp Gly Gln Gly Thr Leu Val Thr Val Ser Ser Gly Ser Ala Ser Ala
```

```
                115                 120                 125
Pro Thr Leu Gly Gly Gly Ser Gly Gly Gly Ser Ala Ala Ala
            130                 135                 140

Gln Ser Ala Leu Thr Gln Pro Pro Ser Val Ser Gly Ser Pro Gly Gln
145                 150                 155                 160

Ser Val Thr Ile Ser Cys Thr Gly Ser Ser Ser Asp Val Gly Tyr Tyr
                165                 170                 175

Asp His Val Ser Trp Tyr Gln His Pro Gly Arg Ala Pro Lys Val
            180                 185                 190

Ile Ile Tyr Asp Val Thr Lys Arg Pro Ser Gly Val Pro Asp Arg Phe
            195                 200                 205

Ser Gly Ser Lys Ser Gly Asn Thr Ala Ser Leu Thr Ile Ser Gly Leu
            210                 215                 220

Gln Ala Glu Asp Glu Ala Asp Tyr Tyr Cys Ser Ser Tyr Ala Gly Ser
225                 230                 235                 240

Tyr Thr Trp Val Phe Gly Gly Gly Thr Glu Leu Thr Val Leu Gly Gln
                    245                 250                 255

Pro Lys Ala Ala Pro Ser Val Thr Leu Phe Pro Pro Ser Ser
            260                 265                 270

<210> SEQ ID NO 116
<211> LENGTH: 323
<212> TYPE: PRT
<213> ORGANISM: Artificial Sequence
<220> FEATURE:
<223> OTHER INFORMATION: Synthetic Polypeptide

<400> SEQUENCE: 116

Ala Ser Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
                35                  40                  45

Gly Val His Thr Phe Pro Ala Val Leu Gln Ser Asp Leu Tyr Thr Leu
            50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Asp Ile Ser
            130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
```

```
                    210                 215                 220
Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
            275                 280                 285

Val Gln Lys Ser Asn Trp Glu Ala Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly

<210> SEQ ID NO 117
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 117

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
                20                  25                  30

Phe Tyr Pro Gly Val Val Thr Val Asp Trp Lys Val Asp Gly Thr Pro
            35                  40                  45

Val Thr Gln Gly Met Glu Thr Thr Gln Pro Ser Lys Gln Ser Asn Asn
        50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
                100                 105

<210> SEQ ID NO 118
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 118

Arg Xaa Xaa Arg
1
```

METHODS FOR ALTERING BODY COMPOSITION BY ADMINISTERING ANTI-PRO/LATENT MYOSTATIN ANTIBODIES

RELATED APPLICATIONS

This application is a continuation of U.S. patent application Ser. No. 15/400,825, filed Jan. 6, 2017 which, in turn, claims priority to U.S. Provisional Patent Application No. 62/276,698, filed Jan. 8, 2016, U.S. Provisional Patent Application No. 62/328,597, filed Apr. 27, 2016, U.S. Provisional Patent Application No. 62/333,816, filed May 9, 2016, U.S. Provisional Patent Application No. 62/333,810, filed May 9, 2016, U.S. Provisional Patent Application No. 62/413,278, filed Oct. 26, 2016, and which is a continuation of International Application No. PCT/US2016/052014, filed on Sep. 15, 2016. The entire contents of each application are incorporated herein by reference.

SEQUENCE LISTING

The instant application contains a Sequence Listing which has been submitted electronically in ASCII format and is hereby incorporated by reference in its entirety. Said ASCII copy, created on Mar. 14, 2019, is named 127036-00308_SL.txt and is 109,022 bytes in size.

BACKGROUND OF THE INVENTION

Myostatin, also known as GDF8, is a member of the TGFβ superfamily, and belongs to a subfamily including two members: Myostatin and GDF11. Like other members of the TGFβ superfamily, Myostatin and GDF11 are both initially expressed as inactive precursor polypeptides (termed pro-myostatin and proGDF11, respectively).

Myostatin is a well-known negative regulator of skeletal muscle mass and is released from an autoinhibitory N-terminal prodomain by two separate protease cleavage steps. These cleavage events that lead to the local release of "mature" myostatin from its inactive complex, may be referred to as supracellular activation. Following activation, mature myostatin signals by binding to a complex of Type I and II cell surface receptors (Alk4/5 and ActRIIB) whose downstream signaling induces muscle atrophy.

There is interest in myostatin as a target for the treatment of muscle wasting. A number of therapeutics targeting the ActRIIB signaling pathway are completing early- to mid-stage clinical trials in muscle wasting conditions, including sarcopenia, muscular dystrophies, cachexia, and hip replacement/hip fracture. To date, however, the primary clinical strategy has focused on directly blocking the interaction between mature myostatin and cell surface receptors, and several therapeutic programs have been discontinued due to lack of specificity (leading to unacceptable toxicities) and/or efficacy. Therefore, there is a need for improved anti-myostatin therapeutics.

SUMMARY OF THE INVENTION

The present invention encompasses the recognition that blocking the activation step of myostatin, rather than targeting already active myostatin, may provide an advantageous mode of selectively inhibiting myostatin signaling in vivo. Thus, the invention may have utility as a therapeutic in any condition where selective reduction of myostatin signaling in vivo is beneficial. More specifically, the invention includes surprising findings that specific inhibition of myostatin activation can effectuate not only muscle mass increase but also enhanced muscle function, as well as prevention of muscle atrophy and metabolic dysregulation. Unexpectedly, beneficial therapeutic effects can also be achieved even below a lesion in a subject having impaired but not complete loss of signaling between a neuron and its target tissue, such as a target muscle. To the best knowledge of the inventors of the present disclosure, this is the first such demonstration achieved in vivo by inhibiting myostatin signaling, despite the fact that there has been a number of antagonists developed for inhibiting myostatin since its discovery some 20 years ago. Thus, in one aspect the invention also includes methods for treating conditions that involve impaired signaling between a motor neuron and its target muscle by the use of a myostatin inhibitor, so as to achieve therapeutic benefits in a subject, including below the lesion.

Accordingly, in one aspect, disclosed herein is a method for inhibiting myostatin activation in a subject, the method comprising a step of administering to the subject a composition comprising a myostatin inhibitor, e.g., an antibody, or antigen binding fragment thereof, that specifically binds pro/latent-myostatin and blocks release of mature myostatin, in an amount effective to cause two or more of the following in the subject: (a) an increase in mass and/or function of a muscle tissue in the subject; (b) an increase in the metabolic rate of the subject; (c) an increase in insulin sensitivity of the subject; (d) an increase in a level of brown adipose tissue in the subject; (e) an increase in a level of beige adipose tissue in the subject; (f) a decrease in a level of white adipose tissue in the subject; (g) a decrease in a level of visceral adipose tissue in the subject; (h) a decrease in ratio of adipose-to-muscle tissue in the subject; (i) an increase in glucose uptake by a brown adipose tissue, a beige adipose tissue, or a muscle tissue in the subject; (j) a decrease in glucose uptake by a white adipose tissue or a liver tissue; (k) a decrease in muscle catabolism of protein and/or muscle release of amino acids in the subject; (l) an increase in insulin dependent glycemic control in the subject; (m) a decrease in intramuscular fat infiltration in the subject; (n) clinically meaningful improvement in a standardized quality-of-life test score; (o) prevention of muscle loss or atrophy in the subject; and/or (p) prevention of developing a metabolic dysregulation associated with muscle dysfunction in the subject, wherein the subject is a human subject, e.g., a human subject who would benefit from reduced myostatin signaling.

In one embodiment, the method further comprises a step of selecting the subject suffering from a muscle condition or disorder. In another embodiment, the method further comprises a step of selecting the subject suffering from, or at risk of developing, a metabolic disorder.

In one embodiment, administration of an effective amount of a myostatin inhibitor, e.g., an antibody or antigen-binding fragment thereof that specifically binds pro/latent myostatin and blocks activation of mature myostatin causes an increase in a level of latent myostatin in serum, as compared to a control, in the subject.

In one embodiment, the subject has a muscle condition selected from the group consisting of: myopathy, muscular atrophy, muscular dystrophy, nerve injury. In one embodiment, the muscular atrophy is associated with a defect in motor neurons. In one embodiment, the defect comprises a genetic mutation. In another embodiment, the muscular atrophy is associated with spinal muscular atrophy (SMA), amyotrophic lateral sclerosis (ALS), or myasthenia gravis. In one embodiment, the nerve injury comprises partial denervation of neurons that innervate muscle, or impaired signaling between a motor neuron and a target muscle. In one embodiment, the nerve injury is SCI. In another embodiment, the SCI is partial/incomplete SCI. The location of a lesion in SCI may be anywhere along the spinal cord. In one embodiment, the SCI comprises a lesion between i) T1-T6; ii) T7-L5; iii) C6-C7; iv) C5-C6; or v) C3-C8. In one embodiment, the subject is in an acute phase of SCI; sub-acute phase of SCI, or chronic phase of SCI. In one embodiment, the subject has, or at risk of developing, a metabolic disorder associated with the SCI. In one embodiment, the metabolic disorder is or comprises insulin resistance, inflammation, abnormal lipid metabolism, or an increase in intramuscular fat infiltration. In one embodiment, the muscle atrophy comprises glucocorticoid-induced muscle atrophy.

In one embodiment, the subject has a metabolic disease selected from the group consisting of type I diabetes, type II diabetes, obesity, metabolic syndrome/pre-diabetes, cardiovascular disease, non-alcoholic steatohepatitis (NASH), spinal cord injury (SCI), a hypo-metabolic state, double diabetes, Cushings disease, and an obesity syndrome.

In one embodiment, the subject is treated with a second therapy. In one embodiment, the second therapy comprises neuroprotective therapy. In another embodiment, the neuroprotective therapy comprises a stem cell therapy. In some embodiments, the neuroprotective therapy is an agent that promotes the survival of motor neurons. In some embodiments, the agent is olesoxime, riluzole, or thyrotropin releasing hormone.

In another embodiment, the second therapy comprises a splice-correction therapy. In one embodiment, the splice-correction therapy is a survival motor neuron (SMN) corrector. In some embodiments, the SMN corrector is an SMN2 splice corrector that increases the expression of functional SMN protein in the subject.

In some embodiments, the SMN2 splice corrector is an antisense molecule. In some embodiments, the SMN2 splice corrector is Spinraza® (Nusinersen). In some embodiments, the antisense molecule is administered by intravenous or intrathecal injection. However, other appropriate routes of administration may be used. In some embodiments, the SMN2 splice corrector is a small molecule. In some embodiments, the SMN2 splice corrector is RG7800 (Roche), RG7916 (Roche), or LMI070 (Novartis). In some embodiments, the small molecule is administered orally or by another suitable method.

In another aspect, disclosed herein is a method of treating or preventing a disease associated with an impaired neurological signaling between a neuron and a target tissue, e.g., a target muscle, in a human subject, the method comprising selecting the human subject suffering from a disease associated with an impaired neurological signaling between a neuron and a target tissue; and administering to the human subject a composition comprising a myostatin inhibitor, e.g., an antibody, or antigen binding fragment thereof, that specifically binds pro/latent-myostatin and blocks release of mature myostatin in an amount effective to treat or prevent the disease, thereby treating or preventing the disease associated with the impaired neurological signaling in the human subject.

In some embodiments, the target tissue expresses myostatin (e.g., myostatin precursors, and/or mature myostatin). In one embodiment, the target tissue is selected from the group consisting of a muscle tissue, an adipose tissue, a brain tissue, a liver tissue, and a blood vessel tissue. In one embodiment, the target tissue is a muscle.

In another aspect, disclosed herein is a method for treating a lesion that causes an impaired but not complete loss of signaling between a neuron and a target muscle in a subject. Such method includes a step of administering to the subject a composition comprising a myostatin inhibitor, e.g., an anti-pro/latent myostatin antibody, in an amount effective to treat the muscle located below the lesion in the subject. In some embodiments, the amount is an amount effective to prevent muscle loss or muscle atrophy below the lesion in the subject. In some embodiments, the amount is an amount effective to increase muscle mass and/or function below the lesion in the subject.

In some embodiments, the lesion is associated with incomplete spinal cord injury.

In one embodiment, the muscle contains fast-twitch muscle fibers. In another embodiment, the muscle located below the lesion is selected from the group of a soleus muscle, a gastrocnemius muscle, a bicep muscle and a tricep muscle. In one embodiment, the amount is effective to increase mass and/or function of a muscle above the lesion in the subject. In another embodiment, the myostatin inhibitor is an agent that blocks, antagonizes or inhibits myostatin signaling in vivo. In some embodiments, such agent is an antibody, or antigen-binding portion thereof, a small molecule, or gene therapy. In some embodiments, the antibody is an antibody that specifically binds pro/latent myostatin and blocks release of mature myostatin in vivo. In some embodiments, the antibody binds mature myostatin. In some embodiments, the antibody selectively (e.g., preferentially) binds mature myostatin over mature GDF11. In some embodiments, the antibody specifically binds mature myostatin but does not bind mature GDF11. In some embodiments, the antibody binds and/or blocks a myostatin receptor.

In some embodiments, the lesion is a spinal cord lesion. In one embodiment, the subject has an incomplete spinal cord injury (SCI). In one embodiment, the incomplete SCI comprises a lesion between: i) T1-T6; ii) T7-L5; iii) C6-C7; iv) C5-C6; or v) C3-C8.

In one embodiment, the amount is effective to treat a metabolic condition in the subject. In one embodiment, the amount is effective to cause in the subject: (a) an increase in mass and/or function of a muscle tissue in the subject; (b) an increase in the metabolic rate of the subject; (c) an increase in insulin sensitivity of the subject; (d) an increase in a level of brown adipose tissue in the subject; (e) an increase in a level of beige adipose tissue in the subject; (f) a decrease in a level of white adipose tissue in the subject; (g) a decrease in a level of visceral adipose tissue in the subject; (h) a decrease in ratio of adipose-to-muscle tissue in the subject; (i) an increase in glucose uptake by a brown adipose tissue, a beige adipose tissue, or a muscle tissue in the subject; (j) a decrease in glucose uptake by a white adipose tissue or a liver tissue; (k) a decrease in muscle catabolism of protein and/or muscle release of amino acids in the subject; (l) an increase in insulin dependent glycemic control in the subject; (m) a decrease in intramuscular fat infiltration in the subject; (n) clinically meaningful improvement in a standardized quality-of-life test score; (o) prevention of muscle loss or atrophy in the subject; and/or, (p) prevention of developing a metabolic dysregulation associated with muscle dysfunction in the subject.

In another aspect, the disclosure provides a method of treating or preventing a metabolic disease in a human subject, the method comprising selecting a human subject suffering from a metabolic disease; and administering to the human subject an effective amount of a myostatin inhibitor, e.g., an antibody, or antigen binding fragment thereof, that specifically binds pro/latent-myostatin, thereby treating or preventing the metabolic disease in the human subject.

In one embodiment, the metabolic disease is selected from the group consisting of type I diabetes, type II diabetes, obesity, metabolic syndrome/pre-diabetes, cardiovascular disease, non-alcoholic steatohepatitis (NASH), spinal cord injury (SCI), a hypo-metabolic state, double diabetes, Cushings disease, and an obesity syndrome. In one embodiment, the obesity is sarcopenic obesity. In one embodiment, the hypo-metabolic state is selected from the group consisting of a state associated with prolonged immobilization, a state associated with bed-rest, a state associated with casting, a state associated with a stroke, a state associated with amputation, and a post-surgery state. In one embodiment, the Cushings disease is selected from the group consisting of corticosteroid-induced Cushings disease and tumor-induced Cushings disease. In one embodiment, the obesity syndrome is selected from the group consisting of Prader Willi, an obesity syndrome associated with a genetic disorder, and an obesity syndrome associated with a hypothalamic disorder.

In another aspect, the disclosure provides a method of treating or preventing a disease associated with an impaired neurological signaling between a neuron and a target tissue in a human subject, the method comprising selecting a human subject suffering from a disease associated with an impaired neurological signaling between a neuron and a target tissue; and administering to the human subject an effective amount of a myostatin inhibitor, e.g., an antibody, or antigen binding fragment thereof, that specifically binds pro/latent-myostatin, thereby treating or preventing the disease associated with the impaired neurological signaling in the human subject. In some embodiments, the target tissue expresses myostatin (e.g., myostatin precursors, and/or mature myostatin).

In one embodiment, the disease associated with an impaired neurological signaling between a neuron and a target tissue is selected from the group consisting of spinal cord injury (SCI), myasthelia gravis, amyotrophic lateral sclerosis (ALS), and spinal muscular atrophy (SMA). In one embodiment, the disease associated with an impaired neurological signaling between a neuron and a target tissue is spinal cord injury (SCI). In one embodiment, the human subject is in an acute spinal cord injury (SCI) phase. In one embodiment, the human subject is in a sub-acute spinal cord injury (SCI) phase. In one embodiment, the human subject is in a chronic spinal cord injury (SCI) phase.

In one aspect, the disclosure provides a method for promoting fiber type switch in a subject. The method comprises administering to the subject a composition comprising a myostatin inhibitor, e.g., an antibody, or antigen binding fragment thereof, that specifically binds pro/latent-myostatin and blocks release of mature myostatin in an amount effective to promote fiber type switch, thereby promoting fiber type switch in the subject.

In another aspect, the disclosure provides a method for preferentially increasing type II or fast twitch fibers over type I or slow twitch fibers in a subject. The method comprises administering to the subject a composition comprising an antibody, or antigen binding fragment thereof, that specifically binds pro/latent-myostatin and blocks release of mature myostatin in an amount effective to preferentially increase type II or fast twitch fibers over type I or slow twitch fibers fiber type switch, thereby preferentially increasing type II or fast twitch fibers over type I or slow twitch fibers in the subject.

In one embodiment, administration of the myostatin inhibitor, e.g., antibody, or antigen binding fragment thereof, increases mass and/or function of a muscle tissue in the human subject. In one embodiment, administration of the myostatin inhibitor, e.g., antibody, or antigen binding fragment thereof, increases mass and/or function of a fast twitch muscle tissue in the human subject. In one embodiment, administration of the myostatin inhibitor, e.g., antibody, or antigen binding fragment thereof, increases mass and/or function of a slow twitch muscle tissue in the human subject.

In one embodiment, administration of the myostatin inhibitor, e.g., antibody, or antigen binding fragment thereof, increases the metabolic rate of the human subject. In one embodiment, administration of the myostatin inhibitor, e.g., antibody, or antigen binding fragment thereof, increases insulin sensitivity in the human subject. In one embodiment, administration of the myostatin inhibitor, e.g., antibody, or antigen binding fragment thereof, increases the level of brown adipose tissue in the human subject. In one embodiment, administration of the myostatin inhibitor, e.g., antibody, or antigen binding fragment thereof, increases the level of beige adipose tissue in the human subject. In one embodiment, administration of the myostatin inhibitor, e.g., antibody, or antigen binding fragment thereof, decreases the level of white adipose tissue in the human subject. In one embodiment, administration of the myostatin inhibitor, e.g., antibody, or antigen binding fragment thereof, decreases the level of visceral adipose tissue in the human subject. In one embodiment, administration of the myostatin inhibitor, e.g., antibody, or antigen binding fragment thereof, decreases the ratio of adipose-to-muscle tissue in the human subject.

In one embodiment, administration of the myostatin inhibitor. e.g., antibody, or antigen binding fragment thereof, increases glucose uptake by a muscle tissue in the human subject. In one embodiment, administration of the myostatin inhibitor, e.g., antibody, or antigen binding fragment thereof, decreases glucose uptake by a target tissue, wherein the target tissue is selected from the group consisting of a white adipose tissue, a liver tissue and a blood vessel tissue.

In one embodiment, administration of the myostatin inhibitor, e.g., antibody, or antigen binding fragment thereof, decreases muscle catabolism of protein and/or muscle release of amino acids in the human subject. In one embodiment, administration of the myostatin inhibitor, e.g., antibody, or antigen binding fragment thereof, increases insulin dependent glycemic control in the human subject.

In another aspect, disclosed herein is a method of increasing metabolic rate in a human subject, the method comprising selecting a human subject who would benefit from an increase in metabolic rate; and administering to the human subject an effective amount of a myostatin inhibitor, e.g., an antibody, or antigen binding fragment thereof, that specifically binds pro/latent-myostatin, thereby increasing the metabolic rate in the human subject.

In another aspect, disclosed herein is a method of increasing the level of brown adipose tissue in a human subject, the method comprising selecting a human subject who would benefit from an increase in the level of brown adipose tissue; and administering to the human subject an effective amount of a myostatin inhibitor, e.g., an antibody, or antigen binding fragment thereof, that specifically binds pro/latent-myostatin, thereby increasing the level of brown adipose tissue in the human subject.

In another aspect, disclosed herein is a method of increasing the level of beige adipose tissue in a human subject, the method comprising selecting a human subject who would benefit from an increase in the level of beige adipose tissue;

and administering to the human subject an effective amount of a myostatin inhibitor, e.g., an antibody, or antigen binding fragment thereof, that specifically binds pro/latent-myostatin, thereby increasing the level of beige adipose tissue in the human subject.

In another aspect, disclosed herein is a method of increasing insulin dependent glycemic control in a human subject, the method comprising selecting a human subject who would benefit from an increase in insulin dependent glycemic control; and administering to the human subject an effective amount of a myostatin inhibitor, e.g., an antibody, or antigen binding fragment thereof, that specifically binds pro/latent-myostatin, thereby increasing insulin dependent glycemic control in the human subject.

In another aspect, disclosed herein is a method of decreasing muscle catabolism of protein and/or muscle release of amino acids in a human subject, the method comprising selecting a human subject who would benefit from a decrease in muscle catabolism of protein and/or muscle release of amino acids; and administering to the human subject an effective amount of a myostatin inhibitor. e.g., an antibody, or antigen binding fragment thereof, that specifically binds pro/latent-myostatin, thereby decreasing muscle catabolism of protein and/or muscle release of amino acids in the human subject.

In another aspect, disclosed herein is a method of decreasing glucose uptake by a target tissue in a human subject, the method comprising selecting a human subject who would benefit from a decrease in glucose uptake by a target tissue selected from the group consisting of a white adipose tissue, a liver tissue and a blood vessel tissue; and administering to the human subject an effective amount of a myostatin inhibitor, e.g., an antibody, or antigen binding fragment thereof, that specifically binds pro/latent-myostatin, thereby decreasing glucose uptake by the target tissue in the human subject.

In one embodiment, the target tissue comprises macrophages, smooth muscle cells and foam cells.

In another aspect, disclosed herein is a method of treating or preventing a metabolic disease in a human subject, the method comprising selecting a human subject suffering from a metabolic disease; and administering to the human subject an amount of a myostatin inhibitor, e.g., an antibody, or antigen binding fragment thereof, that specifically binds pro/latent-myostatin, effective to cause at least two or more of the following in the human subject: (a) an increase in mass and/or function of a muscle tissue in the human subject; (b) an increase in the metabolic rate of the human subject; (c) an increase in insulin sensitivity of the human subject; (d) an increase in the level of brown adipose tissue in the human subject; (e) an increase in the level of beige adipose tissue in the human subject; (f) a decrease in the level of white adipose tissue in the human subject; (g) a decrease in the level of visceral adipose tissue in the human subject; (h) a decrease in the ratio of adipose-to-muscle tissue in the human subject; (i) an increase in glucose uptake by a white adipose tissue, a liver tissue or a blood vessel tissue in the human subject; (j) a decrease in muscle catabolism of protein and/or muscle release of amino acids in the human subject; and/or (k) an increase in insulin dependent glycemic control in the human subject, thereby treating or preventing the metabolic disease in the human subject.

In another aspect, disclosed herein is a method of preventing muscle atrophy below a lesion in a subject who has suffered a lesion, the method comprising selecting a subject who has suffered a lesion; and administering to the human subject an effective amount of a myostatin inhibitor, e.g., an antibody, or antigen binding fragment thereof, that specifically binds pro/latent-myostatin. Such subjects may be at risk of developing muscle dysfunction, e.g., atrophy.

In one embodiment, the lesion is due to a spinal cord injury (SCI). In one embodiment, the human subject is in an acute spinal cord injury (SCI) phase. In one embodiment, the human subject is in a sub-acute spinal cord injury (SCI) phase. In some embodiments, the SCI is an incomplete SCI, characterized in that function of the affected nerves and/or the target muscle(s) is partially retained. In some embodiments, the subject has suffered an incomplete SCI involving partial denervation of motor neurons and is in an acute or sub-acute phase of SCI. In some embodiments, the subject is within 6 months post-SCI, e.g., within 5 months, within 4 months, within 3 months, within 2 months, within 4 weeks, or within 2 weeks post SCI. In some embodiments, the subject has not exhibited atrophy and/or muscle loss below lesion.

In one embodiment, administration of the myostatin inhibitor, e.g., antibody, or antigen binding fragment thereof, further increases mass and/or function of a muscle above the lesion. In one embodiment, administration of the myostatin inhibitor, e.g., antibody, or antigen binding fragment thereof, increases mass and/or function of a fast switch muscle. In one embodiment, administration of the myostatin inhibitor, e.g., antibody, or antigen binding fragment thereof, increases mass and/or function of a slow switch muscle.

In some embodiments, the mass of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor. e.g., antibody, or antigen binding fragment thereof, increases locomotor function in the human subject. In some embodiments, the locomotor function of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the locomotor function of the human subject is increased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor, e.g., antibody, or antigen binding fragment thereof, increases motor coordination and balance in the human subject. In some embodiments, the motor ordination and balance of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the motor ordination and balance of the human subject is increased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor, e.g., antibody, or antigen binding fragment thereof, increases muscle strength in the human subject. In some embodiments, the muscle strength of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the muscle strength of the human subject is increased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor, e.g., antibody, or antigen binding fragment thereof, increases grip strength in the human subject. In one embodiment, administration of the myostatin inhibitor, e.g., antibody, or antigen binding fragment thereof, decreases the level of white adipose tissue in the human subject. In some embodiments, the level of white adipose tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of white adipose tissue is decreased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor, e.g., antibody, or antigen binding fragment thereof, increases total body mass of the human subject. In some embodiments, the level of total body mass is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of total body mass is increased by at least about 1-5%, 5-10%, 10-20%, 1-30%, 1-40%, 1-50%, 10-50%, 20-30%, 20-60%, 30-80%, 40-90%, or 50-100%.

In one embodiment, administration of the myostatin inhibitor, e.g., antibody, or antigen binding fragment thereof, increases metabolic rate of the human subject. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%.

In one embodiment, the muscle is selected from the group of a soleus muscle, a gastrocnemius muscle, a bicep muscle and a tricep muscle.

In one embodiment, the myostatin inhibitor, e.g., antibody, or antigen binding fragment thereof, is administered to the human subject within less than 5, 10, 20, 30, 40, 50, 60 minutes after the human subject has suffered the lesion. In one embodiment, the myostatin inhibitor, e.g., antibody, or antigen binding fragment thereof, is administered to the human subject at least 1, 2, 3, 4, 5, 6, 7, 8, 9, 10, 12 or 24 hours after the human subject has suffered the lesion. In one embodiment, the myostatin inhibitor, e.g., antibody, or antigen binding fragment thereof, is administered to the human subject within at least 1, 2, 3, 4, 5, 6, 7, 8, 9, 10 days or at least 1, 2, 3, 4, 5, 6, 7, 8, 9, 10, 11, 12, 24, 48 or 60 months after the human subject has suffered the lesion. In one embodiment, the myostatin inhibitor, e.g., antibody, or antigen binding fragment thereof, is administered to the human subject for about 1-30 days, about 1-50 days, about 1-100 days, about 1-200 days or about 1-300 days.

In one embodiment, the myostatin inhibitor, e.g., antibody, or antigen binding fragment thereof, is administered to the human subject chronically. In one embodiment, the myostatin inhibitor, e.g., antibody, or antigen binding fragment thereof, is administered to the human subject at a dose in a range of 0.01 mg/kg to 100 mg/kg. In one embodiment, the myostatin inhibitor, e.g., antibody, or antigen binding fragment thereof, is administered to the human subject intraperitoneally, intravenously, intramuscularly, locally or subcutaneously.

In one embodiment, the methods disclosed herein further comprise administering a second therapy to the human subject. In one embodiment, the second therapy is selected from the group consisting of insulin, insulin sensitivity enhancing agents, alpha-glucosidase inhibitors, biguanides, sulfonylureas, insulin secretion-promoting agents, amyrin agonist, phosphotyrosin phosphatase inhibitor, aldose reductase inhibitors, neurotrophic factors, PKC inhibitors, advanced glycation end-product (AGE) inhibitors, active oxygen quenching agents, statins, squalene synthetase inhibitors, fibrate, niacin. PCSK9 inhibitors, triglyceride lowering agents, cholesterol sequesting agents, angiotensin converting enzyme inhibitors, angiotensin II antagonists, calcium channel blockers, ursodiol, pioglitazone, orlistat, betaine, rosiglitazone, central anti-obesity agents, gastrointestinal lipase inhibitors, beta 3-adrenoceptor agonists, peptide-based appetite-suppressing agents, cholecystokinin agonists, dopamine agonists, DPP-4 inhibitors, glucagon-like peptides, meglitinides, sulfonylureas, sodium glucose transporter (SGLT) 2 inhibitors, cyclooxygenase inhibitors, progesterone derivatives, metoclopramide-based agents, tetrahydrocannabinol-based agents, and lipid metabolism improving agents.

In another aspect, disclosed herein is a method of treating a subject, the method comprising selecting a human subject who exhibits either: i) an increase in a level of pro-myostatin in a target muscle, as compared to a control level of pro-myostatin, or ii) a decrease in a level of latent myostatin in the circulation, as compared to a control level of latent myostatin; and administering to the human subject a therapeutically effective amount of a myostatin inhibitor, e.g., an antibody, or an antigen-binding fragment thereof, that specifically binds pro/latent-myostatin and blocks release of mature myostatin; thereby treating the subject. In one embodiment, the subject exhibits both i) and ii).

In one embodiment, the administering step results in an increase in a level of latent myostatin in the target muscle after the administering step. In one embodiment, the increase in latent myostatin in the target muscle after the administering step is detectable within 48 hours after the administration step. In one embodiment, the increase in latent myostatin in the target muscle after the administering step is detectable for at least 28 days after the administration step. In one embodiment, the level of latent myostatin in the target muscle after the administering step is increased at least 1.2-fold as compared to the level of latent myostatin in the target muscle before the administering step.

In one embodiment, the administering step results in an increase in a level of latent myostatin in the circulation of the subject after the administering step. In one embodiment, the increase in latent myostatin in the circulation of the subject after the administering step is detectable within 48 hours after the administration step. In one embodiment, the increase in latent myostatin in the circulation of the subject after the administering step is detectable for at least 28 days after the administration step. In one embodiment, the level of latent myostatin in the circulation of the subject after the administering step is at least 2-fold greater than the level of latent myostatin in the circulation prior to the administering step.

In one embodiment, the selecting step comprises determining the level of pro-myostatin in the target muscle. In one embodiment, the selecting step comprises determining the level of latent myostatin in the circulation.

In one embodiment, the method further comprises a step of determining a level of pro-myostatin in the target muscle after the administering step. In one embodiment, the method further comprises a step of determining a level of latent myostatin in the circulation after the administering step. In one embodiment, the level of pro-myostatin in the target muscle is determined by obtaining a muscle tissue sample from the subject and determining the level of pro-myostatin in the muscle tissue sample. In one embodiment, the level of latent myostatin in the circulation is determined by obtaining a blood sample from the subject and determining the level of latent myostatin in the blood sample.

In one embodiment, the target muscle is a fast twitch muscle. In one embodiment, the target muscle comprises fast oxidative fibers.

In one embodiment, the administering step comprises a single dose of the myostatin inhibitor, e.g., antibody, or antigen-binding fragment thereof. In one embodiment, the administering step comprises at least two doses of the myostatin inhibitor, e.g., antibody, or antigen-binding fragment thereof.

In one embodiment, a reduction in muscle mass is prevented in the subject. In one embodiment, the subject exhibits an increase in muscle mass following the administering step. In one embodiment, the subject exhibits an increase in muscle function following the administering step.

In one embodiment, the subject is a human subject.

In another aspect, disclosed herein is a method of preventing a reduction of and/or increasing muscle mass in a human subject, the method comprising administering to the human subject a single dose of a therapeutically effective amount of a myostatin inhibitor, e.g., an antibody, or an antigen-binding fragment thereof, that specifically binds pro/latent-myostatin and blocks release of mature myostatin, wherein the subject exhibits a sustained increase in muscle mass for at least 8 weeks after the dose is administered, thereby preventing a reduction of and/or increasing muscle mass in the human subject. In one embodiment, the subject exhibits a progressive increase in muscle mass for at least 12 weeks after administration. In one embodiment, the subject exhibits a sustained increase in muscle mass for at least 16 weeks after administration.

In another aspect, disclosed herein is a method of preventing a reduction of and/or increasing muscle mass in a human subject, the method comprising administering to the human subject more than two doses comprising at least a first dose and a second dose of a therapeutically effective amount of a myostatin inhibitor, e.g., an antibody, or an antigen-binding fragment thereof, that specifically binds pro/latent-myostatin and blocks release of mature myostatin, wherein the first dose and the second dose are administered to the subject at least about 4 weeks apart, and wherein the subject exhibits a sustained increase in muscle mass for at least 8 weeks after the first dose is administered, thereby preventing reduction of and/or increasing muscle mass in the human subject. In one embodiment, the first dose and the second dose are administered to the subject at least about 8 weeks apart.

In one embodiment, the subject is one who would benefit from increased muscle mass and/or increased muscle function. In one embodiment, the subject has a myopathy or is at risk of developing a myopathy. In one embodiment, the myopathy is spinal cord injury. In one embodiment, the myopathy is a secondary myopathy. In one embodiment, the secondary myopathy is denervation, genetic muscle weakness, or cachexia.

In one embodiment, the subject has muscle atrophy or is at risk of developing muscle atrophy. In one embodiment, the muscle atrophy is glucocorticoid-induced muscle atrophy. In one embodiment, the glucocorticoid-induced muscle atrophy is muscle atrophy induced by cortisol (hydrocortisone), cortisone, prednisone, prednisolone, methylprednisolone, dexamethasone, betamethasone, triamcinolone, beclometasone, fludrocortisone acetate, deoxycorticosterone acetate (doca), or aldosterone.

In one embodiment, the subject is administered a glucocorticoid following the administration of the myostatin inhibitor, e.g., antibody, or antigen-binding fragment thereof. In one embodiment, the glucocorticoid is administered at a dose sufficient to induce a significant decrease in lean body mass in a control subject who has not been administered the myostatin inhibitor, e.g., antibody or antigen-binding portion thereof.

In one embodiment, the antibody, or antigen-binding fragment thereof, is administered at a dose of about 0.01 mg/kg to about 30 mg/kg. In one embodiment, the myostatin inhibitor, e.g., antibody, or antigen-binding fragment thereof, is administered intraperitoneally, intravenously, intramuscularly, or subcutaneously.

In one embodiment, the myostatin inhibitor. e.g., antibody, or antigen-binding fragment thereof, inhibits myostatin signaling in a subject. In one embodiment, the antibody, or antigen binding fragment thereof, specifically binds to pro/latent Myostatin and not to mature myostatin. In one embodiment, the antibody, or antigen binding fragment thereof, specifically binds to pro/latent myostatin and not to another member of the transforming growth factor Beta family. In one embodiment, the member of the transforming growth factor Beta family is GDF11 or Activin. In one embodiment, the antibody, or antigen binding fragment thereof, does not bind GDF11.

In one embodiment, the antibody, or antigen binding fragment thereof, is cross-reactive with human and murine pro/latent myostatin. In one embodiment, the antibody, or antigen binding fragment thereof, inhibits proteolytic formation of mature myostatin by tolloid protease. In one embodiment, the antibody, or antigen binding fragment thereof, inhibits proteolytic formation of mature myostatin by tolloid protease with an IC50 of less than 1 µM.

In one embodiment, the antibody, or antigen binding fragment thereof, comprises a heavy chain variable domain comprising a complementarity determining region 3 (CDRH3) comprising a sequence as set forth in anyone of SEQ ID NOs:10-11 and 66. In one embodiment, the antibody, or antigen binding fragment thereof, comprises a light chain variable domain comprising a complementarity determining region 3 (CDRL3) comprising a sequence as set forth in any one of SEQ ID NO: 22-23 and 67. In one embodiment, the antibody, or antigen binding fragment thereof, comprises six complementarity determining regions (CDRs): CDRH1, CDRH2, CDRH3, CDRL1, CDRL2, and CDRL3, wherein CDRH1 comprises a sequence as set forth in any one of SEQ ID NOs: 1-3, CDRH2 comprises a sequence as set forth in any one of SEQ ID NOs: 4-9, CDRH3 comprises a sequence as set forth in any one of SEQ ID NOs: 10-11 and 66, CDRL1 comprises a sequence as set forth in any one of SEQ ID NOs: 12-17, CDRL2 comprises a sequence as set forth in any one of SEQ ID NOs: 18-21, and CDRL3 comprises a sequence as set forth in any one of SEQ ID NOs: 22-23 and 67.

In one embodiment, CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12 or 13, CDRL2 comprises a sequence as set forth in SEQ ID NO: 18 or 19, and CDRL3 comprises a sequence as set forth in SEQ ID NO: 22.

In one embodiment, CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14 or 15, CDRL2 comprises a sequence as set forth in SEQ ID NO: 20 or 21, and CDRL3 comprises a sequence as set forth in SEQ ID NO: 23.

In one embodiment, CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11, CDRL1 comprises a sequence as set forth in SEQ ID NO: 16 or 17, CDRL2 comprises a sequence as set forth in SEQ ID NO: 20 or 21, and CDRL3 comprises a sequence as set forth in SEQ ID NO: 23.

In one embodiment, CDRH1 comprises a sequence set forth in SEQ ID NO: 1 or 2, CDRH2 comprises a sequence set forth in SEQ ID NO:4 or 5, CDRH3 comprises a sequence set forth in SEQ ID NO:66, CDRL1 comprises a sequence set forth in SEQ ID NO:12 or 13, CDRL2 comprises a sequence set forth in SEQ ID NO: 18 or 19, and CDRL3 comprises a sequence set forth in SEQ ID NO:67.

In one embodiment, the antibody, or antigen binding fragment thereof, wherein the antibody comprises a heavy chain variable domain sequence as set forth in any one of SEQ ID NOs: 24-29. In one embodiment, the antibody, or antigen binding fragment thereof, comprises a light chain variable domain sequence of as set forth in any one of SEQ ID NOs: 30-35. In one embodiment, the antibody, or antigen binding fragment thereof, comprises a heavy chain variable region comprising an amino acid sequence of SEQ ID NO:25 and a light chain variable region comprising an amino acid sequence of SEQ ID NO:31.

In one embodiment, the antibody, or antigen binding fragment thereof, comprises a heavy chain comprising an amino acid sequence of SEQ ID NO:50. In one embodiment, the antibody, or antigen binding fragment thereof, comprises a light chain comprising an amino acid sequence of SEQ ID NO:51.

In one embodiment, the antibody, or antigen binding fragment thereof, competes for binding to pro/latent myostatin with any other antibody described herein. In one embodiment, the antibody, or antigen binding fragment thereof, binds to pro/latent myostatin at the same epitope as an antibody described herein.

In one embodiment, the antibody, or antigen binding fragment thereof, competes for binding to pro/latent myostatin with an equilibrium dissociation constant, Kd, between the antibody and pro/latent myostatin of less than $10^{-6}$ M. In one embodiment, the Kd is in a range of $10^{-11}$ M to $10^{-6}$ M.

In one embodiment, the antibody, or antigen binding fragment thereof, is a human antibody, a humanized antibody, a diabody, a chimeric antibody, a Fab fragment, a F(ab')2 fragment, or an Fv fragment. In one embodiment, the antibody is a humanized antibody. In one embodiment, the antibody is a human antibody. In one embodiment, the antibody, or antigen binding fragment thereof, comprises a framework having a human germline sequence.

In one embodiment, the antibody, or antigen binding fragment thereof, comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In one embodiment, the antibody comprises a constant domain of IgG4. In one embodiment, the antibody comprises a constant domain of IgG4 having a backbone substitution of Ser to Pro that produces an $IgG_1$-like hinge and permits formation of inter-chain disulfide bonds. In one embodiment, the antibody, or antigen-binding portion thereof, does not bind to GDF11.

BRIEF DESCRIPTION OF THE FIGURES

FIG. 1A shows myostatin secreted as a proprotein, with an inhibitory prodomain followed by a C-terminal growth factor domain, which exists as a disulfide-linked dimer. FIG. 1B shows precursor protein assembled in an inactive conformation where the prodomain (dark gray) encloses the growth factor (light gray) with a "straightjacket" assembly. This figure is an adaption from the structure of latent TGFβI (Shi et al. Nature 2011).

FIG. 3C shows the activation of myostatin involves two distinct protease events, generating three major myostatin species. The biosynthetic precursor protein, pro-myostatin, is processed by two separate proteases. Cleavage of pro-myostatin (and proGDF11) is carried out by a proprotein convertase, such as Furin/PACE3 (Paired Basic Amino acid Cleaving Enzyme 3) or PCSK5 (Proprotein Convertase Subtilisin/Kexin type 5), which cuts at a conserved RXXR (SEQ ID NO:118) site between the prodomain and mature growth factor. This cleavage produces a latent complex, in which the mature growth factor is shielded from binding to its receptors by the prodomain. See FIG. 3B, which illustrates the potential inhibition of a tolloid protease, blocking further cleavage of pro-myostatin. Activation and release of the active growth factor is accomplished after cleavage by an additional protease from the BMP/tolloid family, such as TLL-2 (Tolloid-like protein 2) or BMPL (Bone Morphogenetic Protein 1).

FIGS. 7A-7D show results of an assay evaluating tissue weights. FIG. 7A shows the mean gastrocnemius weight. FIG. 7B shows the mean pectoralis weight. FIG. 7C shows the mean soleus weight. FIG. 7D shows the mean triceps weight. Statistical evaluation was performed using a one-way ANOVA followed by Holm-Sidak's post hoc test in comparison to the Vehicle Control Group (Group 1). Data represent group means±SEM. **p<0.01. Bars indicate from left-to-right Groups 1-5.

FIG. 8A shows the mean tibialis anterior weight. FIG. 8B shows the mean diaphragm weight. FIG. 8C shows the mean quadriceps weight. Statistical evaluation was performed using a one-way ANOVA followed by Holm-Sidak's post hoc test in comparison to the Vehicle Control Group (Group 1). Data represent group means±SEM. *p<0.05. Bars indicate from left-to-right Groups 1-5.

FIG. 9A is a graph showing the calculated percent weight change from Day 0 in animals weighed twice weekly throughout the study. In FIG. 9B, animals underwent EchoMRI (QNMR) to measure body composition on days −4, 7, 14, 21, and 28 and percent lean mass change from Day −1 was calculated. Data represent group means±SEM. For both body weight and lean mass the mean percent change data for each group on day 28 of the study were analyzed using a one-way ANOVA followed by Holm-Sidak's post hoc test in comparison to the IgG Control Group (Group 2). *p<0.0005, p<0.005, *p<0.05, ns (not significant).

FIG. 10A shows the mean quadriceps (rectus femoris) weight, FIG. 10B shows the mean gastrocnemius weight, FIG. 10C shows the mean tibialis anterior weight, and FIG. OD shows the mean diaphragm weight. Percent difference in mean muscle weights of the Ab1 treated groups compared to the IgG control group is noted above each bar. Statistical evaluation was performed using a one-way ANOVA followed by Holm-Sidak's post hoc test in comparison to the IgG Control Group (Group 2). Data represent group means±SEM. **p<0.0001, *p<0.0005, **p<0.005, *p<0.05, ns (not significant).

FIGS. 11A-11B show results of an assay evaluating mean percent body weight and lean mass change. FIG. 11A shows the percent weight change from Day 0 calculated from animals weighed twice weekly throughout the study. (FIG. 11B) Animals underwent EchoMRI (QNMR) to measure body composition on days −1, 6, and 13 and percent lean mass change from Day −1 was calculated. PBS=phosphate buffered saline, Dex=dexamethasone, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. Data represent group means±SEM. Mean percent change data for each group on day 14 (for body weight) and day 13 (for lean mass) were analyzed using a one-way ANOVA followed by a Dunnett's multiple comparisons test vs. group 1 (**p<0.0001, *p<0.0005, **p<0.005, *p<0.05) and vs. group 5 (++++p<0.0001, +++p<0.0005, ++p<0.005, +p<0.05). ns (not significant).

FIGS. 12A-12D are graphs showing results of an assay evaluating the weights of different muscles. FIG. 12A shows the mean gastrocnemius weight (grams), FIG. 12B shows the mean quadriceps (rectus femoris) weight (grams), FIG. 12C shows the mean percent gastrocnemius weight change versus the control animals treated with PBS (IP) and normal drinking water (Group 1), and FIG. 12D shows the mean percent quadriceps (rectus femoris) weight change versus the control animals treated with PBS (IP) and normal drinking water (Group 1). PBS=phosphate buffered saline, Dex=dexamethasone, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. For FIGS. 12A-12B, error bars represent standard deviation (SD). For FIGS. 12C-12D, error bars represent standard error of the mean (SEM). Statistical evaluation was performed using a one-way ANOVA followed by a Dunnett's multiple comparisons test vs. group 1 (**p<0.0001, *p<0.0005. **p<0.005, *p<0.05) and vs. group 5 (++++p<0.0001, +++p<0.0005, ++p<0.005, +p<0.05). ns (not significant). Bars indicate from left-to-right, PBS, water; PBS, dex; IgG Control; Ab1 (20); and Ab1(2).

FIG. 13A shows the percent weight change from Day 0 calculated for animals who were weighed twice weekly throughout the study. FIG. 13B shows the percent lean mass change from Day −1 calculated from animals who underwent EchoMRI (QNMR) to measure body composition on days −1, 7, and 14. PBS=phosphate buffered saline, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. Data represent group means f SEM.

FIG. 14A shows the mean gastrocnemius weight from the casted leg (grams), FIG. 14B shows the mean quadriceps (rectus femoris) weight from the casted leg (grams), FIG. 14C shows the mean percent gastrocnemius weight change versus the control animals treated with PBS (IP) and not casted (Group 1), and FIG. 14D shows the mean percent quadriceps (rectus femoris) weight change versus the control animals treated with PBS (IP) and not casted (Group 1). PBS=phosphate buffered saline, IgG (20)=IgG control antibody dosed at 20 mg/kg/wk, Ab1 (20)=Ab1 antibody dosed at 20 mg/kg/wk, and Ab1 (2)=Ab1 antibody dosed at 2 mg/kg/wk. For FIGS. 14A-14B, error bars represent standard deviation (SD). For FIGS. 14C-14D, error bars represent standard error of the mean (SEM). Statistical evaluation was performed using a one-way ANOVA followed by a Dunnett's multiple comparisons test vs. group 1 (**p<0.0001, *p<0.0005, **p<0.005, *p<0.05) and vs. group 5 (++++p<0.0001, +++p<0.0005, ++p<0.005, +p<0.05). ns (not significant). Bars indicate from left-to-right, PBS, no cast; PBS, casted; IgG Control (1), casted; Ab1(20), casted; and Ab1(2), casted.

FIG. 15 shows results of an assay evaluating the lean mass change at Day 21 (top right) and Day 28 (top left). It also depicts the percent change in lean mass at three different doses, 20 mg/kg/wk (bottom left), 2 mg/kg/wk (bottom middle), and 0.5 mg/kg/wk (bottom right) of the tested antibodies, PBS control, and IgG control. Statistical evaluation was performed using a one-way ANOVA followed by a Dunnett's multiple comparisons test vs. group 1 (**$p<0.0001$, *$p<0.005$, **$p<0.01$, *$p<0.05$) and vs. the IgG control. For the top two panels, bars from left-to-right are: PBS; IgG Ctrl 20 mg/kg/wk; Ab1 20 mg/kg/wk; Ab1 2 mg/kg/wk; Ab1 0.5 mg/kg/wk; Ab2 20 mg/kg/wk; Ab2 2 mg/kg/wk; Ab2 0.5 mg/kg/wk; Ab4 20 mg/kg/wk; Ab4 2 mg/kg/wk; A4 0.5 mg/kg/wk; Ab6 20 mg/kg/wk; Ab6 2 mg/kg/wk; and Ab60.5 mg/kg/wk. For the bottom left panel (20 mg/kg/wk), the data points corresponding to day 28 post dosing, from top to bottom, correspond to Ab1. Ab4, Ab2, Ab6, IgG control, and PBS. For the bottom center panel (2 mg/kg/wk), the data points corresponding to day 28 post dosing, from top to bottom, correspond to Ab2, Ab1, Ab6, Ab4, IgG control, and PBS. For the bottom right panel (0.5 mg/kg/wk), the data points, corresponding to day 28 post dosing, from top to bottom, correspond to IgG control Ab1, Ab2, PBS, Ab4, and Ab6.

FIG. 16A shows the domain structure of pro-myostatin and latent myostatin, with protease cleavage sites indicated. FIG. 16B shows partially proprotein convertase cleaved pro-myostatin run on an SDS PAGE gel. Under reducing conditions, the protein bands consisted of the pro-myostatin monomer (~50 kD), prodomain (~37 kD) and growth factor (12.5 kD).

FIG. 17A shows Ab1 binds specifically to pro-myostatin and latent myostatin, with no binding observed to other members of the TGFB superfamily, most notably the corresponding forms of GDF11. Ab1 was administered at a high concentration (50 ug/mL) to Forte-Bio BLI tips coated with the indicated antigen and the on and off rates were measured to obtain an approximate Kd value. The magnitude of biosensor response, indicating a binding event, is graphically represented by black bars, and the calculated Kd is indicated in orange. FIG. 17B shows that Ab1 blocks the activation of pro-myostatin, but not proGDF11. Following an overnight proteolysis reaction with enzymes from both the proprotein-convertase and tolloid protease families, the release of mature growth factor was measured using a CAGA-based reporter assay in 293T cells. Results were compared to control reactions to calculate the fraction of pro-myostatin or proGDF11 which was released in the assay.

FIGS. 18A-18C show the SCID dose response with the candidate antibodies. FIG. 18A shows the muscle weight of the gastrocnemius and FIG. 18B shows the muscle weight of the quadriceps (rectus femoris). FIG. 18C shows the percent changes in mean muscle weight compared to the PBS control. The bars in FIGS. 18A-18B from left-to-right are: PBS; IgG Ctrl 20 mg/kg/wk; Ab1 20 mg/kg/wk; Ab1 2 mg/kg/wk; Ab1 0.5 mg/kg/wk; Ab2 20 mg/kg/wk; Ab2 2 mg/kg/wk; Ab2 0.5 mg/kg/wk; Ab4 20 mg/kg/wk; Ab4 2 mg/kg/wk; Ab4 0.5 mg/kg/wk; Ab6 20 mg/kg/wk; Ab6 2 mg/kg/wk; and Ab6 0.5 mg/kg/wk.

FIGS. 21A-21B show the heavy chain (FIG. 21A; SEQ ID NO: 50) and light chain (FIG. 21B; SEQ ID NO: 51) of a humanized monoclonal antibody (Ab2) of the IgG4 subtype with Proline substituted for Serine. This generates an IgG1-like hinge sequence and minimizes the incomplete formation of inter-chain disulfide bridges which is characteristic of IgG4. The complementarity-determining regions (CDRs) are underlined. Bolded NST sequence: N-linked glycosylation consensus sequence site; Bolded DP sequences are potential cleavage sites; Bolded NX sequences, wherein X can be S, T, or G are potential deamidation sites; Bolded DX sequences, wherein X can be G, S, T, or SDG are potential isomerization sites; Bolded methionines are potential methionine oxidation sites; Bolded Q is an expected N-terminal pyroglutamic acid.

FIG. 23C shows the affinity-matured variants have a slower off-rate by octet as well.

FIGS. 24A-24B show sequence alignments of the variable heavy regions (FIG. 24A) and variable light regions (FIG. 24B) of parental Ab1 with affinity optimized variants, Ab3 and Ab5. Sequence identifiers from top to bottom correspond to SEQ ID NOs.: 24, 26, 28 (FIG. 24A). Sequence identifiers from top to bottom correspond to SEQ ID NOs.: 30, 32, 34 (FIG. 24B). Complementarity-determining regions (CDRs) are defined using the Kabat (underlined) and IMGT nomenclature (bold). Substitutions from parental Ab1 are shown in light gray.

FIG. 30A shows rats treated with Ab2 show increased lean mass compared to PBS- or IgG control-treated animals. Ab2 and IgG were administered intravenously at 10 mg/kg doses on day 0. Lean mass measured by qNMR (N=8 per group) at baseline (day 0) and 7, 14, 21 and 28 days after dosing. FIG. 30B shows rectus femoris and tibilais anterior muscles were collected from all groups at the end of the study (N=8 per group) and weighed to determine muscle mass. Rats treated with Ab2 show an increase of 14% and 11% in rectus femoris and tibialis anterior muscle masses, respectively.

FIG. 31A shows treatment with Ab2 (top line) increases latent myostatin levels in rat serum by ~20-fold. FIG. 31B shows that in rat muscle (rectus femoris), Ab2 treatment leads to a 1.9× increase in the latent form of myostatin. The bars from left to right correspond to pro-myostatin, latent myostatin, pro-myostatin, and latent myostatin. No statistically significant change in pro-myostatin is observed in rat muscle. These data are from quantitative western analyses with n=3 samples per group.

FIG. 35A shows latent myostatin is elevated in both Ab2- and AbMyo-treated muscles. However, elevation of latent myostatin in AbMyo-treated muscles returns to baseline by day 28, while those in Ab2 treated muscles remain elevated until at least this time (P<0.003 vs. AbMyo treatment). FIG. 35B shows a similar trend is observed with pro-myostatin, though the difference between the Ab2 and AbMyo treated groups at day 28 is not statistically significant (P=0.068).

FIG. 37A in vivo Plantarflexor functional performance after four weeks of treatment with a murine version of Ab1. Maximal force was normalized to limb length. Force measurements produced from electrical stimulus of the plantarflexor muscle group via the sciatic nerve. On average from 40-150 Hz there was a 19% increase in maximal force (p=0.003). Specifically, at 60 Hz an 18% increase in maximal force was measured (p=4.083). FIG. 37B shows the gastrocnemius weight increased after administration of muAb1. FIG. 37C shows that when normalized to gastrocnemius weight, there was no change in maximum force, indicating no change in muscle quality. FIG. 37D shows in vitro extensor digitorum longus muscle function after four weeks of treatment with muAb1. Force measurements of the EDL over increasing stimulus frequencies normalized to EDL length. Increases in muscle force were: 24% at 80 Hz (p=0.024), 28% at 100 Hz (p=0.010), and 27% at 150 Hz (p=0.011). FIG. 37E shows that the EDL weight increased after administration of muAb1. FIG. 37F shows that when normalized to EDL weight, there was no change in maximum force, indicating no change in muscle quality. FIG. 37G shows the Type IIB mean fiber area of muAb1 and PBS. FIG. 37H shows 4 muscle fiber types (%) in PBS and muAb samples.

FIGS. 38A-38I show administration of muAb1 in healthy animals enhances muscle function. FIGS. 38A-38B show maximum rates of relaxation and contraction and force-frequency relationships following in vivo Plantarflexor functional performance after four weeks of treatment with muAb1. FIGS. 38C-38D show maximum rates of relaxation and contraction and force-frequency relationships following in vitro extensor digitorum longus muscle function after four weeks of treatment with muAb1. FIGS. 38E-38I show muscle fiber cross sectional area quantitation from the plantarflexor muscle group.

FIGS. 40A-40C show cross sections of tibilias anterior muscle probed with anti-pro/latent GDF8 antibody, Ab10, that had been incubated in blocking buffer alone (FIG. 40A), incubated in blocking buffer with 10-fold molar excess recombinant mouse GDF8 (FIG. 40B), or incubated in blocking buffer with 10-fold molar excess recombinant mouse GDF11 (FIG. 40C). FIGS. 40A-40C are counterstained with DAPI.

FIGS. 41A-41C show cross sections of tibialis anterior muscle probed with anti-pro/latent GDF8 antibody, Ab10, and anti-laminin, and counterstained with DAPI. Pro/latent GDF8 and laminin colocalize in the interstitial space at muscle fiber vertices (arrow), between muscle fibers (arrow head), and around interstitial nuclei (asterisk).

FIGS. 43A-43D show effects of treatment with Ab2 on change in lean mass in healthy Cynomolgus monkeys. Healthy male Cynomolgus monkeys were dosed by intravenous injection once weekly for 8 weeks at three different doses of Ab2, 3 mg/kg, 10 mg/kg, and 30 mg/kg, with a 4-week recovery phase. Control animals were administered vehicle control (20 mM Citrate and 150 mM Sodium Chloride USP, pH 5.5). Lean mass was measured by Dual Energy X-Ray Absorptiometry (DEXA). FIG. 43A is a graph showing mean percent change in lean mass in muscles from all limbs in Ab2-treated and control animals measured at Day 0, 4 weeks, 8 weeks, and 12 weeks. FIG. 43B is a graph showing mean percent change in lean mass in muscles from all limbs in Ab2-treated and vehicle control animals measured at week 4. FIG. 43C is a graph showing mean percent change in lean mass in limb muscles in Ab2-treated and vehicle control animals measured at week 8. FIG. 43D is a graph showing mean percent change in lean mass in limb muscles in Ab2-treated and vehicle control animals measured at week 12.

FIGS. 44A-44B am graphs showing effects of treatment with Ab2 on muscle weight in biceps brachii and gastrocnemius muscles collected from healthy Cynomolgus monkeys. Healthy male Cynomolgus monkeys were dosed by intravenous injection once weekly for 8 weeks at three different doses of Ab2, 3 mg/kg, 10 mg/kg, and 30 mg/kg, with a 4-week recovery phase to week 12. Control animals were administered vehicle control (20 mM Citrate and 150 mM Sodium Chloride USP, pH 5.5). Muscle weight was measured by tissue weight at week 12.

FIG. 45 shows mean percent change in lean mass from baseline (day 0) and in percent difference in muscle weight in healthy Cynomolgus monkeys treated with Ab2 compared to the vehicle control.

DETAILED DESCRIPTION OF THE INVENTION

Figure 1A:
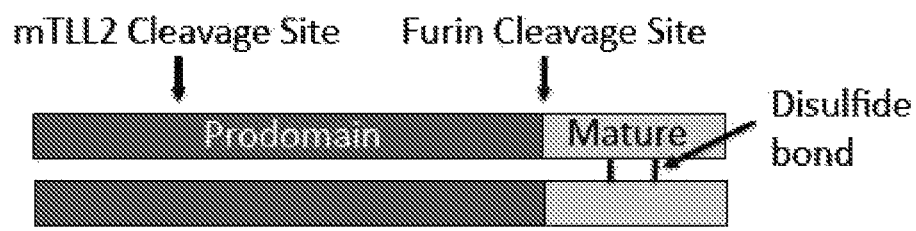
FIGS. 1A-1B show myostatin domain structure and pro-myostatin assembly.

The present disclosure relates to antibodies that are capable of specifically binding to a myostatin precursor or precursor complex and blocking its proteolytic processing into mature myostatin in vivo, thereby inhibiting myostatin signaling so as to elicit a beneficial effect in vivo. Such antibodies are useful for administration to subjects who may benefit from or in need of reduced myostatin signaling.

According to the invention, administration of an effective amount of a myostatin inhibitor, e.g., an anti-pro/latent myostatin antibody, described herein to a subject can produce multiple beneficial biological effects in the subject by selectively inhibiting activation of myostatin in vivo. Such biological effects include two or more, e.g., 3 or more, 4 or more, 5 or more, 6 or more, 2-4, 2-5, 2-6, 3-5 or 3-6 of the following benefits:

a) an increase in mass and/or function of a muscle in the subject;
b) an increase in the metabolic rate of the subject;
c) an increase in insulin sensitivity of the subject;
d) an increase in the level of brown adipose tissue in the subject;
e) an increase in the level of beige adipose tissue in the subject;
f) a decrease in the level of white adipose tissue in the subject;
g) a decrease in the level of visceral adipose tissue in the subject;
h) a decrease in the ratio of adipose-to-muscle tissue in the subject;
i) an increase in glucose uptake by a white adipose tissue, a live tissue or a blood vessel tissue in the subject;
j) a decrease in muscle catabolism of protein and/or muscle release of amino acids in the subject;
k) an increase in insulin-dependent glycemic control in the subject;
l) a decrease in intramuscular fat infiltration in the subject;
m) a clinically meaningful improvement in a standardized quality-of-life test score;

(o) prevention of muscle loss or atrophy in the subject; and/or, (p) prevention of developing a metabolic dysregulation associated with muscle dysfunction in the subject.

Thus, the present invention includes the use of myostatin inhibitors, e.g., antibodies, or antigen binding fragments thereof, that specifically bind pro-myostatin and/or latent myostatin and block activation of mature myostatin in vivo in subjects. e.g., human subjects who benefit from reduced myostatin signaling. The invention includes methods of treating or preventing conditions associated with myostatin dysregulation using antibodies, or antigen binding fragments thereof, that specifically bind pro-myostatin and/or latent myostatin and block activation of myostatin in an amount effective to treat or prevent such conditions. Conditions associated with myostatin dysregulation include muscle diseases and disorders, as well as certain metabolic dysregulation.

In order that the present invention may be more readily understood, certain terms are first defined. In addition, it should be noted that whenever a value or range of values of a parameter are recited, it is intended that values and ranges intermediate to the recited values are also intended to be part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

Definitions

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages may mean±1%. Furthermore, the term "about" can mean within ±1% of a value.

The terms "administer", "administering" or "administration" include any method of delivery of an antibody or an antigen-binding fragment thereof, e.g., a pharmaceutical composition comprising such an antibody or antigen-binding fragment, or an agent, into a subject's system or to a particular region in or on a subject (systemic and local administration, respectively).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The antibodies of the invention are described in further detail in International Patent Application WO2016073853A1 and International Application No. PCT/US2016/052014, filed on Sep. 15, 2016, the entire contents of each of which are incorporated herein by reference. Antibody variants, as known in the art, are also encompassed by the present invention.

The term "antigen binding fragment", "antigen-binding fragment" or "antigen-binding portion" of an antibody (or simply "antibody fragment" or "antibody portion"), as used herein, refers to one or more fragments of an antibody that retain the ability to specifically bind to an antigen (e.g., pro/latent myostatin). It has been shown that the antigen-binding function of an antibody can be performed by fragments of a full-length antibody. Examples of binding fragments encompassed within the term "antigen binding fragment" of an antibody include (i) a Fab fragment, a monovalent fragment consisting of the VL, VH, CL and CH1 domains; (ii) a F(ab')2 fragment, a bivaient fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody. (v) a dAb fragment (Ward et al., (1989) Nature 341:544-546), which consists of a VH domain; and (vi) an isolated complementarity determining region (CDR). Furthermore, although the two domains of the Fv fragment. VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which V H and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) Proc. Natl. Acad. Sci. USA 90:6444-6448; Poljak, R. J. et al. (1994) Structure 2:1121-1123).

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

The term "control" or "control sample." as used herein, refers to any clinically or scientifically relevant comparative sample or counterpart, including, for example, a sample from a healthy subject, a sample from a subject having a deficiency that can cause or make the subject susceptible to a certain disease or condition, a subject with a disease or condition of interest, a sample from a subject treated with a pharmaceutical carrier, a sample from a subject prior to treatment, a sham or buffer treated subject or sample, an untreated subject or sample, and the like.

The term "control level" refers to an accepted or predetermined level of a biological marker, e.g., a level of a marker obtained before treatment or the onset of disease or before administration of a drug, e.g., an antibody or an antigen-binding portion thereof. The level of a biological marker present in a subject or population of subjects having one or more particular characteristics. e.g., the presence or absence of a particular disease or condition.

The term "decrease", as used herein, in the context of a disease symptom refers to a statistically significant decrease in such level. The decrease can be, for example, at least 5%, 10%, 15%, 20%, 25%, 30%, 35%, 40%, 45%, 50%, 55%, 60%, 65%, 70%, 75%, 80%, 85%, 90%, or 95%, or below the level of detection for the detection method. The decrease can also be, for example, about 1-10%, 10-20%, 1-30%, 20-50%, 30-60%, 40-70%, 50-80%, or 60-90% below the level of detection for the detection method. In certain embodiments, the reduction is down to a level accepted as within the range of normal for an individual without such disorder which can also be referred to as a normalization of a level.

As used herein, the term "denervation" refers to loss or perturbation of nerve supply or neuronal input to its target tissue, such as a muscle tissue. Causes of denervation include disease (e.g., genetic disorders of motor neurons), chemical toxicity, physical injury, or intentional surgical interruption of a nerve and the like. Denervation may be partial denervation (also referred to as incomplete denervation) or complete denervation. Partial deneration can be, for example, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95% loss or perturbation of nerve supply or neuronal input to its target tissue. In some embodiments, partial denervation includes about 1-10%, 10-20%, 1-30%, 20-50%, 30-60%, 40-70%, 50-80%, 60-90% of loss or perturbation of nerve supply or neuronal input to its target tissue.

"Determining" as used herein is understood as performing an assay or using a method to ascertain the state of someone or something, e.g., the presence, absence, level, or degree of a certain condition, biomarker, disease state, or physiological condition.

"Development" or "progression" of a disease means initial manifestations and/or ensuing progression of the disease. Development of the disease can be detectable and assessed using standard clinical techniques. However, development also refers to progression that may be undetectable. For purpose of this disclosure, development or progression refers to the biological course of the symptoms. "Development" includes occurrence, recurrence, and onset. As used herein "onset" or "occurrence" of a disease/disorder associated with myopathy includes initial onset and/or recurrence.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. The epitope can be a linear epitope or a conformational epitope.

As used herein, the terms "effective amount" and "effective dose" refer to any amount or dose of a compound or composition that is sufficient to fulfill its intended purpose (s), i.e., a desired biological or medicinal response in a tissue or subject at an acceptable benefit/risk ratio. For example, in certain embodiments of the present invention, the intended purpose may be to inhibit activation of myostatin in vivo, to achieve clinically meaningful outcome associated with the myostatin inhibition.

Measure of the relevant intended purpose may be objective (i.e., measurable by some assay or marker) or subjective (i.e., subject gives an indication of or feels an effect). In some embodiments, a therapeutically effective amount is an amount that, when administered to a patient population that meets certain clinical criteria for a disease, disorder or condition (for example, as determined by symptoms manifested, disease progression/stage, genetic profile, etc.), a statistically significant therapeutic response is obtained among the population.

In some embodiments, an effective amount is an amount that, when administered according to a particular regimen, produces a positive clinical outcome with a reasonably acceptable level of adverse effects (e.g., toxicity), such that the adverse effects, if present, are tolerable enough for a patient to continue with the therapeutic regimen, and the benefit of the therapy overweighs risk of toxicity. Those of ordinary skill in the art will appreciate that in some embodiments of the invention, a unit dosage may be considered to contain an effective amount if it contains an amount appropriate for administration in the context of a dosage regimen correlated with a positive outcome.

A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

The term "human antibody", as used herein, is intended to include antibodies having variable and constant regions derived from human germline immunoglobulin sequences and fragments thereof. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "increase" in the context, e.g., of a disease symptom, such as for example, a loss of function or loss of mass, e.g., muscle mass associated with a disease, refers to a statistically significant increase in such level. The increase can be, for example, at least 5%, 10%, 15%, 20%, 25%, 30%, 35%, 40%, 45%, 50%, 55%, 60%, 65%, 70%, 75%, 80%, 85%, 90%, or 95%, or above the level of detection for the detection method. The increase can also be, for example, about 1-10%, 10-20%, 1-30%, 20-50%, 30-60%, 40-70%, 50-80%, or 60-90% above the level of detection for the detection method. In certain embodiments, the increase is up to a level accepted as within the range of normal for an individual without such disorder which can also be referred to as a normalization of a level. In certain embodiments, the increase is the normalization of the level of a sign or symptom of a disease, an increase in the difference between the subject level of a sign of the disease and the normal level of the sign for the disease. In certain embodiments, the methods include an increase in the mass and/or function of the muscle tissue after treatment of a subject with an antibody that specifically binds pro/latent myostatin. In certain embodiments, the methods include an increase in a level of pro-myostatin in a target muscle, as compared to a control level of pro-myostatin.

An "isolated antibody", as used herein, is intended to refer to an antibody that is substantially free of other antibodies having different antigenic specificities (e.g., an isolated antibody that specifically binds pro/latent-myostatin is substantially free of antibodies that specifically bind antigens other than pro/latent-myostatin). An isolated antibody that specifically binds pro/latent-myostatin may, however, have cross-reactivity to other antigens, such as pro/latent-myostatin molecules from other species. Moreover, an isolated antibody may be substantially free of other cellular material and/or chemicals.

Unless explicitly stated otherwise, the term "mature myostatin" refers to a fully processed, biologically active form of myostatin, unless explicitly stated otherwise. A biologically active form of myostatin is capable of myostatin receptor binding and/or activation. Wild type sequence of mature myostatin is provided as SEQ ID NO: 52. In some cases, mature myostatin may contain one or more mutations, which may exhibit altered structure/function or stability.

67) As used herein, the term "myostatin inhibitor" refers to any compound that inhibits or antagonizes the activity or expression level of myostatin, e.g., pro/latent myostatin. In some embodiments, the myostatin inhibitor may be an antibody (including fragments thereof, such as Domain Antibodies (dAbs) as described in, for example, U.S. Pat. Nos. 6,291,158; 6,582,915; 6,593,081; 6,172,197; and 6,696,245), a small molecule inhibitor, an Adnectin, an Affibody, a DARPin, an Anticalin, an Avimer, a Versabody or a gene therapy. The antibody, or antigen binding fragment thereof, may bind mature myostatin, a myostatin receptor, and/or GDF11. In some embodiments, the myostatin inhibitor is a small molecule inhibitor. In other embodiments, the myostatin inhibitor refers to a gene therapy. In one embodiment, the myostatin inhibitor binds specifically to myostatin, but not GDF11. In one embodiment, the myostatin inhibitor can be used to treat a metabolic disease, a muscle condition or disorder, a disease or disorder associated with an impaired neurological signaling or partial denervation or other condition described herein. In another embodiment, the myostatin inhibitor can be used to treat a disease involving fast twitch fibers, as described herein. In another embodiment, a myostatin inhibitor can be used to provide therapeutic effects below a lesion, as described herein.

As used herein, the phrase "latent myostatin in the circulation" or "circulating latent myostatin" refers to latent myostatin in the blood, plasma, or serum.

As used herein, the term "pro/latent-myostatin" refers to pro-myostatin, latent myostatin, or both (i.e., pro-forms or precursors of myostatin).

"Specific" and "specificity" in the context of an interaction between members of a specific binding pair (e.g., a ligand and a binding site, an antibody and an antigen, biotin and avidin) refer to the selective reactivity of the interaction. The phrase "specifically binds to" and analogous phrases refer to the ability of antibodies (or antigenically reactive fragments thereof) to bind specifically to an antigen (or a fragment thereof) and not bind specifically to other entities. Specific binding is understood as a preference for binding a certain antigen, epitope, receptor ligand, or binding partner with, for example, at least 2-fold, 5-fold, 10-fold, 50-fold, 100-fold, 200-fold, 500-fold, or 1,000-fold preference over a control non-specific antigen, epitope, receptor ligand, or binding partner. "Specific binding" as used herein can also refer to binding pairs based on binding kinetics such as $K_{on}$, $K_{off}$, and $K_D$. For example, a ligand can be understood to bind specifically to its target site if it has a $K_{off}$ of $10^{-2}$ sec$^{-1}$ or less, $10^{-3}$ sec$^{-1}$ or less, $10^{-4}$ sec$^{-1}$ or less, $10^{-5}$ sec$^{-1}$ or less, or $10^{-6}$ sec$^{-1}$ or less; and/or a $K_D$ of $10^{-6}$ M or less, $10^{-7}$ M or less, $10^{-8}$ M or less, $10^{-9}$ M or less, $10^{-10}$ M or less, or $10^{-11}$ M or less, or $10^{-2}$ M or less. It is understood that various proteins can share common epitopes or other binding sites (e.g., kinase reactive sites). In certain embodiments, binding sites may bind more than one ligand, but still can be considered to have specificity based on binding preference as compared to a non-specific antigen and/or by having certain binding kinetic parameters. Methods of selecting appropriate non-specific controls are within the ability of those of skill in the art. Binding assays are typically performed under physiological conditions.

As used herein, the term "slow-twitch", "slow twitch" "Type 1" or "Type I" muscle refers to a muscle enriched in Type I muscle fibers and is used frequently, more postural, and help enable long-endurance feats such as distance running. As used herein, the term "fast-twitch", "fast twitch" "Type 2" or "Type II" muscle refers to a muscle that provides higher energy output and strength and is used in powerful bursts of movements like sprinting, but such a muscle fatigue faster and cannot be used repeatedly. Fast-twitch muscles break down into two categories of fiber types: moderate fast-twitch fibers (Type IIA) and fast-twitch fibers (Type IIB or IIx). Moderate fast-twitch fibers are thicker, quicker to contract, and wear out more rapidly than slow-twitch fibers. Fast-twitch fibers, the most powerful and lowest in endurance, are activated when the body nears maximum exertion. While most muscles tend to be comprised of a mixture of various fiber types, different muscles contain different ratios of fiber types. During development or in response to certain events (e.g., exercise, disease, injury, etc.), fiber types within a muscle or muscle group may undergo fiber type switching, resulting in an altered phynotype in muscle physiology.

As used herein, the term "subject" and "patient" may be used interchangeably. In one embodiment, a subject refers to a vertebrate, in particular a mammal, in need of treatment, e.g., companion animals (e.g., dogs, cats and the like), farm animals (e.g., cows, pigs, horses, sheep, goats, poultry and the like) and laboratory animals (e.g., rats, mice, guinea pigs and the like). In some embodiments, the subject is a human who will benefit from or in need of treatment. In one embodiment, a subject is a human subject.

As used herein, the phrase "sustained increase" in the context of increase of muscle mass refers to an increase of muscle mass for a specified time after the administration a therapeutically effective amount of a myostatin inhibitor, e.g., an anti-pro/latent-myostatin antibody, as described herein. Sustained increase may be continuous or non-continuous, but overall results in an increase in muscle mass for the specified time.

By "treating" or "preventing" a disease or disorder is meant delaying or preventing the onset of such a disease or disorder, reversing, alleviating, ameliorating, inhibiting, slowing down or stopping the progression, aggravation or deterioration, the progression or severity of a condition associated with such a disease or disorder, but not necessarily require a complete treatment or prevention of the disease or disorder. In one embodiment, the symptoms of a disease or disorder are alleviated by at least 5%, at least 10%, at least 20%, at least 30%, at least 40%, or at least 50%.

Myostatin

Figure 1B:
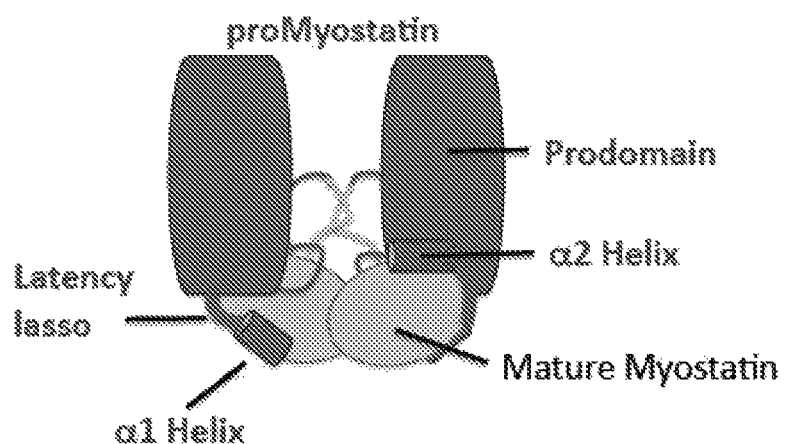
Figure 2:
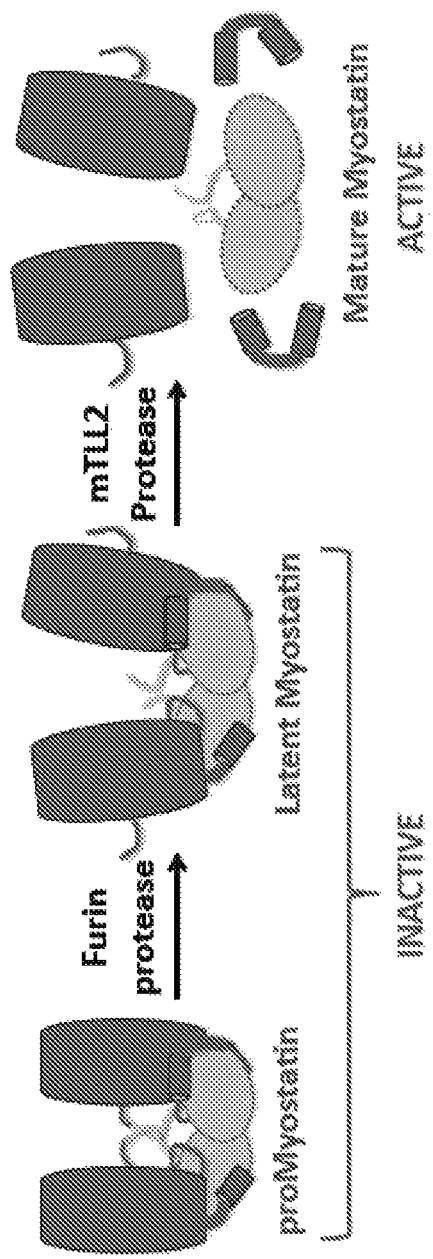
FIG. 2 shows the activation of myostatin involves two distinct protease events, generating three major myostatin species. The biosynthetic precursor protein, pro-myostatin, is processed by two separate proteases. Cleavage of pro-myostatin (and proGDF11) is carried out by a proprotein convertase, such as Furin/PACE3 (Paired basic Amino acid Cleaving Enzyme 3) or PCSK5 (Proprotein Convertase Subtilisin/Kexin type 5), which cuts at a conserved RXXR (SEQ ID NO:118) site between the prodomain and mature growth factor. This cleavage produces a latent complex, in which the mature growth factor is shielded from binding to its receptors by the prodomain. Activation and release of the active growth factor is accomplished after cleavage by an additional protease from the BMP/tolloid family, such as TLL-2 (Tolloid-like protein 2) or BMP1 (Bone Morphogenetic Protein 1). These cleavage events yield a mature form of myostatin, which may be referred to as active myostatin or mature myostatin.

Myostatin, also known as GDF8, is a member of the TGFβ superfamily, and belongs to a subfamily including two members: myostatin and GDF11. Like other members of the TGFβ superfamily, myostatin and GDF11 are both initially expressed as inactive precursor polypeptides (termed pro-myostatin and proGDF11, respectively). The domain structure and nomenclature are shown in FIG. 1A. FIG. 1B illustrates a cartoon model of the overall structure of pro-myostatin, where the mature growth factor is held locked in a cage comprised of two alpha helices connected by a loop termed the "latency lasso".

Myostatin is a well-characterized negative regulator of skeletal muscle mass that is released from an autoinhibitory N-terminal prodomain by two separate protease cleavage steps. These cleavage events, within the muscle fiber microenvironment, for example, may be referred to as supracellular activation. Following activation, mature myostatin signals by binding to a complex of Type I and II cell surface receptors (Alk4/5 and ActRIIB) whose downstream signaling induces muscle atrophy. There is interest in myostatin as a target for the treatment of muscle wasting. A number of therapeutics targeting the ActRIIB signaling pathway are completing early- to mid-stage clinical trials in muscle wasting conditions including sarcopenia, muscular dystrophies, cachexia, and hip replacement/hip fracture. To date, the primary clinical strategy has focused on blocking the interaction between mature myostatin and cell surface receptors. However, several therapeutic programs have been discontinued due to lack of specificity (leading to unacceptable toxicities) and/or efficacy. In vivo, myostatin is primarily in complex with its inhibitory prodomain.

Aspects of the disclosure provided herein relate to an assessment of the extent to which blocking the supracellular activation of myostatin from these inhibitory prodomain complexes provides a means for specifically blocking myostatin pathway signaling. Further aspects of the disclosure relate to an evaluation of a panel of human monoclonal antibodies that selectively bind the myostatin precursor forms, including a subset that inhibit proteolytic activation in vitro. In some embodiments, it has been found that antibodies that block activation are capable of protecting mice from dexamethasone-induced muscle atrophy. Assessment of serum and muscle samples from healthy animals and from those undergoing dexamethasone-induced atrophy demonstrated altered biodistribution of precursor forms during atrophy, a unique finding with important implications in understanding muscle wasting pathologies. Furthermore, treatment of healthy mice with a murine version of a potent activation-blocking antibody promoted robust muscle growth and resulted in significant gains in muscle function. Results provided herein provide insights into the significance of myostatin processing in skeletal muscle protein homeostasis. In addition, blocking the supracellular activation of the growth factor from precursor forms is a potent method for preventing myostatin signaling, a technique offering a novel therapeutic strategy that can also be applied to other members of the TGFβ superfamily.

Activation and release of mature myostatin is accomplished by several discrete protease cleavage events. The first cleavage step of pro-myostatin and proGDF11 is carried out by a proprotein convertase, which cuts at a conserved RXXR (SEQ ID NO:118) site between the prodomain and mature growth factor. This cleavage produces a "latent-myostatin," in which the mature myostatin is shielded from binding to its receptors by the prodomain. Activation and release of the mature, active myostatin growth factor is accomplished after cleavage of latent-myostatin by an additional protease from the BMP/tolloid family, such as mTLL-2. As used herein, the term "mature myostatin" can refer to both full-length mature myostatin, as well as fragments of the full-length mature myostatin which retain biological activity.

The term "pro-myostatin," also known as "proGDF8," refers to an inactive precursor of mature myostatin which comprises a disulfide-linked homodimer, each molecule of the homodimer comprising the amino terminal prodomain covalently bound to the carboxyl terminal mature myostatin domain. In one embodiment, "pro-myostatin" has not been cleaved by either a proprotein convertase, or a protease from the BMP/tolloid family. Exemplary pro-myostatin sequences, variants thereof, and methods of generating pro-myostatin are well known in the art and described in more detail herein.

As used herein the term "latent-myostatin" refers to an inactive precursor of mature myostatin which comprises a disulfide-linked homodimer, each molecule of the homodimer comprising the amino terminal prodomain non-covalently bound to the carboxyl terminal mature myostatin domain. In one embodiment, "latent-myostatin" is generated from a pro-myostatin that has been cleaved by a proprotein convertase, but which has not been cleaved by a protease from the BMP/tolloid family. In another embodiment, "latent-myostatin" can be generated by combining the prodomain and the carboxy terminal mature myostatin domain in vitro and allowing them to fold properly. See, for example, Sengle et al., J. Biol. Chem., 286(7):5087-5099, 2011. Exemplary latent-myostatin sequences, variants thereof, and methods of generating latent-myostatin are well known in the art and described in more detail herein.

Exemplary proGDF8 sequences in the human, rat, mouse and cynomolgus are provided below. In these proGDF8 sequences, a proprotein convertase cleavage site is indicated in bold and a tolloid protease site is indicated by underlining. In some embodiments, the proprotein convertase cleavage site comprises amino acid residues 240 to 243 of SEQ ID NOs: 52-55. In some embodiments, the tolloid protease site comprises amino acid residues 74-75 of SEQ ID NOs: 52-55. It should be appreciated that the exemplary proGDF8 sequences provided herein are not intended to be limiting and additional proGDF8 sequences from other species, including any isoforms thereof, are within the scope of this disclosure.

proGDF8 (human):
(SEQ ID NO: 52)
NENSEQKENVEKEGLCNACTWRQNTKSSRIEAIKIQILSKLRLETAPNIS

KDVIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (rat):
(SEQ ID NO: 53)
NEDSEREANVEKEGLCNACAWRQNTRYSRIEAIKIQILSKLRLETAPNIS

KDAIRQLLPRAPPLRELIDQYDVQRDDSSDGSLEDDDYHATTETIITMPT

ESDFLMQADGKPKCCFFKFSSKIQYNKVVKAQLWIYLRAVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVDRCG

CS.

proGDF8 (mouse):
(SEQ ID NO: 54)
NEGSEREENVEKEGLCNACAWRQNTRYSRIEAIKIQILSKLRLETAPNIS

KDAIRQLLPRAPPLRELIDQYDVQRDDSSDGSLEDDDYHATTETIITMPT

ESDFLMQADGKPKCCFFKFSSKIQYNKVVKAQLWIYLRPVKTPTTVFVQI

LRLIKPMKDGTRYTGIRSLKLDMSPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIAPKRYKANYCSGECEFVFLQKYPH

THLVHQANPRGSAGPCCTPTKMSPINMLYFNGKEQIIYGKIPAMVVGRCG

CS.

proCDF8 (cynomolgus):
(SEQ ID NO: 55)
NENSEQKENVEKEGLCNACTWRQNTKSSRIEAIKIQILSKLRLETAPNIS

KDAIRQLLPKAPPLRELIDQYDVQRDDSSDGSLEDDDYHATTETIITMPT

ESDFLMQVDGKPKCCFFKFSSKIQYNKVVKAQLWIYLRPVETPTTVFVQI

LRLIKPMKDGTRYTGIRSLKLDMNPGTGIWQSIDVKTVLQNWLKQPESNL

GIEIKALDENGHDLAVTFPGPGEDGLNPFLEVKVTDTPKRSRRDFGLDCD

EHSTESRCCRYPLTVDFEAFGWDWIIA.

Myostatin and GDF11 share a relatively high degree of conservation between their mature growth factor domains, with ninety percent identity, but are much less well conserved in their prodomain regions with less than fifty percent amino acid identity between the two. Myostatin and GDF11 bind and signal through the same receptors consisting of a Type I receptor (ALK4/5) in association with a type II receptor (ACTRIIA/B). Engagement of myostatin with Type I and Type II receptors initiates a signaling cascade leading to SMAD phosphorylation and transcriptional activation of muscle atrophy genes. The relatively high degree of conservation in the mature growth factors has made it challenging to identify reagents, such as monoclonal antibodies, that can differentiate between mature myostatin and GDF11.

In some embodiments, pro/latent-myostatin antibodies are provided herein that specifically bind to a chimeric construct that contains the growth factor domain and N terminal propeptide portion of GDF11 and the C terminal portion of the propeptide of GDF8. This chimeric construct, as forth below, is referred as GDF11Arm8.

GDF11Arm8
(SEQ ID NO: 65)
MDMRVPAQLLGLLLLWFSGVLGDYKDDDKHHHHHHLEVLFQGPAEGPAAA

AAAAAAAAAAGVGGERSSRPAPSVAPEPDGCPVCVWRQHSRELRLESIKS

QILSKLRLKEAPNISREVVKQLLPKAPPLRELIDQYDVQRDDSSDGSLED

DDYHATTETIITMPTESDFLMQVDGKPKCCFFKFSSKIQYNKVVKAQLWI

YLRPVETPTTVFVQILRLIKPMKDGTRYTIRSLKLDMNPGTGIWQSIDVK

TVLQNWLKQPESNLGIEIKALDENGHDLAVTFPGPGEDGLNPFLEVKVTD

TPKRSRRNLGLDCDEHSSESRCCRYPLTVDFEAFGWDWIIAPKRYKANYC

SGQCEYMFMQKYPHTHLVQQANPRGSAGPCCTPTKMSPINMLYFNDKQQI

IYGKIPGMVVDRCGCS

Role of Myostatin in Muscle Homeostasis and Metabolic Regulation

Skeletal muscle accounts for approximately 40% of body mass and is a dynamic organ, turning over at a rate of 1-2% per day. Myostatin is believed to play a pivotal role in maintaining the homeostasis of muscle both in healthy and disease conditions. Myostatin is capable of inducing muscle atrophy via its inhibition of myoblast proliferation, increasing ubiquitin-proteasomal activity and downregulating activity of the IGF-Akt pathway. These well-recognized effects are seen in multiple atrophy causing situations, including injury, diseases such as cachexia, disuse and space flight, demonstrating the importance of the myostatin signalling mechanism. Based on this central role, significant work has been pursued to inhibit myostatin's actions in vivo. Indeed, antagonizing myostatin signaling has shown to favor muscle growth/increase.

In addition, muscle is known to be the major protein reservoir of the body and therefore contributes to amino acid homeostasis. Along with glucose (made and stored as glycogen primarily in the liver and the muscles) and lipids (stored in fat tissues), proteins in muscles can act as an energy source (i.e., broken down to generate energy). Impairment or imbalance in the utilization or mobilization of these energy sinks in the body may, at least in part, underlie various types of metabolic dysregulation. It is therefore contemplated that myostatin may play a direct role in the regulation of metabolism by coordinating the balance between breakdown vs. synthesis/storage of glucose, fats and/or muscles in the body. Indeed, while myostatin has been primarily considered as a key regulator of muscle growth/loss since its discovery in 1997, findings presented in more detail herein suggest a broader role of myostatin as a metabolic regulator.

Myostatin Pathway Inhibition

There are several myostatin pathway inhibitors, such as small molecules, antibodies or antigen-binding portions thereof, and gene therapies, in various stages of clinical development towards the treatment of muscle-related conditions. Such pathway antagonists target either the mature growth factor or its type II receptor. Notably, most of these antagonists are not myostatin-specific, such that they antagonize the signaling of multiple TGFβ family members. For example, a number of current clinical candidates block additional growth factors such as Activin A, GDF11, and BMPs 9 and 10, which are regulators of reproductive biology, wound healing, erythropoiesis and blood vessel formation, respectively. Aspects of this disclosure relate to a recognition that the lack of specificity observed in these myostatin antagonists described elsewhere may pose a greater risk to certain patient populations because they block additional biological pathways such as those listed above in addition to myostatin. This may therefore potentially limit the population of patients who can safely undergo therapy due to unacceptable adverse-effects such as abnormal bleeding, wound healing, or reproductive problems caused by off-target antibody binding (Campbell, et al. *Muscle Nerve* (2016); David. L., *Blood* 109, 1953-1961 (2007)). For example, Activin A is involved in both wound healing and reproductive biology, and binding to Activin A would therefore limit use in patients who have recently undergone surgery or injury, or in women of reproductive age. Such increased risk of adverse effects or toxicity may be particularly concerning where i) a patient population requires a long-term treatment (such as chronic conditions); and/or, ii) a patient population is or includes pediatric patients, who may be susceptible to such adverse effects and/or toxicity. Accordingly, the present invention includes a novel approach to inhibiting myostatin signaling in vivo with potentially greater safety profiles.

Accordingly, provided herein are myostatin inhibitors, such as antibodies, or antigen binding fragments thereof, capable of binding to pro-myostatin and/or latent myostatin, thereby inhibiting myostatin activation, and uses thereof for treating diseases and disorders associated with myopathy. In some embodiments, given the prevalence of the latent complex in circulation, treatments are provided herein that specifically target more abundant and longer-lived myostatin precursors e.g., pro-myostatin and latent myostatin, rather than the mature growth factor. Without wishing to be bound by any particular theory, myostatin inhibitors, such as antibodies, or antigen binding fragments thereof, provided herein may prevent the proteolytic activation of pro-myostatin and/or latent myostatin into mature myostatin which is considered the "active" form of myostatin, capable of activating the myostatin pathway, e.g., by binding Type I (ALK4/5) and Type II (ACTRIIA/B) receptors.

As used herein, the term "pro/latent-myostatin" refers to pro-myostatin, latent myostatin, or both. In some embodiments, an anti-pro/latent myostatin antibody, or antigen binding fragment thereof, binds specifically to pro-myostatin. In some embodiments, an anti-pro/latent myostatin antibody, or antigen binding fragment thereof, binds specifically to latent myostatin. In some embodiments, an anti-pro/latent myostatin antibody, or antigen binding fragment thereof, binds specifically to both latent myostatin and pro-myostatin. In preferred embodiments, the anti-pro/latent myostatin antibody, or antigen binding fragment thereof, that binds specifically to pro-myostatin and/or latent myostatin does not bind mature myostatin. In preferred embodiments, the anti-pro/latent myostatin antibody, or antigen binding fragment thereof, that binds specifically to pro-myostatin and/or latent myostatin does not bind pro/latent GDF11 or mature GDF11.

Anti-Pro/Latent Myostatin Antibodies, or Antigen-Binding Fragments thereof, and Production Thereof The present disclosure is based, at least in part, on the surprising discovery that blocking the activation step of myostatin, rather than targeting already active myostatin, may provide an advantageous mode of selectively inhibiting myostatin signaling in vivo. Thus, the invention may have utility as a therapeutic in any condition where selective reduction of myostatin signaling in vivo is beneficial. More specifically, the invention includes surprising findings that specific inhibition of myostatin activation can effectuate not only muscle mass increase but also enhanced muscle function, as well as prevention of metabolic dysregulation. Unexpectedly, beneficial therapeutic effects can also be achieved even below a lesion in a subject having impaired but not complete loss of signaling between a neuron and a target tissue, such as a target muscle.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

Antibodies, or antigen binding fragments thereof, described herein are capable of binding to a pro/latent-myostatin, thereby inhibiting the proteolytic activation of pro/latent-myostatin into mature myostatin. In some instances, antibodies, or antigen binding fragments thereof, described herein can inhibit the proteolytic activation of pro/latent-myostatin by at least 20%. e.g., 30%, 40%, 50%, 60%, 70%, 80%, 90%, 95%, or higher. In some instances, antibodies described herein can inhibit the proteolytic cleavage of pro-myostatin by a proprotein convertase (e.g., furin) by at least 20%, e.g., 30%, 40%, 50%, 60%, 70%, 80%, 90%, 95%, or higher. In some instances, antibodies, or antigen binding fragments thereof, described herein can inhibit the proteolytic cleavage of pro-myostatin or latent myostatin by a tolloid protease (e.g., mTLL2) by at least 20%, e.g., 30%, 40%, 50%, 60%, 70%, 80%, 90%, 95%, or higher.

In some embodiments, inhibition of proteolytic cleavage of pro-myostatin or latent myostatin by a tolloid protease results in a progressive increase in muscle mass. In some embodiments, a subject exhibits a progressive increase in muscle mass for at least 2 weeks, 4 weeks, 6 weeks, 8 weeks, 10 weeks, 12 weeks, 14 weeks, 16 weeks, 18 weeks, or 20 weeks (or any range bracketed by any of the values). The inhibitory activity of an anti-pro/latent-myostatin antibody can be measured by routine methods, for example, by Western blot analysis as described in Example 1 and FIG. 3 disclosed in WO 2016/073853, the entire contents of which are expressly incorporated herein by reference. However, it should be appreciated that additional methods may be used for measuring the inhibitory activity of an anti-pro/latent-myostatin antibody on proteolytic cleavage of pro/latent-myostatin. In some embodiments, inhibition of pro/latent-myostatin cleavage (e.g., by a proprotein convertase and/or tolloid protease) may be reflected as an inhibition constant (Ki), which provides a measure of inhibitor potency, and which it is the concentration of inhibitor (e.g., an anti-pro/latent-myostatin antibody) required to reduce protease activity (e.g., of a proprotein convertase or tolloid protease) by half and is not dependent on enzyme or substrate concentrations.

In some embodiments, a proprotein convertase comprises (i) a catalytic domain that hydrolyzes a peptide bond of a protein containing a proprotein convertase cleavage site, and (ii) a binding pocket that binds to an rTGF with a proprotein convertase cleavage site. Examples of proprotein convertases for use in accordance with the present disclosure include, without limitation, PCSK5/6, PACE4, PACE7 and PACE3 (e.g., furin). A proprotein convertase, in some embodiments, is obtained, e.g., purified from, any mammal including, without limitation, humans, monkeys or rodents (e.g., mice, rats, hamsters). In another embodiment, a proprotein convertase is produced recombinantly.

In some embodiments, a proprotein convertase is homologous to a proprotein convertase selected from the group consisting of: PCSK5/6. PACE4, PACE7 and PACE3 (e.g., furin). For example, a proprotein convertase may be at least 70% identical, at least 80% identical, at least 90% identical, at least 95% identical, at least 96% identical, at least 97% identical, at least 98% identical, at least 99% identical, at least 99.5% identical, or at least about 99.9% identical to PCSK5/6, PACE4, PACE7 or PACE3 (e.g., furin).

A proprotein convertase cleavage site, in some embodiments, is an amino sequence that can be cleaved by a proprotein convertase (e.g., PCSK5/6, PACE4, PACE7 and PACE3). In some embodiments, the proprotein convertase cleavage site comprises the amino acid sequence R-X-X-R, where R is arginine and X is any amino acid. In some embodiments, the proprotein convertase cleavage site comprises the amino acid sequence R-X-(K/R)-R, where R is arginine, K is lysine and X is any amino acid. In some embodiments, the proprotein convertase cleavage site comprises the amino acid sequence is R-V-R-R (SEQ ID NO: 57), where R is arginine and V is valine. Exemplary proprotein convertase cleavage sites for human, rat, mouse, and cynomolgus myostatin are shown, in bold, in SEQ ID NOs: 52-55. In some embodiments, the proprotein convertase cleavage site comprises the amino acid sequence RSRR (SEQ ID NO: 56).

In some embodiments, tolloid proteases for use in accordance with the present disclosure include, without limitation, BMP-1, mTLL-1 and mTLL-2. A tolloid protease may be obtained from any mammal including, without limitation, humans, monkeys, or rodents (e.g., mice, rats, hamsters). In some embodiments, a tolloid protease is homologous to a tolloid protease selected from the group consisting of: BMP-1, mTLL-1 and mTLL-2. For example, a tolloid protease may be at least 70% identical, at least 80% identical, at least 90% identical, at least 95% identical, at least 96% identical, at least 97% identical, at least 98% identical, at least 99% identical, at least 99.5% identical, or at least about 99.9% identical to BMP-1, mTLL-1 and mTLL-2.

A tolloid protease cleavage site, in some embodiments, is an amino sequence that can be cleaved by a tolloid (e.g., BMP-1, mTLL-1 and mTLL-2). Exemplary tolloid protease cleavage sites for human, rat, mouse, and cynomolgus myostatin are shown, in underlining, in SEQ ID NOs: 52-55. In some embodiments, the tolloid cleavage site comprises the amino acid sequence QR, where Q is glutamine and R is arginine.

In some embodiments, antibodies, or antigen binding fragments thereof, described herein are capable of binding to a pro/latent-myostatin, thereby inhibiting myostatin activity. In some instances, the antibodies, or antigen binding fragments thereof, described herein can inhibit myostatin signaling by at least 20%, e.g., 30%, 40%, 50%, 60%, 70%, 80%, 90%, 95%, or higher. In some embodiments, inhibition of Myostatin signaling can be measured by routine methods, for example, using a myostatin activation assay as described in Example 1 disclosed in WO 2016/073853, the entire contents of which are expressly incorporated herein by reference. However, it should be appreciated that additional methods may be used for measuring myostatin signaling activity.

It should be appreciated that the extent of proteolytic cleavage of myostatin, e.g., by a proprotein convertase and/or a tolloid protease, can be measured and/or quantified using any suitable method. In some embodiments, the extent of proteolytic cleavage of myostatin is measured and/or quantified using an enzyme-linked immunosorbent assay (ELISA). For example, an ELISA may be used to measure the level of released growth factor (e.g., mature myostatin). As another example, an antibody, or antigen binding fragment thereof, that specifically binds to pro-myostatin, latent myostatin and/or mature myostatin can be used in an ELISA to measure the level of a specific form of myostatin (e.g., pro/latent/mature-myostatin), to quantify the extent of proteolytic cleavage of myostatin. In some embodiments, the extent of proteolytic cleavage of myostatin is measured and/or quantified using immunoprecipitation followed by SDS-PAGE or mass spectrometry of tryptic peptides, fluorescence anisotropy-based techniques, FRET assays, hydrogen-deuterium-exchange mass spectrometry, and/or NMR spectroscopy.

In some embodiments, antibodies, also known as immunoglobulins, are tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain typically includes an N-terminal variable (V) domain ($V_L$) and a constant (C) domain ($C_L$). Each heavy chain typically includes an N-terminal V domain ($V_H$), three or four C domains ($C_H$1-3), and a hinge region. The $C_H$ domain most proximal to $V_H$ is designated as $C_H$1. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

Anti-pro/latent-myostatin antibodies, or antigen binding fragments thereof, suitable for use in the methods of the present invention include those described in International Patent Application Nos. PCT/US15/59468 and PCT/US16/52014. The entire contents of each of the foregoing applications are incorporated herein by reference in their entireties.

In some embodiments, anti-pro/latent-myostatin antibodies, or antigen binding fragments thereof, of the present disclosure and the nucleic acid molecules of the present disclosure that encode the antibodies, or antigen binding fragments thereof, include the CDR amino acid sequences shown in Tables 1-3.

TABLE 1

| Antibody | CDRH1 (SEQ ID NOs: 1-3) | CDRH2 (SEQ ID NOs: 4-9) | CDRH3 (SEQ ID NOs: 10-11 and 66) | CDRL1 (SEQ ID NOs: 12-17) | CDRL2 (SEQ ID NOs: 18-21) | CDRL3 (SEQ ID NOs: 22-23 and 67) |
|---|---|---|---|---|---|---|
| Ab1 Kabat: IMGT: | SSYGMH (SEQ ID NO: 1) GFTFSSYGMH (SEQ ID NO: 2) | VISYDGSNKY YADSVKG (SEQ ID NO: 4) ISYDGSN (SEQ ID NO: 5) | DLLVRFLEWSHYY GMDV (SEQ ID NO: 10) | SGSSSNIGSNT VH (SEQ ID NO: 12) SSNIGSNT (SEQ ID NO: 13) | SDNQRPS (SEQ ID NO: 18) SDN (SEQ ID NO: 19) | AAWDDSLNGV (SEQ ID NO: 22) |
| Ab2 Kabat: IMGT: | SSYGMH (SEQ ID NO: 1) GFTFSSYGMH (SEQ ID NO: 2) | VISYDGSNKY YADSVKG (SEQ ID NO: 4) ISYDGSN (SEQ ID NO: 5) | DLLVRFLEWSHYY GMDV (SEQ ID NO: 66) | SGSSSNIGSNT VH (SEQ ID NO: 12) SSNIGSNT (SEQ ID NO: 13) | SDNQRPS (SEQ ID NO: 18) SDN (SEQ ID NO: 19) | AAWDDSLNGV (SEQ ID NO: 67) |
| Ab3 Kabat: IMGT: | SSYGMH (SEQ ID NO: 1) GFAFSSYGMH (SEQ ID NO: 3) | VISYDGSIKY YADSVKG (SEQ ID NO: 6) ISYDGSI (SEQ ID NO: 7) | DSSVRFLEWSHKY GMDV (SEQ ID NO: 11) | SGSTSNIGSNT VH (SEQ ID NO: 14) TSNIGSNT (SEQ ID NO: 15) | SDDQRPS (SEQ ID NO: 20) SDD (SEQ ID NO: 21) | AAWDESLNGV (SEQ ID NO: 23) |
| Ab4 Kabat: IMGT: | SSYGMH (SEQ ID NO: 1) GFAFSSYGMH (SEQ ID NO: 3) | VISYDGSIKY YADSVKG (SEQ ID NO: 6) ISYDGSI (SEQ ID NO: 7) | DSSVRFLEWSHKY GMDV (SEQ ID NO: 11) | SGSTSNIGSNT VH (SEQ ID NO: 14) TSNIGSNT (SEQ ID NO: 15) | SDDQRPS (SEQ ID NO: 20) SDD (SEQ ID NO: 21) | AAWDESLNGV (SEQ ID NO: 23) |
| Ab5 Kabat: IMGT: | SSYGMH (SEQ ID NO: 1) GFAFSSYGMH (SEQ ID NO: 3) | VISYDGNNKY YADSVKG (SEQ ID NO: 8) ISYDGNN (SEQ ID NO: 9) | DSSVRFLEWSHKY GMDV (SEQ ID NO: 11) | SGSSSNIGGNT VH (SEQ ID NO: 16) SSNIGGNT (SEQ ID NO: 17) | SDDQRPS (SEQ ID NO: 20) SDD (SEQ ID NO: 21) | AAWDESLNGV (SEQ ID NO: 23) |

In Table 1, the single sequences of CDRH3 and CDRL3 reflect Kabat and IMGT.

TABLE 2

| Description | Amino Acid Sequence (SEQ ID NO) | Nucleic Acid Sequence (SEQ ID NO) |
|---|---|---|
| Heavy chain variable region- Ab1 parental | QIQLVQSGGGVVQPGRSLRLSCAASGFTFS SYGMHWVRQAPGKGLEWVAVISYDGSNKYY ADSVKGRFTISRDNSKNTLYLQMNSLRAED TAVYYCARDLLVRFLEWSHYYGMDVWGQGT TVTVSS (SEQ ID NO: 24) | CAGATCCAGCTGGTGCAGTCTGGGGGAGGCGT GGTCCAGCCTGGGAGGTCCCTGAGACTCTCCT GTGCAGCGTCTGGATTCACCTTCAGTAGCTAT GGCATGCACTGGGTCCGCCAGGCTCCAGGCAA GGGGCTGGAGTGGGTGGCAGTTATATCATATG ATGGAAGTAATAAATACTATGCAGACTCCGTG AAGGGCCGATTCACCATCTCCAGAGACAATTC |

TABLE 2-continued

| Description | Amino Acid Sequence (SEQ ID NO) | Nucleic Acid Sequence (SEQ ID NO) |
|---|---|---|
| | | CAAGAACACGCTGTATCTGCAAATGAACAGCC TGAGAGCCGAGGACACGGCTGTGTATTACTGT GCGAGAGATCTCCTGGTGCGATTTTTGGAGTG GTCGCACTACTACGGTATGGACGTCTGGGGCC AAGGGACCACGGTCACCGTCTCCTCA (SEQ ID NO: 38) |
| Heavy chain variable region-Ab2 germline | QVQLVESGGGVVQPGRSLRLSCAASGFTFS SYGMHWVRQAPGKGLEWVAVISYDGSNKYY ADSVKGRFTISRDNSKNTLYLQMNSLRAED TAVYYCARDLLVRFLEWSHYYGMDVWGQGT TVTVSS (SEQ ID NO: 25) | CAGGTGCAGCTGGTGGAGTCTGGGGGAGGCGT GGTCCAGCCTGGGAGGTCCCTAGACTCTCCTG TGCAGCGTCTGGATTCACCTTCAGTAGCTATG GCATGCACTGGGTCCGCCAGGCTCCAGGCAAG GGGCTGGAGTGGGTGGCAGTTATATCATATGA TGGAAGTAATAAATACTATGCAGACTCCGTGA AGGGCCGATTCACCATCTCCAGAGACAATTCC AAGAACACGCTGTATCTGCAAATGAACAGCCT GAGAGCCGAGGACACGGCTGTGTATTACTGTG CGAGAGATCTCCTGGTGCGATTTTTGGAGTGG TCGCACTACTACGGTATGGACGTCTGGGGCCA AGGGACCACGGTCACCGTCTCCTCA (SEQ ID NO: 39) |
| Heavy chain variable region-Ab3 parental | QIQLVQSGGGVVQPGRSLRLSCAASGFAFS SYGMHWVRQAPGKGLEWVAVISYDGSIKYY ADSVKGRFTISRDNSKNTLYLQMNSLRAED TAVYYCARDLLVRFLEWSHKYGMDVWGQGT TVTVSS (SEQ ID NO: 26) | CAGATCCAGCTGGTGCAGTCTGGGGGAGGCGT GGTCCAGCCTGGGAGGTCCCTGAGACTCTCCT GTGCAGCGTCTGGATTCGCCTTCAGTAGCTAT GGCATGCACTGGGTCCGCCAGGCTCCAGGCAA GGGGCTGGAGTGGGTGGCAGTTATATCATATG ATGGAAGTATCAAATACTATGCAGACTCCGTG AAGGGCCGATTCACCATCTCCAGAGACAATTC CAAGAACACGCTGTATCTGCAAATGAACAGCC TGAGAGCCGAGGACACGGCTGTGTATTACTGT GCGAGAGATCTCCTGGTGCGATTTTTGGAGTG GTCGCACAAGTACGGTATGGACGTCTGGGGCCA AGGGACCACGGTCACCGTCTCCTCA (SEQ ID NO: 40) |
| Heavy chain variable region-Ab4 germline | QVQLVESGGGVVQPGRSLRLSCAASGFAFS SYGMHWVRQAPGKGLEWVAVISYDGSIKYY ADSVKGRFTISRDNSKNTLYLQMNSLRAED TAVYYCARDLLVRFLEWSHKYGMDVWGQGT TVTVSS (SEQ ID NO: 27) | CAGGTGCAGCTGGTGGAGTCTGGGGGAGGCGT GGTCCAGCCTGGGAGGTCCCTGAGACTCTCCT GTCAGCGTCTGGATTCGCCTTCAGTAGCTATG GCATGCACTGGGTCCGCCAGGCTCCAGGCAAG GGGCTGGAGTGGGTGGCAGTTATATCATATGA TGGAAGTATCAAATACTATGCAGACTCCGTGA AGGGCCGATTCACCATCTCCAGAGACAATTCC AAGAACACGCTGTATCTGCAAATGAACAGCCT GAGAGCCGAGGACACGGCTGTGTATTACTGTG CGAGAGATCTCCTGGTGCGATTTTTGGAGTGG TCGCACAAGTACGGTATGGACGTCTGGGGCCA AGGGACCACGGTCACCGTCTCCTCA (SEQ ID NO: 41) |
| Heavy chain variable region-Ab5 parental | QIQLVQSGGGVVQPGRSLRLSCAASGFAFS SYGMHWVRQAPGKGLEWVAVISYDGNNKYY ADSVKGRFTISRDNSKNTLYLQMNSLRAED TAVYYCARDLLVRFLEWSHKYGMDVWGQGT TVTVSS (SEQ ID NO: 28) | CAGATCCAGCTGGTGCAGTCTGGGGGAGGCGT GGTCCAGCCTGGGAGGTCCCTGAGACTCTCCT GTGCAGCGTCTGGATTCGCCTTCAGTAGCTAT GGCATGCACTGGGTCCGCCAGGCTCCAGGCAA GGGGCTGGAGTGGGTGGCAGTTATATCATATG ATGGAAATAATAAATACTATGCAGACTCCGTG AAGGGCCGATTCACCATCTCCAGAGACAATTC CAAGAACACGCTGTATCTGCAAATGAACAGCC TGAGAGCCGAGGACACGGCTGTGTATTACTGT GCGAGAGATCTCCTGGTGCGATTTTTGGAGTG GTCGCACAAGTACGGTATGGACGTCTGGGGCC AAGGGACCACGGTCACCGTCTCCTCA (SEQ ID NO: 42) |
| Heavy chain variable region-Ab6 germline | QVQLVESGGGVVQPGRSLRLSCAASGFAFS SYGMHWVRQAPGKGLEWVAVISYDGNNKYY ADSVKGRFTISRDNSKNTLYLQMNSLRAED TAVYYCARDLLVRFLEWSHKYGMDVWGQGT TVTVSS (SEQ ID NO: 29) | CAGGTGCAGCTGGTGGAGTCTGGGGGAGGCGT GGTCCAGCCTGGGAGGTCCCTGAGACTCTCCT GTGCAGCGTCTGGATTCGCCTTCAGTAGCTAT GGCATGCACTGGGTCCGCCAGGCTCCAGGCAA GGGGCTGGAGTGGGTGGCAGTTATATCATATG ATGGAAATAATAATACTATGCAGACTCCGTGA AGGGCCGATTCACCATCTCCAGAGACAATTCC AAGAACACGCTGTATCTGCAAATGAACAGCCT GAGAGCCGAGGACACGGCTGTGTATTACTGTG CGAGAGATCTCCTGGTGCGATTTTTGGAGTGG TCGCACAAGTACGGTATGGACGTCTGGGGCCA AGGGACCACGGTCACCGTCTCCTCA (SEQ ID NO: 43) |

TABLE 2-continued

| Description | Amino Acid Sequence (SEQ ID NO) | Nucleic Acid Sequence (SEQ ID NO) |
|---|---|---|
| Light chain variable region- Ab1 parental | QPVLTQPPSASGTPGQRVTISCSGSSSNIG SNTVHWYQQLPGTAPKLLIYSDNQRPSGVP DRFSGSKSGTSASLVISGLQSDDEADYYCA AWDDSLNGVFGGGTKLTVL (SEQ ID NO: 30) | CAGCCTGTGCTGACTCAGCCACCCTCAGCGTC TGGGACCCCCGGGCAGAGGGTCACCATCTCTT GTTCTGGAAGCAGCTCCAACATCGGAAGTAAT ACTGTCCACTGGTACCAGCAACTCCCAGGAAC GGCCCCCAAACTCCTCATCTATAGTGATAATC AGCGCCCCTCAGGGGTCCCTGACCGATTCTCT GGCTCCAAGTCTGGCACCTCAGCCTCCCTGGT CATCAGTGGGCTCCAGTCTGACGATGAGGCTG ATTATTACTGTGCAGCATGGGATGACAGCCTG AATGGGGTGTTCGGCGGAGGGACCAAGCTGAC CGTCCTA (SEQ ID NO: 44) |
| Light chain variable region- Ab2 germline | QSVLTQPPSASGTPGQRVTISCSGSSSNIG SNTVHYQQLPGTAPKLLIYSDNQRPSGVPD RFSGSKSGTSASLAISGLQSEDEADYYCAA WDDSLNGVFGGGTKLTVL (SEQ ID NO: 31) | CAGTCTGTGCTGACTCAGCCACCCTCAGCGTC TGGGACCCCCGGGCAGAGGGTCACCATCTCTT GTTCTGGAAGCAGCTCCAACATCGGAAGTAAT ACTGTCCACTGGTACCAGCAACTCCCAGGAAC GGCCCCCAAACTCCTCATCTATAGTGATAATC AGCGCCCCTCAGGGGTCCCTGACCGATTCTCT GGCTCCAAGTCTGGCACCTCAGCCTCCCTGGC CATCAGTGGGCTCCAGTCTGAGGATGAGGCTG ATTATTACTGTGCAGCATGGGATGACAGCCTG AATGGGGTGTTCGGCGGAGGGACCAAGCTGAC CGTCCTA (SEQ ID NO: 45) |
| Light chain variable region- Ab3 parental | QPVLTQPPSASGTPGQRVTISCSGSTSNIG SNTVHWYQQLPGTAPKLLIYSDDQRPSGVP DRFSGSKSGTSASLVISGLQSDDEADYYCA AWDESLNGVFGGGTKLTVL (SEQ ID NO: 32) | CAGCCTGTGCTGACTCAGCCACCCTCAGCGTC TGGGACCCCCGGGCAGAGGGTCACCATCTCTT GTTCTGGAAGCACCTCCAACATCGGAAGTAAT ACTGTCCACTGGTACCAGCAACTCCCAGGAAC GGCCCCCAAACTCCTCATCTATAGTGATGATC AGCGCCCCTCAGGGGTCCCTGACCGATTCTCT GGCTCCAAGTCTGGCACCTCAGCCTCCCTGGT CATCAGTGGGCTCCAGTCTGACGATGAGGCTG ATTATTACTGTGCAGCATGGGATGAGAGCCTG AATGGGGTGTTCGGCGGAGGGACCAAGCTGAC CGTCCTA (SEQ ID NO: 46) |
| Light chain variable region- Ab4 germline | QSVLTQPPSASGTPGQRVTISCSGSTSNIG SNTVHWYQQLPGTAPKLLIYSDDQRPSGVP DRFSGSKSGTSASLAISGLQSEDEADYYCA AWDESLNGVFGGGTKLTVL (SEQ ID NO: 33) | CAGTCTGTGCTGACTCAGCCACCCTCAGCGTC TGGGACCCCCGGGCAGAGGGTCACCATCTCTT GTTCTGGAAGCACCTCCAACATCGGAAGTAAT ACTGTCCACTGGTACCAGCAACTCCCAGGAAC GGCCCCCAAACTCCTCATCTATAGTGATGATC AGCGCCCCTCAGGGGTCCCTGACCGATTCTCT GGCTCCAAGTCTGGCACCTCAGCCTCCCTGGC CATCAGTGGGCTCCAGTCTGAGGATGAGGCTG ATTATTACTGTGCAGCATGGGATGAGAGCCTG AATGGGGTGTTCGGCGGAGGGACCAAGCTGAC CGTCCTA (SEQ ID NO: 47) |
| Light chain variable region- Ab5 parental | QPVTLQPPSASGTPGQRVTISCSGSSSNIG GNTVHWYQQLPGTAPKLLIYSDDQRPSGVP DRFSGSKSGTSALSVISGLQSDDEADYYCA AWDESLNGVFGGGTKLTVL (SEQ ID NO: 34) | CAGCCTGTGCTGACTCAGCCACCCTCAGCGTC TGGGACCCCCGGGCAGAGGGTCACCATCTCTT GTTCTGGAAGCAGCTCCAACATCGGAGGAAAT ACTGTCCACTGGTACCAGCAACTCCCAGGAAC GGCCCCCAAACTCCTCATCTATAGTGATGATC AGCGCCCCTCAGGGGTCCCTGACCGATTCTCT GGCTCCAAGTCTGGCACCTCAGCCTCCCTGGT CATCAGTGGGCTCCAGTCTGACGATGAGGCTG ATTATTACTGTGCAGCATGGGATGAGAGCCTG AATGGGGTGTTCGGCGGAGGGACCAAGCTGAC CGTCCTA (SEQ ID NO: 48) |
| Light chain variable region- Ab6 germline | QSVLTQPPSASGTPGQRVTISCSGSSSNIG GNTVHWYQQLPGTAPKLLIYSDDQRPSGVP DRFSGSKSGTSASLAISGLQSEDEADYYCA AWDESLNGVFGGGTKLTVL (SEQ ID NO: 35) | CAGTCTGTGCTGACTCAGCCACCCTCAGCGTC TGGGACCCCCGGGCAGAGGGTCACCATCTCTT GTTCTGGAAGCAGCTCCAACATCGGAGGAAAT ACTGTCCACTGGTACCAGCAACTCCCAGGAAC GGCCCCCAAACTCCTCATCTATAGTGATGATC AGCGCCCCTCAGGGGTCCCTGACCGATTCTCT GGCTCCAAGTCTGGCACCTCAGCCTCCCTGGC CATCAGTGGGCTCCAGTCTGAGGATGAGGCTG ATTATTACTGTGCAGCATGGGATGAGAGCCTG AATGGGGTGTTCGGCGGAGGGACCAAGCTGAC CGTCCTA (SEQ ID NO: 49) |

TABLE 2-continued

| Description | Amino Acid Sequence (SEQ ID NO) | Nucleic Acid Sequence (SEQ ID NO) |
|---|---|---|
| Ab2-Heavy Chain | QVQLVESGGGVVQPGRSLRLSCAASGFTFS SYGMHWVRQAPGKGLEWVAVISYDGSNKYY ADSVKGRFTISRDNSKNTLYLQMNSLRAED TAVYYCARDLLVRFLEWSHYYGMDVWGQGT TVTVSSASTKGPSVFPLAPCSRSTSESTAA LGCLVKDYFPEPVTVSWNSGALTSGVHTFP AVLQSSGLYSLSSVVTVPSSSLGTKTYTCN VDHKPSNTKVDKRVESKYGPPCPPCPAPEF LGGPSVFLFPPKPKDTLMISRTPEVTCVVV DVSQEDPEVQFNWYVDGVEVHNAKTKPREE QFNSTYRVVSVLTVLHQDWLNGKEYKCKVS NKGLPSSIEKTISKAKGQPREPQVYTLPPS QEEMTKNQVSLTCLVKGFYPSDIAVEWESN GQPENNYKTTPPVLDSDGSFFLYSRLTVDK SRWQEGNVFSCSVMHEALHNHYTQKSLSLS LG (SEQ ID NO: 50) | |
| Ab2-Light Chain | QSVLTQPPSASGTPGQRVTISCSGSSSNIG SNTVHWYQQLPGTAPKLLIYSDNQRPSGVP DRFSGSKSGTSASLAISGLQSEDEADYYCA AWDDSLNGVFGGGTKLTVLGQPKAAPSVTL FPPSSEELQANKATLVCLISDFYPGAVTVA WKADSSPVKAGVETTTPSKQSNNKYAASSY LSLTPEQWKSHRSYSCQVTHEGSTVEKTVA PTECS (SEQ ID NO: 51) | |

TABLE 3

| | CDR-H3 | CDR-L3 | VH | VL | scFV | SEQ ID NOs: from left to right |
|---|---|---|---|---|---|---|
| Ab7 | ESLIRF LEDPQQ GGMDV | NSWTRS NNYI | QVQLQQSGAEVKKPGASV KVSCKASGYTFTSYYMHW VRQAPGQGLEWMGIINPS GGSTSYAQKFQGRVTMTR DTSTSTVYMELSSLRSED TAVYYCARESLIRFLEDP QQGGMDVWGQGTTVTVSS | QSALTQPASVSGSPGQSL TISCTGTSSDIGGYNYVS WYQQHPGKAPKLIIYDVT DRPSGVSGRFSGSKSGNT ASLTISGLQTEDEAEYFC NSWTRSNNYIFGGGTKLT VLGQPKAAPSVTL | QVQLQQSGAEVKKPGASV KVSCKASGYTFTSYYMHW VRQAPGQGLEWMGIINPS GGSTSYAQKFQGRVTMTR DTSTSTVYMELSSLRSED TAVYYCARESLIRFLEDP QQGGMDVWGQGTTVTVSS GSASAPTLGGGGSGGGGS AAAQSALTQPASVSGSPG QSLTISCTGTSSDIGGYN YVSWYQQHPGKAPKLIIY DVTDRPSGVSGRFSGSKS GNTASLTISGLQTEDEAE YFCNSWTRSNNYIFGGGT KLTVLGQPKAAPSVTLFP PSS | 71-75 |
| Ab10 | DRYSSS WGGGFD Y | QSYDAS SLWV | EVQLVQSGGGVVQSGRSL RLSCVASGFSFSNYGMHW VRQAPGKGLEWLAFIWYD GSNKYADSVKGRFTISRD NSKNALYLQMNSLRAEDT AVYYCARDRYSSSWGGGF DYWGQGTVLTVSS | NFMLTQPHSVSESPGRTV TIPCSGRGGSIASDSVQW YQQRPGSAPTTIIYEDNQ RPSGVPDRFSGSVDSSSN SASLTISGLRTEDEADYY CQSYDASSLWVFGGKTKL TVLGQPKAAPSVTL | EVQLVQSGGGVVQSGRSL RLSCVASGFSFSNYGMHW VRQAPGKGLEWLAFIWYD GSNKYADSVKGRFTISR DNSKNALYLQMNSLRAED TAVYYCARDRYSSSWGGG FDYWGQGTVLTVSSGSAS APTLGGGGSGGGGSAAAN FMLTQPHSVSESPGRTVT IPCSGRGGSIASDSVQWY QQRPGSAPTTIIYEDNQR PSGVPDRFSGSVDSSSNS ASLTISGLRTEDEADYYC QSYDASSLWVFGGKTKLT VLGQPKAAPSVTLFPPSS KASGA | 76-80 |
| Ab11 | DRHSLG DFDY | QAWDST TVV | QLQLQQSGGGLVKPGGSL RLSCAASGFTFSSYSMNW VRQAPGKGLEWVSSISSS SSYIYYADSVKGRFTISR DNAKNSLYLQMNSLRAED | SSELTQPSVSVSPGQTAT ITCSGDKLGDKYASWYQD KYASWYQQKPGQSPVLVI YQDTKRPSGIPARFSGSN SGNTATLTISGTQAMDEA | QLQLQQSGGGLVKPGGSL RLSCAASGFTFSSYSMNW VRQAPGKGLEWVSSISSS SSYIYYADSVKGRFTISR DNAKNSLYLQMNSLRAED | 81-85 |

TABLE 3-continued

| | CDR-H3 | CDR-L3 | VH | VL | scFV | SEQ ID NOs: from left to right |
|---|---|---|---|---|---|---|
| | | | TAVYYCVRDRHSLGDFDYWGQGTLVTVSSGS | AYYCQAWDSTTVVFGGGTKLTVLGQPKAAPSVTLFPPSS | TAVYYCVRDRHSLGDFDYWGQGTLVTVSSGSASAPTLGGGGSGGGGSAAASSELTQPPSVSVSPGQTATITCSGDKLGDKYASWYQQKPGQSPVLVIYQDTKRPSGIPARF | |
| Ab9 | HGLMDDSSGYYLSNAFDI | ATWDDSLTGVV | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCANHGLMDDSSGYYLSNAFDIWGQGTMVTVSSGS | QPVLTQPPSASGTPGQRVTISCSGSSSNIGSNTVEWYQQLPGTAPKLLIHSNNQRPSGVPDRFSGSRSGTSASLAISGLQSEDEADYFCATWDDSLTGVVFGGGTTLTVLGQPKAAPSVTLFPPSS | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCANHGLMDDSSGYYLSNAFDIWGQGTMVTVSSGSASAPTLGGGGSGGGGSAAAQPVLTQPPSASGTPGQRVTISCSGSSSNIGSNTVEWYQQLPGTAPKLLIHSNNQRPSGVPDRFSGSRSGTSASLAISGLQSEDEADYFCATWDDSLTGVVFGGGTTLTVLGQPKAAPSVTLFPPSS | 86-90 |
| Ab12 | VGTAAAGDAFDI | AAWDDSLSGWV | QVQLVQSGGGLIQPGGSLRLSCAASGFTVSSYSMNWVRQAPGKGLEWVSYISSSGSTIYYADSVKGRFTISRDNAKNSLYLQMNSLRAEDTALYYCAKVGTAAAGDAFDIWGQGTMVTVSSGS | QPVLTQPPSASGTPGQRVTISCFGSSSNIGSNYVYWYQQLPGTAPKLLIYRNNQRPSGVPDRFSGSKSGTSASLAISGLRSEDEADYYCAAWDDSLSGWVFGGGTKLTVLGQPKAAPSVTLFPPSS | QVQLVQSGGGLIQPGGSLRLSCAASGFTVSSYSMNWVRQAPGKGLEWVSYISSSGSTIYYADSVKGRFTISRDNAKNSLYLQMNSLRAEDTALYYCAKVGTAAAGDAFDIWGQGTMVTVSSGSASAPTLGGGGSGGGGSAAAQPVLTQPPSASGTPGQRVTISCFGSSSNIGSNYVYWYQQLPGTAPKLLIYRNNQRPSGVPDRFSGSKSGTSASLAISGLRSEDEADYYCAAWDDSLSGWVFGGGTKLTVLGQPKAAPSVTLFPPSS | 91-95 |
| Ab8 | VGFYDYVWGSYPYDAFDI | QQYGTSPLT | QIQLVQSGAEVKKPGASVKVSCKASGYTFTSYGISWVRQAPGQGLEWMGWISAYNGNTNYAQKLQGRVTMTTDTSTSTAYMELSSLRSEDTAVYYCARVGFYDYVWGSYPYDAFDIWGQGTMVTVSS | EIVMTQSPGTLSLSPGERATLSCRASQSVSSNYLAWYQQKPGQAPRLLIYDASNRATGIPARFSGSGSGTDFTLTISSLEPEDFALYYCQQYGTSPLTFGGGTKLEIK | QIQLVQSGAEVKKPGASVKVSCKASGYTFTSYGISWVRQAPGQGLEWMGWISAYNGNTNYAQKLQGRVTMTTDTSTSTAYMELSSLRSEDTAVYYCARVGFYDYVWGSYPYDAFDIWGQGTMVTVSSGSASAPTLGGGGSGGGGSAAAEIVMTQSPGTLSLSPGERATLSCRASQSVSSNYLAWYQQKPGQAPRLLIYDASNRATGIPARFSGSGSGTDFTLTISSLEPEDFALYYCQQYGTSPLTFGGGTKLEIKRTVAAPSVF | 96-100 |
| Ab13 | DTSNGGYSSSSFDY | SSYTSSSTLV | EVQLVQSGGGLVQPGRSLRLSCAASGFTFDDYAMHWVRQAPGKGLEWVSGISWNSGSIGYADSVKGRFTISRDNAKNSLYLQMNSLRAEDTALYYCAKDTSNGGYSSSSFDYWGQGTLVTVSS | QSALTQPASVSGSPGQSITISCTGTSSDVGGYNYVSWYQQHPGTAPKLMIYDVSYRPSGVSNRFSGSKSGNTASLTISGLQAEDEADYYCSSYTSSSTLVFGTGTKVTVL | EVQLVQSGGGLVQPGRSLRLSCAASGFTFDDYAMHWVRQAPGKGLEWVSGISWNSGSIGYADSVKGRFTISRDNAKNSLYLQMNSLRAEDTALYYCAKDTSNGGYSSSSFDYWGQGTLVTVSSGSASAPTLGGGGSGGGGSAAAQSALTQPASVSGSPGQSITISCTGTSSDVGGVNYVSWYQQHPGTAPKLMIYDVSYRPSGVSNRFSGSKSGNTASLTISGLQAEDEADYYCSSYTSSSTLVFGTGTKVTVLGQPKANPTVTLFPPSS | 101-105 |
| Ab14 | LVYGGYDEPGYYFDY | AAWDDSLNGWV | EVQLLESRAEVKKPGESLKISCKGSGYSFTSYWIGWVRQMPGKGPEWMGIIYPG | QSVLTQPPSASGTPGQRVTISCSGSSSNIRSNTVNWYQQLPGTAPKLLIYSNNQ | EVQLLESRAEVKKPGESLKISCKGSGYSFTSYWIGWVRQMPGKGPEWMGIIYPG | 106-110 |

TABLE 3-continued

| CDR-H3 | CDR-L3 | VH | VL | scFV | SEQ ID NOs: from left to right |
|---|---|---|---|---|---|
| | | | DSDTRYSPSFQGQVTISA<br>DKSISTAYLQWSSLKASD<br>TAMYYCARLVYGGYDEPG<br>YYFDYWGQGTLVTVSS | RPSGVPDRFSGSKSGTSA<br>SLAISGLQSEDEADYYCA<br>AWDDSLNGWVFGGGTKLT<br>VL | DSDTRYSPSFQGQVTISA<br>DKSISTAYLQWSSLKASD<br>TAMYYCARLVYGGYDEPG<br>YYFDYWGQGTLVTVSSGS<br>ASAPTLGGGGSGGGGSAA<br>AQSVLTQPPSASGTPGQR<br>VTISCSGSSSNIRSNTVN<br>WYQQLPGTAPKLLIYSNN<br>QRPSGVPDRFSGSKSGTS<br>ASLAISGLQSEDEADYYC<br>AAWDDSLNGWVFGGGTKL<br>TVLGQPKAAPSVTLFPPS<br>SKASGA | |
| Ab15 | VDGLEY<br>SSGHNF<br>DY | SSYAGS<br>YTWV | EVQLVQSGGGLVQPGRSL<br>RLSCAASGFTFDDYAMHW<br>VRQAPGKGLEWVSGISWN<br>SGSIGYADSVKGRFTISR<br>DNSKNTLYLQMNSLRAED<br>TAVYYCAKVDGLEYSSGH<br>NFDYWGQGTLVTVSS | QSALTQPPSVSGSPGQSV<br>TISCTGSSSDVGYYDHVS<br>WYQHHPGRAPKVIIYDVT<br>KRPSGVPDRFSGSKSGNT<br>ASLTISGLQAEDEADYYC<br>SSYAGSYTWVFGGGTELT<br>VL | EVQLVQSGGGLVQPGRSL<br>RLSCAASGFTFDDYAMHW<br>VRQAPGKGLEWVSGISWN<br>SGSIGYADSVKGRFTISR<br>DNSKNTLYLQMNSLRAED<br>TAVYYCAKVDGLEYSSGH<br>NFDYWGQGTLVTVSSGSA<br>SAPTLGGGGSGGGGSAAA<br>QSALTQPPSVSGSPGQSV<br>TISCTGSSSDVGYYDHVS<br>WYQHHPGRAPKVIIYDVT<br>KRPSGVPDRFSGSKSGNT<br>ASLTISGLQAEDEADYYC<br>SSYAGSYTWVFGGGTELT<br>VLGQPKAAPSVTLFPPSS | 111-115 |

In some embodiments, anti-pro/latent-myostatin antibody, or antigen-binding portion thereof, of the disclosure include any antibody, or antigen binding fragment thereof, that includes a CDRH1, CDRH2, CDRH3, CDRL1, CDRL2, or CDRL3, or combinations thereof, as provided for any one of the antibodies shown in Tables 1-3. In some embodiments, anti-pro/latent-myostatin antibodies, or antigen-binding portions thereof, comprise the CDRH1, CDRH2, CDRH3, CDRL1, CDRL2, and CDRL3 of any one of the antibodies shown in Tables 1-3. The disclosure also includes any nucleic acid sequence that encodes a molecule comprising a CDRH1, CDRH2, CDRH3, CDRL1, CDRL2, or CDRL3 as provided for any one of the antibodies shown in Tables 1-3. Antibody heavy and light chain CDR3 domains may play a particularly important role in the binding specificity/affinity of an antibody for an antigen. Accordingly, the anti-pro/latent myostatin antibodies, or antigen-binding portions thereof, of the disclosure, or the nucleic acid molecules thereof, may include at least the heavy and/or light chain CDR3s of antibodies as shown in Tables 1-3.

Aspects of the disclosure relate to a monoclonal antibody, or antigen binding fragment, that binds to pro/latent-myostatin protein and that comprises six complementarity determining regions (CDRs): CDRH1, CDRH2, CDRH3. CDRL1. CDRL2, and CDRL3.

In some embodiments, CDRH1 comprises a sequence as set forth in any one of SEQ ID NOs: 1-3. In some embodiments, CDRH2 comprises a sequence as set forth in any one of SEQ ID NOs: 4-9. In some embodiments, CDRH3 comprises a sequence as set forth in any one of SEQ ID NOs: 10-11, 66, 71, 76, 81, 86, 91, 96, 101, 106 and 111. CDRL1 comprises a sequence as set forth in any one of SEQ ID NOs: 12-17. In some embodiments, CDRL2 comprises a sequence as set forth in any one of SEQ ID NOs: 18-21. In some embodiments, CDRL3 comprises a sequence as set forth in any one of SEQ ID NOs: 22-23, 67, 72, 77, 82, 87, 92, 97, 102, 107 and 112.

In some embodiments (e.g., as for anti-pro/latent-myostatin antibody Ab1, shown in Table 1, or an antigen-binding portion thereof), CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 10, CDRL1 comprises a sequence as set forth in SEQ ID NO: 12, or 13, CDRL2 comprises a sequence as set forth in SEQ ID NO: 18 or 19, and CDRL3 comprises a sequence as set forth in SEQ ID NO: 22, and the antibody, or an antigen-binding portion thereof, binds to pro/latent-myostatin.

In some embodiments (e.g., as for anti-pro/latent-myostatin antibody Ab2, shown in Table 1, or an antigen-binding portion thereof), CDRH1 comprises a sequence as set forth in SEQ ID NO: 1 or 2, CDRH2 comprises a sequence as set forth in SEQ ID NO: 4 or 5, CDRH3 comprises a sequence as set forth in SEQ ID NO: 66, CDRL1 comprises a sequence as set forth in SEQ ID NO: 12, or 13, CDRL2 comprises a sequence as set forth in SEQ ID NO: 18 or 19, and CDRL3 comprises a sequence as set forth in SEQ ID NO: 67, and the antibody, or an antigen-binding portion thereof, binds to pro/latent-myostatin.

In some embodiments (e.g., as for anti-pro/latent-myostatin antibody Ab3, shown in Table 1, or an antigen-binding portion thereof), CDRH1 comprises a sequence as set forth in SEQ ID NO: 1 or 3, CDRH2 comprises a sequence as set forth in SEQ ID NO: 6 or 7, CDRH3 comprises a sequence as set forth in SEQ ID NO: 11, CDRL1 comprises a sequence as set forth in SEQ ID NO: 14, or 15. CDRL2 comprises a sequence as set forth in SEQ ID NO: 20 or 21, and CDRL3 comprises a sequence as set forth in SEQ ID NO: 23, and the antibody, or an antigen-binding portion thereof, binds to pro/latent-myostatin.

In some embodiments (e.g., as for anti-pro/latent-myostatin antibody Ab5, shown in Table 1, or an antigen-binding portion thereof), CDRH1 comprises a sequence as set forth in SEQ ID NO: 1 or 3, CDRH2 comprises a sequence as set forth in SEQ ID NO: 8 or 9, CDRH3 comprises a sequence as set forth in SEQ ID NO: 11. CDRL1 comprises a sequence as set forth in SEQ ID NO: 16, or 17, CDRL2 comprises a sequence as set forth in SEQ ID NO: 20 or 21, and CDRL3 comprises a sequence as set forth in SEQ ID NO: 23, and the antibody, or an antigen-binding portion thereof, binds to pro/latent-myostatin.

In some examples, any of the anti-pro/latent-myostatin antibodies, or antigen-binding portions thereof, of the disclosure include any antibody or antigen binding fragment having one or more CDR (e.g., CDRH or CDRL) sequences substantially similar to CDRH1, CDRH2, CDRH3, CDRL1, CDRL2, and/or CDRL3. For example, the antibodies may include one or more CDR sequences as shown in Tables 1-3 (SEQ ID NOs: 1-23, 66, 67, 71, 72, 76, 77, 81, 82, 86, 87, 91, 92, 96, 97, 101, 102, 106, 107, 111 and 112) containing up to 5, 4, 3, 2, or 1 amino acid residue variations as compared to the corresponding CDR region in any one of SEQ ID NOs: 1-23, 66, 67, 71, 72, 76, 77, 81, 82, 86, 87, 91, 92, 96, 97, 101, 102, 106, 107, 111 and 112.

In some embodiments, anti-pro/latent-myostatin antibodies, or antigen-binding portions thereof, of the disclosure include any antibody that includes a heavy chain variable domain of any one of SEQ ID NOs: 24-29, 73, 78, 83, 88, 93, 98, 103, 108 and 113 or a light chain variable domain of any one of SEQ ID NOs: 30-35, 74, 79, 84, 89, 94, 99, 104, 109 and 114. In some embodiments, anti-pro/latent-myostatin antibodies, or antigen-binding portions thereof, of the disclosure include any antibody that includes the heavy chain variable and light chain variable pairs of SEQ ID NOs: 24 and 30; 25 and 31; 26 and 32; 27 and 33; 28 and 34; or 29 and 35).

Aspects of the disclosure provide anti-pro/latent-myostatin antibodies, or antigen-binding portions thereof, having a heavy chain variable and/or a light chain variable amino acid sequence homologous to any of those described herein. In some embodiments, the anti-pro/latent-myostatin antibody, or antigen-binding portions thereof, comprises a heavy chain variable sequence or a light chain variable sequence that is at least 75% (e.g., 80%, 85%, 90%, 95%, 98%, or 99%) identical to the heavy chain variable sequence of any of SEQ ID NOs: 24-29, 73, 78, 83, 88, 93, 98, 103, 108 and 113 or a light chain variable sequence of any one of SEQ ID NOs: 30-35, 74, 79, 84, 89, 94, 99, 104, 109 and 114. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, conservative mutations can be introduced into the CDRs or framework sequences at positions where the residues are not likely to be involved in interacting with pro/latent-myostatin as determined based on the crystal structure. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies, or antigen binding fragments thereof, provided herein comprise mutations that confer desirable properties to the antibodies, or antigen binding fragments thereof. For example, to avoid potential complications due to Fab-arm exchange, which is known to occur with native IgG4 mAbs, the antibodies, or antigen binding fragments thereof, provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like (CPPCP (SEQ ID NO: 58)) hinge sequence. Accordingly, any of the antibodies may include a stabilizing 'Adair' mutation or the amino acid sequence CPPCP (SEQ ID NO: 58).

Anti-pro/latent-myostatin antibodies, or antigen-binding portions thereof, of this disclosure may optionally comprise antibody constant regions or pans thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or an antigen binding portion thereof, combined with any suitable constant regions.

In certain embodiments, the $V_H$ and/or $V_L$ domains may be reverted to germline sequence, e.g., the FR of these domains are mutated using conventional molecular biology techniques to match those produced by the germline cells. For example, the $V_H$ and/or $V_L$ domains may be reverted to germline sequence of IgHV3-30 (SEQ ID NO: 36) and/or IgLV1-44 (SEQ ID NO: 37), respectively. It should be appreciated that any of the $V_H$ and/or $V_L$ domains may be reverted to any suitable germline sequence. In other embodiments, the FR sequences remain diverged from the consensus germline sequences.

IgHV3-30
(SEQ ID NO: 36)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAR

IgLV1-44
(SEQ ID NO: 37)
QSVLTQPPSASGTPGQRVTISCSGSSSNIGSNTVNWYQQLPGTAPKLLIY

YSNNQRPSGVPDRFSGSKSGTSASLAISGLQSEDEADYYCAAWDDSLNG

In some embodiments, anti-pro/latent-myostatin antibodies or antigen binding fragments may or may not include the framework region of the antibodies shown in SEQ ID NOs: 24-35. In some embodiments, anti-pro-latent-myostatin antibodies are murine antibodies and include murine framework region sequences.

In some embodiments, an anti-pro/latent-myostatin antibodies, or antigen binding fragments thereof, can bind to pro/latent-myostatin with relatively high affinity, e.g., with a Kd less than $10^{-6}$ M, $10^{-7}$ M, $10^{-8}$ M, $10^{-9}$ M, $10^{-10}$ M, $10^{-11}$ M or lower. For example, anti-pro/latent-myostatin antibodies, or antigen binding fragments thereof, can bind to pro/latent-myostatin with an affinity between 5 pM and 500 nM, e.g., between 50 pM and 100 nM, e.g., between 500 pM and 50 nM. The invention also includes antibodies or antigen binding fragments that compete with any of the antibodies described herein for binding to pro/latent-myostatin and that have an affinity of 50 nM or lower (e.g., 20 nM or lower, 10 nM or lower, 500 pM or lower, 50 pM or lower, or 5 pM or lower). The affinity and binding kinetics of the anti-pro/latent-myostatin antibody can be tested using any suitable method including but not limited to biosensor technology (e.g., OCTET or BIACORE).

In some embodiments, antibodies, or antigen binding fragments thereof, are disclosed herein that specifically bind pro/latent-myostatin. In some embodiments, any of the antibodies, or antigen binding fragments thereof, provided herein bind at or near a tolloid cleavage site or at or near a tolloid docking site of pro/latent-myostatin. In some embodiments, an antibody binds near a tolloid cleavage site or near a tolloid docking site if it binds within 15 or fewer amino acid residues of the tolloid cleavage site or tolloid docking site. In some embodiments, any of the antibodies, or antigen binding fragments thereof, provided herein bind within 1, 2, 3, 4, 5, 6, 7, 8, 9, 10, 11, 12, 13, 14 or 15 amino acid residues of a tolloid cleavage site or tolloid docking site. In some embodiments, an antibody binds at or near a tolloid cleavage site of GDF8. For example, an antibody may bind an amino acid sequence as set forth in SEQ ID NO: 62 PKAPPLRELIDQYDVQRDDSSDOSLEDDDYHAT (SEQ ID NO: 62). In other embodiments, any of the antibodies, or antigen binding fragments thereof, provided herein bind at or near a proprotein convertase cleavage site or at or near a proprotein convertase docking site of pro/latent-myostatin. In some embodiments, an antibody binds near a proprotein convertase cleavage site or near a proprotein convertase docking site if it binds within 15 or fewer amino acid residues of the proprotein convertase cleavage site or proprotein convertase docking site. In some embodiments, any of the antibodies, or antigen binding fragments thereof, provided herein bind within 1, 2, 3, 4, 5, 6, 7, 8, 9, 10, 11, 12, 13, 14 or 15 amino acid residues of a proprotein convertase cleavage site or proprotein convertase docking site. In some embodiments, an antibody binds at or near a proprotein convertase cleavage site of GDF8. For example, an antibody may bind an amino acid sequence as set forth in SEQ ID NO: 63 (GLNPFLEVKVTDTPKRSRRDFGLDC-DEHSTESRC).

In one example, the anti-pro/latent-myostatin antibodies, or antigen binding fragments thereof, described herein specifically bind pro/latent-myostatin as compared to other forms of Myostatin and/or other members of the TGFβ family of growth factors. Members of the TGFβ family of growth factors include, without limitation AMH, ARTN, BMP10, BMP15, BMP2, BMP3, BMP4, BMP5, BMP6, BMP7, BMP8A, BMP8B, GDF1, GDF10, GDF11, GDF15. GDF2, GDF3, GDF3A, GDF5, GDF6, GDF7, GDF8, GDF9, GDNF, INHA, INHBA, INHBB, INHBC, INHBE, LEFTY1, LEFTY2, NODAL, NRTN, PSPN, TGFβ1, TGFβ2, and TGFβ3 protein. Such antibodies, or antigen binding fragments thereof, may bind pro/latent-myostatin at a much higher affinity as compared to other members of the TGFβ family of growth factors (e.g., at least 2-fold, 5-fold, 10-fold, 50-fold, 100-fold, 200-fold, 500-fold, or 1,000-fold higher). In some embodiments, such antibodies, or antigen binding fragments thereof, may bind pro/latent-myostatin with an affinity of at least 000-fold higher as compared to other members of the TGFβ family of growth factors. In some embodiments, antibodies, or antigen binding fragments thereof, provided herein may bind to pro/latent-myostatin at a much higher affinity as compared to one or more forms of GDF11 or mature myostatin (e.g., at least 2-fold, 5-fold, 10-fold, 50-fold, 100-fold, 200-fold, 500-fold, or 1,000-fold higher). In some embodiments, antibodies, or antigen binding fragments thereof, provided herein may bind to pro/latent-myostatin with an affinity of at least 1,000-fold higher as compared to one or more forms of GDF11 (e.g., proGDF11, latent GDF11 or mature GDF11) or mature myostatin. Alternatively, or in addition, antibodies, or antigen binding fragments thereof, may exhibit a much higher inhibitory activity against proteolytic cleavage of pro/latent-myostatin (e.g., by a proprotein convertase or tolloid protease) as compared with other members of the TGFβ family, such as pro/latent GDF11 (e.g., at least 2-fold, 5-fold, 10-fold, 50-fold, 100-fold, 200-fold, 500-fold, 1,000-fold higher). In another embodiment, the antibodies, or antigen binding fragments thereof, disclosed herein do not bind to GDF11. This avoids potential toxicity issues associated with antibodies that cross-react with both myostatin and GDF11.

In some embodiments, antibodies bind an antigen but cannot effectively eliminate the antigen from the plasma. Thus, in some embodiments, the concentration of the antigen in the plasma may be increased by reducing the clearance of the antigen. However, in some embodiments, antibodies (e.g., sweeping antibodies) provided herein have an affinity to an antigen that is sensitive to pH. Such pH sensitive antibodies may bind to the antigen in plasma at neutral pH and dissociate from the antigen in an acidic endosome, thus reducing antibody-mediated antigen accumulation and/or promoting antigen clearance from the plasma.

Aspects of the disclosure relate to sweeping antibodies. As used herein "sweeping antibodies" or antigen-binding fragments thereof refer to antibodies, or antigen-binding fragments thereof, having both pH-sensitive antigen binding and at least a threshold level of binding to cell surface neonatal Pc receptor (FcRn) at neutral or physiological pH. In some embodiments, sweeping antibodies, or an antigen-binding portion thereof, bind to the neonatal Fc receptor FcRn at neutral pH. For example, sweeping antibodies may bind to the FcRn at a pH ranging from 7.0 to 7.6. In some embodiments, sweeping antibodies, or an antigen-binding portion thereof, can bind to an antigen at an antigen binding site and bind to a cellular FcRn via an Fc portion of the antibody. In some embodiments, sweeping antibodies, or an antigen-binding portion thereof, may then be internalized, releasing antigen in an acidic endosome, which may be degraded. In some embodiments, a sweeping antibody, or an antigen-binding portion thereof, no longer bound to the antigen, may then be released (e.g., by exocytosis) by the cell back into the serum.

In some embodiments, FcRn in the vascular endothelia (e.g., of a subject) extends the half-life of a sweeping antibody, or an antigen-binding portion thereof. In some embodiments, vascular endothelial cells internalize sweeping antibodies, or antigen-binding portions thereof, which in some embodiments are bound to an antigen such as myostatin (e.g., pro-myostatin, latent myostatin or primed myostatin). In some embodiments, a sweeping antibody, or an antigen-binding portion thereof, is recycled back into the bloodstream. In some embodiments, a sweeping antibody, or an antigen-binding portion thereof, has an increased half-life (e.g., in the serum of a subject) as compared to its conventional counterpart. In some embodiments, a conventional counterpart of a sweeping antibody refers the antibody, or an antigen-binding portion thereof, from which the sweeping antibody, or an antigen-binding portion thereof, was derived (e.g., prior to engineering the Fc portion of the conventional antibody to bind FcRn with greater affinity at pH 7). In some embodiments, a sweeping antibody, or an antigen-binding portion thereof, has a half-life in the serum of a subject that is at least 1%, 5%, 10%, 15%, 20%, 25%, 35%, 50%, 75%, 100%, 150%, 200% or 250% longer as compared to its conventional counterpart.

In some embodiments, an Fc portion of a sweeping antibody binds FcRn. In some embodiments, the Fc portion of a sweeping antibody binds to FcRn at a pH of 7.4 with a Kd ranging from $10^{-3}$ M to $10^{-8}$ M. In some embodiments, a sweeping antibody binds to FcRn at a pH of 7.4 with a Kd ranging from $10^{-3}$ M to $10^{-7}$ M, from $10^{-3}$ M to $10^{-6}$ M, from $10^{-3}$ M to $10^{-5}$ M, from $10^{-3}$ M to $10^{-4}$ M, from $10^{-4}$ M to $10^{-8}$ M, from $10^{-4}$ M to $10^{-7}$ M, from $10^{-4}$ M $10^{-6}$M, from $10^{-3}$ to $10^{-5}$ M, from $10^{-5}$ to $10^{-8}$ M, from $10^{-5}$ M to $10^{-7}$ M, from $10^{-5}$ M to $10^{-6}$ M, from $10^{-6}$ M to $10^{-8}$ M, from $10^{-6}$ M to $10^{-7}$ M, or from $10^{-7}$ M to $10^{-8}$ M. In some embodiments, FcRn binds to the CH2-CH3 hinge region of a sweeping antibody. In some embodiments, FcRn binds to the same region as proteinA or protein G. In some embodiments, FcRn binds to a different binding site from FcγRs. In some embodiments, the amino acid residues AA of a sweeping antibody Fc region are required for binding to FcRn. In some embodiments, the amino acid residues AA of a sweeping antibody Fc region affect binding to FcRn.

In some embodiments, any of the antibodies, or antigen binding fragments thereof, provided herein are engineered to bind FcRn with greater affinity. In some embodiments, any of the antibodies, or antigen binding fragments thereof, provided herein are engineered to bind FcRn with greater affinity at pH 7.4. In some embodiments, the affinity of antibodies, or antigen binding fragments thereof, to FcRn is increased to extend their pharmacokinetic (PK) properties as compared to their conventional counterparts. For example, in some embodiments, sweeping antibodies elicit less adverse reactions due to their efficacy at lower doses. In some embodiments, sweeping antibodies, or an antigen-binding portion thereof, are administered less frequently. In some embodiments, transcytosis of sweeping antibodies, or an antigen-binding portion thereof, to certain tissue types are increased. In some embodiments, sweeping antibodies, or antigen-binding portions thereof, enhance efficiency of trans-placental delivery. In some embodiments, sweeping antibodies, or antigen-binding portions thereof, are less costly to produce.

In some embodiments, any of the antibodies, or antigen binding fragments thereof, provided herein are engineered to bind FcRn with lower affinity. In some embodiments, any of the antibodies, or antigen binding fragments thereof, provided herein are engineered to bind FcRn with lower affinity at pH 7.4. In some embodiments, the affinity of sweeping antibodies, or an antigen-binding portion thereof, to FcRn is decreased to shorten their pharmacokinetic (PK) properties as compared to their conventional counterparts. For example, in some embodiments, sweeping antibodies, or an antigen-binding portion thereof, are more rapidly cleared for imaging and/or radioimmunotherapy. In some embodiments, sweeping antibodies, or an antigen-binding portion thereof, promote clearance of endogenous pathogenic antibodies as a treatment for autoimmune diseases. In some embodiments, sweeping antibodies, or antigen-binding portions thereof, reduce the risk of adverse pregnancy outcome, which may be caused by trans-placental transport of material fetus-specific antibodies.

In some embodiments, sweeping antibodies, or an antigen-binding portion thereof, have decreased affinity to an antigen at low pH as compared to a neutral or physiological pH (e.g., pH 7.4). In some embodiments, sweeping antibodies, or an antigen-binding portion thereof, have a decreased affinity to an antigen at an acidic pH (e.g. a pH ranging from 5.5 to 6.5) as compared to a physiological pH (e.g., pH 7.4).

It should be appreciated that any of the antibodies, or antigen binding fragments thereof, provided herein can be engineered to dissociate from the antigen depending on changes in pH (e.g., pH-sensitive antibodies). In some embodiments, sweeping antibodies, or an antigen-binding portion thereof, provided herein are engineered to bind antigen in a pH-dependent manner. In some embodiments, sweeping antibodies, or an antigen-binding portion thereof, provided herein are engineered to bind FcRn in a pH-dependent manner. In some embodiments, sweeping antibodies, or an antigen-binding portion thereof, provided herein are internalized by endocytosis. In some embodiments, sweeping antibodies, or an antigen-binding portion thereof, provided here are internalized by FcRn binding. In some embodiments, endocytosed sweeping antibodies, or antigen-binding portion thereof, release antigen in an endosome. In some embodiments, sweeping antibodies, or antigen-binding portions thereof, are recycled back to the cell surface. In some embodiments, sweeping antibodies remain attached to cells. In some embodiments, endocytosed sweeping antibodies, or an antigen-binding portion thereof, are recycled back to the plasma. It should be appreciated that the Fc portion of any of the antibodies, or antigen binding fragments thereof, provided herein may be engineered to have different FcRn binding activity. In some embodiments, FcRn binding activity affects the clearance time of an antigen by a sweeping antibody. In some embodiments, sweeping antibodies may be long-acting or rapid-acting sweeping antibodies.

In some embodiments, converting a conventional therapeutic antibody, or an antigen-binding portion thereof, into a sweeping antibody, or an antigen-binding portion thereof, reduces the efficacious dose. In some embodiments, converting a conventional therapeutic antibody, or an antigen-binding portion thereof, into a sweeping antibody, or an antigen-binding portion thereof, reduces the efficacious dose by at least 1%, 2%, 5%, 10%, 20%, 30%, 40%, 50%, 60%, 70%, 80%, 90%, 95%, or 99%. In some embodiments, converting a conventional therapeutic antibody, or an antigen-binding portion thereof, into a sweeping antibody, or an antigen-binding portion thereof, reduces the efficacious dose by at least 1.5-fold, 2-fold, 3-fold, 4-fold, 5-fold, 6-fold, 8-fold, 10-fold, 15-fold, 20-fold, 50-fold or 100-fold.

In some embodiments, selecting an appropriate dose of a sweeping antibody, or an antigen-binding portion thereof, for therapy may be performed empirically. In some embodiments, a high dose of a sweeping antibody, or an antigen-binding portion thereof, may saturate FcRn, resulting in antibodies which stabilize antigen in serum without being internalized. In some embodiments, a low dose of a sweeping antibody, or an antigen-binding portion thereof, may not be therapeutically effective. In some embodiments, sweeping antibodies, or antigen-binding portions thereof, are administered once a day, once a week, once every two weeks, once every three weeks, once every four weeks, once every 6 weeks, once every 8 weeks, once every 10 weeks, once every 12 weeks, once every 16 weeks, once every 20 weeks, or once every 24 weeks.

In some embodiments, any of the antibodies, or antigen binding fragments thereof, provided herein may be modified or engineered to be sweeping antibodies. In some embodiments, any of the antibodies, or antigen binding fragments thereof, provided herein may be converted into a sweeping antibody using any suitable method. For example, suitable methods for making sweeping antibodies, or antigen-binding portions thereof, have been previously described in Igawa et al., (2013) "Engineered Monoclonal Antibody with Novel Antigen-Sweeping Activity In vivo," *PLoS ONE* 8(5): e63236; and Igawa et al., "pH-dependent antigen-binding antibodies as a novel therapeutic modality," Biochimica et *Biophysica Acta* 1844 (2014) 1943-1950; the contents of each of which are hereby incorporated by reference. It should be appreciated, however, that the methods for making sweeping antibodies, or an antigen-binding portion thereof, as provided herein are not meant to be limiting. Thus, additional methods for making sweeping antibodies, or an antigen-binding portion thereof, are within the scope of this disclosure.

Some aspects of the disclosure are based on the recognition that the affinity (e.g., as expressed as Kd) of any of the anti-pro/latent-myostatin antibodies, or antigen binding fragments thereof, provided herein are sensitive to changes in pH. In some embodiments, the antibodies, or antigen binding fragments thereof, provided herein have an increased Kd of binding to pro/latent-myostatin at a relatively low pH (e.g., a pH ranging from 4.0-6.5) as compared to a relatively high pH (e.g., a pH ranging from 7.0-7.4). In some embodiments, the antibodies, or antigen binding fragments thereof, provided herein have a Kd of binding to pro/latent-myostatin ranging from $10^{-3}$ M, $10^{-4}$ M, $10^{-5}$ M, $10^{-6}$ M, $10^{-7}$ M, $10^{-8}$ M when the pH is between 4.0 and 6.5. In some embodiments, the antibodies, or antigen binding fragments thereof, provided herein have a Kd of binding to pro/latent-myostatin ranging from $10^{-6}$ M, $10^{-7}$ M, $10^{-8}$ M, $10^{-9}$M, $10^{-10}$M, $10^{-11}$ M when the pH is between 7.0 and 7.4. In some embodiments, the antibodies, or antigen binding fragments thereof, provided herein have a Kd of binding to pro/latent-Myostatin that is at least 2-fold, at least 10-fold, at least 50-fold, at least 100-fold, at least 500-fold, at least 1000-fold, at least 5000-fold, or at least 10000-fold greater at a pH between 4.0 and 6.5 as compared to a pH between 7.0 and 7.4.

In some embodiments, pro/latent-myostatin antibodies, or antigen binding fragments thereof, are provided herein that do not specifically bind to an epitope within the amino acid sequence set forth as (SEQ ID NO: 64). In some embodiments, pro/latent-myostatin antibodies, or antigen binding fragments thereof, provided herein do not specifically bind to the same epitope as an antibody described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-myostatin antibodies, or antigen binding fragments thereof, provided herein do not compete or do not cross-compete for binding to the same epitope as an antibody described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-myostatin antibodies, or antigen binding fragments thereof, provided herein do not specifically bind to the same epitope as an antibody comprising a VH and a VL pair described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015. In some embodiments, pro/latent-myostatin antibodies, or antigen binding fragments thereof, provided herein do not compete or do not cross-compete for binding to the same epitope as an antibody comprising a VH and a VL pair described in Table 2a, 11a, 11b, or 13 of International Patent Application Publication No. WO 2016/098357, which was published on Jun. 23, 2016, and which is based on International Patent Application No. PCT/JP2015/006323, which was filed on Dec. 18, 2015.

Polypeptides

Some aspects of the disclosure relate to a polypeptide having a sequence selected from the group consisting of SEQ ID NO: 24. SEQ ID NO: 25, SEQ ID NO: 26, SEQ ID NO: 27, SEQ ID NO: 28, and SEQ ID NO 29. In some embodiments, the polypeptide is a variable heavy chain domain. In some embodiments, the polypeptide is at least 75% (e.g., 80%, 85%, 90%, 95%, 98%, or 99%) identical to any one of the amino acid sequences set forth in SEQ ID NO: 24, SEQ ID NO: 25, SEQ ID NO: 26, SEQ ID NO: 27, SEQ ID NO: 28, or SEQ ID NO 29.

Some aspects of the disclosure relate to a polypeptide having a sequence selected from the group consisting of SEQ ID NO: 30, SEQ ID NO: 31, SEQ ID NO: 32, SEQ ID NO: 33, SEQ ID NO: 34, and SEQ ID NO 35. In some embodiments, the polypeptide is a variable light chain domain. In some embodiments, the polypeptide is at least 75% (e.g., 80%, 85%, 90%, 95%, 98%, or 99%) identical to any one of the amino acid sequences set forth in SEQ ID NO: 30, SEQ ID NO: 31, SEQ ID NO: 32. SEQ ID NO: 33, SEQ ID NO: 34, or SEQ ID NO 35.

Antibodies, and Antigen-Binding Fragments, that Compete with Anti-Pro/Latent-Myostatin Antibodies, or Antigen Binding Fragments Thereof Aspects of the disclosure relate to antibodies, and antigen-binding fragments thereof, that compete or cross-compete with any of the antibodies, or antigen binding fragments thereof, provided herein. The term "compete", as used herein with regard to an antibody, means that a first antibody binds to an epitope of a protein (e.g., latent myostatin) in a manner sufficiently similar to the binding of a second antibody, such that the result of binding of the first antibody with its epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its epitope or ligand, whether to the same, greater, or lesser extent, the antibodies are said to "cross-compete" with each other for binding of their respective epitope(s). Both competing and cross-competing antibodies are within the scope of this disclosure. Regardless of the mechanism by which such competition or cross-competition occurs (e.g., steric hindrance, conformational change, or binding to a common epitope, or portion thereof), the skilled artisan would appreciate that such competing and/or cross-competing antibodies are encompassed and can be useful for the methods and/or compositions provided herein.

Aspects of the disclosure relate to antibodies, or antigen-binding portions thereof, that compete or cross-compete with any of the antibodies, or antigen binding fragments thereof, provided herein. In some embodiments, an antibody, or an antigen-binding portion thereof, binds at or near the same epitope as any of the antibodies provided herein. In some embodiments, an antibody, or an antigen-binding portion thereof, binds near an epitope if it binds within 15 or fewer amino acid residues of the epitope. In some embodiments, any of the antibodies, or antigen binding fragments thereof, provided herein bind within 1, 2, 3, 4, 5, 6, 7, 8, 9, 10, 11, 12, 13, 14 or 15 amino acid residues of an epitope that is bound by any of the antibodies, or antigen binding fragments thereof, provided herein.

In another embodiment, an antibody, or an antigen-binding portion thereof, competes or cross-competes for binding to any of the antigens provided herein (e.g., pro/latent-myostatin) with an equilibrium dissociation constant, Kd, between the antibody and the protein of less than $10^{-6}$ M. In other embodiments, an antibody, or an antigen-binding portion thereof, competes or cross-competes for binding to any of the antigens provided herein with a Kd in a range from $10^{-11}$ M to $10^{-6}$ M.

Aspects of the disclosure relate to antibodies, or antigen-binding portions thereof, that compete for binding to pro/latent-myostatin with any of the antibodies, or antigen binding fragments thereof, provided herein. In some embodiments, the antibody, or an antigen-binding portion thereof, binds to pro/latent-myostatin at the same epitope as any of the antibodies, or antigen-binding portions thereof, provided herein. For example, in some embodiments any of the antibodies provided herein bind at or near a tolloid cleavage site or at or near a tolloid docking site of pro/latent-myostatin. In other embodiments, any of the antibodies, or antigen binding fragments thereof, provided herein bind at or near a proprotein convertase cleavage site or at or near a proprotein convertase docking site of pro/latent-myostatin. In another embodiment, an antibody, or an antigen-binding portion thereof, competes for binding to pro/latent-myostatin with an equilibrium dissociation constant, Kd, between the antibody, or antigen-binding portion thereof, and pro/latent-myostatin of less than $10^{-6}$ M. In other embodiments, the antibody, or antigen-binding portion thereof, that competes with any of the antibodies, or antigen-binding portions thereof, provided herein binds to pro/latent-myostatin with a Kd in ranging from $10^{-11}$ M to $10^{-6}$ M.

Any of the antibodies, or antigen binding fragments thereof, provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody, or an antigen-binding portion thereof, binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody, or an antigen-binding portion thereof, binds can be determined in a systematic screen by using overlapping peptides derived from the target antigen sequence and determining binding by the antibody, or an antigen-binding portion thereof. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody, or an antigen-binding portion thereof, to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody, or an antigen-binding portion thereof, in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the pro/latent-myostatin polypeptide have been replaced (swapped) with sequences from a closely related, but antigenically distinct protein, such as another member of the TGFβ protein family (e.g., GDF11). By assessing binding of the antibody, or antigen-binding portion thereof, to the mutant pro/latent-myostatin, the importance of the particular antigen fragment to antibody, or antigen-binding portion thereof, binding can be assessed.

Alternatively, competition assays can be performed using other antibodies known to bind to the same antigen to determine whether an antibody, or an antigen-binding portion thereof, binds to the same epitope as the other antibodies, or antigen-binding portions thereof. Competition assays are well known to those of skill in the art.

Any of the suitable methods, e.g., the epitope mapping methods as described herein, can be applied to determine whether an anti-pro/latent-myostatin antibody, or an antigen-binding portion thereof, binds one or more of the specific residues/segments in pro/latent-myostatin as described herein. Further, the interaction of the antibody, or an antigen-binding portion thereof, with one or more of those defined residues in pro/latent-myostatin can be determined by routine technology. For example, a crystal structure can be determined, and the distances between the residues in pro/latent-myostatin and one or more residues in the antibody, or antigen-binding portion thereof, can be determined accordingly. Based on such distance, whether a specific residue in pro/latent-myostatin interacts with one or more residues in the antibody, or antigen-binding portion thereof, can be determined. Further, suitable methods, such as competition assays and target mutagenesis assays can be applied to determine the preferential binding of a candidate anti-pro/latent-myostatin antibody, or n antigen-binding portion thereof, to pro/latent-myostatin as compared to another target such as a mutant pro/latent-myostatin.

Production of Anti-Pro/Latent-Myostatin Antibodies or Antigen Binding Fragments Thereof Numerous methods may be used for obtaining antibodies, or antigen binding fragments thereof, of the disclosure. For example, antibodies, and antigen-binding fragments thereof, can be produced using recombinant DNA methods. Monoclonal antibodies, and antigen-binding fragments thereof, may also be produced by generation of hybridomas (see e.g., Kohler and Milstein (1975) Nature, 256:495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody, or an antigen-binding portion thereof, that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope). One exemplary method of making antibodies, and antigen-binding portions thereof, includes screening protein expression libraries that express antibodies or fragments thereof (e.g., scPv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597 WO92/18619; WO 91/17271; WO 92/20791; WO 92/15679; WO 93/01288; WO 92/01047; WO 92/09690; and WO 90/02809.

In addition to the use of display libraries, the specified antigen (e.g., pro-myostatin) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., chimeric, using suitable recombinant DNA techniques. A variety of approaches for making chimeric antibodies have been described. See e.g., Morrison et al. Proc. Natl. Acad. Sci. U.S.A. 81:6851, 1985; Takeda et al. Nature 314:452, 1985. Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 21770968.

For additional antibody production techniques, see Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serraia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen binding fragments can then be isolated from the growth medium, cellular lysates, or cellular membrane fractions. The isolation and purification of the, e.g., microbially expressed antibodies or antigen binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies, and antigen-binding portions thereof.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen binding fragment may be undertaken by culturing a modified recombinant host under culture conditions appropriate for the growth of the host cells and the expression of the coding sequences. The antibodies or antigen binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the selection of the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in $E.$ $coli$, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, a polynucleotide(s) may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain (s) of the immunoglobulin chains encoding sequences and expression control sequences) can be transferred into the host cell by suitable methods, which vary depending on the type of cellular host.

Modifications

Antibodies and antigen binding fragments of the disclosure may be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of pro/latent-myostatin. The detectable substance may be coupled or conjugated either directly to the polypeptides of the disclosure or indirectly, through an intermediate (such as, for example, a linker) using suitable techniques. Non-limiting examples of suitable enzymes include horseradish peroxidase, alkaline phosphatase, 0-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{66}$Ho, $^{90}$Y, $^{47}$Sc, $^{86}$R, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{133}$Sn, $^{117}$Sn). The detectable substance may be coupled or conjugated either directly to the anti-pro/latent-myostatin antibodies, or antigen-binding portions thereof, of the disclosure or indirectly, through an intermediate (such as, for example, a linker) using suitable techniques. Anti-pro/latent-myostatin antibodies, or antigen-binding portions thereof, conjugated to a detectable substance may be used for diagnostic assays as described herein.

Biological Effects of Myostatin Inhibitors, Such as Anti-Pro/Latent Myostatin Antibodies and Antigen Binding Fragments Thereof Myostatin inhibitors, such as antibodies and antigen-binding fragments thereof, which am encompassed by the present disclosure can be used as a medicament to effectuate beneficial effects (e.g., therapeutic effects) in a subject when administered to the subject in an effective amount. Exemplary such biologically beneficial effects are provided herein. Beneficial biological effects in a subject can be achieved by administration of myostatin inhibitors, e.g., antibodies, or antigen binding fragments thereof, as described herein, that specifically bind pro/latent myostatin. In some embodiments, the antibody, or antigen-binding portion thereof, is administered in an amount effective to cause two or more of the biological effects described below. In some embodiments, the myostatin inhibitor, e.g., antibody, or antigen-binding portion thereof, is administered in an amount effective to cause three or more of the biological effects described below. In some embodiments, the myostatin inhibitor, e.g., the antibody, or antigen-binding portion thereof, is administered in an amount effective to cause four or more of the biological effects described below. In some embodiments, the myostatin inhibitor, e.g., the antibody, or antigen-binding portion thereof, is administered in an amount effective to cause five or more of the biological effects described below. In some embodiments, the myostatin inhibitor, e.g., the antibody, or antigen-binding portion thereof, is administered in an amount effective to cause six or more of the biological effects described below. In some embodiments, the myostatin inhibitor, e.g., the antibody, or antigen-binding portion thereof, is administered in an amount effective to cause seven or more of the biological effects described below. In some embodiments, the myostatin inhibitor, e.g., the antibody, or antigen-binding portion thereof, is administered in an amount effective to cause eight, nine, ten, eleven, twelve, thirteen, fourteen, fifteen, or sixteen of the biological effects described below.

A. Effect on Mass and/or Function of Muscle Tissue in the Human Subject

Administration of a myostatin inhibitor, e.g., an antibody, or antigen binding fragment thereof, that specifically binds pro/latent myostatin increases mass and/or function of a muscle tissue in the human subject. In some embodiments, the muscle tissue is selected from the group consisting of a smooth muscle tissue, a skeletal muscle tissue and a cardiac muscle tissue. Smooth muscle tissue is made up from long tapering cells, generally involuntary and differs from striated muscle in the much higher actin/myosin ratio, the absence of conspicuous sarcomeres and the ability to contract to a much smaller fraction of its resting length. Smooth muscle cells are found particularly in blood vessel walls, surrounding the intestine and in the uterus. Cardiac muscle tissue is a striated but involuntary tissue responsible for the pumping activity of the vertebrate heart. The individual cardiac muscle cells are not fused together into multinucleate structures as they are in striated muscle tissue. Skeletal muscle tissue is under voluntary control. The muscle fibers are syncytial and contain myofibrils, tandem arrays of sarcomeres. There are two general types of skeletal muscle fibers: slow-twitch (type I) and fast-twitch (type II) according to the expression of their particular myosin heavy chain (MHC) isoform. Slow-twitch muscles are better equipped to work aerobically and help enable long-endurance feats such as distance running, while fast-twitch muscles fatigue faster but are better equipped to work anaerobically and are used in powerful bursts of movements like sprinting. The differentiation between slow and fast twitch muscle fibers is based on histochemical staining for myosin adenosine-triphosphatase (ATPase) and the type of myosin heavy chain. The slow twitch muscle fiber (type I fiber) is MHC isoform I and the three fast twitch isoforms (type II fibers) are MHC isoform IIa. MHC isoform IId, and MHC isoform fib (S. Schiaffino, *J. Muscle Res. Cell. Motil.*, 10 (1989), pp. 197-205). In some embodiments, the mass and/or function of a fast twitch muscle tissue in the human subject is increased. In other embodiments, the mass and/or function of a slow twitch muscle tissue in the human subject is increased.

Biological effects of an effective amount of the pharmaceutical compostions provided herein may be associated with a phenotypic change of muscle fiber types, which is a process referred to as fiber type switch. In some embodiments, fiber type switch is triggered by an event, such as an injury and starvation.

In one aspect, the disclosure provides a method for promoting fiber type switch in a subject. The method comprises administering to the subject a composition comprising a myostatin inhibitor, e.g., an antibody, or antigen binding fragment thereof, that specifically binds pro/latent-myostatin and blocks release of mature myostatin in an amount effective to promote fiber type switch, thereby promoting fiber type switch in the subject.

In another aspect, the disclosure provides a method for preferentially increasing type II or fast twitch fibers over type I or slow twitch fibers in a subject. The method comprises
administering to the subject a composition comprising a myostatin inhibitor, e.g., an antibody, or antigen binding fragment thereof, that specifically binds pro/latent-myostatin and blocks release of mature myostatin in an amount effective to preferentially increase type II or fast twitch fibers over type I or slow twitch fibers fiber type switch, thereby preferentially increasing type II or fast twitch fibers over type I or slow twitch fibers in the subject.

In some embodiments, administration of an effective amount of a myostatin inhibitor, e.g., an antibody, or antigen-binding fragment thereof, described herein to a subject can cause an increase in muscle mass. Preferably, such an increase in muscle mass is clinically meaningful to benefit or otherwise improve the health status of the subject. For example, clinically meaningful changes in muscle mass may improve the patient's mobility, self care, metabolism, etc. In some embodiments, the increase in muscle mass is an increase in lean muscle or lean muscles. In some embodiments, such increase in muscle mass is a systemic effect such that muscles in the whole body or substantially whole body show the measurable effect. In other embodiments, effects are localized to certain group/type of muscles. In some embodiments, the mass of the muscle tissue, e.g., lean muscle tissue, is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue, e.g., lean muscle tissue, is increased by at least about 1-5%, 5-10%, 10-20%, 1-30%, 1-40%, 1-50%, 10-50%, 20-30%, 20-60%, 30-80%, 40-90%, or 50-100%. Such increase in muscle mass may be deduced or measured by any suitable known methods, including measurement of cross-sectional area via MRI (e.g., forearm cross section), circumference, diaphragm width (e.g., via ultrasound), etc.

In some embodiments, administration of an effective amount of an antibody or antigen-binding fragments thereof described herein to a subject can cause an enhancement in muscle function. Muscle function may be assessed by a variety of measures, including, without limitation: force generation, grip strength (e.g., maximum grip strength), endurance, muscle oxidative capacity, dynamic grip endurance, etc. In some embodiments, serum creatinine levels are used as a validated biomarker indicative of muscle mass, albeit with limited sensitivity.

In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%. In some embodiments, increased muscle function comprises improved rating, for example, from 1 to 2, 2 to 3, 3 to 4, 4 to 5, 5 to 6, 6 to 7, 7 to 8, 8 to 9, or 9 to 10.

In some embodiments, the myostatin inhibitors, e.g., anti-pro/latent myostatin antibodies, or antigen binding fragments thereof, for use in the methods of the present invention may increase the mass and/or function of the muscle tissue in the subject suffering from a lesion, e.g., due to a spinal cord injury. In some embodiments, the subject is in an acute spinal cord injury phase immediately after injury, where diagnosis between complete and incomplete injury is generally difficult. In other embodiments, the subject is in a sub-acute spinal cord injury phase, where there is a distinction between complete and incomplete spinal cord injury, and recovery is possible through ongoing rehab. In yet another embodiment, the subject is in a chronic spinal cord injury phase. The chronic SCI phase occurs around 4 or 6 month from the date of injury, where patients have demonstrated substantial decrease in rate of recovery or when rehab efforts have reached a plateau despite the ongoing standard of care efforts.

In some embodiments, the mass and/or function of the muscle tissue below a lesion is increased in a subject suffering from a lesion, e.g., a spinal cord injury. In other embodiments, the mass and/or function of the muscle tissue above a lesion is increased in a subject suffering from a lesion, e.g., a spinal cord injury. In some embodiment, the muscle is selected from the group consisting of a soleus muscle, a gastrocnemius muscle, a bicep muscle and a tricep muscle. In some embodiments, the mass of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the mass of the muscle tissue is increased by at least about 1-5%, 5-10%, 10-20%, 1-30%, 1-40%, 1-50%, 10-50%, 20-30%, 20-60%, 30-80%, 40-90%, or 50-100%. In some embodiments, the function of the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the function of the muscle tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., antibody, or antigen binding fragment thereof, that specifically binds pro/latent myostatin increases locomotor function in the human subject, e.g., in a subject suffering from a lesion. In some embodiments, the locomotor function of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the locomotor function of the human subject is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., antibody, or antigen binding fragment thereof, that specifically binds pro/latent myostatin increases the motor ordination and balance in the human subject, e.g., in a subject suffering from a lesion. In some embodiments, the motor ordination and balance of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the motor ordination and balance of the human subject is increased by at least about 1-5%, 5-10%, 10-20%, 1-30%, 1-40%, 1-50%, 10-50%, 20-30%, 20-60%, 30-80%, 40-90%, or 50-100%.

In another embodiment, administration of the myostatin inhibitor, e.g., antibody, or antigen binding fragment thereof, that specifically binds pro/latent myostatin increases the muscle strength in the human subject, e.g., in a subject suffering from a lesion. In some embodiments, the muscle strength of the human subject is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the muscle strength of the human subject is increased by at least about 1-5%, 5-10%, 10-20%, 1-30%, 1-40%, 1-50%, 10-50%, 20-30%, 20-60%, 30-80%, 40-90%, or 50-100%.

In some embodiments, administration of the myostatin inhibitor, e.g., antibody, or antigen binding fragment thereof, that specifically binds pro/latent myostatin can cause clinically meaningful changes in muscle function which corresponds to enhanced functionality of the patient. In some embodiments, enhanced functionality includes improvement in the patient's mobility, self care, metabolism, etc. In some embodiments, administration of an effective amount of the myostatin inhibitor, e.g., antibody, or antigen binding fragment thereof, that specifically binds pro/latent myostatin facilitates or accelerates recovery from a condition, such as injuries, surgeries and other medical procedures. Suitable such conditions may involve a condition that is associated with a nerve damage (whether resulting from an injury or a surgical or other clinical procedure).

For example, suitable subjects include generally healthy individuals, such as a patient who: i) has sustained an acute injury involving a nerve damage that affects muscle function; ii) is scheduled to undergo a surgical procedure (therapeutic or corrective) that may cause an unintended nerve injury (e.g., motor neuron injury); iii) has undergone a surgical procedure that has caused an unintended muscle dysfunction; iv) receives a treatment that involves immobilization of a particular muscle or muscle groups (e.g., cast, etc.); v) is on ventilator (e.g., as a result of acute injury). The administration of the myostatin inhibitor described herein may accelerate recovery in such patients. In some embodiments, such administration may be prophylactic. For example, prior to undergoing or immediately following a surgical procedure that may cause a nerve damage and associated muscle dysfunction, the antibody may be administered to prevent muscle dysfunction. Prevention includes alleviating or lessening the severity of such dysfunction. In these embodiments, administration may be a local administration at or near the site of the affected area, e.g., injury, surgery, etc.

B. Effect on the Metabolic Rate of the Human Subject

Administration of the myostatin inhibitor, e.g., antibody, or antigen binding fragment thereof, that specifically binds pro/latent myostatin increases the metabolic rate of the human subject. In some embodiments, administration of an effective amount of such myostatin inhibitor, e.g., antibody, or antigen-binding fragment thereof, can increase the basal metabolic rate in the subject. Metabolic rates can be calculated by any methods known in the art, for example, by examining the oxygen input and carbon dioxide output, or by indirect calorimetry as demonstrated by Example 11 of the present application. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%.

C. Effect on Insulin Sensitivity of the Human Subject

Administration of the myostatin inhibitor, e.g., antibody, or antigen binding fragment thereof, that specifically binds pro/latent myostatin increases insulin sensitivity of the human subject. Methods for measuring insulin sensitivity are known in the art, for example, glucose tolerance test, and fasting insulin or glucose test. During a glucose tolerance test, a fasting patient takes a 75 gram oral dose of glucose, and then blood glucose levels are measured over the following two hours. A glycemia less than 7.8 mmol/L (140 mg/dl) is considered normal, a glycemia of between 7.8 and 11.0 mmol/L (140 to 197 mg/dl) is considered as impaired glucose tolerance (IGT), and a glycemia of greater than or equal to 11.1 mmol/L (200 mg/dl) is considered diabetes mellitus. For fasting insulin test, a fasting serum insulin level greater than 25 mIU/L or 174 pmol/L is considered insulin resistance. In some embodiments, the metabolic rate is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the metabolic rate is increased by at least about 1-5%, 5-10%, 10-20%, 1-30%, 1-40%, 1-50%, 10-50%, 20-30%, 20-60%, 30-80%, 40-90%, or 50-100%.

D. Effect on the Level of Adipose Tissue in the Human Subject

Administration of the myostatin inhibitor. e.g., antibody, or antigen binding fragment thereof, that specifically binds pro/latent myostatin affects the level of adipose tissue in the human subject. As used herein, the term "adipose tissue" refers to fat including the connective tissue that stores fat. Adipose tissue is derived from preadipocytes. Its main role is to store energy in the form of lipids, although it also cushions and insulates the body. The two types of adipose tissue are white adipose tissue (WAT), which stores energy, and brown adipose tissue (BAT), which generates body heat.

Brown adipose tissue (BAT) is known to function in the dissipation of chemical energy in response to cold or excess feeding, and also has the capacity to modulate energy balance. Activation of brown adipose tissue have been shown to improve glucose homeostasis and insulin sensitivity in humans suggesting that anyone with impaired insulin function might benefit from BAT activation (Stanford et al., *J Clin Invest*. 2013, 123(1): 215-223).

Beige adipose tissues are generated as a result of browning of WAT, also known as beiging. This occurs when adipocytes within WAT depots develop features of BAT. Beige adipocytes take on a multilocular appearance (containing several lipid droplets) and increase expression of uncoupling protein 1 (UCP1). In doing so, these normally energy-storing white adipocytes become energy-releasing adipocytes (Harms et al. Nature Medicine, 2013, 19 (10): 1252-63).

Visceral fat or abdominal fat (also known as organ fat or intra-abdominal fat) is located inside the abdominal cavity, packed between the organs (stomach, liver, intestines, kidneys, etc.). Visceral fat is different from subcutaneous fat underneath the skin, and intramuscular fat interspersed in skeletal muscles. Fat in the lower body, as in thighs and buttocks, is subcutaneous and is not consistently spaced tissue, whereas fat in the abdomen is mostly visceral and semi-fluid. An excess of visceral fat is known as central obesity, or "belly fat", in which the abdomen protrudes excessively and new developments such as the Body Volume Index (BVI) are specifically designed to measure abdominal volume and abdominal fat. Excess visceral fat is also linked to type 2 diabetes, insulin resistance, inflammatory diseases and other obesity-related diseases (Mokdad et al., *JAMA: The Journal of the American Medical Association*. 2001, 289 (1): 76-9).

Mass of adipose tissue can be determined by any method known to a person of ordinary skill in the art. For example, adipose tissue may be measured by dual-energy X-Ray absorptiometry (DXA), as demonstrated in Example 11 of the present application.

Administration of the myostatin inhibitor, e.g., antibody, or antigen binding fragment thereof, that specifically binds pro/latent myostatin increases the level of brown adipose tissue and/or the level of beige adipose tissue in the human subject. On the other hand, administration of the myostatin inhibitor, e.g., anti-pro/latent myostatin antibody, or antigen-binding portion thereof, decreases the level of white adipose tissue and visceral adipose tissue in the human subject.

In some embodiments, the level of brown or beige adipose tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of brown or beige adipose tissue is increased by at least about 1-5%, 5-10%, 10-20%, 1-30%, 1-40%, 1-50%, 10-50%, 20-30%, 20-60%, 30-80%, 40-90%, or 50-100%.

In some embodiments, the level of white or visceral adipose tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the level of white or visceral adipose tissue is decreased by at least about 1-5%, 5-10%, 10-20%, 1-30%, 1-40%, 1-50%, 10-50%, 20-30%, 20-60%, 30-80%, 40-90%, or 50-100%.

E. Effect on the Ratio of Adipose-to-Muscle Tissue in the Human Subject.

Administration of the myostatin inhibitor, e.g., antibody, or antigen binding fragment thereof, that specifically binds pro/latent myostatin decreases the ratio between adipose-to-muscle tissue in the human subject. In some embodiments, the ratio between adipose-to-muscle tissue is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, the ratio between adipose-to-muscle tissue is decreased by at least about 1-5%, 5-10%, 10-20%, 1-30%, 1-40%, 1-50%, 10-50%, 20-30%, 20-60%, 30-80%, 40-90%, or 50-100%.

F. Effect on Glucose Uptake in the Human Subject

Administration of the myostatin inhibitor, e.g., antibody, or antigen binding fragment thereof, that specifically binds pro/latent myostatin affects glucose uptake by tissues in the human subject. In some embodiments, glucose uptake by muscle tissue is increased. For example, glucose uptake by the muscle tissue is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In some embodiments, glucose uptake by the muscle tissue is increased by at least about 1-5%, 5-10%, 10-20%, 1-30%, 1-40%, 1-50%, 10-50%, 20-30%, 20-60%, 30-80%, 40-90%, or 50-100%.

In other embodiments, glucose uptake by white adipose tissue, liver tissue and blood vessel tissue are reduced. In some embodiments, glucose uptake by white adipose tissue, liver tissue and blood vessel tissue are reduced by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, glucose uptake by white adipose tissue, liver tissue and blood vessel tissue are reduced by at least about 1-5%, 5-10%, 10-20%, 1-30%, 1-40%, 1-50%, 10-50%, 20-30%, 20-60%, 30-80%, 40-90%, or 50-100%.

G. Effect on Muscle Catabolism of Protein and/or Muscle Release of Amino Acids in the Human Subject Administration of the myostatin inhibitor, e.g., antibody, or antigen binding fragment thereof, that specifically binds pro/latent myostatin decreases muscle catabolism of protein and/or muscle release of amino acids in the human subject. In some embodiments, muscle catabolism of protein and/or muscle release of amino acids is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, muscle catabolism of protein and/or muscle release of amino acids is decreased by at least about 1-5%, 5-10%, 10-20%, 1-30%, 1-40%, 1-50%, 10-50%, 20-30%, 20-60%, 30-80%, 40-90%, or 50-100%.

H. Effect on Insulin Dependent Glycemic Control in the Human Subject

Administration of the myostatin inhibitor, e.g., antibody, or antigen binding fragment thereof, that specifically binds pro/latent myostatin increases insulin dependent glycemic control in the human subject. In some embodiments, insulin dependent glycemic control is increased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, insulin dependent glycemic control is increased by at least about 1-5%, 5-10%, 10-20%, 1-30%, 1-40%, 1-50%, 10-50%, 20-30%, 20-60%, 30-80%, 40-90%, or 50-100%.

I. Effect on Intramuscular Fat Infiltration in the Human Subject

Administration of the myostatin inhibitor, e.g., antibody, or antigen binding fragment thereof, that specifically binds pro/latent myostatin decreases intramuscular fat infiltration in the human subject. In some embodiments, intramuscular fat infiltration is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, intramuscular fat infiltration is decreased by at least about 1-5%, 5-10%, 10-20%, 1-30%, 1-40%, 1-50%, 10-50%, 20-30%, 20-60%, 30-80%, 40-90%, or 50-100%.

J. Effect on Life Quality of the Human Subject

Assessment of the quality of life in patients with severe or chronic conditions, such as SCI patients, may involve integrated approaches to evaluate various aspects of physical, mental, social and other parameters. Generally, a greater degree of quality of life is associated with factors such as: accessibility to assistive technology; community reintegration; functionality with lower limb and walking and/or wheeled mobility; mental health; severity in neurological impairment and autonomic dysfunction; pain management; functional independence and self-care; upper limb strength; and spasticity control. Administration of the antibody, or antigen binding fragment thereof, that specifically binds pro/latent myostatin increases the quality of life of the human subject to achieve a clinically meaningful improvement as measured by a standardized quality-of-life test/system. A number of suitable tests for assessing the quality of life in patients are known in the art, including: Incontinence Quality of Life Questionnaire (I-QOL); Life Satisfaction Questionnaire (LISAT-9, LISAT-11); Quality of Life Index (QLI)—SCI Version; Quality of Life Profile for Adults with Physical Disabilities (QOLP-PD); Quality of Well Being (QWB) and Quality of Well Being-Self-Administered (QWB-SA); Qualiveen; Satisfaction with Life Scale (SWLS, Deiner Scale); Short Form 36 (SP-36); Sickness Impact Profile 68 (SIP 68); and World Health Organization Quality of Life-BREF (WHOQOL-BREF).

In some embodiments, quality of life is assessed in accordance with the SF-36 Quality of Life Scoring System, which is a validated scoring system, in which an 8 point change is considered clinically meaningful. Typically, for SCI patients, values are in the low 50's. In some embodiments, administration of an effective amount of the antibody, or antigen binding fragment thereof, that specifically binds pro/latent myostatin results in an clinically meaningful improvement in a standardized quality-of-life test score. As used the herein, the term "clinically meaningful improvement" refers to a significant improvement over a standard level. In some embodiments, an SCI patient's SP-36 Quality of Life scores are increased by at least 8 points, following treatment with an effective amount of an antibody or antigen-binding fragments thereof described herein, as compared to the patient's score prior to the treatment. In some embodiments, patients achieve higher scores as assessed by the SF-36 Quality of Life Test, for example, at least 9, 10, 11, 12, 13, 14, 15, 16, 17, 18, 19, 20, 30, 40, or 50 points increase in the scores from the SF-36 Quality of Life Scoring System. In other embodiments, the scores from the SF-36 Quality of Life Scoring System is increased by at least about 8-10, 10-15, 15-20, 20-30, 30-40, 40-50, 8-20, 8-30, 8-40, or 8-50.

In some embodiments, the SCI Neurological Quality of Life Test is employed to assess patients' quality of life before and after treatment with the inhibitors of myostatin signaling disclosed herein. Advantages of this test include: i) it is easy to administer; ii) it assesses both physical function and mental health; and, iii) it is highly validated for a number of clinical indications.

K. Effect on Preventing Muscle Loss or Atrophy in the Human Subject

Administration of an effective amount of the myostatin inhibitor, e.g., antibody, or antigen binding fragment thereof, that specifically binds pro/latent myostatin prevents muscle loss or atrophy in the human subject at risk of developing muscle loss and/or atrophy. In some embodiments, muscle loss or atrophy is decreased or prevented by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, muscle loss or atrophy is decreased or prevented by at least about 1-5%, 5-10%, 10-20%, 1-30%, 1-40%, 1-50%, 10-50%, 20-30%, 20-60%, 30-80%, 40-90%, or 50-100%.

In some embodiments, a suitable subject is a subject who has not developed atrophy but is considered at risk of developing atrophy. In some embodiments, a subject has a disease or condition associated with a neurological defect that impairs motor neuron function. In some embodiments, such conditions are caused by muscular dystrophy or atrophy. In some embodiments, the neurological defect is caused by a nerve injury. In some embodiments, the nerve injury involves partial denervation of motor neurons, which causes partial impairment of function in the affected muscle. In some embodiments, such condition is caused by SCI. In some embodiments, the subject with SCI is in an acute or sub-acute phase of SCI (e.g., not yet reached a chronic phase).

In some embodiments, when a composition comprising an effective amount of an inhibitor of myostatin signaling described herein is administered to a population of patients who are at risk of developing muscle atrophy associated with partial devervation of motor neurons, the composition i) prevents manifestation or aggravation of the muscle atrophy in a statistically significant fraction of the patient population; or, ii) lessens the severity of the muscle atrophy in the statistically significant fraction of the patient population.

Prevention of muscle loss or atrophy by the use of a myostatin inhibitor, e.g., an antibody or antigen-binding fragment thereof, described herein can be readily monitored or assessed by any suitable methods to evaluate motor function involving affected muscles.

In some embodiments, administration of an effective amount of such antibody also prevents or lessens an early-onset axonal polyneuropathy in affected limbs.

L. Effect on Preventing Development of Metabolic Disease in the Subject

Administration of an effective amount of the myostatin inhibitor, e.g., antibody, or antigen binding fragment thereof, that specifically binds pro/latent myostatin prevents development of metabolic disease in the subject, e.g., a human subject. In some embodiments, development of metabolic disease is decreased by at least 1%, 2%, 3%, 4%, 5%, 6%, 7%, 8%, 9%, 10%, 15%, 20%, 25%, 30%, 35%, 40%, 45%, 50%, 60%, 70%, 80%, 90% or 100%. In other embodiments, development of metabolic disease is decreased by at least about 1-5%, 5-10%, 10-20%, 1-30%, 1-40%, 1-50%, 10-50%, 20-30%, 20-60%, 30-80%, 40-90%, or 50-100%.

In some embodiments, a suitable subject is a subject who has not fully developed a metabolic disease but is considered at risk of developing such a condition. In some embodiments, a subject has a disease or condition associated with muscle dysfunction. In some embodiments, the muscle dysfunction is associated with partial denervation of motor neurons, which causes partial impairment of function in the affected muscle. In some embodiments, such conditions are caused by muscular dystrophy or atrophy. In some embodiments, such condition is caused by SCI. In some embodiments, the subject with SCI is in an acute or sub-acute phase of SCI (e.g., not yet reached a chronic phase).

In some embodiments, when a composition comprising an effective amount of an inhibitor of myostatin signaling described herein is administered to a population of patients who are at risk of developing a metabolic disorder associated with muscle dysfunction, the composition i) prevents manifestation or aggravation of the metabolic disorder in a statistically significant fraction of the patient population; or, ii) lessens the severity of the metabolic disease in the statistically significant fraction of the patient population.

In some embodiments, effects on metabolism may be monitored or measured by insulin resistance, lipid panel/markers (e.g., leptin), inflammatory markers and oxidative stress markers, including, but are not limited to: IL-6, TNF, CRP, plasma total antioxidant status, lipid oxidation and erythrocyte glutathione peroxidase activity.

Use of Myostatin Inhibitors, Such as Anti-pro/latent Myostatin Antibodies and Antigen Binding Fragments Thereof Pharmaceutical Compositions Myostatin inhibitors, e.g., antibodies, or antigen binding fragments thereof, described herein may be formulated into pharmaceutical compositions suitable for administration in human or non-human subjects. Such pharmaceutical compositions may be intended for therapeutic use, or prophylactic use. One or more of the myostatin inhibitors, e.g., anti-pro/latent-myostatin antibodies can be mixed with a pharmaceutically acceptable carrier (excipient), including buffer, to form a pharmaceutical composition for administering to a patient who may benefit from reduced myostatin signaling in vivo. "Pharmaceutically acceptable" means that the carrier must be compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In one example, a pharmaceutical composition described herein contains more than one myostatin inhibitor, e.g., more than one anti-pro/latent-myostatin antibody, or antigen-binding portion thereof, that recognize different epitopes/residues of the target antigen.

In some examples, the pharmaceutical composition described herein comprises emulsion-based or lipid-based formulations, such as liposomes containing a myostatin inhibitor, e.g., anti-pro/latent-myostatin antibody or antigen-binding portion thereof, which can be prepared by any suitable method, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporations method with a lipid composition comprising phosphatidylcholine, cholesterol and PEG-derivatized phosphatidylethanolamine (PEG-PE). Liposomes are extruded through filters of defined pore size to yield liposomes with the desired diameter.

The myostatin inhibitor, e.g., anti-pro/latent-myostatin antibody, or antigen-binding portion thereof, may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, or antigen-binding portion thereof, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an anti-pro-myostatin antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The Subject

Pharmaceutical compositions described herein are suitable for administration in human or non-human subjects. Accordingly, the myostatin inhibitor, e.g., anti-pro/latent-myostatin antibodies, and antigen-binding portions thereof, described herein are useful as medicament for administering to a subject who is likely to benefit from reduced myostatin signaling. In some embodiments, suitable subjects include healthy individuals who may nonetheless benefit from enhanced muscle mass/function, as well as improved metabolism. In some embodiments, suitable subjects have an existing muscle condition and/or associated metabolic dysfunction. In some embodiments, suitable subjects are at risk of developing such condition(s). In some embodiments, suitable subjects are those on a therapy comprising another therapeutic agent to treat a muscle/metabolic condition, but which is associated with adverse effects or toxicity.

In some embodiments, preferred subjects meet at least two of the following criteria: i) the subject has a condition associated with partial denervation of a motor neuron; ii) the condition involves a muscle containing or enriched with fast twitch fibers; and, iii) the subject retains an anabolic capability (e.g., generally healthy adults with injury) and/or is in a growth phase (e.g., young children, etc.).

In some embodiments, such medicament is suitable for administration in a pediatric population, an adult population, and/or an elderly population.

The pediatric population in need for the myostatin inhibitor, e.g., anti-pro/latent-myostatin antibodies and antigen-binding portions thereof, described herein may range between 0 and 6 months of age, between 0 and 12 months of age, between 0 and 18 months of age, between 0 and 24 months of age, between 0 and 36 months of age, between 0 and 72 months of age, between 6 and 36 months of age, between 6 and 36 months of age, between 6 and 72 months of age, between 12 and 36 months of age, between 12 and 72 months of age. In some embodiments, the pediatric population suitable for receiving the myostatin inhibitor, e.g., antibody or antigen-binding fragment, described herein who is likely to benefit from such treatment may range between 0 and 6 years of age, between 0 and 12 years of age, between 3 and 12 years of age, between 0 and 17 years of age. In some embodiments, the population has an age of at least 5 years, e.g., 6, 7, 8, 9, 10, 11, 12, 13, 14, 15, 16, or 17 years. In some embodiments, the pediatric population may be aged below 18 years old. In some embodiments, the pediatric population may be (a) at least 5 years of age and (b) below 18 years of age.

The adult population in need for the myostatin inhibitor, e.g., anti-pro/latent-myostatin antibodies and antigen-binding portions thereof, described herein may have an age of at least 18 years, e.g., at least 19, 20, 25, 30, 35, 40, 45, 50, 55, 60 or 65 years. In some embodiments, the adult population may be below 65 years of age. In some embodiments, the adult population may of (a) at least 18 years of age and (b) below 65 years of age.

The elderly population in need for the myostatin inhibitor, e.g., anti-pro/latent-myostatin antibodies and antigen-binding portions thereof, described herein may have an age of 65 years or older (i.e., ≥65 years old), e.g., at least 70, 75 or 80 years.

A human subject who is likely to benefit from the treatment may be a human patient having, at risk of developing, or suspected of having a metabolic disease/disorder associated with impaired neurological signaling, such as those described below. A subject having a pro/latent-myostatin-associated disease or disorder can be identified by routine medical examination, e.g., laboratory tests, organ functional tests. CT scans, or ultrasounds. A subject suspected of having any of such disease/disorder might show one or more symptoms of the disease/disorder. A subject at risk for the disease/disorder can be a subject having one or more of the risk factors for that disease/disorder.

A control subject, as described herein, is a subject who provides an appropriate reference for evaluating the effects of a particular treatment or intervention of a test subject or subject. Control subjects can be of similar age, race, gender, weight, height, and/or other features, or any combination thereof, to the test subjects.

In some embodiments, a myostatin assay (e.g., myostatin ELISA) is used to determine a subject requiring treatment of an anti-pro/latent myostatin antibody. Methods for assaying myostatin can be found in Lakshman et al. Molecular and Cell Endocrinology (2009) 302:26-32 (myostatin ELISA) and Bergen et al. Skeletal Muscle (2015) 5:21 (liquid chromatography with tandem mass spectrometry, both of which are incorporated by reference herein.

In some embodiments, methods are provided for improving muscle performance in a subject. The subject may or may not have or be at risk of having a condition associated with decreased muscle mass and/or decreased muscle function. As used herein, the term "muscle performance" generally refers to the capacity of the muscle to contract and/or to apply a force (e.g., to an external object). In some embodiments, muscle performance may relate to the capacity of the muscle to consume energy. For example, in some embodiments, muscle performance may relate to the capacity of the muscle to produce and/or consume adenosine triphosphate (ATP) molecules to facilitate muscle contraction. In some embodiments, muscle performance refers to the capacity of the muscle to contract repeatedly for a particular duration of time. In some embodiments, muscle performance refers to the capacity of the muscle to apply a force to an object, e.g., to move the object over a measurable distance. In some embodiments, muscle performance refers to the capacity of the muscle to apply a force to an object for a particular duration of time (e.g., to move the object over a measurable distance for a particular duration of time).

In some embodiments, the myostatin inhibitor, e.g., anti-pro/latent-myostatin antibody and antigen-binding portions thereof, described herein is administered to a subject in need of the treatment at an amount sufficient to inhibit the proteolytic activation of pro/latent-myostatin to active myostatin by at least 20% (e.g., 30%, 40%, 50%, 60%, 70%, 80%, 90% or greater) in vivo. In other embodiments, a myostatin inhibitor, e.g., antibody or antigen-binding portion thereof, is administered in an amount effective in reducing the pro/latent-myostatin or latent myostatin level by at least 20% (e.g., 30%, 40%, 50%, 60%, 70%, 80%, 90% or greater).

In some embodiments, the myostatin inhibitor, e.g., anti-pro/latent-myostatin antibody or antigen-binding portion thereof, described herein is administered to a subject who will benefit from increased muscle mass. In some embodiments, the myostatin inhibitor, e.g., anti-pro/latent-myostatin antibody or antigen-binding portion thereof, described herein is administered to a subject who will benefit from increased muscle-to-fat ratios. In some embodiments, the myostatin inhibitor, e.g., anti-pro/latent-myostatin antibody or antigen-binding portion thereof, described herein is administered to a subject who will benefit from increased muscle function. In some embodiments, the subject may or may not have or be at risk of having a condition associated with decreased muscle mass and/or decreased muscle function. In some embodiments, the subject has or is at risk of having a condition associated with decreased muscle mass and/or decreased muscle function.

The methods of the present invention further comprising selecting a subject. In some embodiment, the subject suffer from or is at risk of developing a muscle condition or disorder. In some embodiment, the subject suffer from or is at risk of developing a metabolic disorder. In some embodiment, the subject suffer from or is at risk of developing a disease or disorder associated with impaired neurological signaling.

Routes of Administration

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-pro/latent-myostatin antibodies can be aerosolized using a fluorocarbon formulation and a metered dose inhaler, or inhaled as a lyophilized and milled powder.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, a myostatin inhibitor, e.g., anti-pro/latent-myostatin antibody or antigen-binding portion thereof, is administered via site-specific or targeted local delivery techniques. Examples of site-specific or targeted local delivery techniques include various implantable depot sources of the myostatin inhibitor. e.g., anti-pro/latent-myostatin antibody or antigen-binding portion thereof, or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The particular dosage regimen, e.g., dose, timing and repetition, used in the method described herein will depend on the particular subject and that subject's medical history.

Treatment efficacy for a disease/disorder associated with myopathy can be assessed using any suitable methods. For example, treatment efficacy for a disease/disorder associated with myopathy can be assessed by evaluating muscle weakness (e.g., assessing the pattern and severity of weakness), electromyography, evaluating blood chemistries (e.g., assessing electrolytes, assessing endocrine causes, measuring creatinine kinase level, determining erythrocyte sedimentation rate and performing antinuclear antibody assays), and evaluating biopsies (e.g., by histologic, histochemical, electron microscopic, biochemical, and genetic analysis).

"An effective amount" as used herein refers to the amount of each active agent required to confer a therapeutic effect on the subject, either alone or in combination with one or more other active agents. For example, an effective amount refers to the amount of a myostatin inhibitor, e.g., an antibody, or antigen binding fragment thereof, of the present disclosure which is sufficient to achieve a biological effect, e.g., an increase in muscle mass or muscle fiber diameter, a switch in muscle fiber type, an increase in the amount of force generated by the muscle, an increase in mass and/or function of a muscle tissue in the subject; an increase in the metabolic rate of the subject; an increase in insulin sensitivity of the subject; an increase in a level of brown adipose tissue in the subject; an increase in a level of beige adipose tissue in the subject; a decrease in a level of white adipose tissue in the subject; a decrease in a level of visceral adipose tissue in the subject; a decrease in ratio of adipose-to-muscle tissue in the subject; an increase in glucose uptake by a brown adipose tissue, a beige adipose tissue, or a muscle tissue in the subject; a decrease in glucose uptake by a white adipose tissue or a liver tissue; a decrease in muscle catabolism of protein and/or muscle release of amino acids in the subject; an increase in insulin dependent glycemic control in the subject; or a decrease in intramuscular fat infiltration in the subject; or a clinically significant outcome, e.g., a partial or complete recovery of the ability to perform physical tasks after injury; a clinically meaningful improvement in quality of life as assessed by a standardized system, such as SF-36 Quality of Life Scoring System; prevention of muscle loss or atrophy in the subject; and/or prevention of developing a metabolic disease in the subject.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, in the context of an increase in the level of pro-myostatin in the target muscle, the increase is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to a control level of pro-myostatin. In one embodiment, the increase in the level of pro-myostatin in the target muscle is an increase in a range of 1-fold to 3-fold, 1.2-fold to 10-fold, 2-fold to 9-fold, 3-fold to 8-fold, 4-fold to 7-fold, 2-fold to 7-fold, etc. compared to the control level of pro-myostatin.

In some embodiments, in the context of an increase in latent myostatin in the target muscle after the administering step, the increase is detectable within 4 hours, 24 hours, 48 hours, 7 days, 14 days, 21 days, 28 days or 30 days (or any time range bracketed by any of the listed duration of times)

after the administering step. In one embodiment, an increase in latent myostatin in the target muscle after the administering step is detectable for at least 5 days, 7 days, 14 days, 21 days, 28 days, or 30 days (or any time range bracketed by any of the listed duration of times) after the administering step. In one embodiment, an increase in the level of latent myostatin in the target muscle after the administering step is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to the level of latent myostatin in the target muscle before the administering step. In one embodiment, an increase in the level of latent myostatin in the target muscle after the administering step is an increase in a range of 1-fold to 3-fold, 1.2-fold to 10-fold, 2-fold to 9-fold, 3-fold to 8-fold, 4-fold to 7-fold, 2-fold to 7-fold, etc., compared to the level of latent myostatin in the target muscle before the administering step.

In some embodiment, in the context of an increase in latent myostatin in the circulation after the administering step, an increase is detectable within 4 hours, 24 hours, 48 hours, 7 days, 14 days, 21 days, 28 days, or 30 days (or any time range bracketed by any of the listed duration of times) after the administering step. In one embodiment, an increase in latent myostatin in the circulation after the administering step is detectable for at least 5 days, 7 days, 14 days, 21 days, 28 days, or 30 days (or any time range bracketed by any of the listed duration of times) after the administering step. In one embodiment, an increase in the level of latent myostatin in the circulation after the administering step is at least 1-fold, 2-fold, 3-fold, 5-fold, 10-fold, 15-fold, 20-old, 25-fold, 30-old, 35-fold, 40-fold, 45-fold, or 50-fold or more (or any range bracketed by any of the values), compared to the level of latent myostatin in the circulation before the administering step. In one embodiment, an increase in the level of latent myostatin in the target muscle after the administering step is an increase in a range of 1-fold to 3-fold, 1.2-fold to 10-fold, 2-fold to 9-fold, 3-fold to 8-fold, 4-fold to 7-fold, 2-fold to 7-fold, etc., compared to the level of latent myostatin in the target muscle before the administering step.

In some embodiments, in the context of a decrease in the level of latent myostatin in the circulation, the decrease is at least 1-fold, 1.2-fold, 1.5-fold, 2-fold, 2.5-fold, 3-fold, 4-fold, 5-fold, 6-fold, 7-fold, 8-fold, 9-fold, or 10-fold or more (or any range bracketed by any of the values), compared to a control level of latent myostatin. In one embodiment, a decrease in the level of latent myostatin in the circulation is a decrease in a range of 1-fold to 3-fold, 1.2-fold to 10-fold, 2-fold to 9-fold, 3-fold to 8-fold, 4-fold to 7-fold, 2-fold to 7-fold, etc. compared to the control level of latent myostatin.

As discussed above, in some embodiments, in the context of administration of a myostatin inhibitor, e.g., a pro/latent-myostatin antibody, or antigen binding fragment thereof, to a subject, an effective amount is an amount effective to increase mass of a target muscle in the subject compared with a control muscle mass. In some embodiments, muscle treated with an effective amount of the antibody is increase by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, etc., as compared with a control muscle mass that is not treated with an effective amount of the antibody. In some embodiments, such muscle mass increase is achieved in a select group or type of muscles in the subject.

In some embodiments, in the context of administration of a myostatin inhibitor, e.g., pro/latent-myostatin antibody, or antigen binding fragment thereof, to a subject, an effective amount is an amount effective to switch fiber types in the subject. In some embodiments, an effective amount of the antibody can promote a fiber type switch from type I to type II. In some embodiments, an effective amount of the myostatin inhibitor, e.g., antibody or antigen-binding portion thereof, can promote a fiber type switch from type I to type IIB. In some embodiments, an effective amount of the myostatin inhibitor, e.g., antibody or antigen-binding portion thereof, can promote type II fibers, relative to other types of fibers. In some embodiments, an effective amount of the myostatin inhibitor, e.g., antibody or antigen-binding portion thereof, can promote type IIB fibers, relative to other types of fibers. In some embodiments, such phenotypic switch in fibers may occur without significant change in overall muscle mass. In other embodiments, such phenotypic switch in fibers may coincide an increase in overall muscle mass.

In some embodiments, in the context of administration of a myostatin inhibitor, e.g., pro/latent-myostatin antibody, or antigen binding fragment thereof, to a subject, an effective amount is an amount effective to increase diameter of muscle fiber in the subject compared with a control muscle fiber. In some embodiments, the increase in the diameter of the muscle fiber is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control muscle fiber. In some embodiments, the increase in the diameter of muscle fiber is an increase in a range of I-fold to 5-fold, 2-fold to 10-fold, 1-fold to 1.5-fold, 1-fold to 2-fold, etc. compared with a control muscle fiber.

In some embodiments, in the context of administration of a myostatin inhibitor, e.g., pro/latent-myostatin antibody, or antigen binding fragment thereof, to a subject, an effective amount is an amount effective to increase muscle-to-fat ratio in the subject compared with a control muscle mass. In some embodiments, the increase in the muscle-to-fat ratio is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control subject. In some embodiments, the increase in the muscle-to-fat ratio is an increase in a range of I-fold to 5-fold, 2-fold to 10-fold, 1-fold to 1.5-fold, 1-fold to 2-fold, etc. compared with a control subject.

In some embodiments, in the context of administration of a myostatin inhibitor, e.g., a pro/latent-myostatin antibody, or antigen binding fragment thereof, to a subject, an effective amount is an amount effective to decrease intramuscular fat infiltration in the subject compared with a control muscle mass. In some embodiments, the decrease in the intramuscular fat infiltration is a decrease of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control subject. In some embodiments, the decrease in intramuscular fat infiltration is a decrease in a range of 1-fold to 5-fold, 2-fold to 10-fold, 1-fold to 1.5-fold, 1-fold to 2-fold, etc. compared with a control subject.

In some embodiments, a method of preventing a reduction of and/or increasing muscle mass in a human subject includes administering a myostatin inhibitor, e.g., a pro/latent-myostatin antibody, or antigen binding fragment thereof, to a subject that inhibits proteolytic formation of mature myostatin by a tolloid protease. In one embodiment, inhibition of proteolytic cleavage of pro-myostatin or latent myostatin by a tolloid protease results in a progressive increase in muscle mass. In one embodiment, a subject exhibits a progressive increase in muscle mass for at least 2 weeks, 4 weeks, 6 weeks, 8 weeks, 10 weeks, 12 weeks, 14 weeks, 16 weeks, 18 weeks, or 20 weeks (or any range bracketed by any of the values). In some embodiments, a method of preventing a reduction of and/or increasing muscle mass in a human subject includes administering a myostatin inhibitor, e.g., a pro/latent-myostatin antibody, or antigen binding fragment thereof, to a subject comprising more than two doses. In one embodiment, administering a myostatin inhibitor, e.g., a pro/latent-myostatin antibody, or antigen binding fragment thereof, comprises at least a first dose and a second dose, the first dose and the second dose are administered to the subject at least about 2 weeks apart, 4 weeks apart, 6 weeks apart, 8 weeks apart, or 12 weeks apart.

In some embodiments, in the context of administration of a myostatin inhibitor, e.g., a pro/latent-myostatin antibody, or antigen binding fragment thereof, to a subject, an effective amount is an amount effective to increase function of a target muscle in the subject compared with a control muscle function. In some embodiments, the increase in muscle function is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control muscle function. In some embodiments, the increase in muscle function is an increase in a range of 1-fold to 5-fold, 2-fold to 10-fold, 1-fold to 1.5-fold, 1-fold to 2-fold, etc. compared with a control muscle function.

As used herein, the term "control muscle mass" refers to a reference standard useful for evaluating effects of a condition (e.g., treatment with a myostatin inhibitor, e.g., a pro/latent-myostatin antibody, or antigen binding fragment thereof) on the mass of a target muscle in a subject. In some embodiments, a control muscle mass is a predetermined value. In some embodiments, a control muscle mass is experimentally determined. In some embodiments, a control muscle mass is the mass of a target muscle in a subject who has not been administered the myostatin inhibitor, e.g., pro/latent-myostatin antibody, or antigen binding fragment thereof. In some embodiments, a control muscle mass is the mass (e.g., the average mass) of a target muscle in a population of subjects who have not been administered the myostatin inhibitor, e.g., pro/latent-myostatin antibody, or antigen binding fragment thereof. In some embodiments, a control muscle mass is the mass of a target muscle in a subject prior to (e.g., immediately prior to) being administered the myostatin inhibitor, e.g., pro/latent-myostatin antibody, or antigen binding fragment thereof. In some embodiments, a control muscle mass is the mass of a target muscle in a subject who has been administered, in place of the myostatin inhibitor, e.g., pro/latent-Myostatin antibody, or antigen binding fragment thereof, a normal antibody (e.g., of the same isotype as the pro/latent-Myostatin antibody) that has been obtained from an animal that has not been exposed to the antigen to which the pro/latent-myostatin antibody, or antigen binding fragment thereof, is directed. In some embodiments, a control muscle mass is the mass of a target muscle in a subject who has been administered, in place of the myostatin inhibitor, e.g., pro/latent-myostatin antibody, or antigen binding fragment thereof, a vehicle, e.g., saline.

In some embodiments, in the context of administration of a myostatin inhibitor, e.g., pro/latent-myostatin antibody, or antigen binding fragment thereof, to a subject, an effective amount is an amount effective to increase force generation capacity (e.g., a maximal force generation as determined in vitro with a muscle lever system adapted with a horizontal perfusion bath) of a target muscle in the subject compared with a control force generation capacity. In some embodiments, the increase in force generation capacity is an increase of at least 1.1-fold, at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 4-fold, at least 5-fold or more compared with a control force generation capacity. In some embodiments, the increase in force generation capacity is an increase in a range of 1-fold to 5-fold, 2-fold to 10-fold, 1-fold to 1.5-fold, 1-fold to 2-fold, etc. compared with a control force generation capacity.

As used herein, the term "control force generation capacity" refers to a reference standard useful for evaluating effects of a condition (e.g., treatment with a pro/latent-myostatin antibody, or antigen binding fragment thereof) on the force generation capacity of a muscle in a subject. In some embodiments, a control force generation capacity is a predetermined value. In some embodiments, a control force generation capacity is experimentally determined. In some embodiments, a control force generation capacity is the force generation capacity of a target muscle in a subject who has not been administered the myostatin inhibitor, e.g., pro/latent-myostatin antibody, or antigen binding fragment thereof. In some embodiments, a control force generation capacity is the force generation capacity (e.g., the average force generation capacity) of a target muscle in a population of subjects who have not been administered the myostatin inhibitor, e.g., pro/latent-myostatin antibody, or antigen binding fragment thereof. In some embodiments, a control force generation capacity is the force generation capacity of a target muscle in a subject prior to (e.g., immediately prior to) being administered the myostatin inhibitor. e.g., pro/latent-myostatin antibody, or antigen binding fragment thereof. In some embodiments, a control force generation capacity is the force generation capacity of a target muscle in a subject who has been administered, in place of the myostatin inhibitor, e.g., pro/latent-myostatin antibody, a normal antibody (e.g., of the same isotype as the pro/latent-myostatin antibody) that has been obtained from an animal that has not been exposed to the antigen to which the pro/latent-myostatin antibody is directed. In some embodiments, a control force generation capacity is the force generation capacity of a target muscle in a subject who has been administered, in place of the myostatin inhibitor, e.g., pro/latent-myostatin antibody, or antigen binding fragment thereof, a vehicle, e.g., saline.

In some embodiments, the target muscle is a plantarflexor muscle. In some embodiments, the target muscle is a muscle containing type 2 fibers. In some embodiments, the target muscle is a muscle containing fast oxidative fibers or fast glycolytic fibers. In some embodiments, the target muscle is a muscle containing type IIB fibers. In some embodiments, the administration of myostatin inhibitor, e.g., pro/latent-myostatin antibody, or antigen binding fragment thereof, results in increase in type IIB fiber cross-sectional area by at least 1%, 5%, 10%, 15%, 20%, 25%, 30%, 35%, 40%, 45%, or 50% (or any range bracketed by any of the values), compared to the cross-sectional area before the administering step.

Dosages

Empirical considerations, such as the half-life, generally will contribute to the determination of the dosage. For example, antibodies and antigen-binding portions thereof that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a disease/disorder associated with myopathy. Alternatively, sustained continuous release formulations of a myostatin inhibitor, e.g., an anti-pro/latent-myostatin antibody, or antigen-binding portion thereof, may be appropriate. Various formulations and devices for achieving sustained release would be apparent to the skilled artisan and are within the scope of this disclosure.

In one example, dosages for a myostatin inhibitor, e.g., an anti-pro/latent-myostatin antibody, or antigen binding fragment thereof, as described herein may be determined empirically in individuals who have been given one or more administration(s) of the myostatin inhibitor, e.g., antibody, or antigen binding fragment thereof. Individuals are given incremental dosages of the antagonist. To assess efficacy of the antagonist, an indicator of the disease/disorder can be followed.

Generally, for administration of any of the antibody, or antigen binding fragment thereof, described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a disease or disorder associated with pro/latent-myostatin, or a symptom thereof. An exemplary dosing regimen comprises administering an initial dose of about 2 mg/kg, followed by a weekly maintenance dose of about 1 mg/kg of the antibody, or antigen binding fragment thereof, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, every 4 months, every 5 months, every 6 months, every 8 months, every 10 months, every year, or longer. The progress of this therapy is easily monitored by conventional techniques and assays. The dosing regimen (including the antibody used) can vary over time.

In some embodiments, the administration of any of the myostatin inhibitors, e.g., antibodies, or antigen binding fragments thereof, described herein comprises a single dose. In some embodiments, the administration of any of the myostatin inhibitors, e.g., antibodies, or antigen binding fragments thereof, described herein comprises multiple doses (e.g., at least 2, 3, 4, 5, 6, 7, 8, 9, or 10 doses). Administering may comprise more than two doses. In some embodiments, the administration comprises at least a first dose and a second dose of a therapeutically effective amount of the myostatin inhibitor, e.g., antibody or antigen-binding portion thereof. In one embodiment, the first dose and the second dose are administered to the subject at least about 4 weeks apart, 6 weeks apart, 8 weeks apart, or 12 weeks apart.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of a myostatin inhibitor, e.g., an anti-pro/latent-myostatin antibody, or antigen binding fragment thereof, will depend on the specific antibody (or compositions thereof) employed, the type and severity of the disease/disorder, whether the antibody is administered for preventive or therapeutic purposes, previous therapy, the patient's clinical history and response to the antagonist, and the discretion of the attending physician. In some embodiments, a clinician will administer a myostatin inhibitor, e.g., an anti-pro/latent-myostatin antibody or antigen-binding portion thereof, until a dosage is reached that achieves the desired result. Administration of a myostatin inhibitor, e.g., an anti-pro/latent-myostatin antibody or antigen-binding portion thereof, can be continuous or intermittent, depending, for example, upon the recipient's physiological condition, whether the purpose of the administration is therapeutic or prophylactic, and other factors known to skilled practitioners. The administration of a myostatin inhibitor, e.g., an anti-pro/latent-myostatin antibody, or antigen binding fragment thereof, may be essentially continuous over a preselected period of time or may be in a series of spaced dose, e.g., either before, during, or after developing a disease or disorder associated with pro/latent-myostatin.

As used herein, the term "treating" refers to the application or administration of a composition including one or more active agents to a subject, who has a disease/disorder associated with myopathy, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease/disorder.

Alleviating a disease/disorder associated with pro/latent-myostatin includes delaying the development or progression of the disease, or reducing disease severity. Alleviating the disease does not necessarily require curative results. As used therein, "delaying" the development of a disease/disorder associated with pro/latent-myostatin means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

Combination Therapies

The invention encompasses pharmaceutical compositions and related methods used as combination therapies for treating subjects who may benefit from myostatin inhibition in vivo. In any of these embodiments, such subjects may receive combination therapies that include a first composition comprising at least one myostatin inhibitor, e.g., antibody or antigen-binding portion thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat myopathy associated with a disease, while the second composition may treat inflammation or fibrosis associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, the invention provides pharmaceutical compositions and methods for use in combination therapies for the enhancement of muscle mass/function and for the treatment or prevention of metabolic diseases or diseases associated with an impaired neurological signaling, including diabetes, obesity and spinal cord injury. Accordingly, the methods or the pharmaceutical compositions further comprise a second therapy. In some embodiments, the second therapy may be useful in treating or preventing metabolic diseases or diseases associated with an impaired neurological signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action.

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

The one or more anti-myostatin antibodies or other myostatin inhibitors of the invention may be used in combination with one or more of additional therapeutic agents. Examples of the additional therapeutic agents which can be used with an anti-myostatin antibody of the invention include, but are not limited to, diabetes mellitus-treating agents, diabetic complication-treating agents, cardiovascular diseases-treating agents, anti-hyperlipemic agents, hypotensive or anti-hypertensive agents, anti-obesity agents, nonalcoholic steatohepatitis (NASH)-treating agents, chemotherapeutic agents, immunotherapeutic agents, immunosuppressive agents, and the like. Such combination therapies may advantageously utilize lower dosages of the administered therapeutic agents, thus avoiding possible toxicities or complications associated with the various monotherapies.

Examples of agents for treating diabetes mellitus include insulin formulations (e.g., animal insulin formulations extracted from a pancreas of a cattle or a swine; a human insulin formulation synthesized by a gene engineering technology using microorganisms or methods), insulin sensitivity enhancing agents, pharmaceutically acceptable salts, hydrates, or solvates thereof (e.g., pioglitazone, troglitazone, rosiglitazone, netoglitazone, balaglitazone, rivoglitazone, tesaglitazar, farglitazar, CLX-0921, R-483, NIP-221, NIP-223, DRF-2189, GW-7282TAK-559, T-131, RG-12525, LY-510929, LY-519818, BMS-298585, DRF-2725, GW-1536, GI-262570, KRP-297, TZD18 (Merck), DRF-2655, and the like), alpha-glycosidase inhibitors (e.g., voglibose, acarbose, miglitol, emiglitate and the like), biguanides (e.g., phenformin, metformin, buformin and the like) or sulfonylureas (e.g., tolbutamide, glibenclamide, gliclazide, chlorpropamide, tolazamide, acetohexamide, glyclopyramide, glimepiride and the like) as well as other insulin secretion-promoting agents (e.g., repaglinide, senaglinide, nateglinide, mitiglinide, GLP-1 and the like), amyrin agonist (e.g., pramlintide and the like), phosphotyrosin phosphatase inhibitor (e.g., vanadic acid and the like) and the like.

Examples of agents for treating diabetic complications include, but are not limited to, aldose reductase inhibitors (e.g., tolrestat, epalrestat, zenarestat, zopolrestat, minairestat, fidareatat, SK-860, CT-112 and the like), neurotrophic factors (e.g., NGF, NT-3, BDNF and the like), PKC inhibitors (e.g., LY-333531 and the like), advanced glycation end-product (AGE) inhibitors (e.g., ALT946, pimagedine, pyradoxamine, phenacylthiazolium bromide (ALT766) and the like), active oxygen quenching agents (e.g., thioctic acid or derivative thereof, a bioflavonoid including flavones, isoflavones, flavonones, procyanidins, anthocyanidins, pycnogenol, lutein, lycopene, vitamins E, coenzymes Q, and the like), cerebrovascular dilating agents (e.g., tiapride, mexiletene and the like).

Anti-hyperlipemic agents include, for example, statin-based compounds which am cholesterol synthesis inhibitors (e.g., pravastatin, simvastatin, lovastatin, atorvastatin, fluvastatin, rosuvastatin and the like), squalene synthetase inhibitors or fibrate compounds having a triglyceride-lowering effect (e.g., fenofibrate, gemfibrozil, bezafibrate, clofibrate, sinfibrate, clinofibrate and the like), niacin, PCSK9 inhibitors, triglyceride lowing agents or cholesterol sequesting agents.

Hypotensive agents include, for example, angiotensin converting enzyme inhibitors (e.g., captopril, enalapril, delapril, benazepril, cilazapril, enalapril, enalaprilat, fosinopril, lisinopril, moexipril, perindopril, quinapril, ramipril, trandolapril and the like) or angiotensin II antagonists (e.g., losartan, candesartan cilexetil, olmesartan medoxomil, eprosartan, valsartan, telmisartan, irbesartan, tasosartan, pomisartan, ripisartan forasartan, and the like) or calcium channel blockers (e.g., amlodipine) or aspirin.

Nonalcoholic steatohepatitis (NASH)-treating agents include, for example, ursodiol, pioglitazone, orlistat, betaine, rosiglitazone.

Anti-obesity agents include, for example, central antiobesity agents (e.g., dexfenfluramine, fenfluramine, phentermine, sibutramine, amfepramone, dexamphetamine, mazindol, phenylpropanolamine, clobenzorex and the like), gastrointestinal lipase inhibitors (e.g., orlistat and the like), beta 3-adrenoceptor agonists (e.g., CL-316243, SR-58611-A, UL-TG-307, SB-226552, AJ-9677, BMS-196085 and the like), peptide-based appetite-suppressing agents (e.g., leptin, CNTF and the like), cholecystokinin agonists (e.g., lintitript, FPL-15849 and the like) and the like.

Chemotherapeutic agents include, for example, alkylating agents (e.g., cyclophosphamide, iphosphamide and the like), metabolism antagonists (e.g., methotrexate, 5-fluorouracil and the like), anticancer antibiotics (e.g., mitomycin, adriamycin and the like), vegetable-derived anticancer agents (e.g., vincristine, vindesine, taxol and the like), cisplatin, carboplatin, etoposide and the like. Among these substances, 5-fluorouracil derivatives such as furtulon and neofurtulon are preferred.

Immunotherapeutic agents include, for example, microorganisms or bacterial components (e.g., muramyl dipeptide derivative, picibanil and the like), polysaccharides having immune potentiating activity (e.g., lentinan, sizofilan, krestin and the like), cytokines obtained by a gene engineering technology (e.g., interferon, interleukin (IL) and the like), colony stimulating factors (e.g., granulocyte colony stimulating factor, erythropoetin and the like) and the like, among these substances, those preferred are IL-1, IL-2, IL-12 and the like.

Immunosuppressive agents include, for example, calcineurin inhibitor/immunophilin modulators such as cyclosporine (Sandimmune, Gengraf, Neoral), tacrolimus (Prograf, FK506), ASM 981, sirolimus (RAPA, rapamycin, Rapamune), or its derivative SDZ-RAD, glucocorticoids (prednisone, prednisolone, methylprednisolone, dexamethasone and the like), purine synthesis inhibitors (mycophenolate mofetil, MMF, CellCept®, azathioprine, cyclophosphamide), interleukin antagonists (basiliximab, daclizumab, deoxyspergualin), lymphocyte-depleting agents such as anti-thymocyte globulin (Thymoglobulin, Lymphoglobuline), anti-CD3 antibody (OKT3), and the like.

In addition, agents whose cachexia improving effect has been established in an animal model or at a clinical stage, such as cyclooxygenase inhibitors (e.g., indomethacin and the like), progesterone derivatives (e.g., megestrol acetate), glucosteroid (e.g., dexamethasone and the like), metoclopramide-based agents, teutahydrocannabinol-based agents, lipid metabolism improving agents (e.g., eicosapentanoic acid and the like), growth hormones, IGF-1, antibodies against TNF-α, LIP, IL-6 and oncostatin M may also be employed concomitantly with an anti-myostatin antibody according to the present invention. Additional therapeutic agents for use in the treatment of diseases or conditions related to metabolic disorders and/or impaired neurological signaling would be apparent to the skilled artisan and are within the scope of this disclosure.

In some embodiments, second agents suitable for administration as a combination therapy in conjunction with the antibodies described herein are anti-fibrotic agents, such as TGFβ1 inhibitors.

In some embodiments, second agents suitable for administration as a combination therapy in conjunction with the antibodies described herein are modulators (e.g., agonists and antagonists) of certain members of the TGFβ super family of growth factors, such as BMP6, BMP7, GDP11, TGFβ2, TGFβ3, RGMc, etc.

Any of the above-mentioned agents can be administered in combination with the myostatin antibody of the invention to treat a metabolic disease, or a disease associated with an impaired neurological signaling between a neuron and a target tissue, e.g., spinal cord injury, muscular atrophy, and muscular dystrophy.

Use of Myostatin Inhibitors, Such as Anti-Pro/Latent-Myostatin Antibodies and Antigen Binding Fragments Thereof, for Treating Diseases/Disorders Pharmaceutical compositions described herein are suitable for administration to human patients for the treatment or prevention of diseases and conditions where reduced myostatin signaling is desirable. Such diseases and conditions include, but are not limited to: muscle conditions or disorders, metabolic disorders, and diseases associated with impaired neurological signaling, e.g., spinal cord injury. Exemplary conditions for which the compositions and methods of the present invention may be useful are further described below.

A. Muscle Conditions and Disorders

In some embodiments, the methods of the present invention are suitable for treating or preventing muscle conditions and disorders. As used herein, the term "muscle condition" or "muscle disorder" refers to a disease, condition, or disorder, where the muscle does not function normally, or a disease, condition, or disorder, where the function of muscle is normal, but there are less force generated by the muscle due to a reduced amount of muscle available. A muscle condition or disorder may include, without limitation, a myopathy, muscular atrophy, a muscular dystrophy, etc. Such conditions may be caused by a defect or defects in a motor neuron, a genetic mutation, or an injury, such as a nerve injury.

In one embodiment, the muscle condition is a myopathy. As used herein, the term "myopathy" refers to a muscular condition characterized by impaired muscle structure or function, typically resulting in muscular weakness. A "myopathy" may also include a muscular condition characterized by normal muscle structure but impaired or abnormal neuronal input, which in turn affects muscle function. A "myopathy" may also include inflammatory myopathies and/or autoimmune myopathies. e.g., myasthenia gravis.

Myopathies include muscular conditions that are neuromuscular or musculoskeletal in nature. In some embodiments, the myopathy is an inherited myopathy. Inherited myopathies include, without limitation, dystrophies, myotonias, congenital myopathies (e.g., nemaline myopathy, multi/minicore myopathy, and centronuclear myopathy), mitochondrial myopathies, familial periodic myopathies, inflammatory myopathies and metabolic myopathies (e.g., glycogen storage diseases and lipid storage disorder). In some embodiments, the myopathy is an acquired myopathy. Acquired myopathies include, without limitation, external substance induced myopathy (e.g., drug-induced myopathy and glucocorticoid myopathy, alcoholic myopathy, and myopathy due to other toxic agents), myositis (e.g., dermatomyositis, polymyositis and inclusion body myositis), myositis ossificans, rhabdomyolysis, and myoglobinurias, and disuse atrophy. In some embodiments, the myopathy is disuse atrophy, which may be caused by prolonged disuse of muscles, leading to deterioration of normal muscle function. Disuse atrophy may be a result of hospitalization, bone fracture (e.g. a hip fracture) or by nerve injury. In some embodiments the myopathy is related to a disease or disorder such as amyotrophic lateral sclerosis (ALS), spinal muscular atrophy (SMA), cachexia syndromes due to renal failure. AIDS, cardiac conditions and/or cancer. In some embodiments the myopathy is related to ageing. In some embodiments the myopathy is related to sarcopenia. In some embodiments, the myopathy is related to paraspinal muscle atrophy (PMA).

In some embodiments, the myopathy is a primary myopathy. In one embodiments, a primary myopathy comprises disuse atrophy. In some embodiments, the disuse atrophy is associated with hip fracture, elective joint replacement, critical care myopathy, spinal cord injury or stroke. In some embodiments, the myopathy is a genetic muscle weakness associated with, for example, a muscular dystrophy.

In some embodiments, the myopathy is a secondary myopathy, in which muscle loss or dysfunction is secondary to a disease pathology. In some embodiments, secondary myopathy comprises denervation or cachexia. In some embodiments, the secondary myopathy is caused by a denervation associated with monitor neuron dysfunction. In some embodiments, motor neuron dysfunction is due to genetic mutation(s) that affect motor neurons. Diseases known to involve mutations in motor neurons include, but are not limited to, amyotrophic lateral sclerosis (ALS) and spinal muscular atrophy (SMA). In some embodiments, the secondary myopathy is a cachexia associated with renal failure, AIDS, a cardiac condition, cancer or aging. In some embodiments, the secondary myopathy is caused by a nerve injury, including unwanted nerve injury sustained during a medical procedure, such as surgeries. Detrimental effects of such injury to the function of a target tissue (e.g., target muscle) may be effectively treated by administration of a myostatin inhibitor described herein. For example, such administration may prevent and/or alleviate myopathy, and/or facilitate recovery.

In some embodiments, the methods of the present invention are suitable for treating or preventing muscle conditions and disorders, including vocal cord paresis/paralysis. As used herein, the term "vocal cord paresis/paralysis" refers to a condition that results from abnormal nerve input into the voice box muscles (laryngeal muscles). Paralysis may involve the total interruption of nerve impulse, resulting in no movement; paresis may involve the partial interruption of nerve impulse, resulting in weak or abnormal motion of laryngeal muscles. In some embodiments, the anti-myostatin antibody, or antigen binding fragment thereof, is administered locally, for example, via direct local injection into the affected vocal cord muscle(s). Unilateral injection is needed when only one side of the vocal cord is affected, for example, due to a nerve injury on one side. In other embodiments, both sides of the vocal cord are affected when nerves on both sides are injured and, thus, bilateral injection is preferred.

The anti-myostatin antibody, or antigen binding fragment thereof, for use in the methods of the present invention may increase the vocal cord muscle mass locally to close the gap between the two vocal cord folds to restore function. In severe cases, where the gap is too large, surgery may be required to correct it. In such cases of severe vocal cord paresis/paralysis, anti-myostatin antibody, or antigen binding fragment thereof, may be used as an adjunctive therapy with surgery to further close the gap. In some embodiments, the methods of the present invention are suitable for treating or preventing mild vocal cord paresis/paralysis for which vocalization function is affected but where a corrective surgery is not necessary. In other embodiments, the methods of the present invention are suitable for treating or preventing severe vocal cord paresis/paralysis as an adjunct to surgery or as a primary therapy in situations when surgery is not feasible or too risky.

In some embodiments, the methods of the present invention are suitable for treating or preventing muscle conditions and disorders, including paraspinal muscle atrophy (PMA). In one embodiment, the antibodies, or antigen binding fragments thereof, described herein are used in methods of treatment of a paraspinal muscle atrophy that is a postoperative paraspinal muscle atrophy. i.e., a paraspinal muscle atrophy after a surgery. In one embodiment, the methods of treatment include treating a nerve injury-dependent muscle atrophy. In one embodiment, the methods of treatment as described herein include treating a postoperative nerve injury-dependent muscle atrophy. In one embodiment, the methods of treatment include treating a postoperative muscle atrophy, in which the surgery is a spinal surgery. In one embodiment, the methods of treatment include treating a postoperative muscle atrophy, in which the spinal surgery is a lumbar spine surgery or a lumbar spine procedure, e.g., a lumbar fusion procedure, a lumbar nonfusion procedure, a posterior lumbar fusion procedure, an anterior lumbar fusion procedure, a minimally invasive (MIS) posterior lumbar decompression procedure, a minimally invasive (MIS) posterior lumbar fusion procedure, a non-MIS equivalent procedure, etc. In one embodiment, the methods of treatment include treating a paraspinal muscle atrophy after a lumbar spine fusion procedure. In one embodiment, the methods of treatment include treating a paraspinal muscle atrophy after a posterior lumbar spine fusion procedure. In one embodiment, the methods of treatment include treating a paraspinal muscle atrophy after a non-MIS lumbar fusion procedure. In one embodiment, methods of treatment with the myostatin inhibitors, e.g., antibodies, or antigen binding fragments thereof, described herein results in at least 1%, 2%, 3%, 4%, 5%, 6%, 7%, 8%, 9%, 10%, 12%, 15%, 18%, 20%, or 25% decrease in postoperative paraspinal muscle atrophy. In one embodiment, methods of treatment with the myostatin inhibitors, e.g., antibodies, or antigen binding fragments thereof, described herein results in at least 1%, 2%, 3%, 4%, 5%, 6%, 7%, 8%, 9%, 10%, 12%, 15%, 18%, 20%, or 25% decrease in postoperative nerve injury-dependent paraspinal muscle atrophy.

Another aspect of the disclosure includes a method of treating a subject having a disease or condition related to congenital myopathies. Exemplary congenital myopathies include, without limitation, X-linked my tubular myopathy, autosomal dominant centronuclear myopathy, autosomal recessive centronuclear myopathy, nemaline myopathy, and congenital fiber-type disproportion myopathy.

Another aspect of the disclosure includes a method of treating a subject having a muscle disease or condition related to muscular dystrophies. Exemplary muscular dystrophies include, without limitation, Duchenne's, Becker's, facioscapulohumeral (FSH), and Limb-Girdle muscular dystrophies.

Another aspect of the disclosure includes a method of treating a subject having a urogynecological related disease or condition, glottic disorders (stenosis), extraocular myopathy, carpel tunnel, Guillain-Barré, or osteosarcoma.

B. Metabolic Disorders and Diseases

The invention provides methods for treating or preventing a metabolic disease in a subject. As used herein, the term "metabolic disease" refers to any undesirable condition involving perturbation of the normal physiological state of homeostasis due to an alteration in metabolism (anabolism and/or catabolism). Metabolic disorders affect how the body processes substances needed to carry out physiological functions and are generally associated with aberrant glucose, lipid and/or protein metabolism and pathological consequences arising from such disorder. A number of metabolic disorders of the invention share certain characteristics, e.g., they are associated with a loss of fat-free or lean muscle mass, an excess of fat mass, a lower metabolic rate, insulin resistance, lack of ability to regulate blood sugar, weight gain, and/or increase in body mass index. As discussed in more detail herein, metabolic disorders can occur secondarily to, or occur as a result of, a muscle condition or disorder.

The present invention is based, at least in part, on the discovery that administration of a myostatin inhibitor, e.g., an antibody, or antigen binding fragment thereof, that specifically binds to pro/latent myostatin, to subjects having a metabolic disease significantly improves both the physiological and the functional characteristics of the injured subjects. In particular, the present inventors have surprisingly discovered that administration of a myostatin inhibitor, e.g., an anti-myostatin antibody or antigen-binding portion thereof, significantly increases the metabolic rate or energy expenditure in subjects having metabolic disease. Administration of a myostatin inhibitor, e.g., an anti-myostatin antibody or antigen-binding portion thereof, also significantly attenuated SCI-induced reduction in sub-lesional muscle mass and overall body mass and, while at the same time reducing the mass of undesirable adipose tissue such as white and visceral adipose tissue. In addition, subjects who received a myostatin inhibitor, e.g., an anti-myostatin antibody or antigen-binding portion thereof, treatment exhibited a significant improvement in their locomotor function, muscle strength, as well as motor coordination and balance skills.

Accordingly, the present invention provides methods for treating or preventing metabolic diseases in a human subject. The methods include selecting a human subject suffering from a metabolic disease, and administering to the human subject an effective amount of a myostatin inhibitor. e.g., an antibody, or antigen binding fragment thereof, that specifically binds myostatin, thereby treating or preventing the metabolic disease in the human subject. Preferably, the antibody, or antigen binding fragment thereof, specifically binds to pro/latent myostatin, but does not bind to GDF11. Antibodies that specifically recognize pro/latent myostatin, but not GDF11, are beneficial and avoid undesirable toxicity caused by off-target binding of antibodies to GDF11 in the subject.

Examples of metabolic diseases that may be treated or prevented by the methods of the present invention include but are not limited to, type I diabetes, type 2 diabetes, metabolic syndrome, pre-diabetes, obesity, cardiovascular diseases, non-alcoholic stetohepatitis (NASH), spinal cord injury (SCI), hypo-metabolic states, double diabetes, Cushings disease, obesity syndrome, insulin resistance, insulin insufficiency, hyperinsulinemia, impaired glucose tolerance (IGT), abnormal glycogen metabolism, hyperlipidemia, hypoalbuminemia, hypertriglyceridemia, syndrome X and fatty liver disease. In some embodiments, metabolic diseases include diseases associated with impaired neurological signaling or partial denervation.

Additional diseases or conditions related to metabolic disorders and/or body composition that would be apparent to the skilled artisan and are within the scope of this disclosure.

Diabetes refers to a group of metabolic diseases characterized by high blood sugar (glucose) levels which result from defects in insulin secretion or action, or both. There are two most common types of diabetes, namely type 1 diabetes and type 2 diabetes, which both result from the body's inability to regulate insulin. Insulin is a hormone released by the pancreas in response to increased levels of blood sugar (glucose) in the blood.

The term "type I diabetes," as used herein, refers to a chronic disease that occurs when the pancreas produces too little insulin to regulate blood sugar levels appropriately. Type I diabetes is also referred to as insulin-dependent diabetes mellitus, IDDM, and juvenile onset diabetes. People with type I diabetes (insulin-dependent diabetes) produce little or no insulin at all. Although about 6 percent of the United States population has some form of diabetes, only about 10 percent of all diabetics have type I disorder. Most people who have type I diabetes developed the disorder before age 30. Type I diabetes represents is the result of a progressive autoimmune destruction of the pancreatic R-cells with subsequent insulin deficiency. More than 90 percent of the insulin-producing cells (beta cells) of the pancreas are permanently destroyed. The resulting insulin deficiency is severe, and to survive, a person with type I diabetes must regularly inject insulin.

In type II diabetes (also referred to as noninsulin-dependent diabetes mellitus, NDDM), the pancreas continues to manufacture insulin, sometimes even at higher than normal levels. However, the body develops resistance to its effects, resulting in a relative insulin deficiency. Type II diabetes may occur in children and adolescents but usually begins after age 30 and becomes progressively more common with age: about 15 percent of people over age 70 have type II diabetes. Obesity is a risk factor for type II diabetes, and 80 to 90 percent of the people with this disorder are obese.

In some embodiments, diabetes includes pre-diabetes. "Pre-diabetes" refers to one or more early diabetic conditions including impaired glucose utilization, abnormal or impaired fasting glucose levels, impaired glucose tolerance, impaired insulin sensitivity and insulin resistance. Prediabetes is a major risk factor for the development of type 2 diabetes mellitus, cardiovascular disease and mortality. Much focus has been given to developing therapeutic interventions that prevent the development of type 2 diabetes by effectively treating prediabetes.

In some embodiments, diabetes includes double diabetes, which is a combination of type I diabetes with features of insulin resistance and type 2 diabetes.

Diabetes can be diagnosed by the administration of a glucose tolerance test. Clinically, diabetes is often divided into several basic categories. Primary examples of these categories include, autoimmune diabetes mellitus, non-insulin-dependent diabetes mellitus (type 1 NDDM), insulin-dependent diabetes mellitus (type 2 IDDM), non-autoimmune diabetes mellitus, non-insulin-dependent diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) 14th ed., New York, McGraw-Hill).

Obesity is another prevalent metabolic disease that can be treated or prevented by the methods of the present invention. "Obesity" refers to a chronic condition defined by an excess amount body fat. The normal amount of body fat (expressed as percentage of body weight) is between 25-30% in women and 18-23% in men. Women with over 30% body fat and men with over 25% body fat are considered obese. Obesity can be defined using any clinically relevant definitions. For example, in adults, body mass index (BMI, $kg/m^2$) is frequently used as a measure of overweight and obesity, with overweight being defined as a BMI 25-29.9 $kg/m^2$, obesity as a BMI equal to or greater than 30 $kg/m^2$, and morbid obesity being defined as BMIs over 40 $kg/m^2$. Obesity can also be defined in adults by central adiposity as measured by waist circumference, with raised waist circumference defined as equal to or greater than 102 cm in men and equal to or greater than 88 cm in women. Subject with obesity may exhibit other symptoms such as increased fasting plasma glucose, increased fasting plasma triglycerides, decreased fasting high density lipoprotein (HDL) level, and increased blood pressure. Obesity may also cause various orthopedic problems, skin disorders and swelling of the feet and ankles. Severe complications of obesity include a much higher risk of coronary artery disorder and of its major risk factors type II diabetes, hyperlipidemia and hypertension. Much of the morbidity associated with obesity is associated with type II diabetes, as poorly controlled diabetes and obesity lead to a constellation of symptoms that are together known as syndrome X, or metabolic syndrome. In some embodiments, the obesity is sarcopenic obesity.

The methods of the present invention are also suitable for treating or preventing metabolic disease such as metabolic syndromes. As used herein, "metabolic syndrome" refers to the concept of a clustering of metabolic risk factors that come together in a single individual and lead to a high risk of developing diabetes and/or cardiovascular diseases. The main features of metabolic syndrome include insulin resistance, hypertension (high blood pressure), cholesterol abnormalities, dyslipidemia, triglyceride abnormalities, an increased risk for clotting and excess body weight, especially in the abdomen, or obesity. The American Heart Association suggests that metabolic syndrome be diagnosed by the presence of three or more of the following components: (1) an elevated waist circumference (men, equal to or greater than 40 inches (102 cm); women, equal to or greater than 35 inches (88 cm)); (2) elevated triglycerides (equal to or greater than 150 mg/dL); (3) reduced High Density Lipoprotein cholesterol or HDL (men, less than 40 mg/dL; women, less than 50 mg/dL); (4) elevated blood pressure (equal to or greater than 130/85 mm Hg); and (5) elevated fasting glucose (equal to or greater than 100 mg/dL).

In another aspect, the methods of the present invention are suitable for treating or preventing metabolic disease such as obesity syndromes. The term "obesity syndrome" refers any disorder or conditions causing a subject to be grossly fat or overweight. Like other metabolic diseases, people with obesity syndrome are usually associated a loss of fat-free or lean muscle mass, an excess of fat mass, a lower metabolic rate, insulin resistance, lack of ability to regulate blood sugar, weight gain, and increase in body mass index. In some embodiments, the obesity syndrome is selected from the group consisting of Prader Willi, an obesity syndrome associated with a genetic disorder, and an obesity syndrome associated with a hypothalamic disorder.

The methods of the present invention are also suitable for treating or preventing metabolic diseases associated with a hypo-metabolic state. The term "a hypo-metabolic state" refers to a state of reduced metabolism or metabolic activity, where the body is not producing enough energy. Patients with a hypo-metabolic state generally have a lower metabolic rate, a loss of fat-free or lean muscle mass, an excessive gain of fat mass, insulin resistance, lack of ability to regulate blood sugar, weight gain, and an increase in body mass index. In some embodiments, the hypo-metabolic state is selected from the group consisting of a state associated with prolonged immobilization, a state associated with bed-rest, a state associated with casting, a state associated with a stroke, a state associated with amputation, and a post-surgery state. In some embodiments, the hypo-metabolic state is a post-surgery state, e.g., paraspinal muscle atrophy after lumbar spine surgery. In one embodiment, the paraspinal muscle atrophy is a nerve injury-dependent muscle atrophy. In one embodiment, the surgery is a spinal surgery. In one embodiment, the spinal surgery is a lumbar spine surgery or a lumbar spine procedure, e.g., a lumbar fusion procedure, a lumbar nonfusion procedure, a posterior lumbar fusion procedure, a anterior lumbar fusion procedure, a minimally invasive (MIS) posterior lumbar decompression procedure, a minimally invasive (MIS) posterior lumbar fusion procedure, a non-MIS equivalent procedure, etc.

In another aspect, the methods of the present invention are suitable for treating or preventing metabolic diseases such as Cushings disease. The term "Cushings disease" refers to a condition in which the pituitary gland releases too much adrenocorticotropic hormone (ACTH). Symptoms of Cushing disease may include upper body obesity (above the waist) and thin arms and legs, round, red, full face (moon face) and slow growth rate in children. In some embodiments, the Cushings disease is selected from the group consisting of corticosteroid-induced Cushings disease and tumor-induced Cushings disease.

In yet another aspect, the methods of the present invention are suitable for treating or preventing metabolic diseases such as cardiovascular disease. The term "cardiovascular disease" refers to any disease of the heart or blood vessels. Cardiovascular or heart disease includes but is not limited to, for example, angina, arrhythmia, coronary artery disease (CAD), coronary heart disease, cardiomyopathy (including dilated cardiomyopathy, restrictive cardiomyopathy, arrhythmogenic right ventricular cardiomyopathy, and diabetic cardiomyopathy), heart attack (myocardial infarction), heart failure, hypertrophic cardiomyopathy, mitral regurgitation, mitral valve prolapse, pulmonary stenosis, etc. Blood vessel disease includes but is not limited to, for example, peripheral vascular disease, artery disease, carotid artery disease, deep vein thrombosis, venous diseases, and atherosclerosis.

Another aspect of the disclosure includes a method of treating a subject having a metabolic disease or condition related to aging. Exemplary diseases and conditions related to ageing include, without limitation, sarcopenia (age-related muscle loss), frailty, and androgen deficiency.

Another aspect of the disclosure includes a method of treating a subject having a metabolic disease or condition related to disuse atrophy/trauma. Exemplary diseases and conditions related to disuse atrophy/trauma include, without limitation, muscle weakness related to time spent in an intensive care unit (ICU), hip/joint replacement, hip fracture, stroke, bed rest, SCI, rotator cuff injury, knee replacement, bone fracture, and burns.

C. Diseases Associated with Impaired Neurological Signaling

The present disclosure is based, at least in part, on the surprising discovery that inhibition of myostatin signaling may be particularly useful for the intervention of conditions involving defects in communication between muscle and its innervating neurons. Thus, the disclosure provides methods for treating or preventing diseases associated with impaired neurological signaling between a neuron and a target tissue that expresses myostatin in subjects, e.g., human subjects. In some embodiments, the methods include administering to a subject suffering from a disease associated with an impaired neurological signaling between a neuron and a target tissue an effective amount of a myostatin inhibitor, e.g., an antibody, or antigen binding fragment thereof, that specifically binds myostatin and inhibits myostatin signaling, thereby treating or preventing the disease associated with the impaired neurological signaling in the subject. Preferably, the antibody, or antigen binding fragment thereof, specifically binds to pro/latent myostatin, but does not bind to GDF11.

As used herein, term "disease with an impaired neurological signaling" refers to any disease or disorder that is caused by, or associated with, a disrupted signal transduction or a breakdown in communication between a neuron and its target tissue(s), e.g., a muscle tissue, a brain tissue, a liver tissue, a blood vessel tissue, or an adipose tissue. In some embodiments, the impaired neurological signaling occurs due to a damage in the neuron structure, where neurons are incapable of transmitting signals towards their targets. In other embodiments, the structures of neurons remain intact, but there are functional disruption or defects, for example, a blockage at the neuromuscular junction, such that the ability of neurons to transmit signals is affected.

In some embodiments, "disease with an impaired neurological signaling" refers to disease or condition associated with denervation, e.g., a partial loss or perturbation of nerve supply or neuronal input to its target, such as muscle. In some embodiments, denervation is induced by injury. In some embodiments, denervation is associated with a disease. Non-limiting examples of diseases with an impaired neurological signaling include, for example, vocal cord paresis/paralysis, spinal cord injury (SCI), myasthelia gravis, amyotrophic lateral sclerosis (ALS), and spinal muscular atrophy (SMA).

Spinal Cord Injury

The methods of the present invention are also suitable for treating or preventing conditions with an impaired neurological signaling due to nerve injury. In some embodiments, such condition is spinal cord injury (SCI). As used herein, the term "spinal cord injury" refers to damages to any part of the spinal cord or nerves at the end of the spinal canal. Spinal cord injury often causes permanent changes in strength, sensation and other body functions below the site of the injury. Each year, it is estimated that there are 12,500 new cases of spinal cord injury (US). Prevalence is 275,000 cases in the US and roughly 60% have paraplegia. There are no therapies in development directed at reversing or reducing muscle atrophy in SCI and this represents a large unmet need. While there is significant patient heterogeneity based on time since injury, level and completeness of injury, and extent of disability, physical rehabilitation to improve muscle function and metabolic outcomes is standard of care.

SCI patients are stratified based on the level (paraplegia vs. tetraplegia) and the completeness of the lesion (complete vs incomplete). This stratification has been developed into the ASIA scale, with two broad groups based on level of paralysis: complete (AIS grades A/B) and incomplete (AIS grades C/D/E), defined below:

A: Complete motor and sensory loss
B: Motor loss with retained sensory perception (still can feel touch, pressure)
C and D: Incomplete motor loss
E: Most function is regained: this represents a low proportion of the population.

There are 7 cervical (neck), 12 thoracic (chest), 5 lumbar (back), and 5 sacral (tail) vertebrae. A lesion in SCI may occur at any location along the vertebrae. The key muscles that need to be tested to establish neurologic level are as follows:

C5: Elbow flexors (biceps, brachialis)
C6: Wrist extensors (extensor carpi radialis longus and brevis)
C7: Elbow extensors (triceps)
C8: Long finger flexors (flexor digitorum profundus)
T1: Small finger abductors (abductor digiti minimi)
L2: Hip flexors (iliopsoas)
L3: Knee extensors (quadriceps)
L4: Ankle dorsiflexors (tibialis anterior)
L5: Long toe extensors (extensor hallucis longus)
S1: Ankle plantar flexors (gastrocnemius, soleus)

With a complete spinal cord injury, the cord can't send signals below the level of the injury. As a result, patients are paralyzed below the injury. With an incomplete injury, patients will have some movement and sensation below the injury.

There are multiple phases associated with spinal cord injury. Subjects may be in an acute spinal cord injury phase immediately after injury, where diagnosis between complete and incomplete injury is generally difficult, due in part to the trauma and associated inflammation. Typically, the acute phase is defined as the initial in-hospital period following the event/injury in acute medical/surgical care, which is generally around ~2 weeks. A subject may be in a sub-acute spinal cord injury phase, where there is a distinction between complete and incomplete spinal cord injury, and recovery is possible through ongoing rehab. Typically the sub-acute phase constitutes ~2 weeks up to ~18 months post injury (e.g., 3-6 months post-injury). Yet further, a subject may be in a chronic spinal cord injury phase which generally starts around 6-12 months after the time of injury, where patients have demonstrated substantial decrease in rate of recovery or when rehab efforts have reached a stable phase (e.g., plateau) despite the ongoing standard of care efforts.

Muscle strength always should be graded according to the maximum strength attained, no matter how briefly that strength is maintained during the examination. The muscles are tested with the patient supine. Motor level is determined by the most caudal key muscles that have muscle strength of 3 or above while the segment above is normal (=5).

Motor index scoring uses the 0-5 scoring of each key muscle, with total points being 25 per extremity and with the total possible score being 100.

Lower extremities motor score (LEMS) uses the ASIA key muscles in both lower extremities, with a total possible score of 50 (i.e., maximum score of 5 for each key muscle [L2, L3, L4, L5, and S1] per extremity). A LEMS of 20 or less indicates that the patient is likely to be a limited ambulator. A LEMS of 30 or more suggests that the individual is likely to be a community ambulator.

ASIA recommends use of the following scale of findings for the assessment of motor strength in spinal cord injury:

0: No contraction or movement
1: Minimal movement
2: Active movement, but not against gravity
3: Active movement against gravity
4: Active movement against resistance
5: Active movement against full resistance Monitoring functional outcomes and quality of life in SCI patients is a complex task as selection of the appropriate functional measure depends upon the completeness and level of injury. One common measure which is applicable to all patients is the functional independence measure (FIM) which is a 7 point scale designed to quantify the dependence of a patient on a caregiver. An additional metric for measuring quality of life which has had recent attention is the SCI-QOL, which integrates both functional skills and emotional health of the patient (Tulsky 2015, *J Spinal Cord Med.* 38(3): 257-69). Many other functional outcome measures have been outlined by the SCIRE project.

In some embodiments, meaningful clinical effects achieved by administration of an effective amount of the myostatin inhibitor described herein to SCI patients may correspond to at least a 6 point (≥6) increase from baseline in total motor score of ASIA at, e.g., week 24. In some embodiments, meaningful clinical effects achieved by administration of an effective amount of the myostatin inhibitor described herein to SCI patients may correspond to statistically significant difference in the meantotal SCIM III score between treated and untreated/control groups at Day 112 (+/−7 days). In some embodiments, meaningful clinical effects achieved by administration of an effective amount of the myostatin inhibitor described herein to SCI patients may correspond to greater than a 4 point (>4) increase in Functional Independence Measure for Locomotion (FIM-L) score.

Individuals with spinal cord injury have an increased prevalence of abnormalities in carbohydrate and lipid metabolism associated with immobilization, muscle atrophy, and increased adiposity. The body composition is substantially altered and typified by rapid and long-term decline in metabolically active muscle mass and bone with stark increases in central adiposity. The latter contributes to a maladaptive metabolic profile favoring substantial gain in body mass occurring 2-7 months following injury. Occurring together these co-morbid risk factors incite all-cause cardiovascular disease, diabetes, and risk clustering as cardiometabolic disease, the latter including component hazards for dyslipidemia, glucose intolerance and insulin resistance.

Rapid and profound muscle wasting affects those with a spinal cord injury and impacts the entire body, not just the denervated limbs. Muscle loss is believed to be due to a combination of factors including denervation (of the paretic limbs), immobilization, inflammation, factors released by the paralyzed muscle, steroid use, infections, and lack of nutrition. A large percentage (~30%) of lean muscle mass is lost in the first six weeks following injury (the acute phase). This accelerated rate of lean mass loss continues on into chronic conditions with a decrease in lean mass (per decade) of 3% for tetraplegia and 2.4% for paraplegia (as compared to a decline of 1% seen in healthy controls) (Spungen 2003). This accelerated muscle atrophy contributes to premature sarcopenia.

An SCI patient experiences profound changes in total body composition. In particular, lean muscle mass is replaced with fat mass, on average an SCI patient has 13% more fat tissue per unit BMI than a healthy control, with a significant increase in intramuscular fat (Spungen 2003, Gorgey 2007). This whole-body change in composition (~60-70% are obese) has profound impacts on metabolism which is evidenced by increased prevalence of cardiovascular disease, type II diabetes, and thyroid disorders.

Mechanical unloading following spinal cord injury also translates into disruptions in bone homeostasis. SCI patients have reduced bone mineral content, develop osteoporosis, and suffer from increased rates of fractures (as many as 50% of SCI patients will experience a fracture post injury) (Battaglino 2013). A fracture leads to hospitalization and can have profound consequences by increasing the risk for developing pressure ulcers, contractures of the knee and hip, and for experiencing a hypertensive crisis.

Overall increases in lean mass and decrease in fat mass in SCI patients can be monitored by several well-validated methods, such as thigh or upper arm muscle volume by magnetic resonance imaging, or total body composition by dual-energy x-ray absorptiometry or DEXA. Such measurements are routinely performed in the field.

Outcome or progress of therapy (e.g., overall clinical effects) may be measured by using any of well-characterized tests commonly employed for evaluating SCI clinical practice. These tests are useful for i) providing information on each measure's clinical utility and psychometric properties; ii) assisting clinicians to select appropriate measures tailored to particular patient(s); iii) identifying individuals who may benefit from a certain therapy; iv) monitoring progress; v) evaluating whether treatments are effective; and/or, vi) help programs improve services to patients and medical professionals. Suitable clinical evaluation tools/tests available for patients include, but are not limited to the following:

For evaluating Assistive Technology, useful tests include: Assistive Technology Device Predisposition Assessment (ATD-PA); Quebec User Evaluation of Satisfaction with Assistive Technology (QUEST 2.0); and Wingate Anaerobic Testing (WAnT).

For evaluating Community Reintegration, useful tests include: Assessment of Life Habits Scale (LIFE-H); Community Integration Questionnaire (CIQ); Craig Handicap Assessment & Reporting Technique (CHART); Impact on Participation and Autonomy Questionnaire (IPAQ); Physical Activity Recall Assessment for People with Spinal Cord injury (PARA-SCI); Physical Activity Scale for Individuals with Physical Disabilities (PASIPD); and Reintegration to Normal Living (RNL) Index.

For evaluating Lower Limb & Walking, useful tests include: 10 Meter Walking Test (10 MWT); 6-Minute Walk Test (6MWT); Berg Balance Scale (BBS); Clinical Outcome Variables Scale (COVS); Functional Standing Test (FST); Spinal Cord Injury Functional Ambulation Inventory (SCI-FAI); Timed Up and Go Test (TUG); and Walking Index for Spinal Cord Injury (WISCI) and WISCI II.

For evaluating Mental Health, useful tests include: Beck Depression Inventory (BDI); Brief Symptom Inventory (BSI); CAGE Questionnaire; Center for Epidemiological Studies Depression Scale (CES-D and CES-D-10); Depression Anxiety Stress Scale-21 (DASS-21): Fatigue Severity Scale (FSS); Hospital Anxiety and Depression Scale (HADS); Patient Health Questionnaire-9 (PHQ-9); Scaled General Health Questionnaire-28 (GHQ-28); Symptom Checklist-90-Revised (SCL-90-R); and Zung Self-Rating Depression Scale (SDS).

For evaluating Neurological Impairment and Autonomic Dysfunction, useful tests include: American Spinal Injury Association Impairment Scale (AIS): International Standards for Neurological Classification of Spinal Cord Injury; and Surface Electromyography (sEMG).

Other useful evaluation systems for Affected Physiological Systems include: Exercise Self-Efficacy Scale (ESES); Moorong Self-Efficacy Scale (MSES); Spinal Cord Injury Secondary Conditions Scale (SCI-SCS); Spinal Cord Lesion Coping Strategies Questionnaire (SCL CSQ); Spinal Cord Lesion Emotional Wellbeing Questionnaire (SCL EWQ); and Wingate Anaerobic Testing (WAnT).

For assessing Pain, useful tests include: Brief Pain Inventory (BPI); Classification System for Chronic Pain in SCI; Donovan SCI Pain Classification System; Multidimensional Pain Inventory (MPI)—SCI version; Multidimensional Pain Readiness to Change Questionnaire (MPRCQ2); Quantitative Sensory Testing (QST); Tunk's Classification Scheme; and Wheelchair Users Shoulder Pain Index (WUSPI).

For evaluating Quality of Life and Health Status, useful tests include: Incontinence Quality of Life Questionnaire (I-QOL); Life Satisfaction Questionnaire (LISAT-9, LISAT-11); Quality of Life Index (QLI)—SCI Version; Quality of Life Profile for Adults with Physical Disabilities (QOLP-PD); Quality of Well Being (QWB) and Quality of Well Being-Self-Administered (QWB-SA); Qualiveen; Satisfaction with Life Scale (SWLS, Deiner Scale); Short Form 36 (SF-36); Sickness Impact Profile 68 (SIP 68); and World Health Organization Quality of Life-BREF (WHOQOL-BREF).

For evaluating Self Care & Daily Living, useful tests include: Appraisals of DisAbility: Primary and Secondary Scale (ADAPSS); Barthel Index (BI); Frenchay Activities Index (FAI); Functional Independence Measure (FIM); Functional Independence Measure Self-Report (FIM-SR); Klein-Bell Activities of Daily Living Scale (K-B Scale); Lawton Instrumental Activities of Daily Living scale (IADL); Quadriplegia Index of Function (QIF); Quadriplegia Index of Function Modified (QIP-Modified); Quadriplegia Index of Function-Short Form (QIF-SF); Rivermead Mobility Index (RMI); Self Care Assessment Tool (SCAT); Self Reported Functional Measure (SRFM); Spinal Cord Independence Measure (SCIM); and Spinal Cord Injury Lifestyle Scale (SCILS).

For Sexuality and Reproduction, useful tests include: Emotional Quality of the Relationship Scale (EQR); Knowledge, Comfort, Approach and Attitude towards Sexuality Scale (KCAASS); Sexual Attitude and Information Questionnaire (SAIQ); Sexual Behaviour Scale (SBS); Sexual Interest and Satisfaction Scale (SIS); Sexual Interest, Activity an; and Satisfaction (SIAS)/Sexual Activity and Satisfaction (SAS) Scales.

For evaluating Skin Health, useful tests include: Abruzzese Scale; Braden Scale; Gosnell Measure; Norton Measure; Skin Management Needs Assessment Checklist (SMNAC); Spinal Cord Injury Pressure Ulcer Scale—Acute (SCIPUS-A); Spinal Cord Injury Pressure Ulcer Scale (SCIPUS) Measure; Stirling's Pressure Ulcer Severity Scale; and. Waterlow Scale.

For evaluating Spasticity, useful tests include: Ashworth and Modified Ashworth Scale (MAS); Pendulum Test (Wartenberg); Penn Spasm Frequency Scale (PSFS); Spinal Cord Assessment Tool for Spastic Reflexes (SCATS); Spinal Cord Injury Spasticit; and Evaluation Tool (SCI-SET).

For evaluating Upper Umb Functionality, useful tests include: Box and Block Test (BBT); Capabilities of Upper Extremity Instrument (CUE); Graded Redefined Assessment of Strength, Sensibility and Prehension (GRASSP); Grasp and Release Test (GRT); Hand-Held Myometer; Jebsen Hand Function Test (JHFT); Modified Functional Reach Test (mFRT); Six-Minute Arm Test (6-MAT); Sollerman Hand Function Test; Tetraplegia Hand Activity Questionnaire (THAQ); and Van Lieshout Test Short Version (VLT-SV).

And, for evaluating Wheeled Mobility, useful tests include: 4 Functional Tests for Persons who Self-Propel a Manual Wheelchair (4FTPSMW); Timed Motor Test (TMT); Tool for assessing mobility in wheelchair-dependent paraplegics; Wheelchair Circuit (WC); and Wheelchair Skills Test (WST).

Based on the effects of myostatin on muscle mass and metabolism, a myostatin inhibitor, e.g., an anti-myostatin antibody or antigen-binding portion thereof, can potentiate a number of long-term health consequences (which may be measured by one or more standardized tests/tools such as those listed above) which affect those living with SCI, and would cause clinically meaningful benefits to patients at the time of injury and/or in chronic conditions. Indeed, the present inventors surprisingly discovered that specific inhibition of myostatin activation by a myostatin inhibitor, e.g., an anti-pro/latent myostatin antibody had a positive impact on muscle function in the subjects, including in muscles below the injury or lesion. Specifically, administration of the myostatin inhibitor, e.g., anti-pro/latent myostatin antibody, to a partial denervation animal model not only prevented muscle atrophy and increased muscle mass in the injured subjects, but also enhanced the function of the injured muscle, as well as prevented metabolic dysregulation associated with neuron injuries and, thus, improving the overall metabolic health of the subjects which may provide significant long term benefits.

D. Other Diseases

Another aspect of the disclosure includes a method of treating a subject having a disease or condition related to Cachexia. Exemplary diseases and conditions related to cachexia include, without limitation, cancer, chronic heart failure, acquired immune deficiency syndrome (AIDS), chronic obstructive pulmonary disease (COPD), and chronic kidney disease (CKD).

Another aspect of the disclosure includes a method of treating a subject having a disease or condition related to rare diseases. Exemplary rare diseases and conditions include, without limitation, osteogenesis imperfecta, sporadic inclusion body myositis, and acute lymphoblastic leukemia.

Kits

The present disclosure also provides kits for use in alleviating diseases/disorders associated with myopathy. Such kits can include one or more containers comprising a myostatin inhibitor, e.g., an anti-pro/latent-myostatin antibody, or antigen binding fragment thereof, e.g., any of those described herein.

In some embodiments, the kit can comprise instructions for use in accordance with any of the methods described herein. The included instructions can comprise a description of administration of the myostatin inhibitor, e.g., anti-pro/latent-myostatin antibody, or antigen binding fragment thereof, to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of a myostatin inhibitor, e.g., an anti-pro/latent-myostatin antibody, or antigen binding fragment thereof, generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with myopathy. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-pro/latent-myostatin antibody, or antigen binding fragment thereof, as those described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

Assays for Detecting Pro/Latent-Myostatin

In some embodiments, methods and compositions provided herein relate to a method for detecting pro/latent-myostatin in a sample obtained from a subject. As used herein, a "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is a patient or a healthy volunteer. In some embodiments, the subject is a "healthy subject" (e.g., who is not at risk of developing a muscle condition, such as muscle atrophy, but may nevertheless benefit from increased muscle mass and/or function). In some embodiments, the subject has or at risk of developing muscle atrophy or weakness. In some embodiments, the subject has or at risk of developing muscle atrophy or weakness and will benefit from increased muscle mass and/or function.

In some embodiments, a method for detecting a pro/latent-myostatin in a sample obtained from a subject involves (a) contacting the sample with the anti-pro/latent-myostatin antibody, or antigen binding fragment thereof, under conditions suitable for binding of the antibody to the antigen, if the antigen is present in the sample, thereby forming binding complexes; and (b) determining the level of the antibody or antigen binding fragment bound to the antigen (e.g., determining the level of the binding complexes).

As used herein a binding complex refers to a biomolecular complex of antibody (including antigen binding fragments) bound to antigen (e.g., pro/latent-myostatin protein). Binding complexes may comprise antibodies with a single specificity or two or more antibodies or antigen binding fragments with different specificities. In one embodiment, a binding complex comprises two or more antibodies recognizing different antigenic sites on the same antigen. In some instances, an antibody may be bound to an antigen, having bound to it other biomolecules such as RNA, DNA, polysaccharides or proteins. In one embodiment, a binding complex comprises two or more antibodies recognizing different antigens. In some embodiments, an antibody in a binding complex (e.g., an immobilized antibody bound to antigen), may itself by bound, as an antigen, to an antibody (e.g., a detectably labeled antibody). Thus, binding complexes may, in some instances, comprise multiple antigens and multiple antibodies or antigen binding fragments.

Antigens present in binding complexes may or may not be in their native in situ conformation. In some embodiments, a binding complex is formed between an antibody and a purified protein antigen, or isolated proteins comprising antigen, in which the antigen is not in its native in situ conformation. In some embodiments, a binding complex is formed between an antibody and a purified protein antigen, in which the antigen is not in its native in situ conformation and is immobilized on solid support (e.g., a PVDF membrane). In some embodiments, a binding complex is formed with an antibody and, for example, a cell surface protein that is present in situ in a native confirmation (e.g., on the surface of a cell).

Antibodies in binding complexes may or may not be detectably labeled. In some embodiments, binding complexes comprise detectably labeled antibodies and non-labeled antibodies. In some embodiments, binding complexes comprise detectably labeled antigen. In some embodiments, antibodies, in binding complexes, are immobilized to one or more solid supports. In some embodiments, antigens, in binding complexes, are immobilized to one or more solid supports. Exemplary solid supports are disclosed herein and will be apparent to one of ordinary skill in the art. The foregoing examples of binding complexes are not intended to be limiting. Other examples of binding complexes will be apparent to one or ordinary skill in the art.

In any of the detection, diagnosis, and monitoring methods, the antibody, (including antigen binding fragments) or antigen may be conjugated to a solid support surface, either directly or indirectly. Methods for conjugation to solid supports are standard and can be accomplished via covalent and non-covalent interactions. Non-limiting examples of conjugation methods include: adsorption, cross-linking, protein A/G—antibody interactions, and streptavidin-biotin interactions. Other methods of conjugation will be readily apparent to one of ordinary skill in the art.

In some aspects, detection, diagnosis, and monitoring methods include comparing the level of the antibody (including antigen binding fragments) bound to the antigen (e.g., pro/latent-myostatin) to one or more reference standards. The reference standard may be, for example, the level of a corresponding pro/latent-myostatin in a subject that does or does not have a pro/latent-myostatin. In one embodiment, the reference standard is the level of pro/latent-myostatin detected in a sample that does not contain pro/latent-myostatin (e.g., a background level). Alternatively, a background level can be determined from a sample that contains a particular pro/latent-myostatin, by contacting the sample with non-specific antibodies (e.g., antibodies obtained from non-immune serum). Then again, the reference standard may be the level of pro/latent-myostatin detected in a sample that does contain pro/latent-myostatin (e.g., a positive control). In some cases, the reference standard may be a series of levels associated with varying concentrations of pro/latent-myostatin in a sample and useful for quantifying the concentration of pro/latent-myostatin in the test sample. The foregoing examples of reference standards are not limiting and other suitable reference standard will be readily apparent to one of ordinary skill in the art. In some embodiments, the level of the antibody bound to pro/latent-Myostatin is compared to the level of mature myostatin. In some instances, the level of pro/latent myostatin is compared to mature myostatin to determine the ratio of inactive to active myostatin in the sample.

The level of pro/latent-myostatin may be measured, as provided herein, from a biological sample. A biological sample refers to any biological material which may be obtained from a subject or cell. For example, a biological sample may be whole blood, plasma, serum, saliva, cerebrospinal fluid, urine, cells (or cell lysate) or tissue (e.g., normal tissue or tumor tissue). In some embodiments, a biological sample is a fluid sample. In some embodiments, a biological sample is a solid tissue sample. For example, a tissue sample may include, without limitation skeletal muscle, cardiac muscle, adipose tissue as well as tissue from other organs. In some embodiments, a biological sample is a biopsy sample. In some embodiments, a solid tissue sample may be made into a fluid sample using routine methods in the art.

A biological sample may also include one or more cells of a cell line. In some embodiments, a cell line includes human cells, primate cells (e.g., vero cells), rat cells (e.g., GH3 cells. OC23 cells) or mouse cells (e.g., MC3T3 cells). There are a variety of human cell lines, including, without limitation, human embryonic kidney (HEK) cells, HeLa cells, cancer cells from the National Cancer Institute's 60 cancer cell lines (NCI60), DU145 (prostate cancer) cells, Lncap (prostate cancer) cells, MCF-7 (breast cancer) cells, MDA-MB-438 (breast cancer) cells, PC3 (prostate cancer) cells, T47D (breast cancer) cells, THP-1 (acute myeloid leukemia) cells, U87 (glioblastoma) cells, SHSY5Y human neuroblastoma cells (cloned from a myeloma) and Saos-2 (bone cancer) cells.

A further embodiment relates to a method for monitoring a disease, a condition, or any treatment thereof (e.g., myopathy or myopathy treatment) in a subject having, or at risk of having, the disease or condition comprising: (a) obtaining a biological sample from the subject, (b) determining the level of a pro/latent-myostatin in the biological sample using an antibody that detects pro/latent-myostatin, and (c) repeating steps (a) and (b) on one or more occasions. Myostatin has been used as a biomarker for muscle atrophy, however, the currently available commercial methods and reagents (e.g., antibodies used in ELISAs and Western Blots) are either not specific for myostatin, detect only mature myostatin or do not detect myostatin at all. Thus, provided herein are methods and reagents (e.g., antibodies) for detecting pro/latent-myostatin in the context of diseases and/or conditions (e.g., muscle atrophy) for diagnostic purposes. As one example, the level of pro/latent-myostatin may be measured in a subject, or biological sample therefrom, to detect or monitor the progression of a disease or condition. As another example, the level of pro/latent-myostatin may be measured in a subject, or biological sample therefrom, to monitor the response to a treatment for a disease or condition. It should be appreciated that the level of pro/latent-myostatin may be monitored over any suitable period of time, which may differ depending on the disease or condition, the subject has or any treatment regimen that the subject may be subject to.

Another embodiment relates to a diagnostic composition comprising any one of the above described antibodies, antigen binding fragments, polynucleotides, vectors or cells and optionally suitable means for detection. The antibodies are, for example, suited for use in immunoassays in which they can be utilized in liquid phase or bound to a solid phase carrier. Examples of immunoassays which can utilize the antibody are competitive and non-competitive immunoassays in either a direct or indirect format. Examples of such immunoassays are the Enzyme Linked Immunoassay (ELISA), radioimmunoassay (RIA), the sandwich (immunometric assay), flow cytometry, the western blot assay, immunoprecipitation assays, immunohistochemistry, immuno-microscopy, lateral flow immuno-chromatographic assays, and proteomics arrays. The antigens and antibodies can be bound to many different solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

By a further embodiment, antibodies (including antigen binding fragments) provided herein may also be used in a method for evaluating pro/latent-myostatin expression in a subject by obtaining a biological sample from the subject which may be a tissue sample, a blood sample or any other appropriate body fluid sample. The procedure may comprise contacting the blood sample (whole blood, serum, plasma), a tissue sample, or protein sample isolated therefrom, with an antibody, under conditions enabling the formation of binding complexes between antibody and antigen. The level of such binding complexes may then be determined by any suitable method. In some embodiments, the biological sample is contacted with the antibody under conditions suitable for binding of the antibody to a pro/latent-myostatin protein, if the antigen is present in the sample, and formation of binding complexes consisting of antibody, bound to the antigen. This contacting step is typically performed in a reaction chamber, such as a tube, plate well, membrane bath, cell culture dish, microscope slide, and the like. In some embodiments, an antibody is immobilized on a solid support. In some embodiments, the antigen is immobilized on a solid support. In some embodiments, the solid support is the surface of the reaction chamber. In some embodiments, the solid support is of a polymeric membrane (e.g., nitrocellulose strip, Polyvinylidene Difluoride (PVDF) membrane, etc.). Other appropriate solid supports may be used.

In some embodiments, an antibody is immobilized on the solid support prior to contacting with the antigen. In other embodiments, immobilization of the antibody is performed after formation of binding complexes. In still other embodiments, antigen is immobilized on a solid support prior to formation of binding complexes. A detection reagent is added to the reaction chamber to detect immobilized binding complexes. In some embodiments, the detection reagent comprises a detectably labeled secondary antibody directed against the antigen. In some embodiments, the primary antibody is itself detectable labeled, and is thereby the detection reagent.

In one aspect, detection methods comprise the steps of immobilizing antibodies to a solid support; applying a sample (e.g., a biological sample or isolated protein sample) to the solid support under conditions that permit binding of antigen to the antibodies, if present in the sample; removing the excess sample from the solid support; applying detectably labeled antibodies under conditions that permit binding of the detectably labeled antibodies to the antigen-bound immobilized antibodies; washing the solid support and assaying for the presence of label on the solid support.

In some embodiments, the antigen is immobilized on the solid support, such as a PVDF membrane, prior to contacting with the antibody in a reaction chamber (e.g., a membrane bath). A detection reagent is added to the reaction chamber to detect immobilized binding complexes. In some embodiments, the detection reagent comprises a detectably labeled secondary antibody directed against the antigen. In some embodiments, the detection reagent comprises a detectably labeled secondary antibody directed against the primary antibody. As disclosed herein, the detectable label may be, for example, a radioisotope, a fluorophore, a luminescent molecule, an enzyme, a biotin-moiety, an epitope tag, or a dye molecule. In some embodiments, the primary antibody is itself detectable labeled, and is thereby the detection reagent. Suitable detectable labels are described herein, and will be readily apparent to one of ordinary skill in the art.

Accordingly, diagnostic kits, suitable for home or clinical use (point of care service), are provided that comprise (a) detectably labeled and/or non-labeled antibodies, as antigen binding reagents (e.g., pro/latent-myostatin binding reagents); (b) a detection reagent; and, optionally. (c) complete instructions for using the reagents to detect antigens in a sample. In some embodiments, the diagnostic kit includes the antibody, and/or pro/latent-myostatin immobilized on a solid support. Any of the solid supports described herein are suitable for incorporation in the diagnostic kits. In a preferred embodiment, the solid support is the surface of a reaction chamber of a plate well. Typically, the plate well is in a multi-well plate having a number of wells selected from: 6, 12, 24, 96, 384, and 1536, but it is not so limited. In other embodiments, the diagnostic kits provide a detectably labeled antibody. Diagnostic kits are not limited to these embodiments and other variations in kit composition will be readily apparent to one of ordinary skill in the art.

The present invention is further illustrated by the following examples, which are not intended to be limiting in any way. The entire contents of all references, patents and published patent applications cited throughout this application, as well as the Figures and Sequence Listing, are hereby incorporated herein by reference.

EXAMPLES

Example 1: Generation and Selection of Antibodies

Antibody Summary

Ab2 is a fully human anti-pro/latent-myostatin monoclonal antibody of the IgG4/lambda isotype that binds to human pro- and latent-myostatin with high affinity (Kd=3420 pM by ForteBio BLI). The antibody is capable of inhibiting the proteolytic activation of pro/latent-myostatin with 1C50 values in the 0.5 micromolar range (which is at or near the limit of the assay). The theoretical molecular weight of the polypeptide is 144,736 Da and its theoretical pI is 6.7. Affinity optimization using antibody display was performed to identify higher affinity variants Ab4 and Ab6. The affinity optimized variants are similarly constructed on the human IgG4/lambda isotype frameworks.

TABLE 4

Biochemical properties of candidate anti-Pro/latent-Myostatin antibodies

| Antibody | Affinity (Octet) pM | Theoretical MW (Da) *aglycosylated | Calculated pI |
|---|---|---|---|
| Ab1 | 4760 | 144809.8 | 6.9 |
| Ab2 | 3420 | 144735.6 | 6.7 |
| Ab4 | 472 | 144661.7 | 6.7 |
| Ab6 | 331 | 144629.5 | 6.7 |

Platform and Identification of Parental Antibody

The parental Ab1 antibody was identified via selection of a naïve phage display library using pro- and latent-myostatin as the primary antigens for selection. Phage selection and initial screening were performed using a library displaying conventional scFv in a format similar to that described by McCafferty et al. (McCafferty et al., 1990). Each round of selection consisted of pre-clearing (for removal of nonspecific phage antibodies), incubation with antigen, washing, elution and amplification. Selections were performed via multiple rounds using both solid phase (biotinylated antigens coated on immunotubes) and solution phase (biotinylated antigens, captured using streptavidin coated beads) panning strategies.

In total, 10,000 individual scFv clones were screened for binding to pro- or latent-myostatin through two separate campaigns. The first program utilized pro/latent-myostatin as an antigen, while a second campaign used latent myostatin as an antigen. DNA for scFv clones of interest were sequenced and 216 unique clones were identified. Positive binding scFv clones were counter-screened for binding to proGDF11 as well as to a panel of unrelated proteins to confirm specificity for pro/latent-myostatin. From the panel of unique scFv clones, 101 (of 134 GDF8 specific clones) were converted to full length IgG (IgG1 isotype) for additional characterization.

Full-length IgG antibodies were further characterized by ELISA for binding to the human and murine pro- and latent-forms of myostatin and GDF11. Antibodies were also screened for binding to the myostatin prodomain, proTGFβ (human and murine), the mature growth factor of myostatin, the GDF11 mature growth factor, the Activin A growth factor, and proActivin A. Lead antibodies were selected based on their cross-reactivity with pro- and latent human and murine myostatin, with no interactions with GDF11, Activin, or TGFβ proteins.

Two forms of epitope binning were employed. First, chimeric constructs which swapped portions of the prodomains of myostatin and GDF11 were designed and produced. These chimeric proteins were assayed for interaction with screening antibodies by ELISA. Epitope binning was carried out using a ForteBio BLI instrument, in which the biotinylated pro/latent-myostatin antibody was immobilized on a streptavidin coated biosensor chip, and cross-blocking of antibodies was evaluated by sensor response. These epitope binning experiments, along with data from the ELISA binding experiments, allowed for the segregation of our functionally active lead antibodies (see below) into three distinct epitope groups (see Table 5).

TABLE 5

Ranking of five anti-pro/latent-Myostatin IgG1 antibodies

| Clone ID | proGDF8 Kd (µM) (octet) | Human proGDF8 IC50$^2$ (µM) Reporter assay | Murine proGDF8 IC50$^2$ (µM) Reporter assay | % body weight increase in 6 weeks 25 mg/kg/week | % lean mass increase in 4 weeks 20 mg/kg/week | Epitope bin |
|---|---|---|---|---|---|---|
| Ab1 | 11.5 | 0.996 | 1.46 | 14.58* | 14.1* | 1 |
| Ab7 | 28 | 0.983 | 1.68 | 12.42* | ND | 1 |
| Ab8 | 0.5 | 6.037 | 139$^1$ | 10.33* | 7.4 | 2 |
| Ab9 | 22 | 12.16 | 19.86 | 7.44 | ND | 3 |
| Ab10 | 0.3 | 0.772 | ND | ND | 14.3* | 1 |

*Statistical significance by one-way ANOVA with Dunnett.
Ab8 does not bind latent myostatin, only pro-myostatin. Murine pro/latent-Myostatin preparations have ~40% latent material which reduces the apparent efficacy in functional assays.
ND: Not determined.

In order to evaluate the ability of antibodies to bind and inhibit the activation of pro/latent-myostatin, a number of biochemical and cellular assays were established. Binding kinetics to pro- and latent-myostatin was measured by ForteBio Octet, in which the biotinylated substrate protein was immobilized on streptavidin coated sensor chips. The equilibrium dissociation constants of candidates from screening are shown in Table 5.

To measure the ability of the IgGs to inhibit myostatin signaling, a myostatin activation assay was developed. Conditioned medium from cells overexpressing either mTll2 (the tolloid protease require for myostatin activation) or Furin (the proprotein convertase which cleaves the mature growth factor from the prodomain) were produced. Following pre-incubation with the test antibody, pro/latent-myostatin or latent myostatin was incubated with either a mixture of mTll2 and Furin conditioned media (pro-myostatin) or mTll2 conditioned media (latent myostatin). Following an overnight proteolysis reaction, the release of mature growth factor was measured using a CAGA-based reporter assay in 293T cells. Antibodies were further validated by dose response, in the same assay, the results of which are shown in Table 5.

Five parental antibodies (Table 5) demonstrated consistently potent selectivity and activity in all of the above assays and were further chosen for further characterization in vivo (discussed in Example 2). For consistency, the binding and activity of these antibodies towards pro/latent-myostatin is summarized, as Ab8 does not recognize latent myostatin.

Figure 3A:
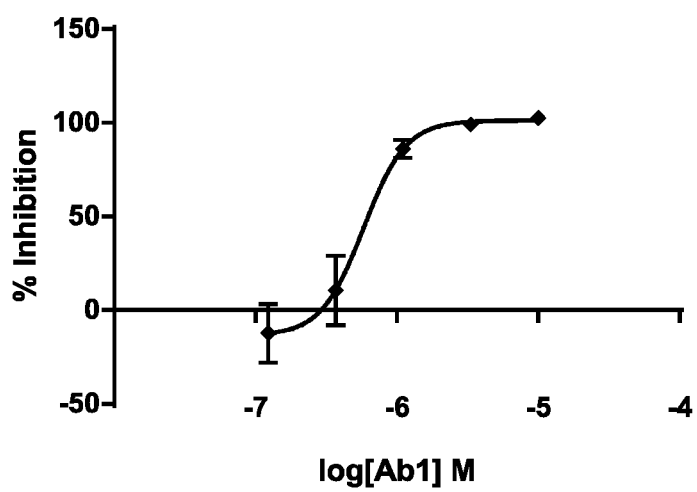
FIGS. 3A-3C show that Ab1 blocks cleavage of pro-myostatin by members of the tolloid family of proteases. Latent myostatin samples, preincubated with increasing amounts of Ab1, were analyzed in a myostatin activation assay. Following analysis of myostatin release by reporter assay (FIG. 3A), samples were then run under reducing conditions and probed by western blot with an antibody raised towards the prodomain of myostatin (FIG. 3B). An ~18 kDa band (box), corresponding to the ARM portion of the prodomain generated after tolloid cleavage, decreased proportionally with increasing doses of Ab1. The latent and pro-myostatin standards (45 ng loaded) show the migration of pro-myostatin at ~50 kDa, and the prodomain at ~37 kDa.
Figure 3B:
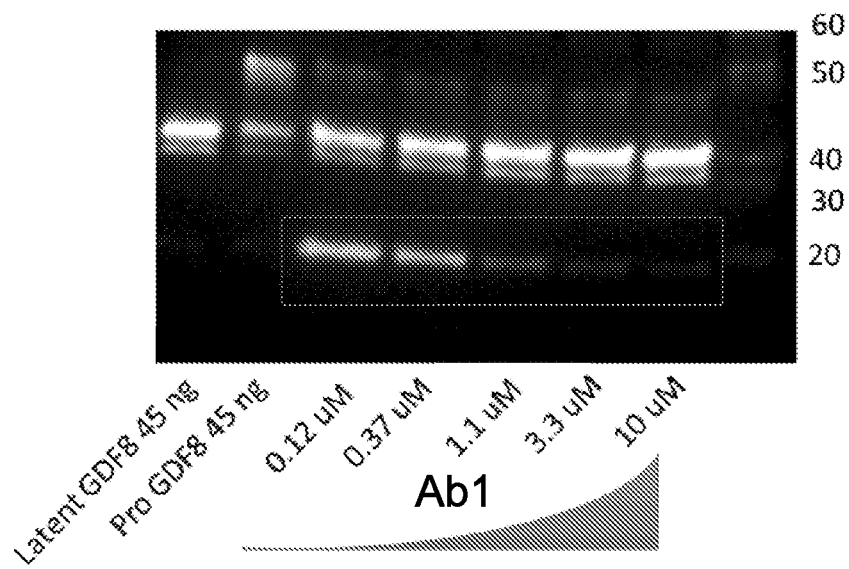
Figure 3C:
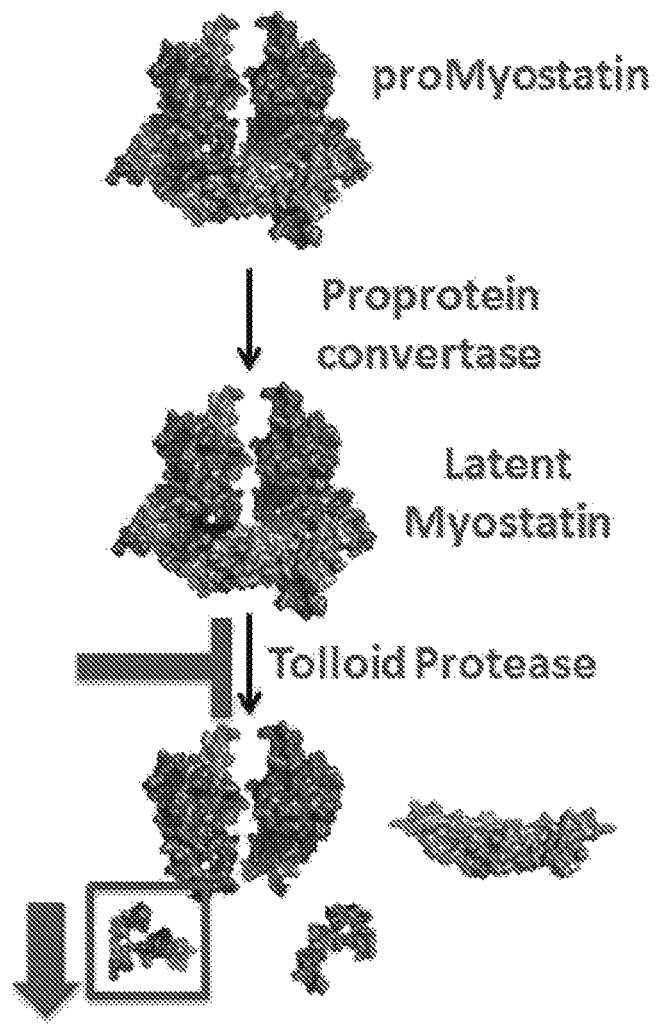

To determine the mechanism of action of antibody candidates, samples were analyzed by western blotting using a polyclonal antibody raised against the prodomain of myostatin, as shown in FIG. 3. This allowed for tracking of a fragment (boxed) of the myostatin prodomain which is generated after mTll2 cleavage. A dose-dependent decrease was seen in the generation of this fragment as the concentration of Ab1 is increased. This experiment indicates that the antibodies in epitope bin 1 act by blocking the cleavage of pro- and latent-myostatin by the tolloid family of proteases.

Based on the in vitro and in vivo activity of the active anti-pro/latent-myostatin antibodies, Ab1 was selected as the lead for further optimization, including affinity maturation, germlining and manufacturability analysis.

Optimization of Ab1

The Ab1 antibody was selected for further optimization. The affinity for pro/latent-myostatin was optimized using yeast display. Additionally, the sequence of Ab1 was germlined to reduce the potential immunogenicity liability of non-germline amino acid positions within the human variable regions frameworks.

Affinity Optimization of Ab1 by Yeast Display

Figure 23A:
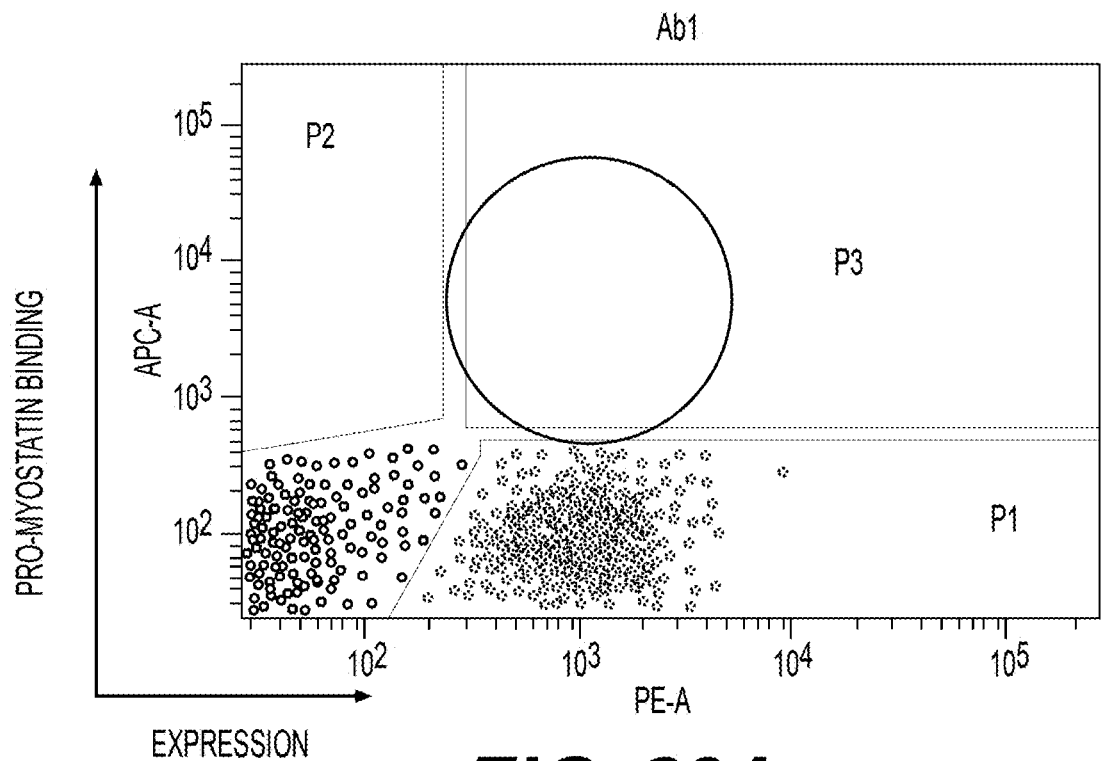
FIGS. 23A-23C show the optimization of Ab1. Optimized candidates which bind specifically to pro-myostatin were chosen, resulting in dozens of clones with increased affinity. FACS was performed to show the increased binding of the yeast clones (FIG. 23B) compared to Ab1 (FIG. 23A).
Figure 23B:
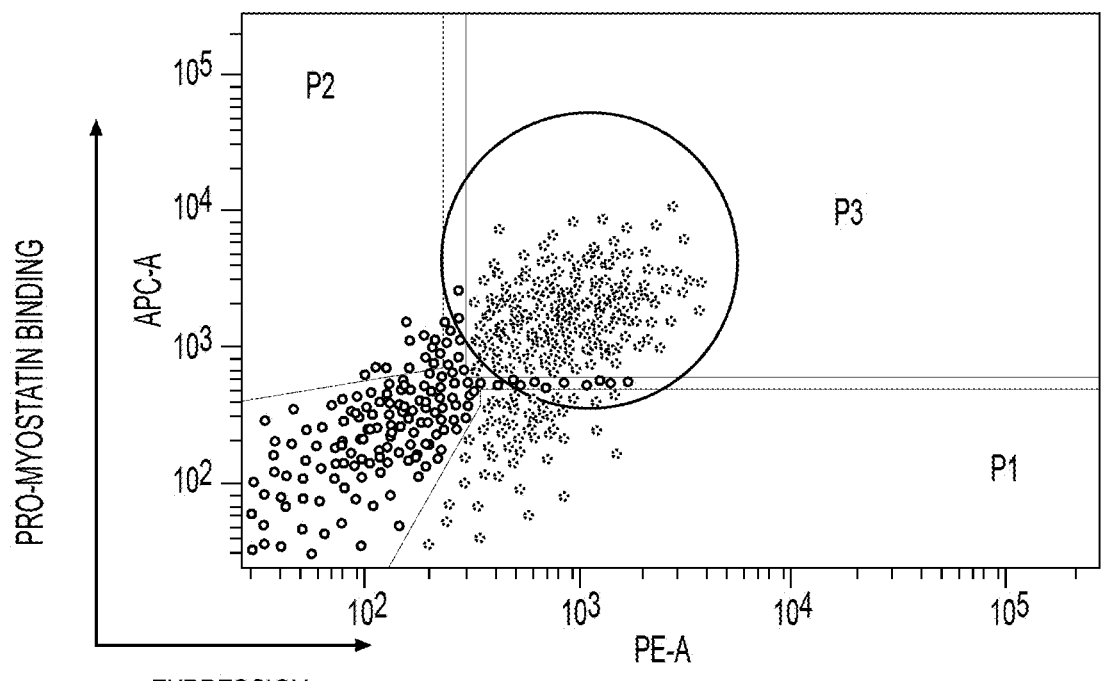
Figure 23C:
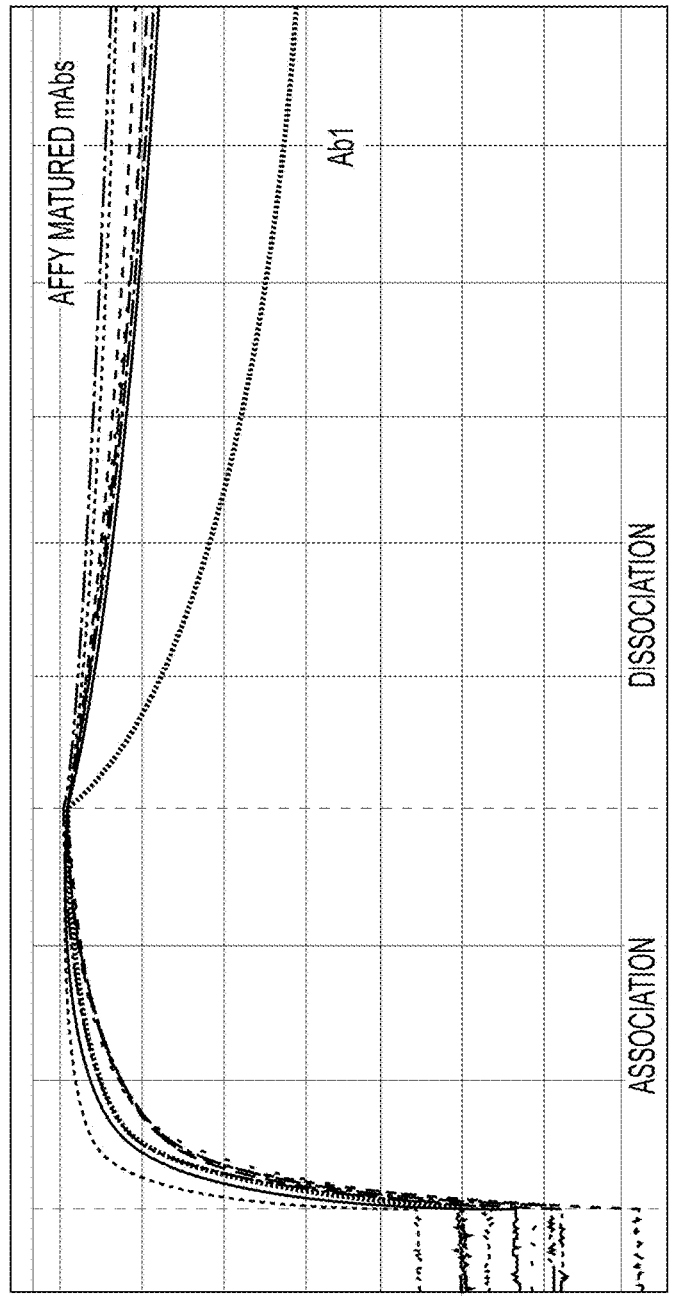

The Ab1 parental antibody was optimized for binding to pro/latent-myostatin using an scFv display approach based in yeast. Briefly, three different scFv libraries were created to introduce point mutations to selected CDR positions based on the amino acid frequency observed in natural human antibody repertoires using antibody deep sequencing corresponding to the human frameworks utilized by Ab1. Each library contained scFv based on the Ab1 sequence with single point mutations introduced in each CDR such that each variant of the resulting heavy chain or light chain would have three total substitutions, one in each CDR. The three libraries were used for FACS-based sorting and selection to identify pools of clones with higher binding affinity for pro/latent-myostatin (FIG. 23). Direct binding of yeast expressed scFv clones was used to select antibodies for conversion to full length IgG expressed in mammalian cell culture.

Many of the higher affinity scFv clones identified in the yeast campaign contained a substitution at position 28 of the heavy chain. For some clones, substitution of threonine to asparagine resulted in the incorporation of a non-canonical N-glycosylation motif within CDRH1. As N-glycosylation within the variable region of an antibody may be undesirable, any clone which contained a glycosylation motif was further substituted to contain alanine at this position.

The binding kinetics to pro- and latent-myostatin were then assessed by octet for each of the affinity optimized constructs and compared to that of the parental Ab1 (discussed in Example 2). All of the clones showed significantly increased binding affinity for myostatin, and two, Ab3 and Ab5, were selected based on the selective binding profile over GDF11.

Primary Sequence and Backbone of Anti-Pro/Latent-Myostatin Antibodies

The sequence alignment of the variable regions of parental Ab1 with its affinity optimized variants is shown below. Complementarity-determining regions (CDRs) are defined using the Kabat (underlined) and IMGT nomenclature (bold). Substitutions from parental Ab1 are shown in lower case red (below and FIG. 24A-24B).

```
A. Heavy Chain Variable Region
             FRAMEWORK 1            CDR1       FRAMEWORK 2
Ab1 parental QIQLVQSGGGVVQPGRSLRLSCAASGFTFSSYGMHWVRQAPGKGLEWVA
Ab3          QIQLVQSGGGVVQPGRSLRLSCAASGFaFSSYGMHWVRQAPGKGLEWVA
Ab5          QIQLVQSGGGVVQPGRSLRLSCAASGFaFSSYGMHWVRQAPGKGLEWVA
             CDR2                  FRAMEWORK 3
Ab1 parental VISYDGSNKYYADSVKGRFTISRDNSKNTLYLQMNSLRAEDTAVYYCAR
Ab3          VISYDGS1KYYADSVKGRFTISRDNSKNTLYLQMNSLRAEDTAVYYCAR
Ab5          VISYDGnNKYYADSVKGRFTISRDNSKNTLYLQMNSLRAEDTAVYYCAR
             CDR3              FRAMEWORK 4
Ab1 parental DLLVRFLEWSHYYGMDVWGQGTTVTVSS (SEQ ID NO: 24)
Ab3          DLLVRFLEWSHkYGMDVWGQGTTVTVSS (SEQ ID NO: 26)
Ab5          DLLVRFLEWSHkYGMDVWGQGTTVTVSS (SEQ ID NO: 28)

B. Light Chain Variable Region
             FRAMEWORK 1             CDR1        FRW2
Ab1 parental QPVLTQPPSASGTPGQRVTISCSGSSSNIGSNTVHWYQQLPGTAPKLLIY
Ab3          QPVLTQPPSASGTPGQRVTISCSGSSSNIGSNTVHWYQQLPGTAPKLLIY
Ab5          QPVLTQPPSASGTPGQRVTISCSGSSSNIGSNTVHWYQQLPGTAPKLLIY
             CDR2 FRAMEWORK 3
Ab1 parental SDNQRPSGVPDRFSGSKSGTSASLVISGLQSDDEADYYC
Ab3          SDgQRPSGVPDRFSGSKSGTSASLVISGLQSDDEADYYC
Ab5          SDgQRPSGVPDRFSGSKSGTSASLVISGLQSDDEADYYC
             CDR3         FRAMEWORK 4
Ab1 parental AAWDDSLNGVFGGGTKLTVL (SEQ ID NO: 30)
Ab3          AAWDeSLNGVFGGGTKLTVL (SEQ ID NO: 32)
Ab5          AAWDeSLNGVFGGGTKLTVL (SEQ ID NO: 34)
```

Antibody Engineering and Rationale for Isotype Selection

In some embodiments, an antibody useful for myostatin blockade will lack effector function. Thus for the humanized construct, an IgG4-Fc region was selected. Antibodies of the IgG4 isotype poorly bind complement C1q and therefore do not significantly activate complement. These antibodies also bind weakly to Fcγ receptors, leading to inefficient or absent antibody-dependent cell-mediated cytotoxicity (ADCC).

To avoid potential complication due to Fab-arm exchange, which is known to occur with native IgG4 mAbs, Ab1 and its variants were engineered with the stabilizing 'Adair' mutation (Angal, 1993), where serine 228 (EU numbering; residue 241 Kabat numbering) is converted to proline resulting in an IgG1-like (CPPCP (SEQ ID NO: 58)) hinge sequence. This engineered Fc-sequence is used in the production of the approved antibodies Keytruda, Mylotarg and Tysabri, as well as in a number of current late-stage clinical candidate mAbs.

Germlining and Immunogenicity Risk Assessment

Figure 22:
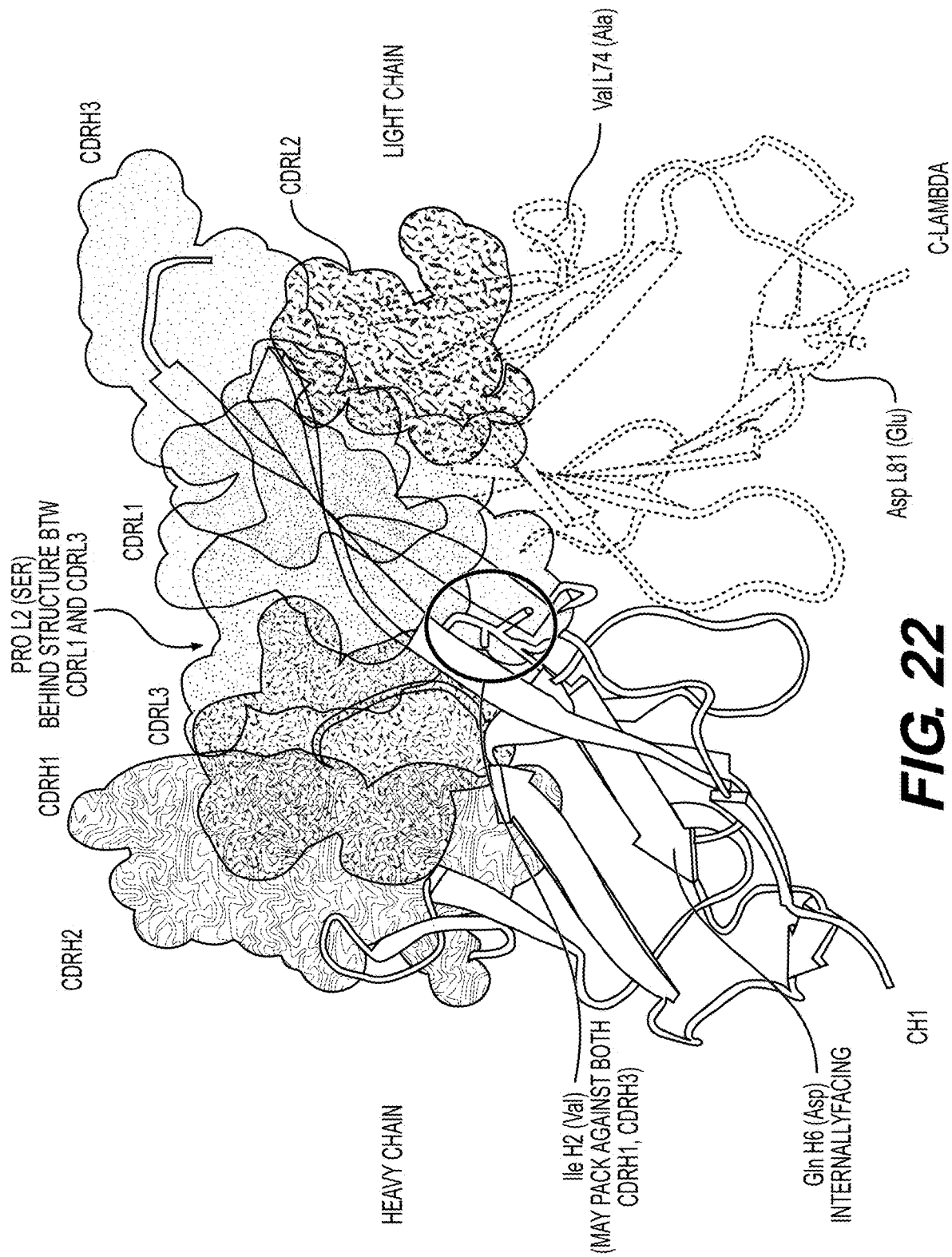
FIG. 22 is a schematic showing the reduced immunogenicity risk by germlining. 24H4 (WT) contains 5 non-germline amino acids within framework regions, as indicated in the schematic.

The Ab1 parental antibody and its variants are fully human IgG4 (S228P), lambda antibodies derived from phage display. The Fc portion of the antibody contains a single stabilizing mutation to prevent Fab arm exchange (described above). The IgG4 Fc is not expected to have measurable binding to Fc gamma receptors (see Example 2). The variable framework regions of Ab1 as isolated from the fully human naïve phage library contains five non-germline amino acids (see below and FIG. 22). Complementarity determining regions (CDRs) are defined using the Kabat nomenclature and are underlined. Non-germline residues are shown in lower case.

```
A. Heavy Chain Variable Region
            <-------------FR1-------------><CDR><-----FR2----><-----CDR2------>
    Ab1     QIQLVQSGGGVVQPGRSLRLSCAASGFTFSSYGMHWVRQAPGKGLEWVAVISYDGSNKYYADSVKG
    IgHV3-30 .v...e............................................................

<-------------FR3-------------><------CDR3-----><---FR4--->
    Ab1     RFTISRDNSKNTLYLQMNSLRAEDTAVYYCARDLLVRFLEWSHYYGMDVWGQGTTVTVSS
            (SEQ ID NO: 24)
    IgHV3-30 ............................. (SEQ ID NO: 36)
    JH6                                                      ................ (SEQ ID NO: 59)

B. Light Chain Variable Region
            <---------FR1--------><----CDR1---><-----FR2-----><CDR2>
    Ab1     QPVLTQPPSASGTPGQRVTISCSGSSSNIGSNTVHWYQQLPGTAPKLLIYSDNQRPS
    IgLV1-44 .s................................n................n.....

<-------------FR3-------------><--CDR3--><---FR4-->
    Ab1     GVPDRFSGSKSGTSASLVISGLQSDDEADYYCAAWDDSLNGVFGGGTKLTVL (SEQ ID NO: 30)
    IgLV1-44 ................s......e....... (SEQ ID NO: 60)
    JL1/2/3                                            ........... (SEQ ID NO: 61)
```

To mitigate the potential for immunogenicity, additional variants of Ab1 molecules were created which substitute the non-germline framework residues to their corresponding germline amino acids. In some embodiments, the substitution pertaining to Ab1 may be similarly applied to Ab3 and Ab4, or any antibody disclosed herein for which germlining is appropriate.

A sequence alignment of variable regions of Ab1 with its affinity optimized variants is shown below. A.) heavy chain, B.) light chain. Complementarity determining regions (CDRs) are defined using the Kabat (underlined) and IMGT nomenclature (bold). Framework regions substitutions present in parental Ab1 are shown in lower case.

```
A. Heavy Chain Variable Region
            FRAMEWORK 1                   CDR1         FRAMEWORK 2
IgHV3-30    QVQLVESGGGVVQPGRSLRLSCAASGFTFSSYGMHWVRQAPGKGLEWVA
Ab1         QlQLVqSGGGVVQPGRSLRLSCAASGFTFSSYGMHWVRQAPGKGLEWVA
Ab2         QVQLVESGGGVVQPGRSLRLSCAASGFTFSSYGMHWVRQAPGKGLEWVA
Ab4         QVQLVESGGGVVQPGRSLRLSCAASGFAFSSYGMHWVRQAPGKGLEWVA
Ab6         QVQLVESGGGVVQPGRSLRLSCAASGFSFSSYGMHWVRQAPGKGLEWVA
                CDR2                 FRAMEWORK 3
IgHV3-30    VISYDGSNKYYADSVKGRFTISRDNSKNTLYLQMNSLRAEDTAVYYCAR
Ab1         VISYDGSNKYYADSVKGRFTISRDNSKNTLYLQMNSLRAEDTAVYYCAR
Ab2         VISYDGSNKYYADSVKGRFTISRDNSKNTLYLQMNSLRAEDTAVYYCAR
Ab4         VISYDGSIKYYADSVKGRFTISRDNSKNTLYLQMNSLRAEDTAVYYCAR
Ab6         VISYDGNNKYYADSVKGRFTISRDNSKNTLYLQMNSLRAEDTAVYYCAR
                CDR3                FRAMEWORK 4
IgHV3-30    ---------------------------      (SEQ ID NO: 36)
Ab1         DLLVRFLFEWSHYYGMDVWGQGTTVTVSS    (SEQ ID NO: 24)
Ab2         DLLVRFLFEWSHYYGMDVWGQGTTVTVSS    (SEQ ID NO: 25)
Ab4         DLLVRFLFEWSHKYGMDVWGQGTTVTVSS    (SEQ ID NO: 27)
Ab6         DLLVRFLFEWSHKYGMDVWGQGTTVTVSS    (SEQ ID NO: 29)

B. Light Chain Variable Region
            FRAMEWORK 1                 CDR1        FRW2
IgLV1-44    QSVLTQPPSASGTPGQRVTISCSGSSSNIGSNTVNWYQQKPGTAPKLLIY
Ab1         QSVLTQPPSASGTPGQRVTISCSGSSSNIGSNTVNWYQQKPGTAPKLLIY
Ab2         QSVLTQPPSASGTPGQRVTISCSGSSSNIGSNTVNWYQQKPGTAPKLLIY
Ab4         QSVLTQPPSASGTPGQRVTISCSGSTSNIGSNTVNWYQQKPGTAPKLLIY
Ab6         QSVLTQPPSASGTPGQRVTISCSGSSSNIGGNTVNWYQQKPGTAPKLLIY
                CDR2         FRAMEWORK 3
IgLV1-44    SNNQRPSGVPDRFSGSKSGTSASLAISGLQSEDEADYYC
Ab1         SDNQRPSGVPDRFSGSKSGTSASLAISGLQSaDEADYYC
Ab2         SDNQRPSGVPDRFSGSKSGTSASLAISGLQSEDEADYYC
Ab4         SDDQRPSGVPDRFSGSKSGTSASLAISGLQSEDEADYYC
Ab6         SDDQRPSGVPDRFSGSKSGTSASLAISGLQSEDEADYYC
```

Three of the five substitutions were found to be away from CDR regions and therefore have no impact on binding. A Proline at position 2 of the light chain packs against CDRL3 and substitution to germline Serine actually improves binding to pro/latent-myostatin by stabilizing the CDR conformation.

The overall antibody is greater than 99% human (calculated as 100% minus the % non-germline AA excluding CDRH3). There are no chemical conjugations. The heavy chain CDRH2 sequence contains a potential isomerization liability (Asp-Gly) which is also present in the germline IgHV3-30 sequence.

Example 2: Pharmacological Characterization

In Vitro Pharmacological Assays

A total of 24 optimized Ab1 variants were expressed and purified as IgG4 and assayed for improved binding and functional activity. The changes to these molecules included germlining mutations to the parental variable region, along with mutations in the CDRs which conferred increased binding to pro/latent-myostatin in the affinity maturation screen (see Example 1).

The Ab1 variants were screened in several different ELISA-based assays, in which the binding to the pro-myostatin and latent myostatin proteins (human, murine, and cynomolgus) was re-assessed, along with a large screen of negative control proteins to verify that non-specific binding was not introduced as a result of the affinity maturation. Negative controls included GDF11 proteins (proGDF11, latent GDF11 and mature GDF11), TGFβ proteins, and Activin proteins (proActivin). Additionally, the antibodies were assessed for polyspecificity (which can lead to rapid clearance) in a screen similar to that published previously (Hotzel et al., 2012). Any antibodies with significant interactions to negative control proteins, or with baculovirus particles in the polyspecificity screen were not considered further as candidates for a development program.

The 24 optimized variants of Ab1 were also assessed in the pro-myostatin activation assay to determine their functional efficacy, and EC50 values from dose response curves were compared to the parental Ab1 antibody. Most antibodies had equivalent or improved EC50 values, with a few displaying reduced efficacy in this assay. Those with reduced efficacy in the activity assay were excluded from further analysis.

Three variants of Ab1 with improved binding to pro- and latent myostatin while retaining specificity for pro- and latent myostatin were identified. Binding and activity data for these three variants and the parental Ab1 molecule are summarized in Tables 4-7, sequences are shown in Example 1.

TABLE 6

Binding characteristics of antibodies to human/cynomolgus/mouse proMyostatin to parental Ab1 IgG4.

| | Ab1 | | | |
|---|---|---|---|---|
| | Activity Assay - 293T cells | Kinetics Analysis - Fortebio Octet | | |
| | EC50 (µM) | kon(1/Ms) | kdis(1/s) | Kd (M) |
| Human | 0.274 | 4.18E+05 | 1.99E-03 | 4.76E-09 |
| Cynomolgus | 0.5842 | 3.05E+05 | 1.75E-03 | 5.75E-09 |
| Mouse | 0.8386 | 2.37E+05 | 2.62E-03 | 1.10E-08 |

TABLE 7

Binding characteristics of antibodies to human/cynomolgus/mouse proMyostatin to Ab1 IgG4 with the correct germline residues replaced (Ab2) for non-germlined residues.

| | Ab2 | | | |
|---|---|---|---|---|
| | Activity Assay - 293T cells | Kinetics Analysis - Fortebio Octet | | |
| | EC50 (µM) | kon(1/Ms) | kdis(1/s) | Kd (M) |
| Human | 0.248 | 4.57E+05 | 1.56E-03 | 3.42E-09 |
| Cynomolgus | 0.6168 | 2.78E+05 | 1.41E-03 | 5.08E-09 |
| Mouse | 0.7138 | 2.35E+05 | 1.97E-03 | 8.39E-09 |

TABLE 8

Binding characteristics of antibodies to human/cynomolgus/mouse proMyostatin to Ab3 IgG4 containing the corrected germline residues (Ab4).

| | Ab4 | | | |
|---|---|---|---|---|
| | Activity Assay - 293T cells | Kinetics Analysis - Fortebio Octet | | |
| | EC50 (µM) | kon(1/Ms) | kdis(1/s) | Kd (M) |
| Human | 0.179 | 4.98E+05 | 2.35E-04 | 4.72E-10 |
| Cynomolgus | 0.4451 | 3.01E+05 | 2.34E-04 | 7.76E-10 |
| Mouse | 0.4466 | 2.53E+05 | 2.72E-04 | 1.08E-09 |

TABLE 9

Binding characteristics of antibodies to human/cynomolgus/mouse proMyostatin to Ab5 IgG4 containing the corrected germline residues (Ab6).

| | Ab6 | | | |
|---|---|---|---|---|
| | Activity Assay - 293T cells | Kinetics Analysis - Fortebio Octet | | |
| | EC50 (nM) | kon(1/Ms) | kdis(1/s) | Kd (M) |
| Human | 0.151 | 5.27E+05 | 2.51E-04 | 4.77E-10 |
| Cynomolgus | 0.4037 | 3.50E+05 | 2.57E-04 | 7.35E-10 |
| Mouse | 0.3068 | 2.94E+05 | 2.81E-04 | 9.54E-10 |

Cell-Based, Ex Vivo and In Vivo Biological Activity Assays

Figure 4:
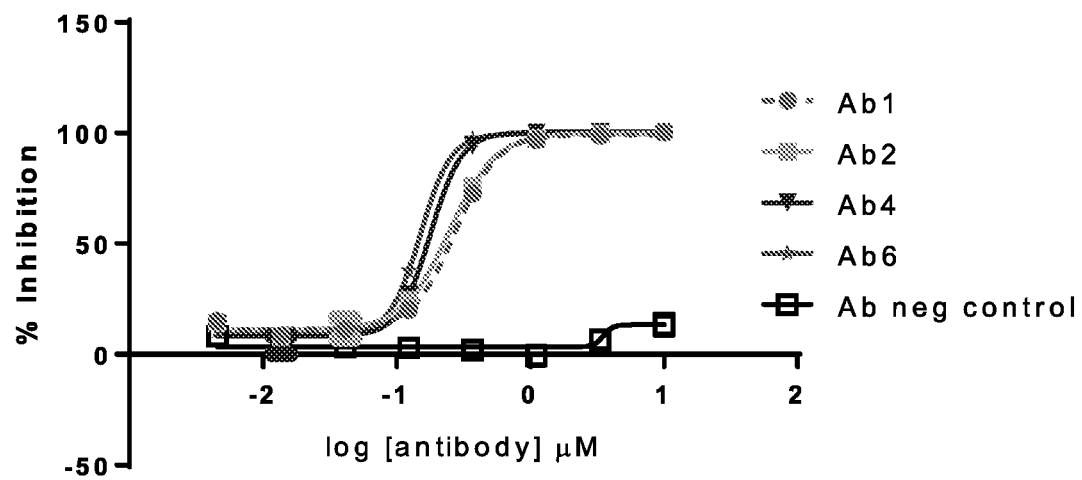
FIG. 4 shows the performance of the parental Ab1 antibody and other candidates in the cell-based reporter assay. Following an overnight proteolysis reaction with enzymes from both the proprotein-convertase and tolloid protease families, the release of mature growth factor was measured using a CAGA-based reporter assay in 293T cells. Results were compared to control reactions to calculate the fraction of pro-myostatin or proGDF11 which was released in the assay. Standard deviation for an average of 3 replicates is shown, but not visible on the graph for most data points due to their low magnitude.
Figure 5:
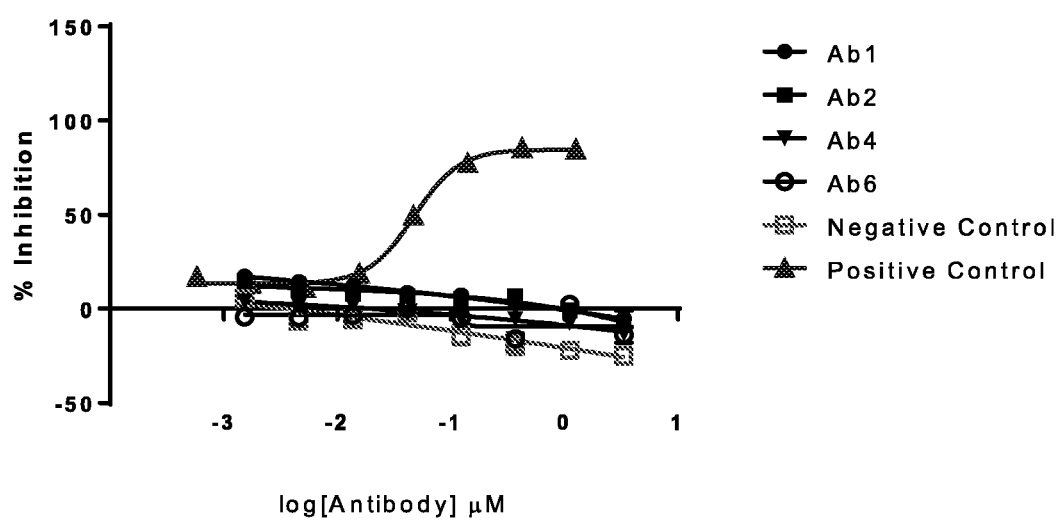
FIG. 5 shows graphically that Ab1, Ab2, Ab4, and Ab6 antibodies do not inhibit proGDF11 activation.

Ab1 optimized variants were assessed in the GDF8 activation assay in a dose response study. In these experiments, 0.5 µM pro-myostatin was pre-incubated with increasing amounts of the test article. Following this pre-incubation step, conditioned media from HEK293 cells overexpressing the mTll2 and Furin proteases was added to release the mature growth factor from pro-myostatin. Following incubation at 30° C. overnight, the material was added to 293T cells carrying a SMAD-based luciferase reporter plasmid, and the activity of the released material was recorded. Data from a screen are shown in FIG. 4.

Selectivity for Myostatin Over Other TGFβ Family Members

The selectivity of the candidate antibodies was also assessed by both binding and functional assays to verify the lack of cross reactivity to other members of the TGFβ family. Human myostatin and GDF11 share 90% identity in the mature growth factor domain, and 47% identity in the prodomain regions. From the epitope mapping studies, it was determined that the parental Ab1 molecule recognizes an epitope on the prodomain of pro-myostatin and latent myostatin because ELISA assays have shown binding of this antibody to a construct consisting of the prodomain of myostatin. Even though the prodomains of myostatin and GDF11 share less than 50% identity, and we do not expect significant cross reactivity, the specificity of the lead antibodies was carefully assessed.

A sensitive assay for detecting interactions between the antibodies of interest and negative control reagents was developed. In this assay, biotinylated proGDF11 or biotinylated pro-myostatin was immobilized on a ForteBio BLI streptavidin-coated sensor tip, which was applied to wells containing 30 µg/mL of antibody. Interactions of the analyte with the protein immobilized on the chip are measured by the magnitude of the response of the biosensor chip. The biosensor response after 5 minutes of association (a saturating signal for proGDF8) was compared between the two antigens, and expressed as the percent response for GDF8 binding. AU antibodies had minimal interactions with proGDF11, compared to the robust binding events measured for pro-myostatin.

TABLE 10

Interactions with proGDF11 at high concentrations of the candidate molecules

| | GDF11 response, expressed as a percentage of GDF8 response |
|---|---|
| Ab1 | 1.33% |
| Ab2 | 0.81% |
| Ab4 | 2.51% |
| Ab6 | 2.07% |

The antibody candidates were also evaluated in a GDF11 activation assay. In this assay, 50 nM proGDF11 is preincubated with increasing concentrations of the antibody. Following preincubation, conditioned medium from HEK293 cells overexpressing BMP-1 (a tolloid family protease) and PCSK5 (a furin family member specific for GDF11) was added to proteolytically activate proGDF11. Following overnight incubation at 30° C., the reaction mixtures are assessed for GDF11 activity in a SMAD-based reporter cell line. As is shown in Table 10, the anti-myostatin antibodies do not inhibit proGDF11 activation, while a positive control antibody imparts dose-dependent inhibition of GDF11 activation.

Binding affinities of antibody candidates were determined using the ForteBio Octet QKe dip and read label free assay system utilizing bio-layer interferometry. Antigens were immobilized to biosensors (streptavidin-coated biosensors for proGDF8, proGDF11 and proActivin; direct amine coupling for all others) in each experiment and the antibodies/ constructs were presented in solution at high concentration (50 μg/mL) to measure binding interactions.

TABLE 11

Comparison of antibodies for binding to different forms of several TGFβ family members.

|  | Ab2 | Ab4 | Ab6 | Ab1 |
|---|---|---|---|---|
| Pro GDF8 | 7.35E–09 | 9.24E–10 | 8.89E–10 | 6.23E–09 |
| Latent GDF8 | 7.84E–09 | 1.10E–09 | 1.12E–09 | 9.06E–09 |
| Mature GDF8 | – | – | – | – |
| Pro GDF11 | – | *1.25E–07 | *6.07E–08 | – |
| Mature GDF11 | – | – | – | – |
| Pro Activin A | – | – | – | – |
| Mature Activin A | – | – | – | – |
| BMP 9 | – | – | – | – |
| BMP10 | – | – | – | – |
| Mature TGFB1 | – | – | – | – |

*Non-specific binding.

Results from an antigen binding study are summarized in Table 11. There are some calculated Kd values which were fitted to data with poor binding response, which is indicated in the table as weak non-specific binding.

As the proGDF8 sample used in Table 11 contained approximately 10-15% latent GDF8, a separate experiment was used to confirm proGDF8 binding to human and murine GDF8 antigens specifically. In addition, primed GDF8, in which proGDF8 is proteolytically cleaved by both a pro-protein convertase and tolloid protease was also assessed for binding affinity to Ab2 and AbMyo. For these experiments, a homogenous preparation of human proGDF8 was purified from stably integrated 293 cells cultured in the presence of 30 μM decanoyl-RVKR-CMV. Primed human GDF8 was produced by in-vitro cleavage of proGDF8 utilizing conditioned media from mTll2-overexpressing cells and purified Furin protease. In the binding experiments with these proteins, 150 nM of Ab2 or AbMyo was used to saturate the immobilization sites on human Fc capture tips (FortéBio), and the association and dissociation of 150 nM analyte was evaluated.

Analysis of binding affinities to murine proteins were also assessed and are reported in Table 12. Murine proGDF8 protein was produced by removing all mature and latent murine GDF8 from the sample via negative selection with an antibody that tightly recognizes latent and mature GDF8 (AbMyo2), 50 nM of antibody was used to saturate an anti-human Fc capture tip (FortéBio). Initially, all antibodies were tested against a single 200 nM concentration of murine proGDF8, murine latent GDF8, and mature GDF8. If binding was observed, a Kd value was determined by immobilizing the antibody as previously described and using analyte in titration from 200 to 0.82 nM by 3-fold dilutions. The Kd was determined using a global fit with FortéBio data analysis software 8.2. For binding to mature myostatin, 5 ug/mL of growth factor (R&D systems) was coupled to amine reactive sensor tips (FortéBio) in acetate buffer at pH 5. All antibodies were initially tested at 333 nM for binding to this myostatin-coupled sensor. Antibodies that showed binding were then tested in concentrations ranging from 333 to 1.37 nM by 3-fold dilutions. A global fit was used to determine the Kd of the interaction using FortéBio data analysis 8.2.

TABLE 12

Comparison of antibodies for binding to different forms of human and murine GDF8.

|  | Ab2 | AbMyo |
|---|---|---|
| Human Pro GDF8 | 2.9E–09 | — |
| Human latent GDF8 | 2.4E-9 | 3.87E–10 |
| Human primed GDF8 | 8.66E–09 | 8.83E–10 |
| Mature GDF8 | — | 4.7E–11 |
| Murine ProGDFS | 2.3E–09 | — |
| Murine Latent GDF8 | 2.0E–09 | <1E–12 |

Results from an antigen binding study are summarized in Table 12. Experiments with no detectable binding are noted by a minus sign (–). Some values, labeled as <1 E-12, had very slow dissociation rates making the high affinity unable to be quantified. Surprisingly, AbMyo was unable to recognize recombinant proGDF8, which is different than results reported in Latres ea a/2015, in which the authors reported association of AbMyo with proGDF8 in an immunoprecipitation experiment from serum of mice that were dosed with the antibody which could produce artifacts. Another surprising result is the interaction between Ab2 and primed GDF8, a complex of GDF8 with tolloid-cleaved prodomain. This result is unexpected because Ab2 blocks tolloid cleavage of the prodomain and suggests that the interaction of Ab2 with proGDF8 and latent GDF8 does not require an intact tolloid cleavage site.

Evaluation of Fc-Region Functionality

In some embodiments, anti-pro/latent-myostatin therapy involves binding to a soluble target (pro/latent-myostatin) and preventing proteolytic activation. In some embodiments, antibody dependent cell-mediated cytotoxicity and complement fixation are not involved in this process. Ab1 and its related variants were engineered to contain an IgG4-Fc region. It is understood that IgG4 antibodies generally lack effector function due to their weak binding to complement component C1q and Fcγ receptors.

To demonstrate the reduced capacity for effector function, Ab1 and related antibodies were tested for binding to CD64 (FcgRI) and C1q by ELISA. For comparison, an IgG1 variant of Ab1 was also prepared. In this assay, all IgG4 antibodies showed significantly weaker binding (10- to 20-fold) to CD64 and C1q compared to IgG1. The relative binding values at the EC50 are listed in Table 13.

TABLE 13

Relative binding affinities of Ab2 and related antibodies to CD64.

| Antibody | Isotype | Relative CD64 Binding @ EC50(%) | Relative C1q Binding @ EC50(%) |
|---|---|---|---|
| Ab1-G1 | IgG1 | 100 | 100 |
| Ab1 | IgG4 (S228P) | 10 | ND |
| Ab2 | IgG4 (S228P) | 5 | 8 |
| Ab3 | IgG4 (S228P) | 5 | 5 |
| Ab5 | IgG4 (S228P) | 8 | 9 |

Not determined

The apparent binding affinities of Ab1 and its related variants to CD64 and C1q are similar to other IgG4 clinical candidate antibodies, and are considerably reduced compared to antibodies of the IgG1 isotype. Based on the biology of IgG4 antibodies, it is therefore concluded that the anti-pro/latent-myostatin antibodies will not induce appreciable effector function in vivo.

Efficacy in Animal Models

Based on in vitro characterization, four antibodies were chosen to test in an in vivo study (Ab7, Ab1, Ab8 and Ab9). The objective of the study was to assess the ability of these four candidate antibodies to modulate muscle mass mice. Five (5) groups of ten (10) female SCID mice received test article administration by intraperitoneal (IP) injection once per week on Days 0, 7, 14, 21, 28, and 35. Prior to test article administration (Day 0), all animals underwent grip strength evaluation. Grip strength evaluation was also performed on the last day of the study (Day 42). On Day 0, blood was collected via retro-orbital bleed for assessment of complete blood counts (CBC). Following dosing, animals were evaluated daily for body weight and general health observations. On Day 42, following grip strength assessment, animals were sacrificed via $CO_2$ overdose and blood was collected via cardiac puncture for CBC assessment. Additional blood was collected for the preparation of plasma. Various tissues were isolated and weighed. The muscles collected were: gastrocnemius, pectoralis, soleus, triceps, tibialis anterior, quadriceps (rectus femoris) and diaphragm. The organs collected were: heart, kidney, spleen, liver and inguinal white adipose tissue. All tissues were weighed and snap frozen except for the gastrocnemius muscles which were fixed in formalin (leg 1) and OCT (leg 2) for histologic analysis.

Summary

Figure 6:
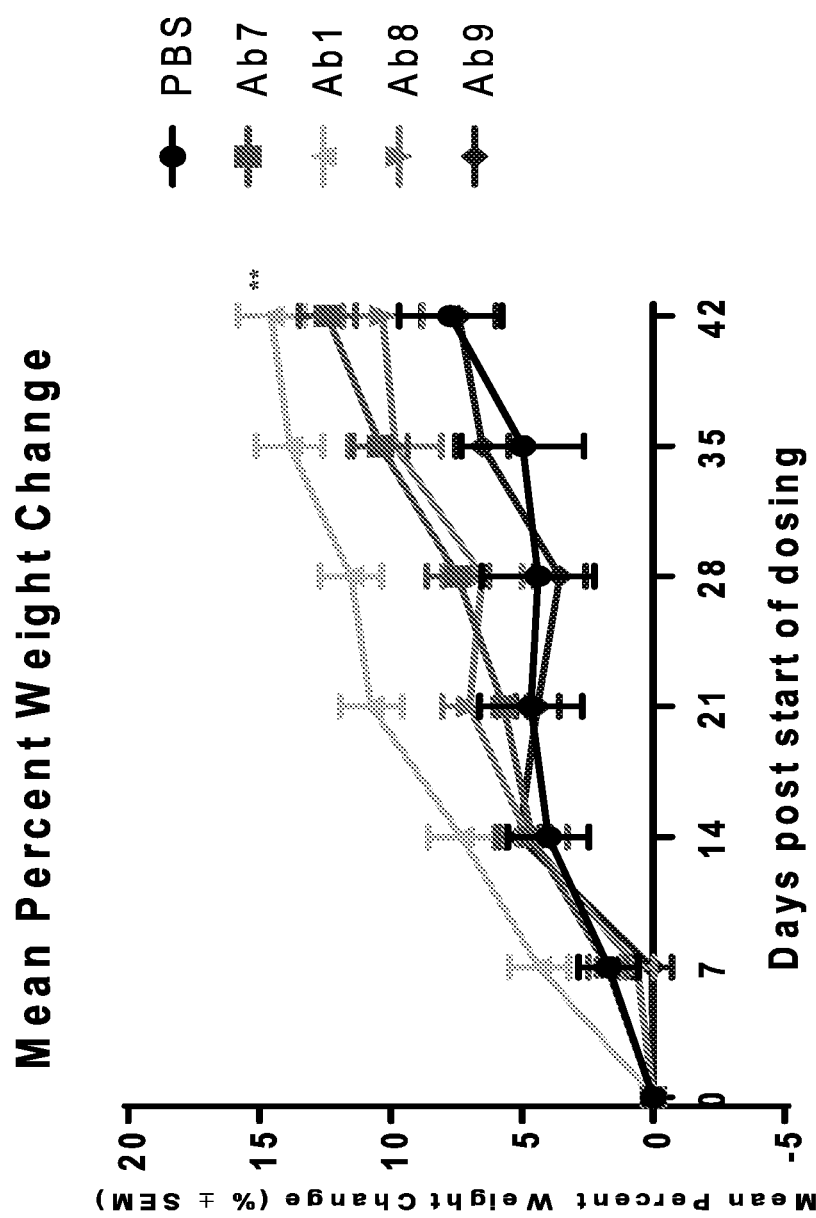
FIG. 6 shows results of an assay evaluating mean percent body weight change. Animals were weighed daily and the percent weight change from Day 0 was calculated. Data represent group means±SEM. The mean percent change data for each group on day 42 of the study were analyzed using a one-way ANOVA followed by Holm-Sidak's post hoc test in comparison to the PBS Control Group, **p<0.01.

The mean daily percent weight change data for animals in study SCH-02 are shown in FIG. 6. Animals in all five groups gained weight on a weekly basis. Animals treated with the antibody Ab1 had the largest increase in body weight (14.6%) as depicted in FIG. 6. Only animals treated with Ab1 had a statistically significant increase in mean percent body weight change in comparison to animals in the vehicle (PBS) control group (FIG. 6).

Figure 8A:
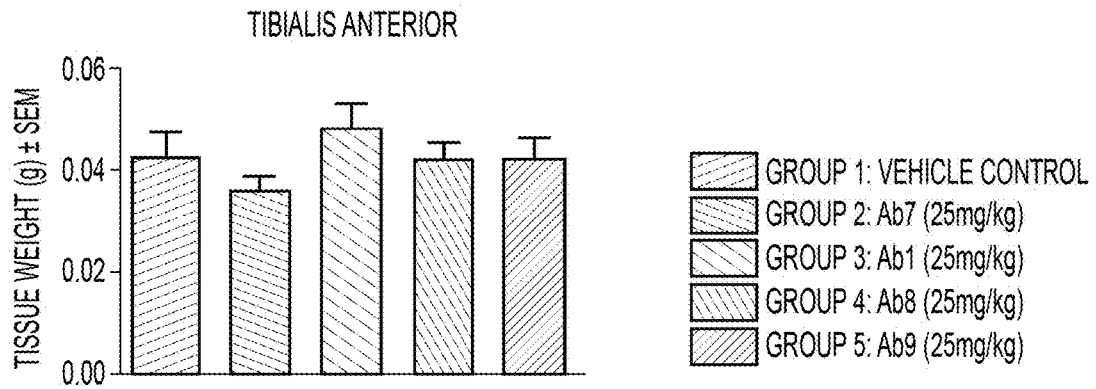
FIGS. 8A-8C show results of an assay evaluating tissue weights.
Figure 8B:
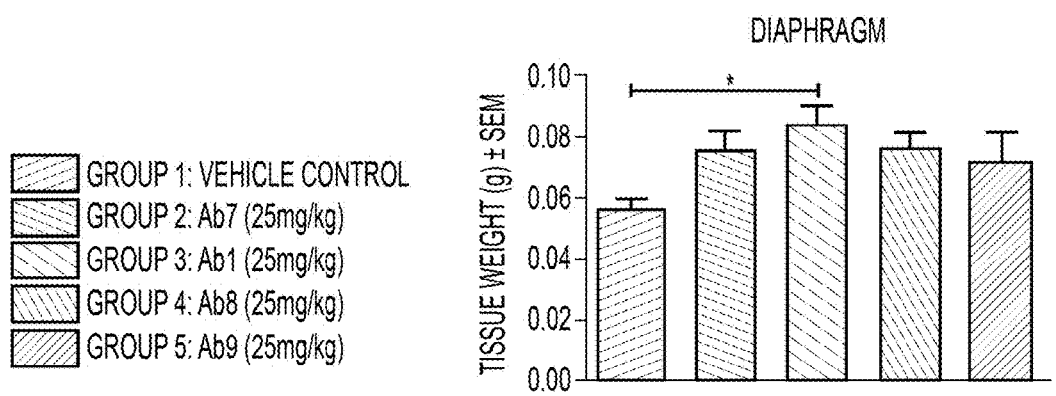
Figure 8C:
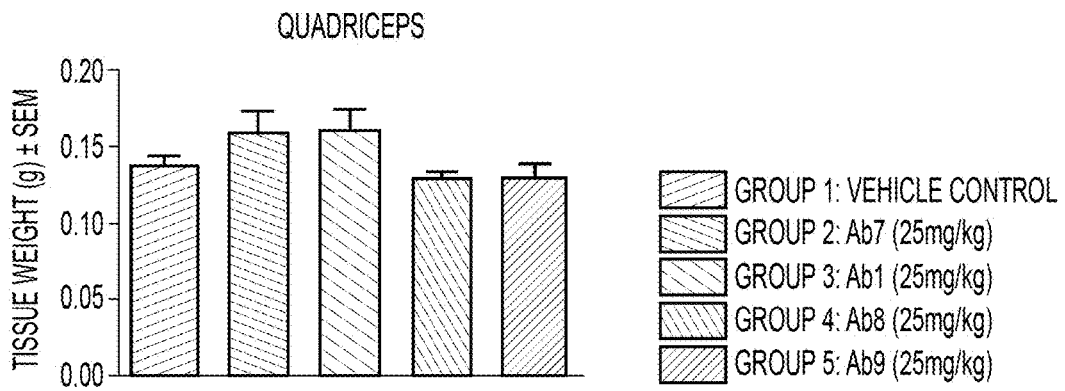

The weights for the dissected muscles are plotted in FIGS. 7 and 8. Animals treated with Ab1 had statistically significant increases in gastrocnemius (FIG. 7A) and diaphragm (FIG. 8B) weights compared to vehicle (PBS) control treated animals, 27.6% and 49.8%, respectively. Additional muscles from Ab1 treated animals showed increases in weight compared to the PBS control, but these differences were not statistically significant. There were no statistically significant differences between treatment groups for the mean tissue weights of heart, spleen, kidney, liver, and adipose tissue.

SCID Dose Response Study

In the in vivo study (above) animals dosed with Ab1 at 25 mg/kg once weekly for 6 weeks showed statistically significant increases in body weight and muscle weights (gastrocnemius and diaphragm) compared to animals dosed with the vehicle (PBS). This muscle enhancing activity of Ab1 was next investigated in more detail in a dose response study in SCID mice. In this study, whether the magnitude of the effect on muscle mass could be increased by increasing the dose of Ab1 to as high as 60 mg/kg/wk and whether the magnitude of the effect on muscle mass could be decreased by decreasing the dose of Ab1 to as low as 2 mg/kg/wk were examined. In this study, the activity of Ab1 was compared to two more antibodies (Ab8, which was originally tested in the study described above Ab10).

Ten (10) groups of ten (10) female SCID mice received test article administration by intraperitoneal (IP) injection (10 ml/kg) twice per week on Days 0, 3, 7, 10, 14, 17, 21, and 24. The doses of test articles were as follows: Ab1 (30 mg/kg, 10 mg/kg, 3 mg/kg and 1 mg/kg), Ab10 (10 mg/kg and 3 mg/kg), and Ab8 (10 mg/kg and 3 mg/kg). Control groups were dosed with PBS and IgG-control (30 mg/kg). Treatment groups are described in Table 14. Animals were 10 weeks old at the start of the study. Body weight was measured on day −4 and twice per week throughout the study, corresponding with dosing days. Body mass composition parameters (fat mass, lean mass and water content) were measured by Echo MRI (QNMR) on days −4, 7, 14, 21 and 28. Thirty (30) days after the first dose of antibody, animals were sacrificed via $CO_2$ overdose and blood was collected via cardiac puncture for CBC assessment and plasma preparation. Additionally, upon study termination, various tissues were isolated and weighed. The muscles collected were: gastrocnemius, soleus, tibialis anterior, quadriceps (rectus femoris) and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the gastrocnemius muscles which were fixed in formalin (left leg) and OCT (right leg) for histologic analysis.

TABLE 14

Study design

| Treatment Group | Test Article dose | # doses per week | Total dose per week | Animal IDs |
|---|---|---|---|---|
| 1 | PBS Control | 2 | 0 | 1-10 |
| 2 | IgG Control (30 mg/kg) | 2 | 60 mg/kg/wk | 11-20 |
| 3 | Ab1 (30 mg/kg) | 2 | 60 mg/kg/wk | 21-30 |
| 4 | Ab1 (10 mg/kg) | 2 | 20 mg/kg/wk | 31-40 |
| 5 | Ab1 (3 mg/kg) | 2 | 6 mg/kg/wk | 41-50 |
| 6 | Ab1 (1 mg/kg) | 2 | 2 mg/kg/wk | 51-60 |
| 7 | Ab10 (10 mg/kg) | 2 | 20 mg/kg/wk | 61-70 |
| 8 | Ab10 (3 mg/kg) | 2 | 6 mg/kg/wk | 71-80 |
| 9 | Ab8 (10 mg/kg) | 2 | 20 mg/kg/wk | 81-90 |
| 10 | Ab8 (3 mg/kg) | 2 | 6 mg/kg/wk | 91-100 |

Figure 9A:
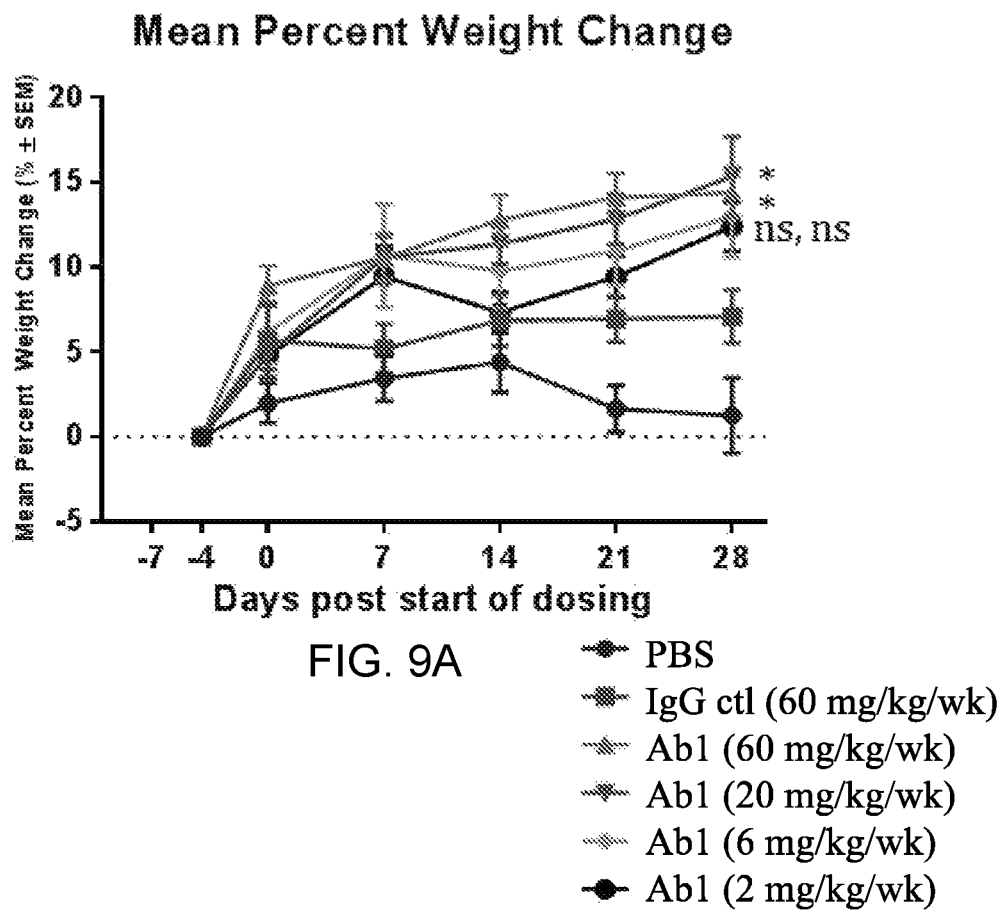
FIGS. 9A-9B show results of an assay evaluating mean percent body weight and lean mass change.
Figure 9B:
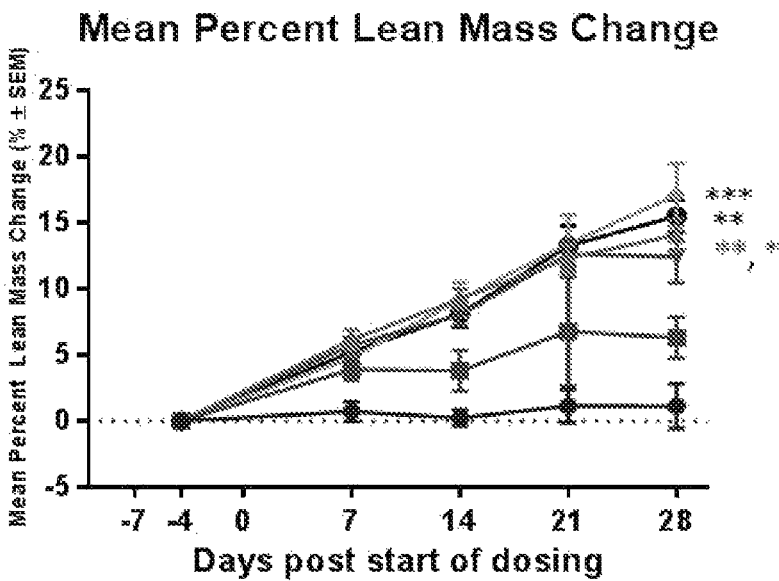

Mean percent weight change and mean percent lean mass change data for animals treated with vehicle (PBS), IgG control and different doses of Ab1 are shown in FIG. 9. Animals treated with Ab1 at 20 and 60 mg/kg/wk doses had significant increases in body weight on day 28 of the study compared to IgG control treated animals, 15.3% and 14.4%, respectively (FIG. 9A). All four groups of animals treated with Ab1 (60, 20, 6 and 2 mg/kg/wk doses) had statistically significant increases in lean mass on day 28 of the study compared to IgG control treated animals, 14.1%, 12.4%, 17.1%, and 15.5%, respectively (FIG. 9B).

Figures 10A, 10B:
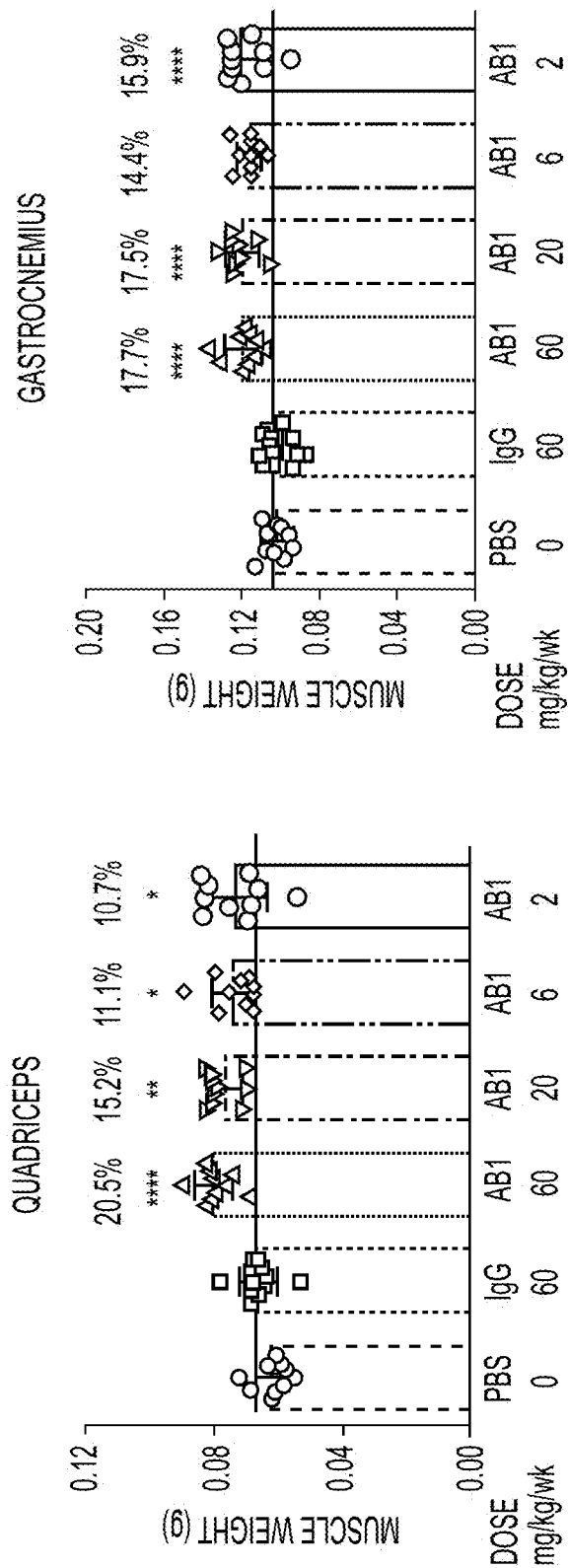
FIGS. 10A-10D are graphs showing results of an assay evaluating muscle weights.
Figures 10C, 10D:
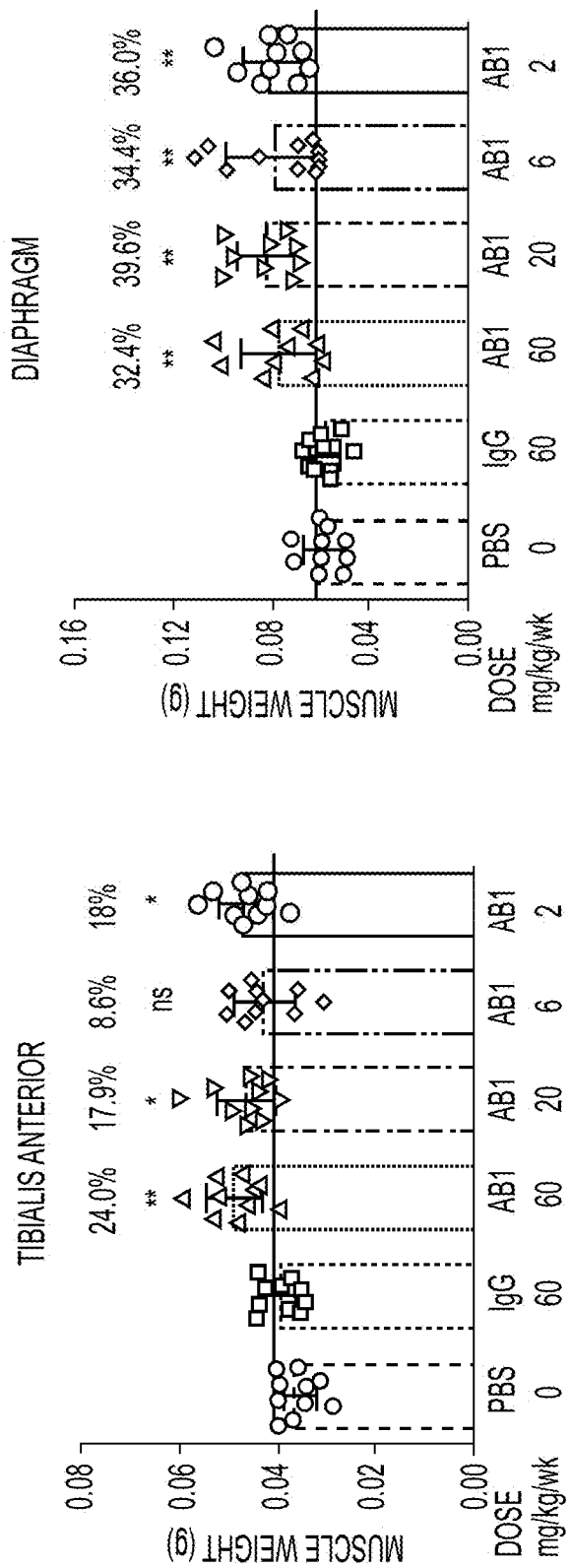

The weights for four muscles (quadriceps (rectus femoris), gastrocnemius, tibialis anterior and diaphragm) are plotted in FIG. 10. The soleus muscle was also dissected, but the small size of the muscle resulted in an extremely variable data set. Animals treated with all doses of Ab1 had statistically significant increases in muscle weights compared to IgG control animals (FIG. 10). The mean percent changes in muscle mass compared to IgG control are shown above the corresponding bar on each muscle graph. Mean percent weight changes for quadriceps (rectus femoris) muscle ranged from 20.5% for the highest dose to 10.7% for the lowest dose (FIG. 10A). Mean percent weight changes for gastrocnemius muscle ranged from 17.7% for the highest dose to 15.9% for the lowest dose (FIG. 10B). Mean percent weight changes for tibialis anterior muscle ranged from 24.0% for the highest dose to 18.0% for the lowest dose (FIG. 10C). Mean percent weight changes for diaphragm muscle were greater than 30% for all dose groups (FIG. 10D). There were no statistically significant differences between treatment groups for the mean tissue weights of heart, spleen, kidney, liver, and adipose tissue.

Anti-Myostatin Antibody Treatment in a Dexamethasone Induced Muscle Atrophy Model Given the ability of the anti-myostatin antibody Ab1 to build muscle mass in healthy SCID mice, it was determined whether Ab1 treatment could also protect animals from treatments that induce muscle atrophy. A model of corticosteroid-induced muscle atrophy was established by treating animals for two weeks with dexamethasone in their drinking water. The dose chosen (2.5 mg/kg/day) was able to induce significant decreases in lean body mass and the mass of individual hindlimb muscles. In the following experiment, animals were treated with different doses of Ab1 to determine if it could protect animals from this dexamethasone-induced muscle atrophy.

In this study, eight (8) groups of ten (10) male mice (C57BL/6) were enrolled in the study at 13.5 weeks of age. Starting on day 0 of the study, mice were given either normal drinking water (groups 1-4) or water containing dexamethasone (groups 5-8). Test articles were administered by intraperitoneal (IP) injection (10 ml/kg) twice per week on Days 0, 3, 7, and 10. The test articles and doses were as follows: PBS (groups 1 and 5), 10 mg/kg IgG Ctl (groups 2 and 6), 10 mg/kg Ab1 (groups 3 and 7), and 1 mg/kg Ab1 (groups 4 and 8). Treatment groups are described in Table 15. Body weight was measured at least twice per week throughout the study. Body mass composition parameters (fat mass, lean mass and water content) were measured by Echo MRI (QNMR) on days −1, 6, and 13. Fourteen (14) days after the first dose of antibody, animals were sacrificed via $CO_2$ overdose and blood was collected via cardiac puncture for plasma preparation. Additionally, upon study termination, various tissues were isolated and weighed. The muscles collected were: gastrocnemius, soleus, tibialis anterior, quadriceps (rectus femoris) and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the gastrocnemius muscles which were fixed in formalin (left leg) and OCT (right leg) for histologic analysis.

animals in the non-diseased control group (group 1) and the dexamethasone treated groups (groups 5-8) are shown in FIG. 11. There were no significant differences in mean percent body weight change between any of these treatment groups on day 14 (FIG. 11A). Treatment of mice with dexamethasone for two weeks led to a significant decrease in lean body mass (groups 5 and 6) compared to a control group (group 1) that was given normal drinking water (FIG. 11B). However, mice treated with both dexamethasone and the antibody Ab1 at 20 mg/kg/wk (group 7) showed no significant difference in percent change in lean body mass on day 14 of the study compared to the control group (group 1). Animals treated with Ab1 at 20 mg/kg/wk, but not 2 mg/kg/wk, showed a significant difference in percent change in lean body mass on day 14, when compared to either of the dexamethasone treated control groups (groups 5 and 6).

Figure 12C:
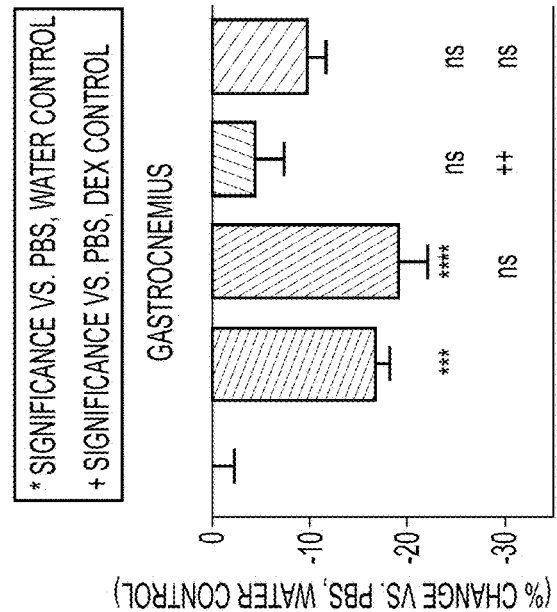
Figure 12D:
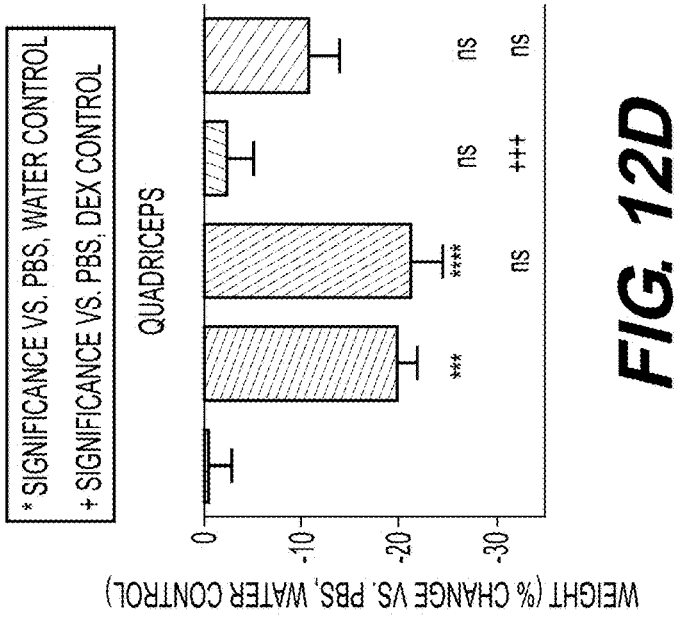

At the end of the two-week treatment with dexamethasone and the test articles, individual muscles were dissected and weighed. The weight data for two muscles (gastrocnemius and quadriceps (rectus femoris)) are plotted in FIGS. 12A-12B. Animals that received dexamethasone via their drinking water and also received either PBS or IgG Control antibody showed significant atrophy in gastrocnemius and quadriceps (rectus femoris) muscles (groups 5 and 6) compared to the non-diseased control group (group 1). Animals treated with both dexamethasone and Ab1 at 20 mg/kg/wk (group 7), but not 2 mg/kg/wk, showed a significant difference in muscle weights when compared to either of the dexamethasone treated control groups (groups 5 and 6). In addition, mice treated with both dexamethasone and the antibody Ab1 at 20 mg/kg/wk (group 7) showed no significant difference in gastrocnemius and quadriceps (rectus femoris) weights when compared to the non-diseased control group (group 1). The mean percent difference in muscle weight of each group compared to the mean muscle weight of the control group (group 1, PBS and water) is shown in FIGS. 12C-12D. The percent decreases in gastrocnemius mass induced by dexamethasone treatment in the PBS and IgG Ctl groups were 16.5% and 18.9%, respectively. In contrast, animals treated with both dexamethasone and 20 mg/kg/wk of Ab1 only had a 4.0% decrease in gastrocnemius muscle mass which was not statistically different from the non-diseased control group (group 1). While animals treated with both dexamethasone and 2 mg/kg/wk Ab1 (group 8) only had a 10% decrease in gastrocnemius muscle mass, the muscle mass decrease for this group was not

TABLE 15

Treatment groups for Dexamethazone-induced atrophy model study

| Treatment Group | Dexamethasone in drinking water | Test Article dose | # doses per week | Total dose per week | Animal IDs |
|---|---|---|---|---|---|
| 1 | none | PBS Control | 2 | 0 | 1-10 |
| 2 | none | IgG Control (10 mg/kg) | 2 | 20 mg/kg/wk | 11-20 |
| 3 | none | Ab1 (10 mg/kg) | 2 | 20 mg/kg/wk | 21-30 |
| 4 | none | Ab1 (1 mg/kg) | 2 | 2 mg/kg/wk | 31-40 |
| 5 | 2.5 mg/kg/day | PBS Control | 2 | 0 | 51-60 |
| 6 | 2.5 mg/kg/day | IgG Control (10 mg/kg) | 2 | 20 mg/kg/wk | 61-70 |
| 7 | 2.5 mg/kg/day | Ab1 (10 mg/kg) | 2 | 20 mg/kg/wk | 71-80 |
| 8 | 2.5 mg/kg/day | Ab1 (1 mg/kg) | 2 | 2 mg/kg/wk | 81-90 |

In this experiment it was determined whether treatment of mice with the anti-myostatin antibody Ab1 could protect animals from corticosteroid induced muscle atrophy. During the study body weight was measured twice weekly and lean mass by QNMR on days −1, 6 and 13. The mean percent weight change and mean percent lean mass change data for statistically different than the decreases for the PBS and IgG control groups (groups 5 and 6). Similar results were seen for the quadriceps (rectus femoris) muscle (FIG. 12D).

Ab1 Treatment in a Casting Induced Muscle Atrophy Model

Given the ability of the anti-myostatin antibody Ab1 to build muscle mass in healthy SCID mice, whether Ab1 treatment could also protect animals from treatments that induce muscle atrophy was investigated. A model of disuse atrophy was established by casting the right leg of mice for two weeks. Casting the right leg with the foot in a plantar flexion position for this time period was able to induce significant decreases in the mass of individual hindlimb muscles. In the following experiment animals were treated with different doses of Ab1 to determine the extent to which it protects animals from this casting induced muscle atrophy.

TABLE 16

Treatment groups for casting-induced atrophy model study

| Treatment Group | Casting | Test Article dose | # doses per week | Total dose per week | Animal IDs |
|---|---|---|---|---|---|
| 1 | No cast | PBS Control | 2 | 0 | 1-10 |
| 2 | No cast | IgG Control (10 mg/kg) | 2 | 20 mg/kg/wk | 11-20 |
| 3 | No cast | Ab1 (10 mg/kg) | 2 | 20 mg/kg/wk | 21-30 |
| 4 | No cast | Ab1 (1 mg/kg) | 2 | 2 mg/kg/wk | 31-40 |
| 5 | Casted | PBS Control | 2 | 0 | 51-60 |
| 6 | Casted | IgG Control (10 mg/kg) | 2 | 20 mg/kg/wk | 61-70 |
| 7 | Casted | Ab1 (10 mg/kg) | 2 | 20 mg/kg/wk | 71-80 |
| 8 | Casted | Ab1 (1 mg/kg) | 2 | 2 mg/kg/wk | 81-90 |

In this study, eight (8) groups of ten (10) male mice (C57BL/6) were enrolled in the study at 14.5 weeks of age. Starting on day 0 of the study, mice were placed under anesthesia and a cast was applied to the right hindlimb with the foot in a plantar flexion position (groups 5-8). The control groups (groups 1-4) were also placed under anesthesia but no cast was placed on the hindlimb. Test articles were administered by intraperitoneal (IP) injection (10 ml/kg) twice per week on Days 0, 3, 7, and 10. The test articles and doses were as follows: PBS (groups 1 and 5), 10 mg/kg IgG Ctl (groups 2 and 6), 10 mg/kg Ab1 (groups 3 and 7), and 1 mg/kg Ab1 (groups 4 and 8). Treatment groups are described in Table 16. Body weight was measured at least twice per week throughout the study. Body mass composition parameters (fat mass, lean mass and water content) were measured by Echo MRI (QNMR) on days −1, 7, and 14. Fourteen (14) days after the first dose of antibody, animals were sacrificed via $CO_2$ overdose and blood was collected via cardiac puncture for plasma preparation.

Additionally, various tissues were isolated and weighed. The muscles collected were: gastrocnemius, soleus, plantaris, tibialis anterior, and quadriceps (rectus femoris). For analysis the weights of the individual muscles from the right hindlimb of the animals were collected. The other tissues collected were: heart, adipose and spleen. All tissues were weighed and then snap frozen except for the gastrocnemius muscles which were fixed in formalin for histologic analysis.

Summary

Figure 13B:
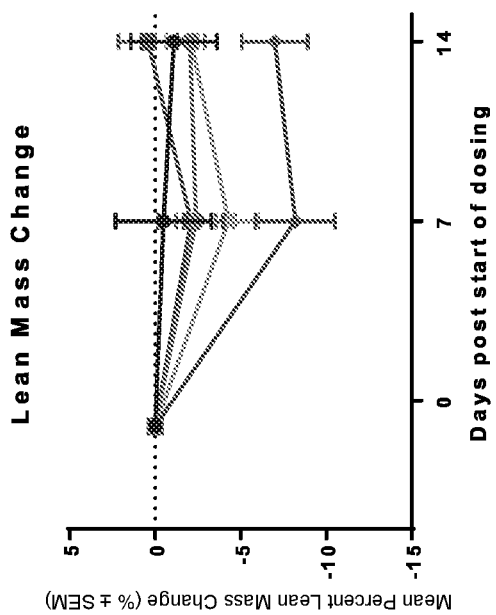
FIGS. 13A-13B show results of an assay evaluating the mean percent body weight and lean mass change.
Figure 13A:
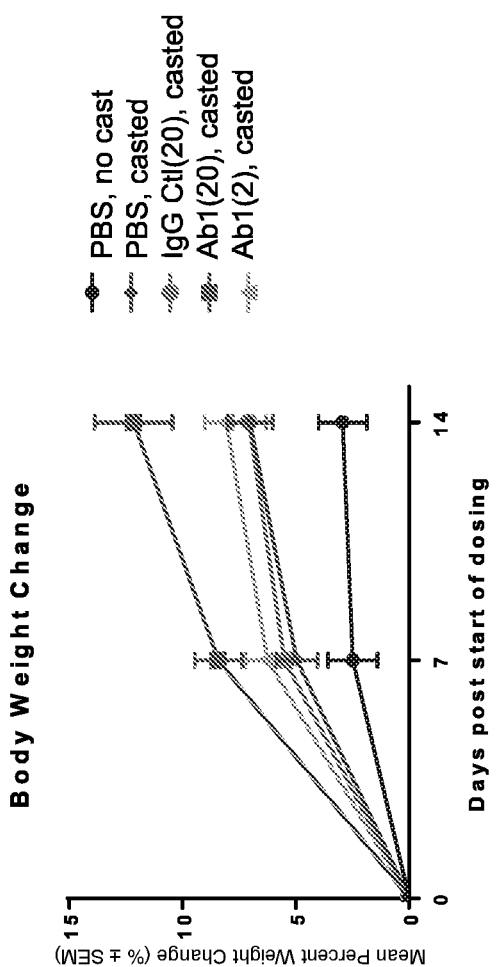

In this experiment, whether treatment of mice with the anti-myostatin antibody Ab1 could protect mice from disuse muscle atrophy induced by casting of the right hindlimb was tested. During the study, body weight was measured twice weekly and lean mass was measured by QNMR on days −1, 7 and 14. The mean percent weight change and mean percent lean mass change data for animals in the non-diseased control group (group 1) and the groups that were casted for two weeks (groups 5-8) are shown in FIG. 13. Casting of the right hind limb did not have any negative effects on body weight gain (FIG. 13A) and any differences in lean mass of groups were not significant (FIG. 13B).

Figure 14B:
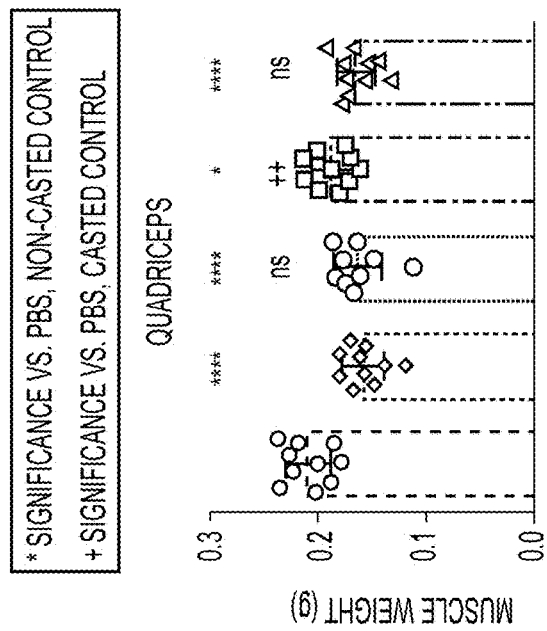
FIGS. 14A-14D show results of an assay evaluating muscle weights.
Figure 14A:
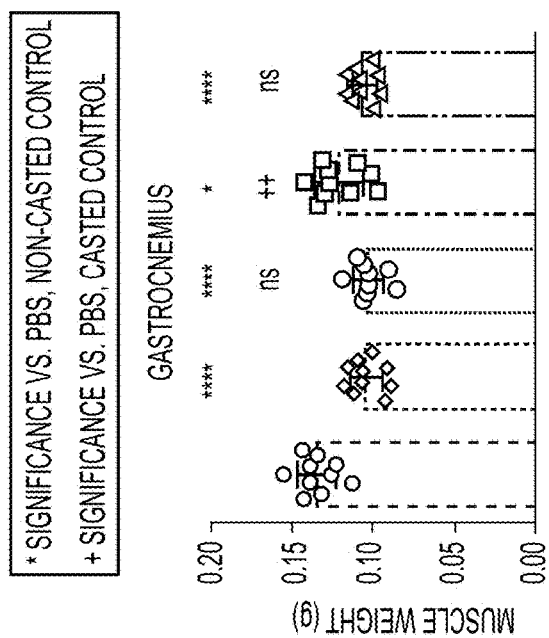
Figures 14C, 14D:
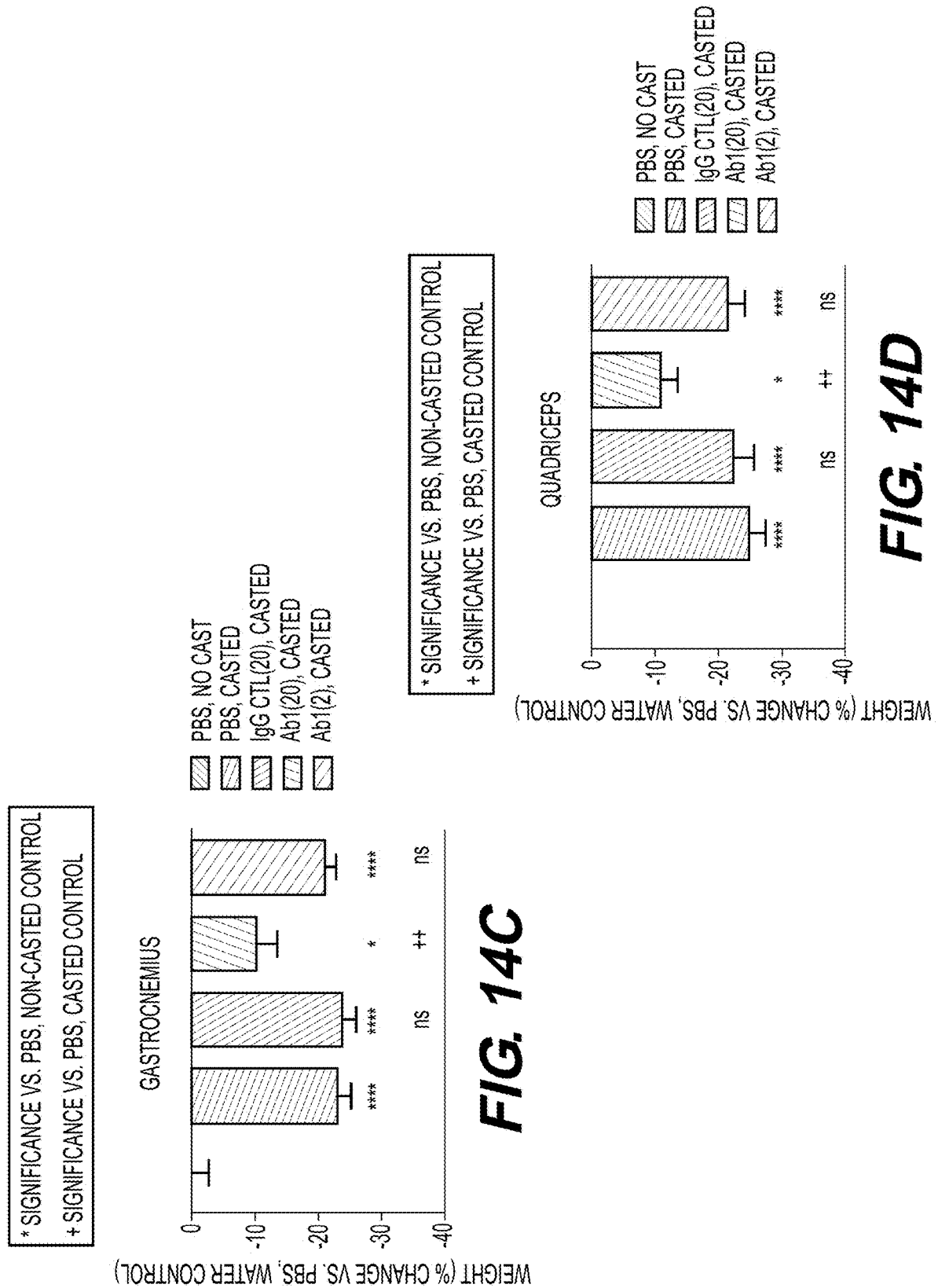

At the end of the two-week study individual muscles were dissected and weighed. The weight data for two muscles (gastrocnemius and quadriceps (rectus femoris)) are plotted in FIGS. 14A-14B). Animals that bad their leg casted and also received either PBS or IgG Control antibody showed significant atrophy in gastrocnemius and quadriceps (rectus femoris) muscles (groups 5 and 6) compared to the non-casted control group (group 1). Animals that were both casted and dosed with Ab1 at 20 mg/kg/wk (group 7), but not 2 mg/kg/wk, showed a significant difference in muscle weights when compared to either of the casted control groups (groups 5 and 6). In addition, casted mice that were treated with the antibody Ab1 at 20 mg/kg/wk (group 7) showed no significant difference in gastrocnemius and quadriceps (rectus femoris) weights when compared to the non-casted control group (group 1). The mean percent difference in muscle weight of each group compared to the mean muscle weight of the non-casted control group (group 1) is shown in FIGS. 14C-14D. The percent decreases in gastrocnemius mass induced by casting in the PBS and IgG Ctl groups were 22.8% and 23.5%, respectively. In contrast, casted mice that were treated with 20 mg/kg/wk of Ab1 only had a 10.0% decrease in gastrocnemius muscle mass. This difference was found to be statistically different from the casted control groups that received PBS and IgG Ctl antibody (group 5 and 6). The muscle mass decrease for the casted mice treated with 2 mg/kg/wk Ab1 was not statistically different than the decreases for the PBS and IgG control groups (groups 5 and 6). Similar results were seen for the quadriceps (rectus femoris) muscle (FIG. 14D).

Figures 16A, 16B:
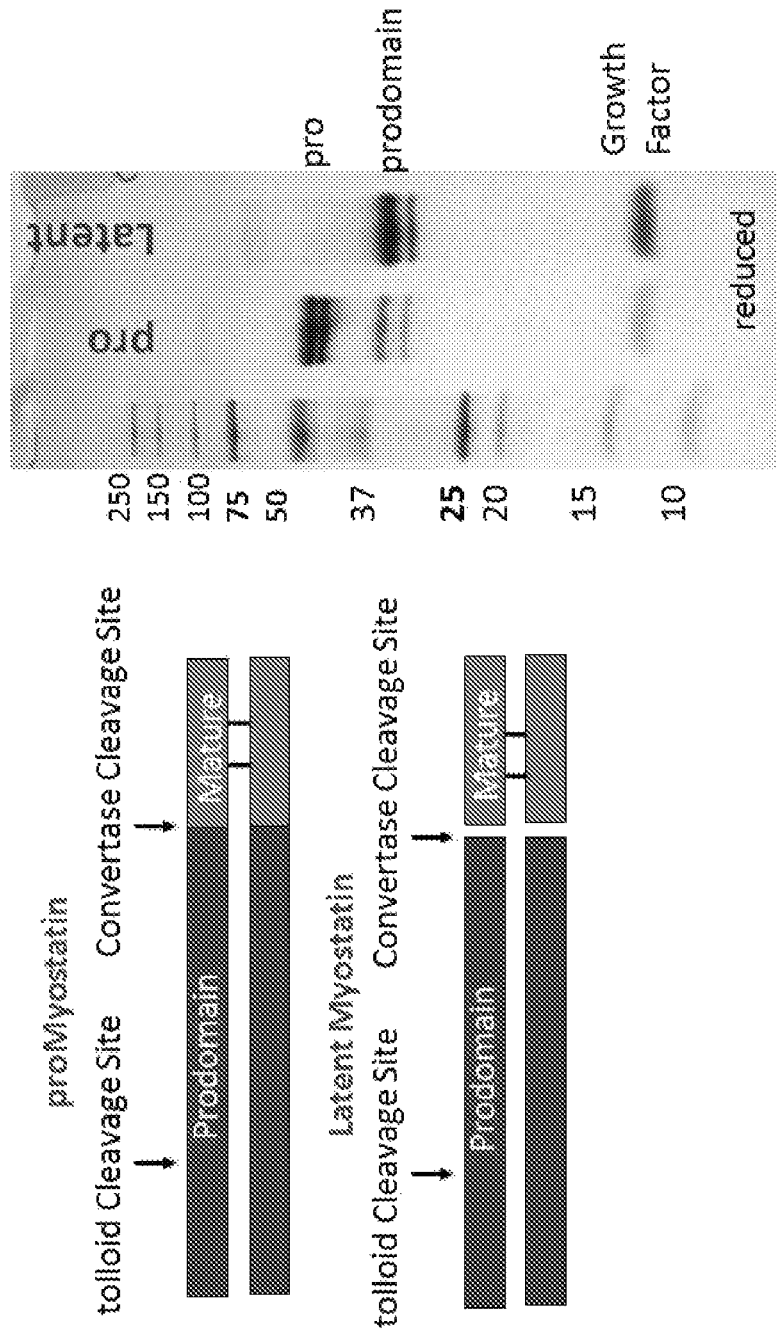
FIGS. 16A-16B show the domain structure and evaluation of myostatin precursor forms.

The domain structure of pro-myostatin and latent myostatin, with protease cleavage sites indicated, is shown in FIG. 16A. An example of partially proprotein convertase cleaved pro-myostatin run on an SDS PAGE gel is shown in FIG. 16B. Under reducing conditions, the protein bands consisted of the pro-myostatin monomer (~50 kD), prodomain (~37 kD) and growth factor (12.5 kD).

Figure 17B:
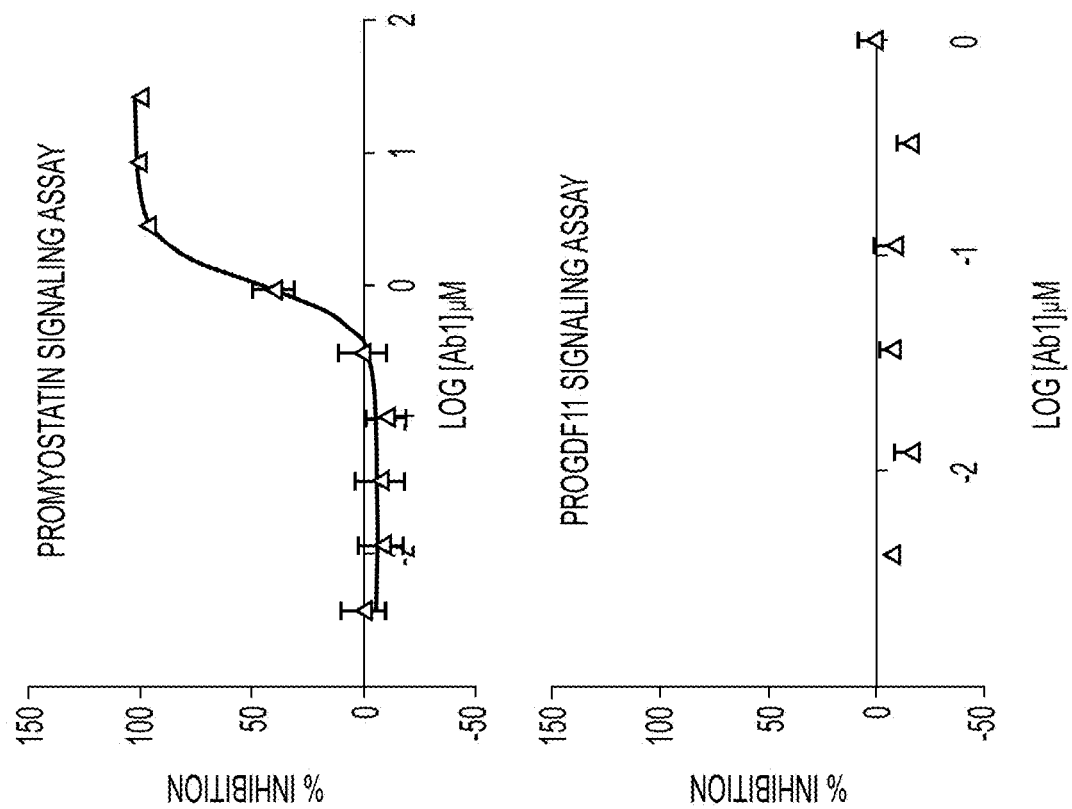
FIGS. 17A-17B show Ab1 is specific for myostatin.
Figure 17A:
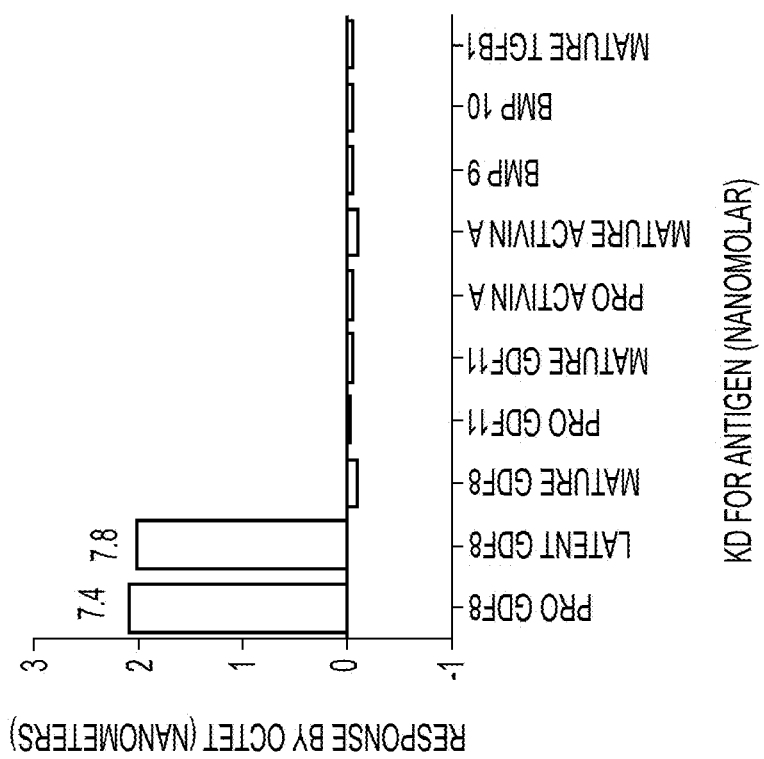

Ab1 binds specifically to pro-myostatin and latent myostatin, with no binding observed to other members of the TGFβ superfamily, most notably the corresponding forms of GDF11 (FIG. 17A). Ab1 was administered at a high concentration (50 ug/mL) to Forte-Bio BLI tips coated with the indicated antigen and the on and off rates were measured to obtain an approximate Kd value. The magnitude of biosensor response, indicating a binding event, is graphically represented by black bars, and the calculated Kd is indicated in orange. Furthermore Ab1 blocks the activation of pro-myostatin, but not proGDF11 (FIG. 17B).

SCID Dose Response Study with Ab1, Ab2, Ab4 and Ab6

The previous in vivo studies with Ab1 have demonstrated that Ab1 can increase muscle mass in healthy animals as well as prevent muscle loss in mouse models of muscle atrophy (dexamethasone and casting induced atrophy). Antibody engineering efforts identified three antibodies with in vitro characteristics that were better than Ab1. In this study, in SCID mice, the in vivo activity of these antibodies was compared at three different doses to the already established activity of Ab1.

Fourteen (14) groups of eight (8) female SCID mice received test article administration by intraperitoneal (IP) injection (10 ml/kg) twice per week on Days 0, 3, 7, 10, 14, 17, 21, and 24. The doses of test articles were as follows: Ab1, Ab2, Ab4 and Ab6 were given at 3 different doses (10 mg/kg, 1 mg/kg, and 0.25 mg/kg) and the IgG-Ctl antibody was given at 10 mg/kg. Treatment groups are described in Table 17. Animals were 10 weeks old at the start of the study. Body weight was measured twice per week throughout the study, corresponding with dosing days. Body mass composition parameters (fat mass, lean mass and water content) were measured by Echo MRI (QNMR) on days 0, 7, 14, 21 and 28. Twenty-eight (28) days after the first dose of antibody, animals were sacrificed via $CO_2$ overdose and blood was collected via cardiac puncture for plasma preparation.

Additionally, various tissues were isolated and weighed. The muscles collected were: gastrocnemius, soleus, tibialis anterior, quadriceps (rectus femoris), extensor digitorum longus, and diaphragm. Muscles were dissected from both the right and left legs of study mice. For analysis the weights of the individual muscles from both legs were combined and the average muscle weight in grams was calculated. The other tissues collected were: heart, kidney, spleen, liver and adipose tissue. All tissues were weighed and then snap frozen except for the left gastrocnemius muscles which was fixed in formalin for histologic analysis.

TABLE 17

Treatment groups for dose response model study

| Treatment Group | Test Article dose | # doses per week | Total dose per week | Animal IDs |
|---|---|---|---|---|
| 1 | PBS Control | 2 | 0 | 1-8 |
| 2 | IgG Control (10 mg/kg) | 2 | 20 mg/kg/wk | 9-16 |
| 3 | Ab1 (10 mg/kg) | 2 | 20 mg/kg/wk | 17-24 |
| 4 | Ab1 (1 mg/kg) | 2 | 2 mg/kg/wk | 25-32 |
| 5 | Ab1 (0.25 mg/kg) | 2 | 0.5 mg/kg/wk | 33-40 |
| 6 | Ab2 (10 mg/kg) | 2 | 20 mg/kg/wk | 41-48 |
| 7 | Ab2 (1 mg/kg) | 2 | 2 mg/kg/wk | 49-56 |
| 8 | Ab2 (0.25 mg/kg) | 2 | 0.5 mg/kg/wk | 57-64 |
| 9 | Ab4 (10 mg/kg) | 2 | 20 mg/kg/wk | 65-72 |
| 10 | Ab4 (1 mg/kg) | 2 | 2 mg/kg/wk | 73-80 |
| 11 | Ab4 (0.25 mg/kg) | 2 | 0.5 mg/kg/wk | 81-88 |
| 12 | Ab6 (10 mg/kg) | 2 | 20 mg/kg/wk | 89-96 |
| 13 | Ab6 (1 mg/kg) | 2 | 2 mg/kg/wk | 97-104 |
| 14 | Ab6 (0.25 mg/kg) | 2 | 0.5 mg/kg/wk | 105-112 |

Mean percent lean mass changes (from day 0) data for animals treated with vehicle (PBS), IgG control, and different doses of Ab1, Ab2, Ab4 and Ab6 are shown in FIG. 15. Animals treated with Ab1, Ab2, Ab4, and Ab6 at a 20 mg/kg/wk dose level had significant increases in lean mass on day 21 and day 28 of the study compared to IgG control and vehicle (PBS) treated animals. Animals treated with Ab1 and Ab2 at a 2 mg/kg/wk dose level also had significant changes in lean mass at day 21 and day 28 of the study. There were no significant changes in lean mass from the control groups for animals treated with Ab1, Ab2, Ab4 and Ab6 at a 0.5 mg/kg/wk dose level.

Figure 18A:
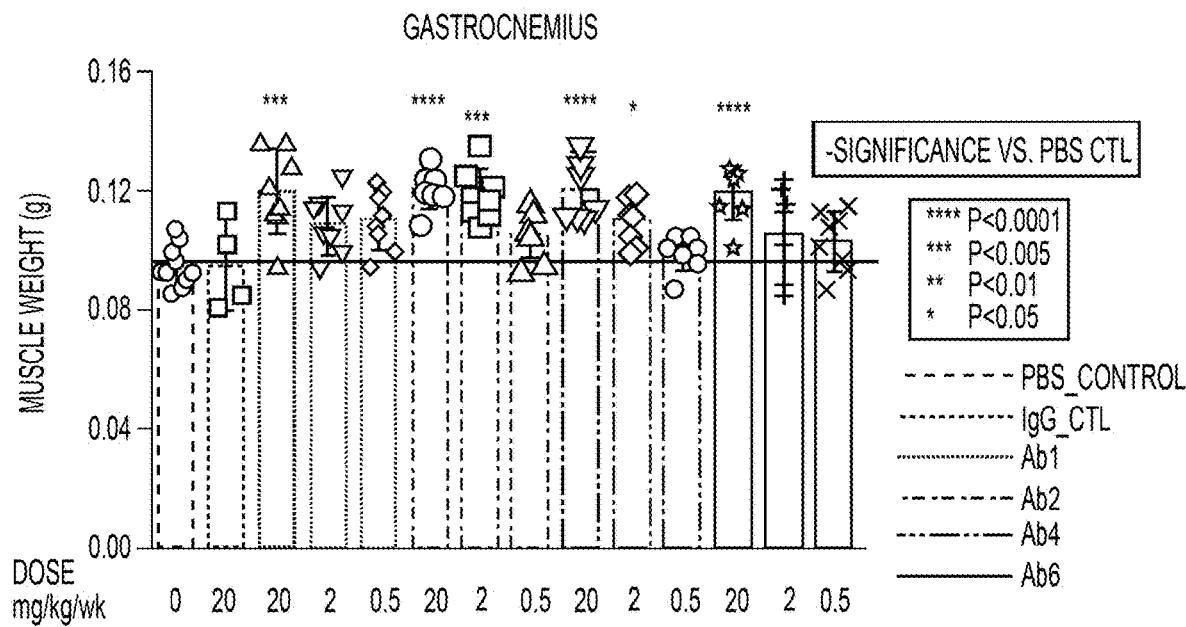
Figure 18B:
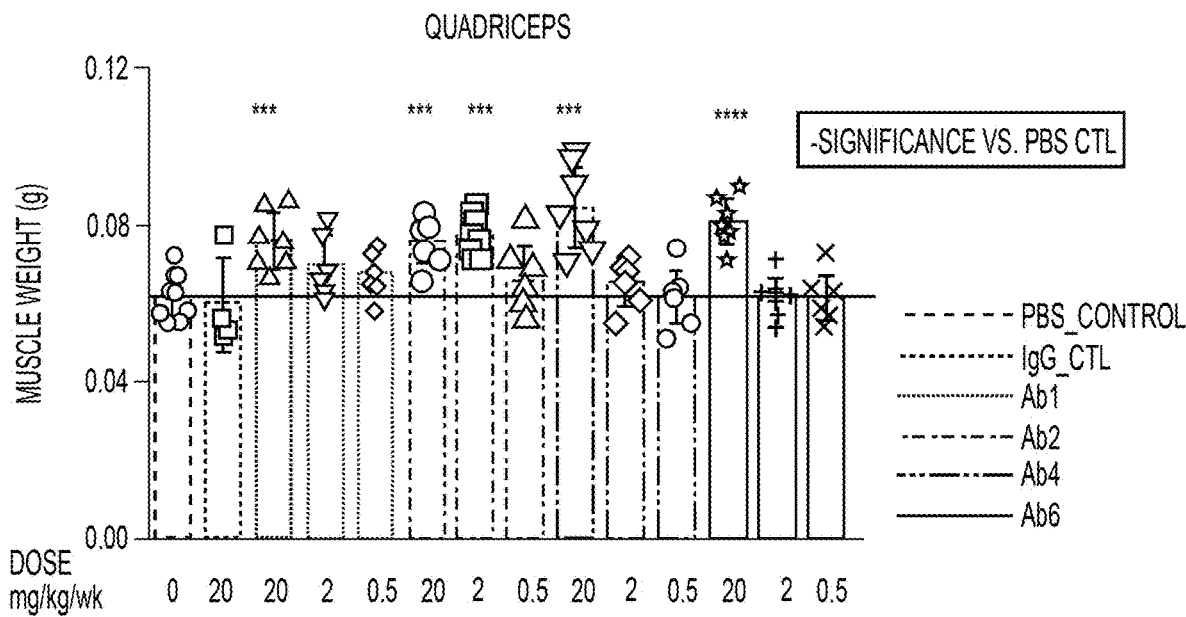

At the end of the study (day 28) muscles were collected and weighed. The weights for quadriceps (rectus femoris) and gastrocnemius muscles are plotted in FIGS. 18A and 18B. Animals treated with Ab1, Ab2, Ab4, and Ab6 at a 20 mg/kg/wk dose level had significant increases in gastrocnemius and quadriceps (rectus femoris) muscle weights compared to vehicle (PBS) treated animals. Animals treated with Ab2 and Ab4 at a 2 mg/kg/wk dose level also had significant changes in gastrocnemius muscle weights. Animals treated with Ab2 at a 2 mg/kg/wk dose level also had significant changes in quadriceps (rectus femoris) muscle weights. There were no significant changes in muscle mass from the control groups for animals treated with Ab1, Ab2, Ab4 and Ab6 at a 0.5 mg/kg/wk dose level. Percent differences in gastrocnemius and quadriceps (rectus femoris) muscle weights (when compared to the vehicle group) of animals treated with different doses of Ab1, Ab2, Ab4 and Ab6 are listed in FIG. 18C.

Duration of Action Study with Ab1 in SCID Mice

The ability of Ab1 to increase lean mass in SCID mice after a single dose and after 3 weekly doses was tested. Seven (7) groups of eight (8) female SCID mice received test article administration by intraperitoneal (IP) injection (10 ml/kg) either once at day 0 (groups 1-4) or once per week on days 0, 7 and 14 (groups 5-7). See Table 18. Antibodies (IgG control, Ab1 and AbMyo) were dosed at 10 mg/kg. Animals were 10 to 11 weeks old at the start of the study. Body weight was measured twice per week throughout the study, corresponding with dosing days. Body mass composition parameters (fat mass, lean mass and water content) were measured by Echo MRI (QNMR) on days 0, 7, 14, and 21.

TABLE 18

Treatment groups and dosing frequency.

| Treatment Group | Test Article | Dose (mg/kg) | Dosing Frequency |
|---|---|---|---|
| 1 | PBS Control | 0 | Once |
| 2 | IgG CTL | 10 | Once |
| 3 | Ab1 | 10 | Once |
| 4 | AbMyo | 10 | Once |
| 5 | IgG CTL | 10 | Once Weekly |
| 6 | Ab1 | 10 | Once Weekly |
| 7 | AbMyo | 10 | Once Weekly |

Figure 19:
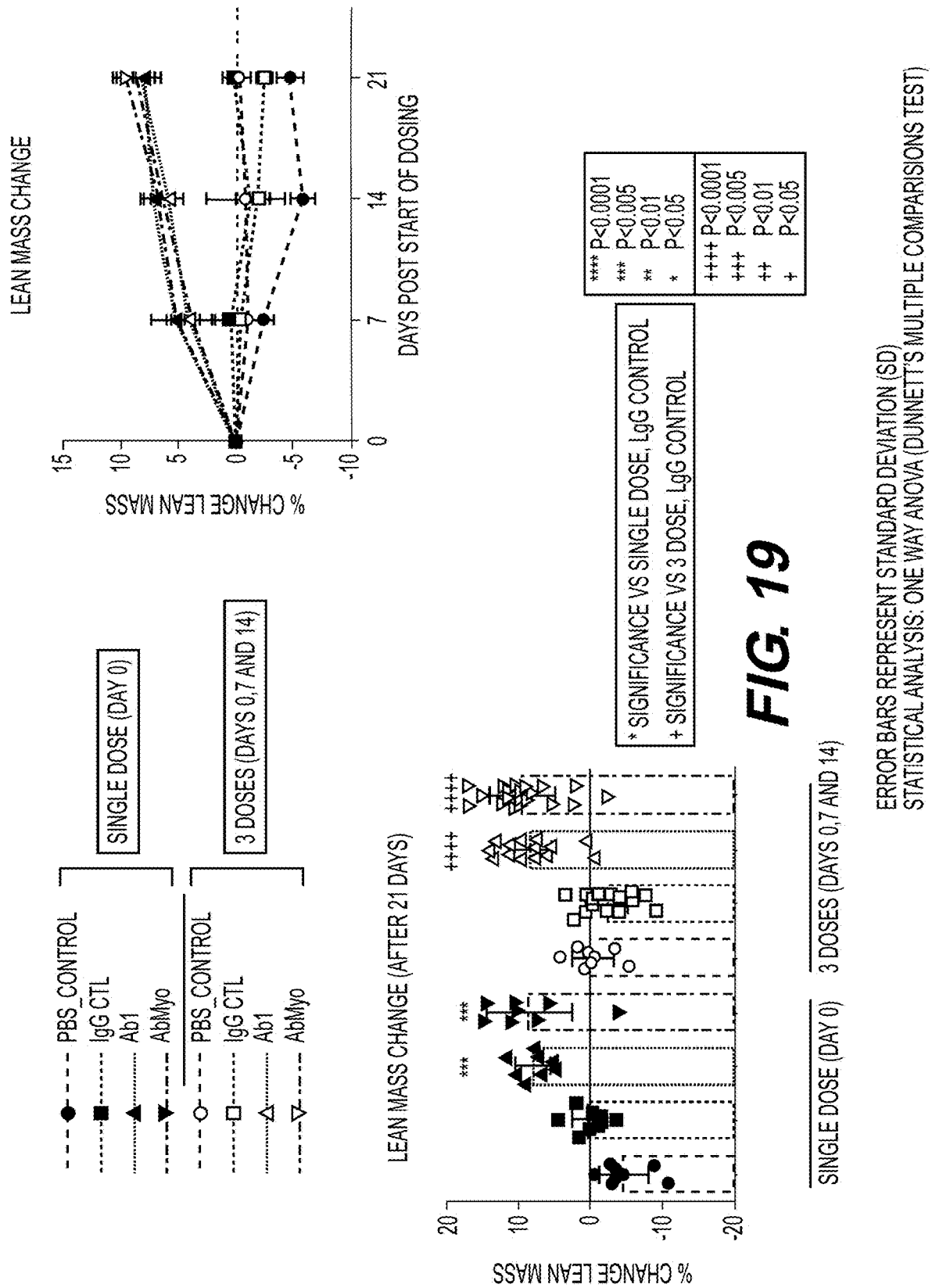
FIG. 19 shows the results of a duration of action study comparing Ab1 to an existing myostatin antibody (AbMyo). PBS was used as a negative control; IgG was used as a positive control. The lean mass change was examined under different dosing protocols after 21 days.
Figure 20:
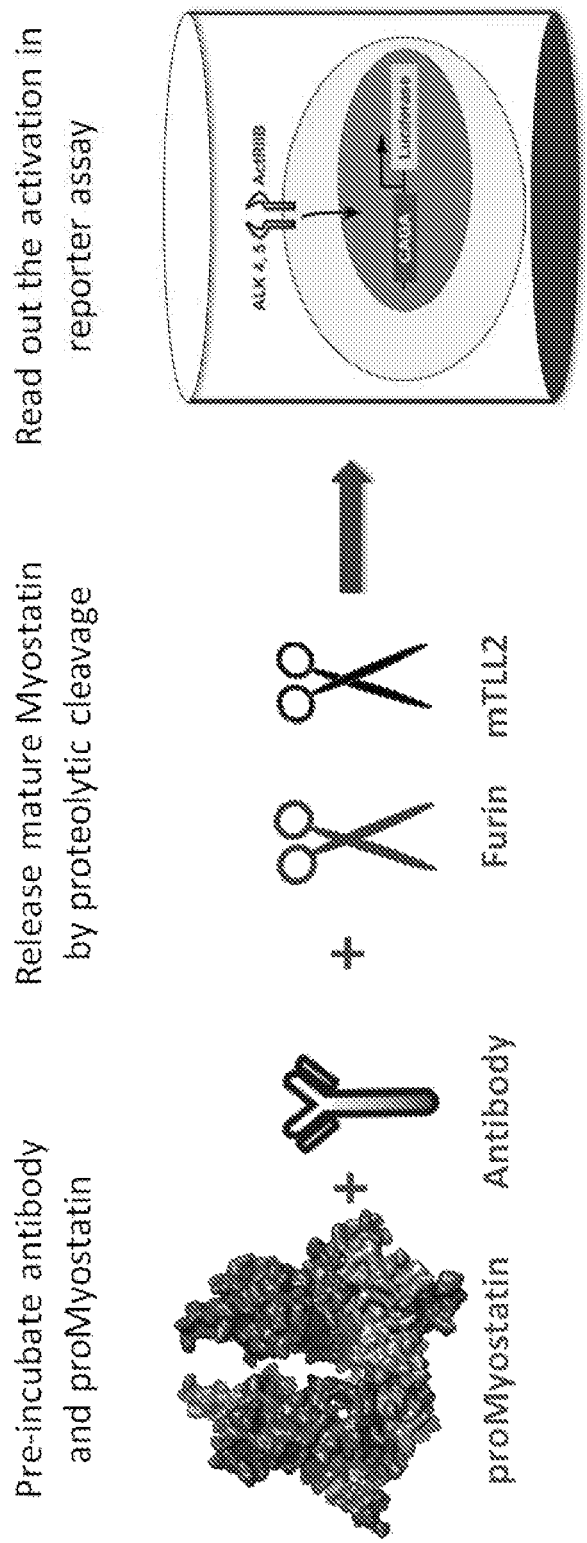
FIG. 20 is a schematic illustrating an assay that reconstitutes myostatin activation in vitro.

Mean percent lean mass change data for animals treated with vehicle (PBS), IgG control. Ab1, AbMyo are shown in FIG. 19. The data are expressed as change in lean mass from day 0 of the study. At 21 days after a single dose of test article, animals treated with Ab1 (group 3) had significant increases in lean mass (compared to IgG control animals-group 1) that were indistinguishable from the lean mass changes after 3 doses of Ab1 (group 6). These changes in lean mass were also comparable to changes seen in animals treated with a single dose (group 4) or with 3 weekly doses (group 7) of AbMyo.

Example 3: Chemistry/Pharmaceutical Sciences

Ab2 is a humanized monoclonal antibody of the IgG4 subtype with Proline substituted for Serine at position 228. This generates an IgG1-like hinge sequence and minimizes the incomplete formation of inter-chain disulfide bridges which is characteristic of IgG4. The complete amino acid sequence of the heavy and light chains of Ab2 are shown below. The complementarity-determining regions (CDRs) are underlined, purple: N-linked glycosylation consensus sequence site; light blue: potential cleavage site; red: potential deamidation site; light green: potential isomerization site; Dark blue: potential methionine oxidation site; Bold: expected N-terminal pyroglutamic acid (FIGS. 21A-21B).

Molecular modeling of Ab1 identified several potential sites of post-translational modifications. Two asparagines in the light chain and seven asparagines in the heavy chain are susceptible to deamidation. Two of these residues are located within CDR regions of the heavy chain.

Native IgG4 mAbs may have incomplete formation of inter-heavy chain disulfide bridges, with the two half molecules (each containing one heavy and one light chain) maintained in the intact antibody structure by noncovalent interactions. IgG4 molecules may be prone to exchange of half-molecules in vitro and in vivo, and the level of half molecules must be consistent across manufacturing batches. The substitution of Ser to Pro in the backbone of the IgG4 structure results in an IgG1-like hinge sequence, thereby enabling the formation of inter-chain disulfide bonds and markedly stabilizing the antibody structure. The integrity and stability of the hinge region is monitored during development with extended characterization, using such assays as non-reducing capillary electrophoresis and quantitation of free sulfhydryls. The potential for chain swapping is monitored in vivo.

Summary

A pro/latent-myostatin-specific antibody that blocks the activation of pro-myostatin and/or latent myostatin is provided herein. Administration of this activation-blocking antibody to healthy mice increases lean body mass and muscle size, with only a single dose needed to sustain the muscle-enhancing effect over a 1-month period. Additionally, antibody administration protects healthy mice from muscle atrophy in two separate models of muscle wasting. The data demonstrate that blocking myostatin activation promotes robust muscle growth and prevents muscle atrophy in vivo, and represents an alternative mechanism for therapeutic interventions of muscle wasting.

Example 4: Analysis of Pro- and Latent-Myostatin in Muscle Atrophy

Western blots were performed to determine the presence of pro and latent myostatin in muscle tissue and in circulation during muscle atrophy as well as during normal conditions. A standard model of muscle atrophy involves treating mice with 2.5 mg/kg/week Dexamethasone (dosed in drinking water) and muscle and plasma were collected after 2 weeks of treatment. This model regularly leads to 15-25% decrease in muscle mass over the course of treatment. Control muscle and plasma were collected at the same time from mice not treated with Dexamethasone. Rectus femoris, tibialis anterior, and soleus muscles were dissected out, flash frozen in liquid nitrogen, and stored at −80° C. until ready to use. Muscle lysates were generated by pulverization, followed by lysis in T-PER buffer supplemented with protease and phosphatase inhibitors. Plasma was collected by standard methods and stored at −80° C.

Figure 25:
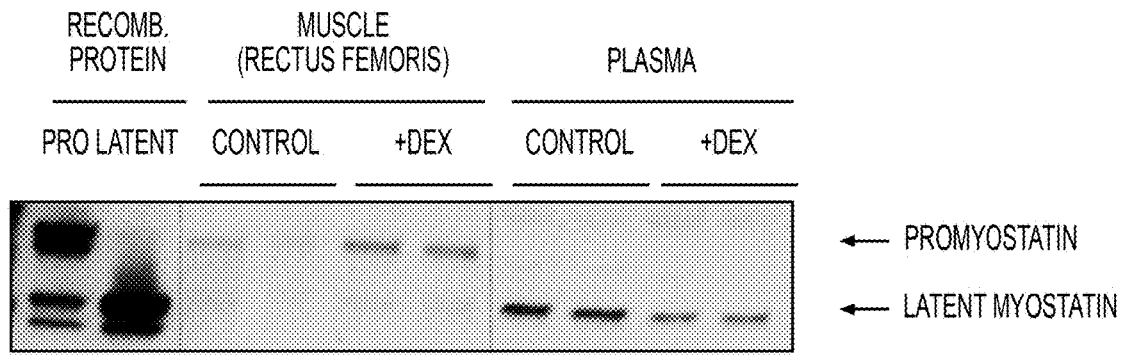
FIG. 25 shows the expression of pro- and latent-myostatin in muscle and plasma from normal and atrophic mice.

Multiple samples containing equal concentrations of protein were separated by PAGE gels and Western blotted onto PVDF membrane. For muscle lysates, 10-50 ng total protein was loaded onto the gel. Plasma was diluted 1:10 in PBS and 10 μl of each sample was loaded onto the gel. As size standards, 0.1-1 ng recombinant pro and/or latent myostatin were also loaded onto the gel. Identification of myostatin protein was accomplished using an antibody recognizing the prodomain of myostatin (AF1539, R&D Systems). This analysis shows that pro-myostatin is the predominant form in muscle, while the latent myostatin is the primary form in Plasma (FIG. 25). Furthermore, it was demonstrated that, in mice with muscle atrophy induced by Dexamethasone, pro-myostatin is increased in muscle tissue, while latent myostatin is decreased in plasma.

Figure 26:
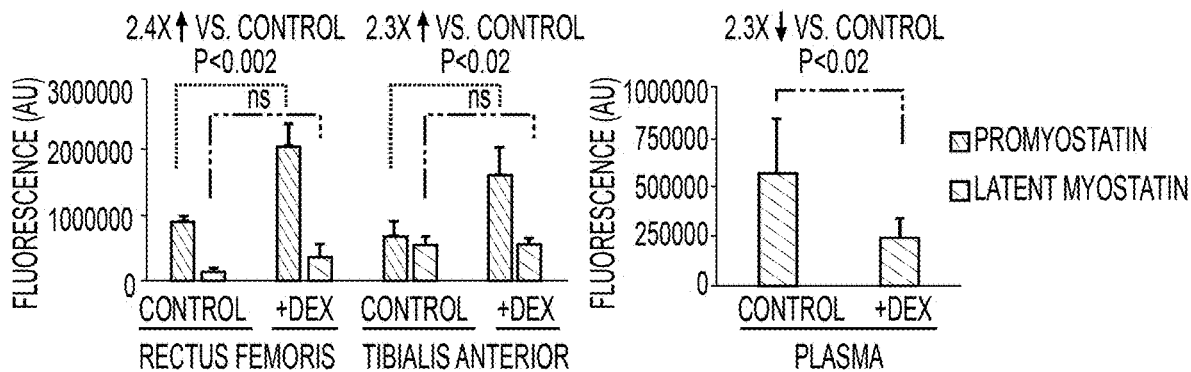
FIG. 26 shows the quantitation of changes in pro and latent myostatin in muscle and plasma. The bars from left to right show pro-myostatin in control muscle, latent myostatin in control muscle, pro-myostatin in dexamethasone (DEX)-treated muscle, latent myostatin in dexamethasone (DEX)-treated muscle, and latent myostatin in serum from control and DEX-treated mice.

To confirm these results, the Western blots were repeated using fluorescent labeling and detection (Azure Biosystems). The relative levels of each of the myostatin forms in plasma and in rectus femoris and tibialis anterior muscles from normal and Dexamethasone-treated mice were quantified. These data confirm the results described above, showing a 2- to 2.5-fold increase in pro-myostatin in both muscles, and a 2.3-fold decrease in latent myostatin in plasma (FIG. 26).

Figure 28A:
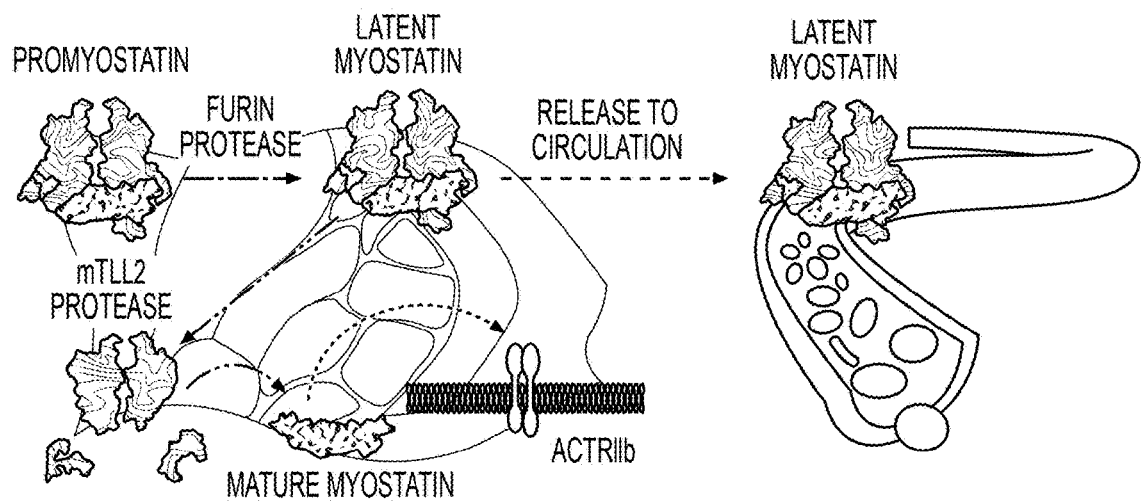
FIGS. 28A-28B provide a model for myostatin flux in normal and atrophic muscle. In normal muscle (FIG. 28A), pro-myostatin is produced in muscle and converted to latent myostatin through cleavage by Furin protease, which may occur either inside or outside of the cell. Some fraction of the latent myostatin in muscle is then released into the circulation, forming a circulating pool of latent myostatin. In muscle atrophy (FIG. 28B), an increase in the active myostatin growth factor is caused by upregulation of pro-myostatin levels in muscle and increased conversion of latent myostatin to the active growth factor. As a consequence, circulating latent myostatin is decreased as the muscle pool of latent myostatin is redirected towards formation of mature myostatin by mTLL2 cleavage.
Figure 28B:
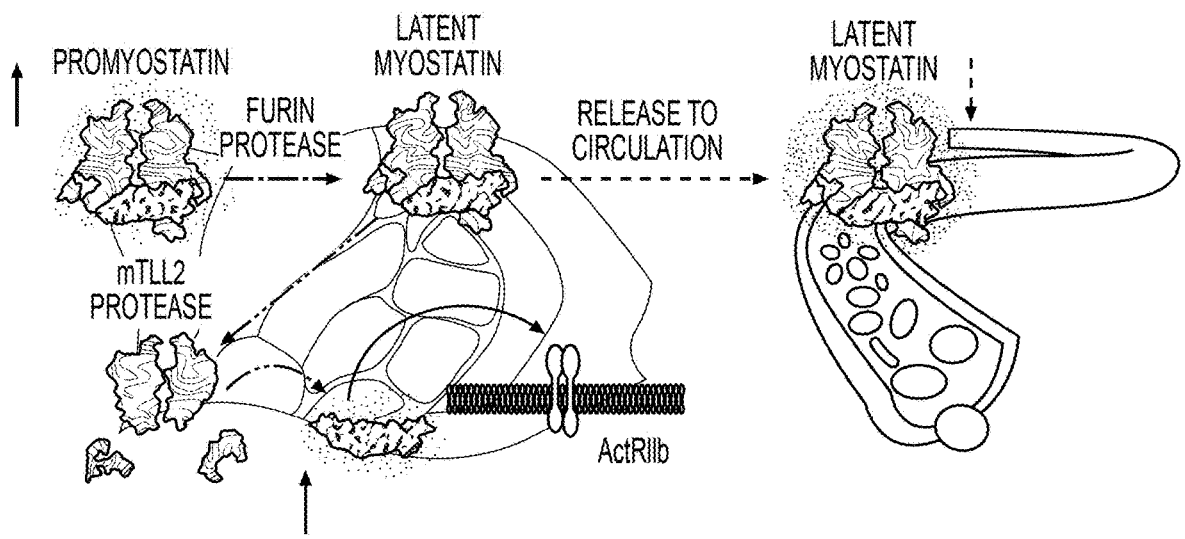

Based on these data, a model for myostatin "flux" in normal and diseased muscle is given. As demonstrated, in normal muscle (FIG. 28A), pro-myostatin is produced in muscle and converted to latent myostatin through cleavage by Furin protease, which may occur either inside or outside of the cell (Anderson et al., 2008). Some fraction of the latent myostatin in muscle is then released into the circulation, forming a circulating pool of latent myostatin. In muscle atrophy, an increase in the active myostatin growth factor is produced, driving muscle atrophy. This increase is thought to be caused by the upregulation of pro-myostatin levels in muscle and the increased conversion of latent myostatin to the active growth factor (FIG. 28B). The data outlined here directly support the first step of this model, showing increased pro-myostatin in muscle. The data also support the second step as decreased muscle mass in Dexamethasone-treated mice was observed, indicating an increased production of mature myostatin, without a concomitant increase in latent Myostatin in muscle. Accordingly, the level of myostatin is plasma was decreased, suggesting an increased conversion to mature myostatin.

Example 5: Immunoprecipitation from Murine Serum and Muscle Tissue

Figure 27:
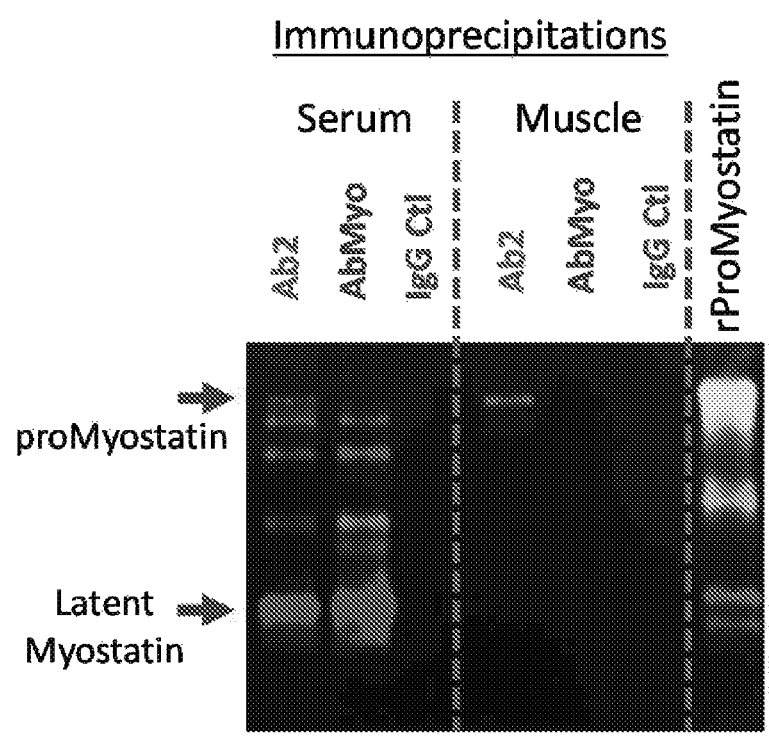
FIG. 27 shows that Ab2 uniquely recognizes pro-myostatin and latent myostatin, binding to the major forms of myostatin in both serum and muscle. Non-reducing Western blot for prodomain (darker gray) and the mature growth factor (lighter gray). Recombinant pro-myostatin (rPro-myostatin) shows the migration of pro-myostatin and myostatin prodomain (latent myostatin) on the gel, highlighted by arrows. In serum, both Ab2 and AbMyo bind to latent myostatin (prodomain band) and multiple partially processed precursors, however only Ab2 recognized pro-myostatin (top band). In muscle, Ab2 precipitated pro-myostatin, with no interaction of AbMyo with pro-myostatin in the muscle tissue.

Immunoprecipitations were performed to determine the presence of pro-myostatin in circulation, and to investigate the binding of Ab2 and AbMyo to endogenous myostatin precursors in serum and muscle. Ab2 recognizes the major form of myostatin in muscle. Results shown in FIG. 27 demonstrate that a pool of serum pro-myostatin precipitates with Ab2, suggesting that there is extracellular pro-myostatin present in vivo. In addition to binding to pro-myostatin, latent myostatin, and other partially processed forms of myostatin in serum, Ab2 immunoprecipitated pro-myostatin from muscle extracts. In contrast, AbMyo efficiently bound to latent myostatin and partially processed precursors in serum, with no detectable interactions with pro-myostatin in the muscle. Given that the muscle is the site where myostatin signaling occurs, this could provide important advantages to the Ab2 mechanism of action.

Homogenized muscle lysate was prepared as follows: frozen mouse quadriceps (rectus femoris) were pulverized using a CryoPrep pulverizer (Covaris, Woburn MA). The pulverized muscle was then resuspended to a concentration of 50 mg/mL in M-Per buffer (ThermoFisher Scientific) with 1× Halt™ Protease and Phosphatase Inhibitor Cocktail without EDTA (ThermoFisher Scientific) The tissue was then crushed using a plastic pestle, (Bio-Plas Cat #4030-PB) and homogenized further with repeated pipetting with a cut-off pipette tip. Muscle samples were then incubated 30 minutes at 4C with end-over-end rotation. Finally, samples were centrifuged at 16.100 g for 10 minutes to pellet the insoluble fraction. The soluble fraction was aspirated off and used in downstream experiments.

For immunoprecipitation, Ab2, IgGCtl, or AbMyo antibodies were covalently conjugated to agarose beads using the Thermo Scientific Pierce™ Co-Immunoprecipitation Kit according to the manufacturer's specifications. 75 ug of each antibody was conjugated to 50 uL of bead slurry, and 30 ug of antibody was utilized in each immunoprecipitation. The immunoprecipitation was performed against 3 mL of pooled normal mouse serum (Bioreclamation) or 1.05 mL of homogenized soluble mouse quadriceps prepared as described above. Antibody conjugated beads and samples were incubated at 4C with end-over-end rocking overnight. After incubation, the beads were recovered by passing the entire sample volume through the spin filters included in the co-immunoprecipitation kit using the QIAvac 24 Plus vacuum manifold (Qiagen). The beads were then washed 3x with 200 uL of IP lysis/wash buffer, and once with 100 µL of 1× conditioning buffer according to the specifications of the kit. Elutions were performed with 50 µL of elution buffer for five minutes and were then mixed with 5 µL of 1M Tris, pH 9.5 in the collection tube.

Myostatin species pulled down by the test antibodies were visualized by Western blotting utilizing AF1539, (R&D systems) ab124721, (Abcam) Alexa Fluor® 680 AffiniPure Donkey Anti-Sheep IgG (H+L), (Jackson ImmunoResearch) and IRDye® 800CW Donkey anti-Rabbit IgG (H+L) (LI-COR Biosciences) Thermo Scientific. SEA BLOCK blocking buffer was utilized for the blocking and primary antibody incubations.

Example 6: Increased Muscle Mass and Altered Myostatin Protein Expression in Rats Treated with Ab2

Seven to eight week old female Sprague-Dawley rats were administered a single intravenous dose of either Ab2 (10 mg/kg), a nonfunctional human IgG control antibody (10 mg/kg), or an equivalent volume of phosphate buffered saline (PBS). During the course of the study, serum was collected from 3 rats per group at 4 hours, 48 hours, 7 days, 14 days, 21 days, and 28 days after dosing. Collection was done by standard methods and samples were stored at −80° C. Lean mass was measured by quantitative nuclear magnetic resonance (qNMR) at baseline (prior to day 0 dosing) and on days 7, 14, 21, and 28 (8 rats/group) and skeletal muscles (rectus femoris, tibialis anterior, and soleus) were collected at the end of study (day 28), weighed, and flash frozen in liquid nitrogen for storage at −80° C.

Figure 29:
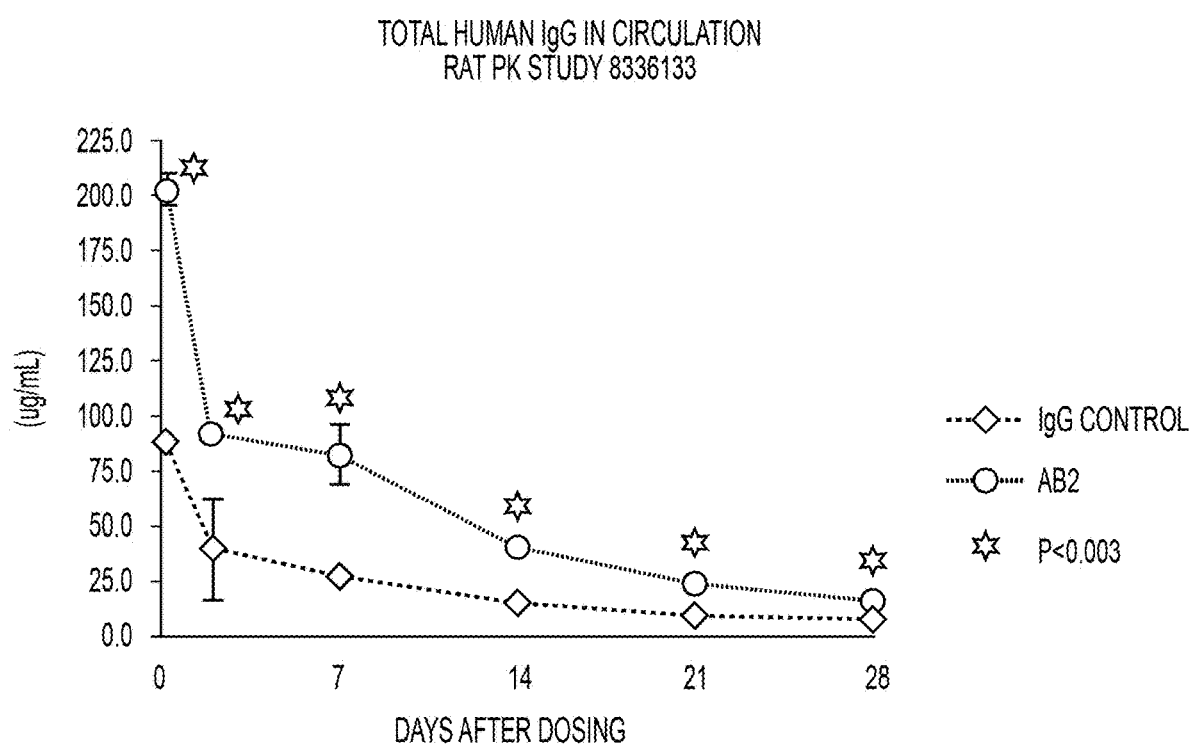
FIG. 29 shows detection of Ab2 (top line) and IgG control (bottom line) antibody in serum from dosed rats. Ab2 exhibits elevated levels in the circulation as compared to the IgG control, with an average of 17.1 µg/ml of Ab2 in serum at the end of the study. Ab2 levels determined by human IgG-specific ELISA with known quantities of each antibody used as a reference standard.

Drug exposure was measured in serum samples using an ELISA specific to human IgG with known quantities of each drug used as a reference standard. As shown in FIG. 29, 4 hours after injection, both Ab2 and the IgG control antibody are detected in rat serum. As the study progresses, Ab2 exhibits elevated circulating drug levels compared to the IgG control, with an average of 17.1 µg/ml drug in serum at the end of the study.

Figure 30A:
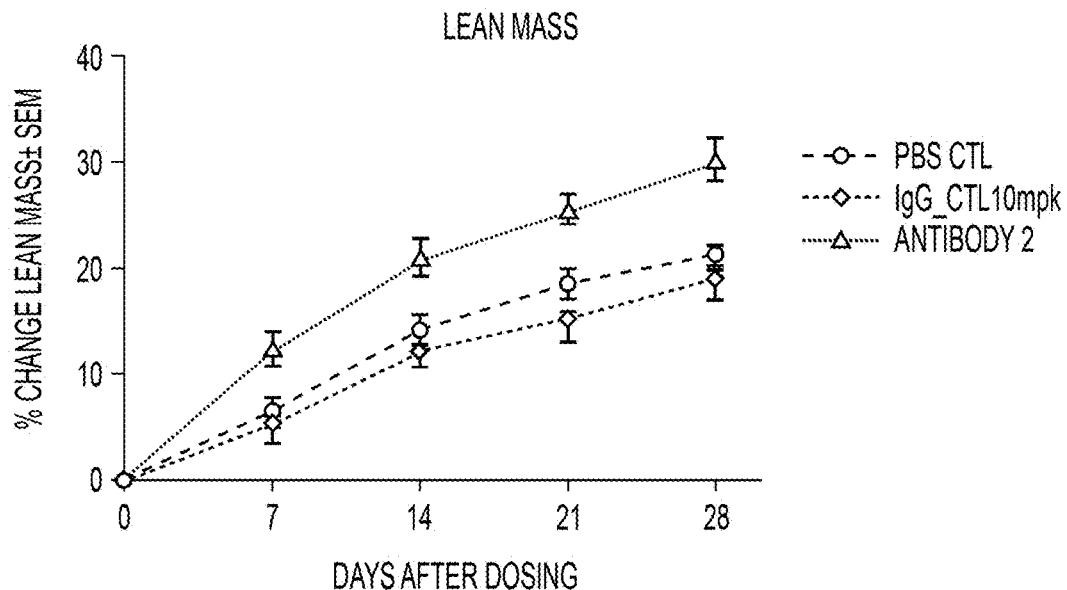
FIGS. 30A-30B shows pharmacodynamic effects of Ab2 in treated rats.
Figure 30B:
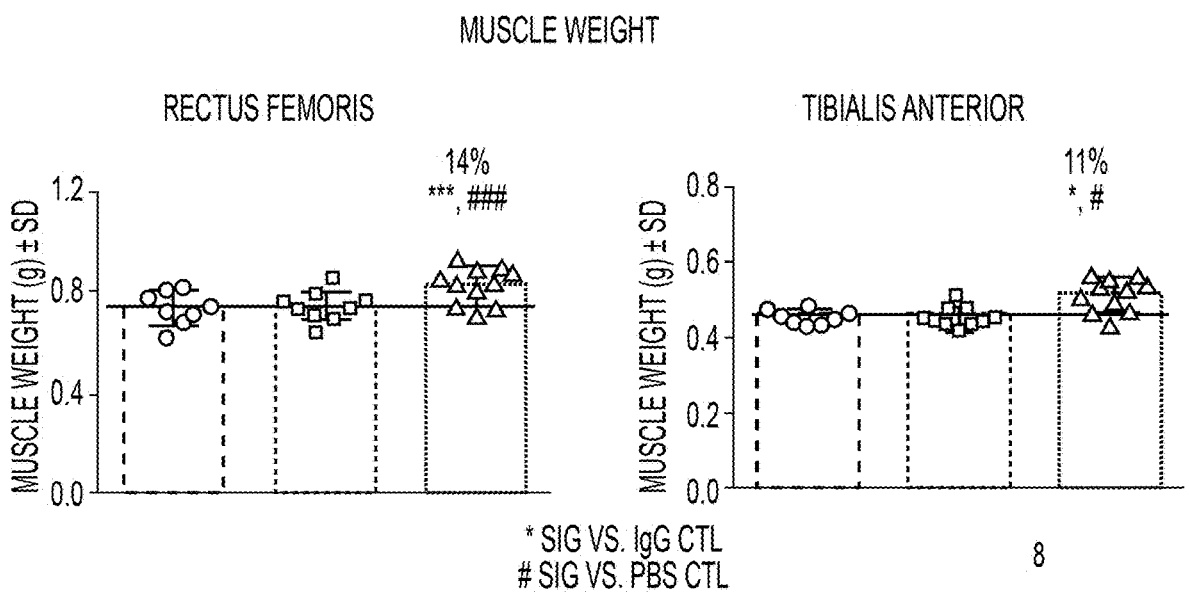

Pharmacodynamic effects of Ab2 treatment were assessed both by measuring lean mass (by qNMR) during the course of the study and by determining the weights of dissected muscle at the end of the study. FIG. 30A shows lean mass measurements during the course of the study, where rats treated with Ab2 demonstrate a clear increase in lean mass compared to rats treated with PBS or with human IgG Control antibody. Muscle mass was measured by collecting and weighing whole skeletal muscles at the end of the study (28 days). As shown in FIG. 30B, rats treated with Ab2 show an increase of 14% and 11% in rectus femoris and tibialis anterior muscle masses, respectively. Together, these data indicate that treatment of rats with a single dose of Ab2 leads to long-lasting increases in muscle mass.

Relative levels of pro and latest myostatin was determined by quantitative western blotting of muscle lysate or serum samples. Muscle lysates were generated from flash frozen muscle samples by pulverization, followed by lysis in T-PER buffer supplemented with protease and phosphatase inhibitors. After lysis, samples containing equal concentrations of protein were separated by PAGE gels and Western blotted onto low fluorescence PVDF membrane. For muscle lysates, 10-50 ng total protein was loaded onto the gel. Plasma was diluted 1:10 in PBS and 10 µl of each sample loaded onto the gel. As size standards, 0.1-1 ng recombinant pro and/or latent myostatin were also loaded onto the gel. Identification of myostatin protein was accomplished using an antibody recognizing the prodomain of latent myostatin (AF1539, R&D Systems), followed by detection with a fluorescently labeled secondary antibody. For all western blot analyses, a minimum of three samples per group were assayed.

Figures 31A, 31B:
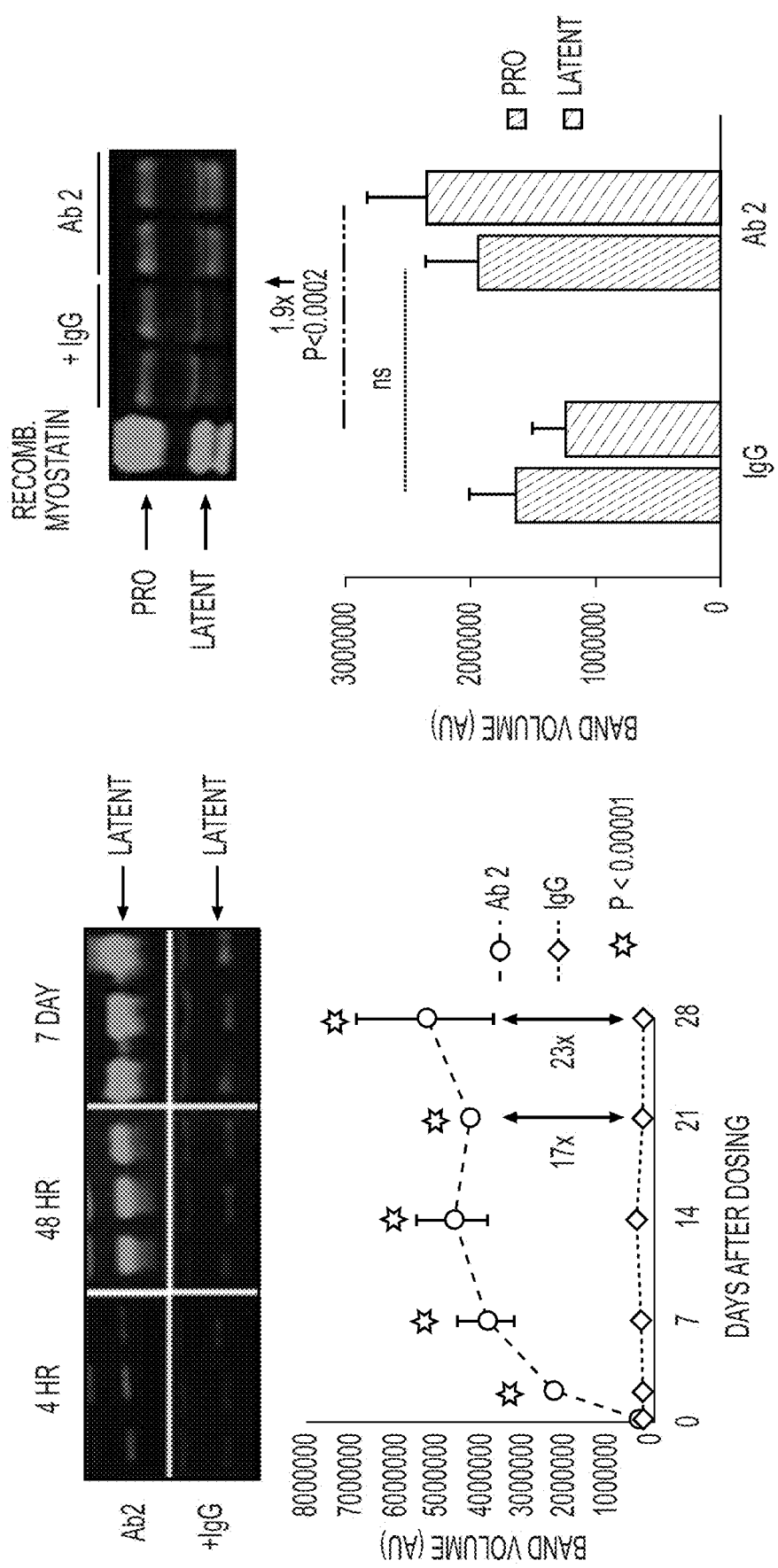
FIGS. 31A-31B show pro/latent-myostatin pro/latent-myostatin levels in Ab2-treated rats.

Treatment with Ab2 increases latent myostatin levels in rat serum by ~20-fold (FIG. 31A) compared to IgG control-treated rats. These data are consistent with effects seen with other antibody drugs, reflecting binding of the drug target in circulation. In rat muscle (rectus femoris), Ab2 treatment leads to a 1.9x increase (vs. IgG control-treated rats) in the latent form of myostatin. No statistically significant change in pro-myostatin is observed. These data indicate that Ab2 binds its target, pro/latent myostatin, and alters myostatin processing in muscle as well as in circulation. It was also observed that Ab2 treatment increases latent, but not pro-myostatin in Rat muscle (FIG. 31B).

Example 7: Increased Muscle Mass and Alteration of Myostatin Protein Expression in Mice Treated with Ab2 and Comparison to a Comparator Anti-Myostatin Antibody Ten week old male SCID mice were administered a single intraperitoneal dose (5 mg/kg) of either Ab2, a nonfunctional human IgG control antibody, or a comparator antibody (AbMyo) that acts by blocking the myostatin/receptor interaction. During the course of the study, serum and skeletal muscle were collected at 1 hour, 4 hours, 48 hours, 7 days, 14 days, 21 days, 28 days, and 56 days after dosing. Serum collection was done by standard methods and samples were stored at −80° C. Skeletal muscles (rectus femoris, tibialis anterior, and soleus) were collected, weighed, and flash frozen in liquid nitrogen for storage at −80° C. Lean mass was measured by quantitative nuclear magnetic resonance (qNMR) at baseline (prior to day 0 dosing) and weekly throughout the course of the study.

Figure 32:
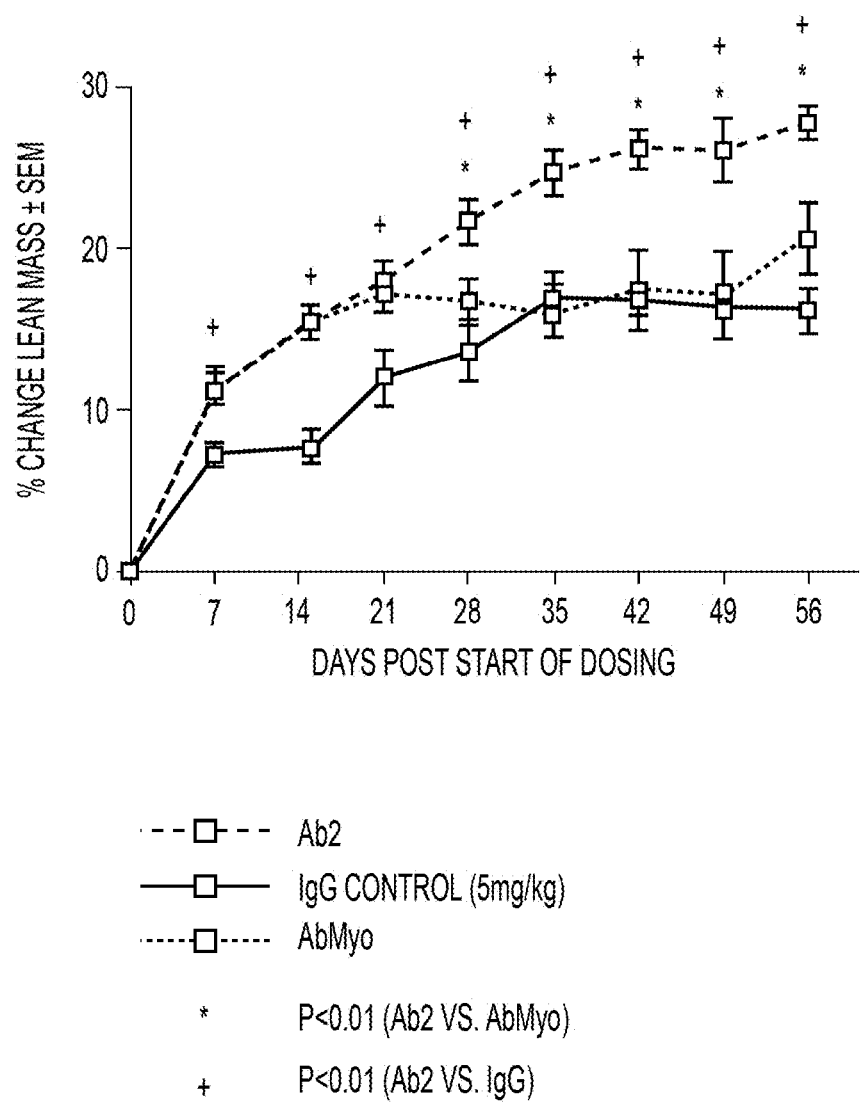
FIG. 32 shows treatment with Ab2 (Ab2) or with the comparator antibody (AbMyo) leads to increased lean mass in mice by as early 7 days after antibody dosing. Increases in lean mass are equivalent for Ab2 and AbMyo until 21 days after dosing. By 28 days after dosing, however, increases in lean mass are lost in the AbMyo-treated group, while increases in the Ab2-treated group are maintained throughout the duration of the study. The top line corresponds to Ab2, the middle line corresponds to AbMyo, and the bottom line corresponds to IgG Control (5 mg/kg).

Pharmacodynamic effects of Ab2 treatment were assessed by measuring lean mass (by qNMR) during the course of the study. FIG. 32 shows lean mass measurements during the course of the study, where mice treated with Ab2 demonstrate a clear increase in lean mass compared to mice treated with human IgG Control antibody. For the first three weeks of the study, mice treated with the comparator antibody (AbMyo) show increases in lean mass equivalent to those in the Ab2 group. However, by 28 days after dosing, AbMyo-treated mice do not maintain increased lean mass. In contrast, mice in the Ab2-treated group maintain their increased lean mass throughout the duration of the study (56 days). These data suggest that Ab2 has a longer duration of action that AbMyo.

Figure 42A:
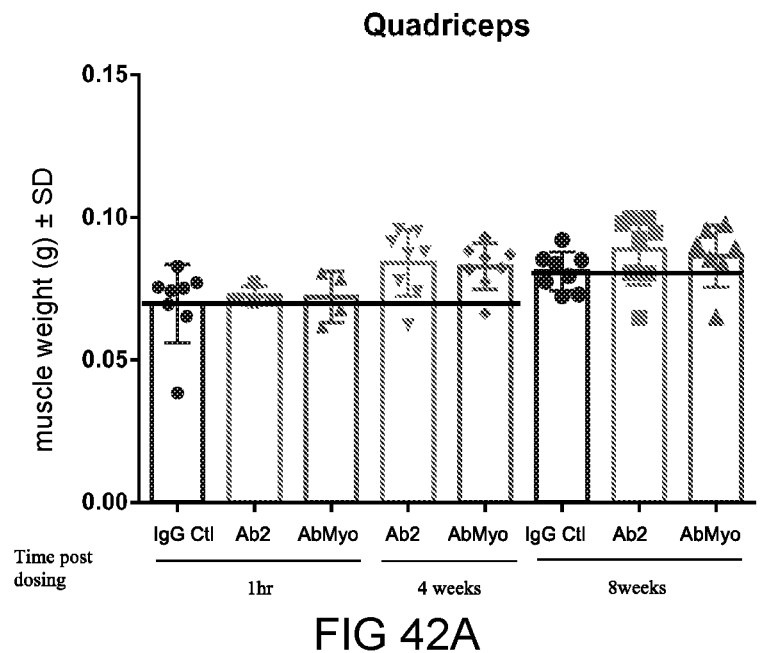
FIGS. 42A-42B show different muscle weights after 1 hour, 4 weeks, and 8 weeks in a single dose pharmacokinetic/pharmacodynamics duration of action study.
Figure 42B:
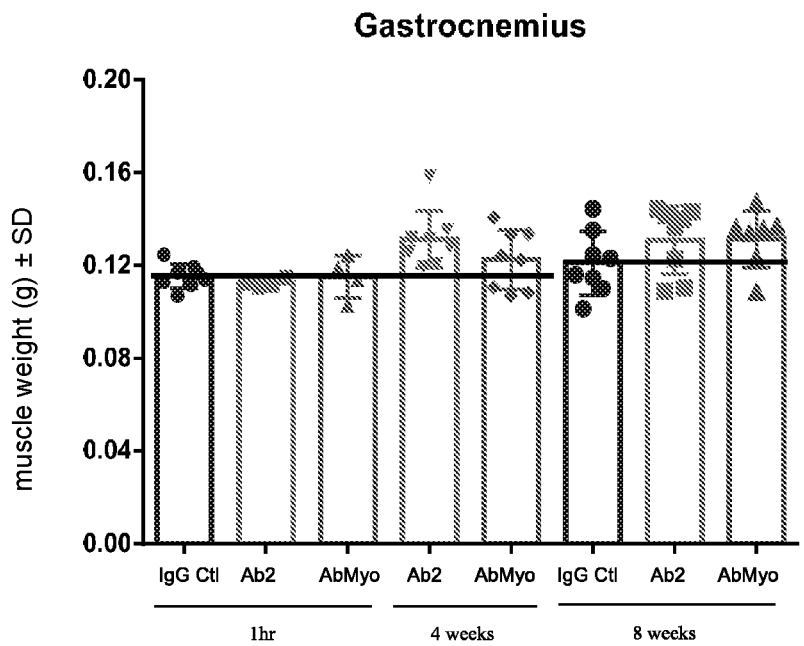

Muscle tissue weights were also measured. In quadriceps (rectus femoris), four weeks after dosing, the muscle weight in the two treatment groups increased. Eight weeks after dosing, the quadriceps (rectus femoris) muscle in both the Ab2 and the AbMyo groups was increased above that of the IgG control, with the Ab2 group showing a slight increase compared to that of the AbMyo group (FIG. 42A). In gastrocnemius, the Ab2 and AbMyo groups showed approximately equivalent muscle weights compared to the IgG control one hour after dosing. Four weeks later, the Ab2 and AbMyo groups showed greater weights than that of the IgG control one hour after the treatment with the Ab2 group showing a slight increase compared to that of the AbMyo group. Eight weeks after treatment, the gastrocnemius muscles of the Ab2 and AbMyo groups were higher than that of the IgG control group (FIG. 42B).

Figure 33:
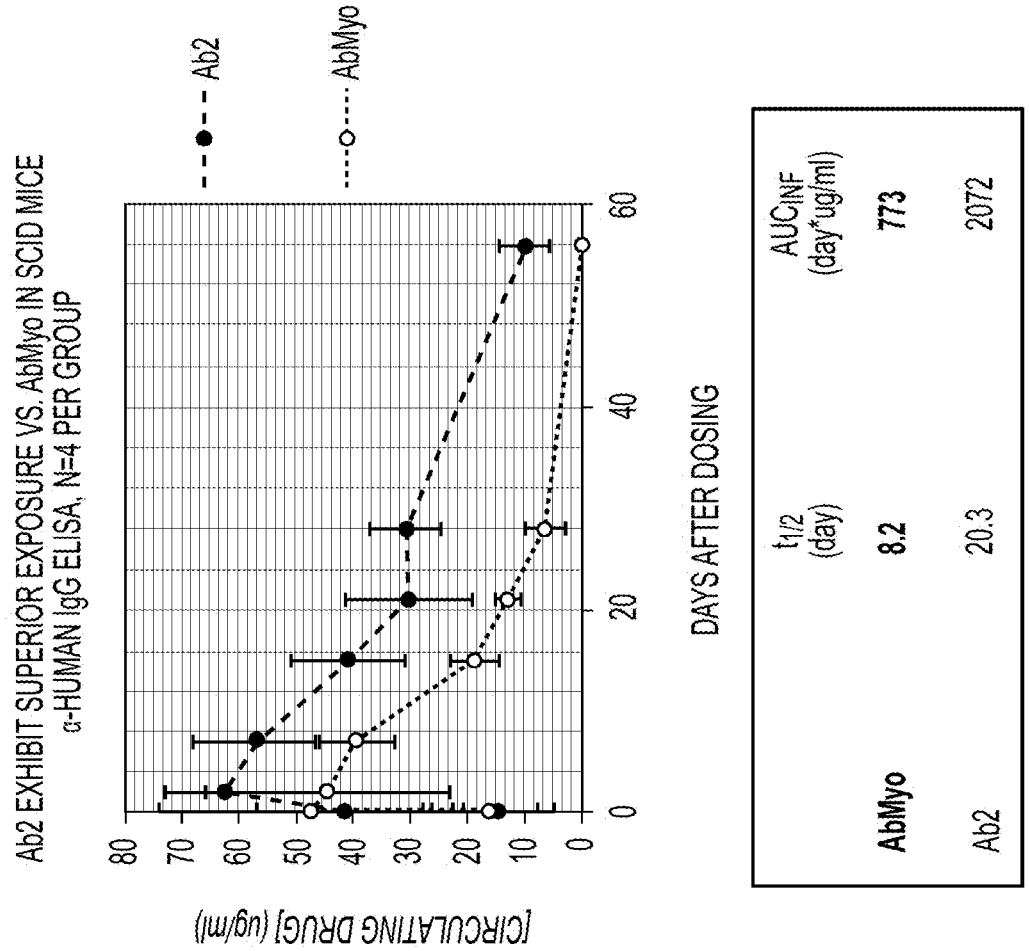
FIG. 33 shows that after a single, 5 mg/kg dose of Ab2 (top line) or of comparator antibody (AbMyo; bottom line), serum levels of drug were measured using an anti-human IgG ELISA. Drug is detected in serum as early as 1 hour after dosing, and levels >1 µg/ml of both antibodies can be detected throughout the study. However, Ab2 exhibits a significantly longer half-life and inferred area under the curve (AUCINF) than AbMyo, suggesting that, at similar doses, Ab2 exhibits significantly greater exposure than AbMyo.

Drug exposure was measured in serum samples using an ELISA specific to human IgG with known quantities of each drug used as a reference standard. As shown in FIG. 33, as early as 1 hour after injection, both Ab2 and the comparator antibody (AbMyo) are detected in serum and levels >1 µg/ml of both antibodies can be detected throughout the study. However, Ab2 exhibits a significantly longer half-life and inferred area under the curve (AUCINF) than AbMyo, suggesting that, at similar doses, Ab2 exhibits significantly greater exposure than AbMyo.

Relative levels of pro and latent myostatin was determined by quantitative western blotting of muscle lysate or serum samples. Muscle lysates were generated from flash frozen muscle samples by pulverization, followed by lysis in T-PER buffer supplemented with protease and phosphatase inhibitors. After lysis, samples containing equal concentrations of protein were separated by PAGE gels and Western blotted onto low fluorescence PVDF membrane. For muscle lysates, 10-50 ng total protein was loaded onto the gel. Plasma was diluted 1:10 in PBS and 10 µl of each sample loaded onto the gel. As size standards, 0.1-1 ng recombinant pro and/or latent myostatin were also loaded onto the gel. Identification of myostatin protein was accomplished using an antibody recognizing the prodomain of latent myostatin (AF1539, R&D Systems), followed by detection with a fluorescently labeled secondary antibody. For all western blot analyses, a minimum of three samples per group were assayed.

Figure 34:
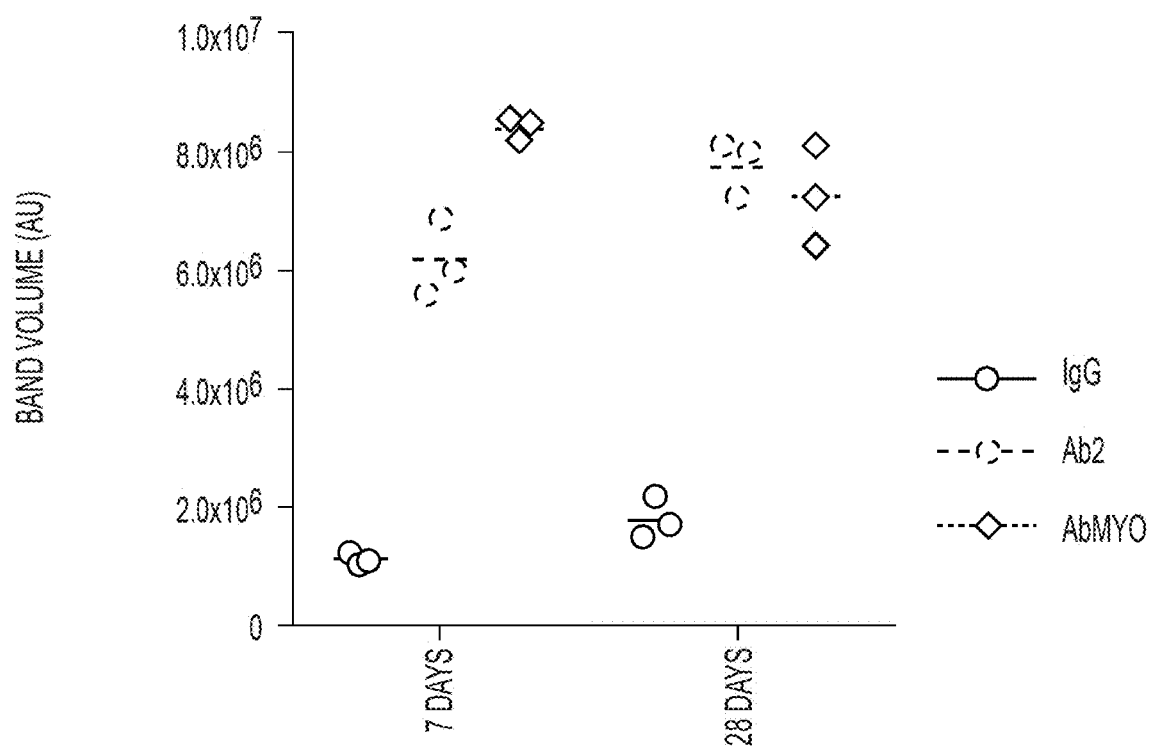
FIG. 34 shows serum myostatin was measured in drug treated mice and in controls using fluorescent western blotting. Despite the increased serum exposure of Ab2, serum latent myostatin levels in both Ab2- and AbMyo-treated mice were similar. These data suggest that the circulating levels of free drug are sufficiently in excess to the level of target that the increased serum exposure of Ab2 does not lead to a greater increase in circulating latent myostatin than is observed in the AbMyo group. Groups of data from left to right correspond to IgG, Ab2, AbMyo, IgG, Ab2, and AbMyo.

Serum myostatin was measured in drug treated mice and in controls using fluorescent western blotting. Despite the increased serum exposure of Ab2, serum latent myostatin levels in both Ab2- and AbMyo-treated mice were similar (FIG. 34). These data suggest that the circulating levels of free drug (not bound to target) are sufficiently greater than the level of target, such that the increased serum exposure of Ab2 does not translate to larger increases in circulating latent myostatin than those observed with AbMyo.

Figure 35A:
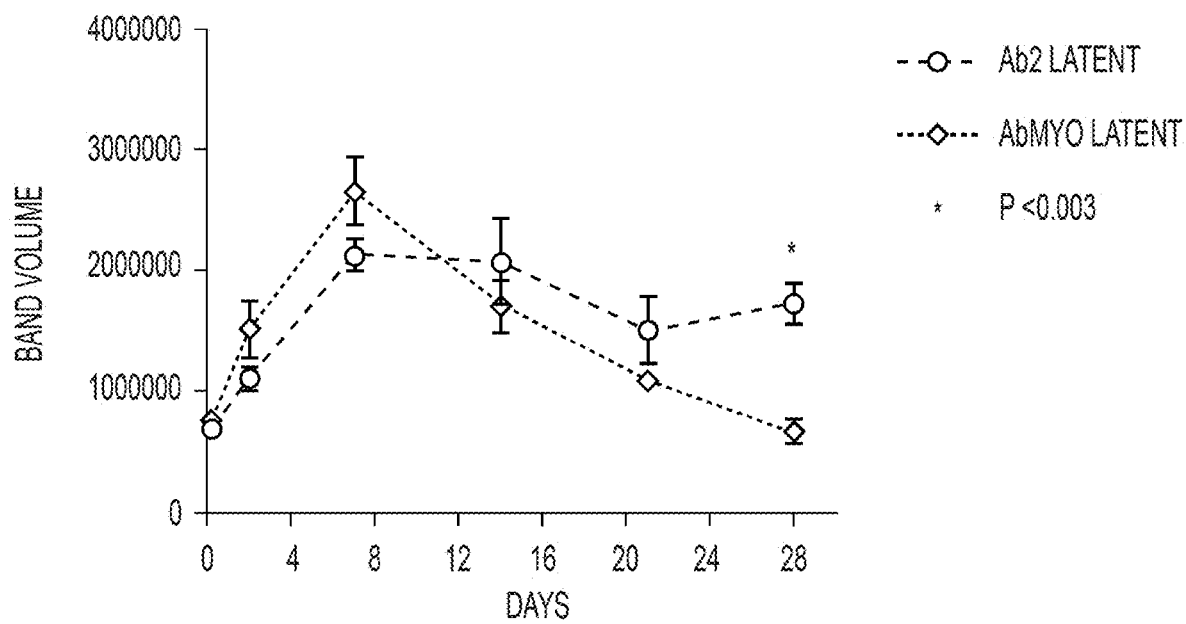
FIGS. 35A-35B shows relative levels of latent and pro-myostatin were measured in mouse muscle lysates by fluorescent western blot.
Figure 35B:
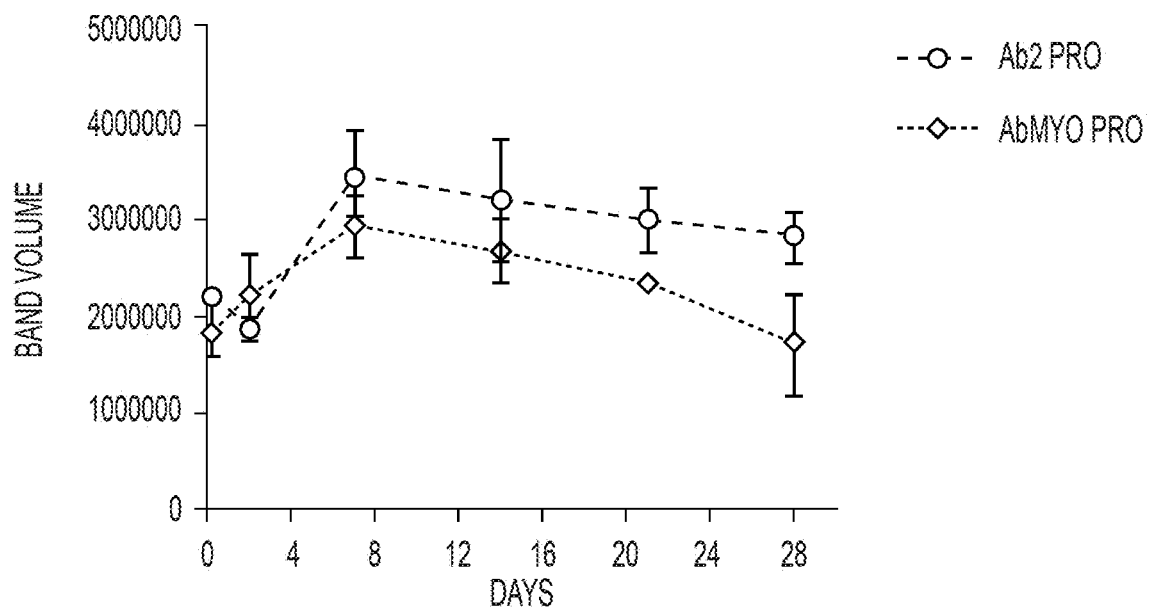

Myostatin levels in muscle (rectus femoris) were also evaluated by fluorescent western blotting. Relative levels of latent and pro-myostatin were measured in mouse muscle lysates by fluorescent western blot. Latent myostatin is elevated in both Ab2 and AbMyo treated muscles (FIG. 35A). However, elevation of latent myostatin in AbMyo-treated muscles returns to baseline by day 28, while those in Ab2 treated muscles remain elevated until at least this time (P<0.003 vs. AbMyo treatment). A similar trend is observed with pro-myostatin (FIG. 35B), though the difference is not statistically significant (P=0.068). These data suggest a longer duration of action of Ab2 at site of drug action, the skeletal muscle.

Example 8: Blockade of Myostatin Activation Prevents Atrophy in a Murine Dexamethasone Model A panel of ten myostatin precursor-specific antibodies was used to interrogate whether or not binding to myostatin is sufficient to block myostatin signaling or whether preventing the release of the growth factor prevents signaling in vivo. This work evaluated the extent to which blocking the proteolytic activation of myostatin from precursor forms could protect otherwise healthy mice from dexamethasone-induced muscle atrophy.

Figure 36A:
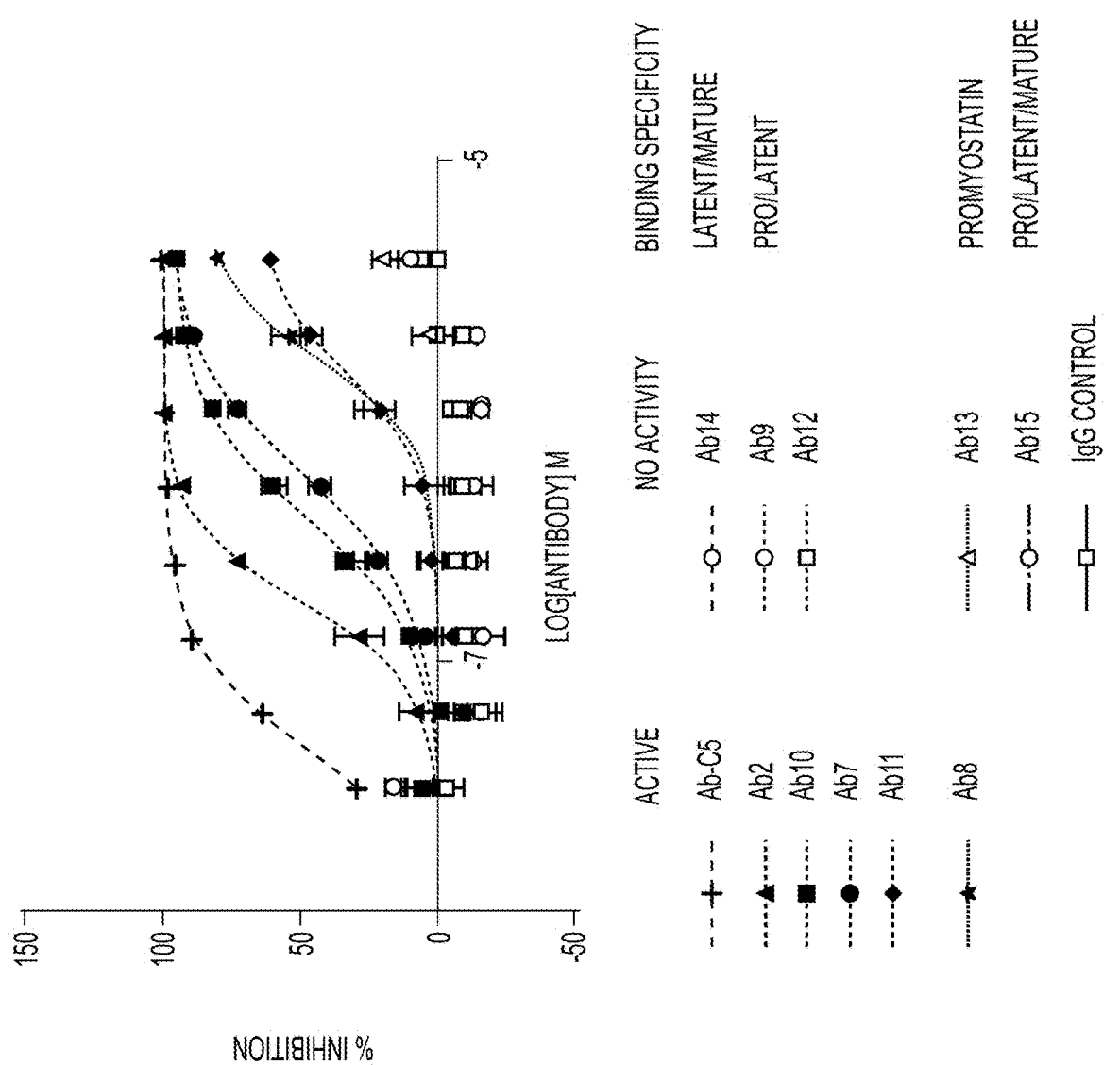
FIG. 36A shows myostatin binding and blocking activity of a panel of antibodies.
Figure 36B:
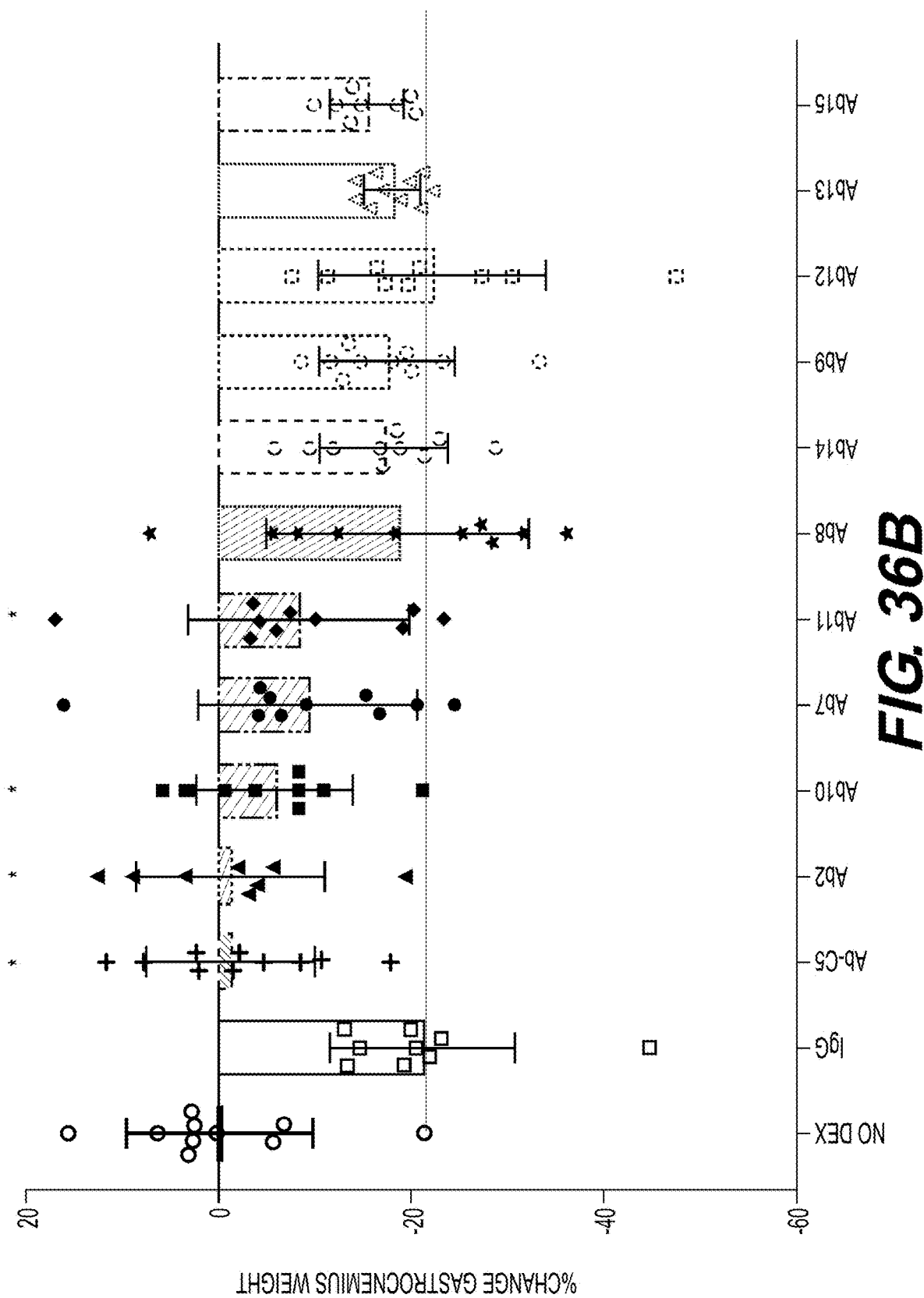
FIG. 36B relates myostatin binding and blocking activity with effects on muscle atrophy.

A model of glucocorticoid-induced muscle atrophy was established by dosing male C57/BL6 mice for two weeks with dexamethasone in their drinking water. Changes in lean body mass were tracked with quantitative NMR (QNMR), and muscles were weighed at the end of the treatment period to monitor muscle atrophy. A dose was selected (2.5 mg/kg/day) that was able to induce significant decreases in lean body mass (~10.9%) and the mass of individual hindlimb muscles (~24.5% and ~21.9% in rectus femoris and gastrocnemius respectively) after two weeks of dosing (FIG. 36B, IgG control in black open squares).

Animals were dosed at 20 mg/kg/wk with fully human antibodies for two weeks, hypothesizing that immune responses would not be mounted against these antibodies in this period of time. Included were not only antibodies which blocked the activation of recombinant myostatin in an in vitro reporter assay, but also antibodies that bound tightly to the precursor and/or mature forms of myostatin and did not inhibit myostatin signaling in vitro (FIG. 36A). For each antibody with functional activity in the in vitro assay, there was another antibody in the panel with a similar binding profile that lacked this functional activity.

At the end of the two-week treatment with dexamethasone and the test articles, individual muscles were dissected and weighed. The percent change in the gastrocnemius muscle weights are plotted in FIG. 36B. Animals that received dexamethasone via their drinking water and also received IgG Control antibody or antibodies which bind to myostatin but do not block its signaling in the in vitro myostatin activation assay showed significant atrophy in gastrocnemius muscles (~20%) compared to the non-diseased control group (black bars).

Interestingly, of five antibodies with in vitro functional activity, four of them recognized both pro and latent myostatin. Three of these antibodies, Ab2, Ab10, and Ab11 prevented atrophy (vs diseased IgG control p=0.0003, p=0.0076, p=0.0309, respectively). The fourth antibody, Ab7 trended towards statistical significance (p=0.0572). Importantly, none had statistically significant deviation in gastrocnemius weights from the non-diseased control cohort over the course of the two week period, reflecting a protection from dexamethasone-induced atrophy by all four of the antibodies.

One antibody with functional activity that did not belong to the predominant functional epitope binding profile, Ab8, did not prevent atrophy in this model (vs non-diseased control p=0.0003, vs IgG control p=0.9991).

Another control antibody was included, Ab-C5, which recognizes the mature and latent forms of myostatin (and GDF11) (Table 23). This antibody inhibits myostatin and GDF11 signaling by blocking the interaction between the myostatin growth factor and cell surface receptors. Treatment of mice with this antibody also prevented dexamethasone-induced atrophy to a similar degree as Ab2 (FIG. 36B). Ab14, which also recognizes mature and latent GDF8 (but not GDF11), and does not block activation was unable to prevent atrophy in this model. These data indicate that blocking activation of myostatin from precursor forms is at least as efficacious as blocking receptor-growth factor recognition.

TABLE 23

Binding profile of ten myostatin precursor-binding antibodies to murine GDF8 and GDF11

|  | Kd Murine Pro-myostatin (nM) | Kd Murine Latent Myostatin (nM) | Kd mature Myostatin (nM) | Kd murine pro + latent GDF11 (nM) | Kd murine Latent GDF11 (nM) | EC50 Activation Assay (nM) |
|---|---|---|---|---|---|---|
| Ab2 | 2.3 ± .069 | 2.0 ± .058 | [1]n.b. | n.b. | n.b. | 174 |
| Ab7 | 32.9 ± 1.647 | 28.4 ± 1.360 | [1]n.b. | n.b. | n.b. | 555 |
| Ab10 | 3.7 ± .121 | 4.2 ± .130 | [1]n.b. | n.b. | n.b. | 373 |
| Ab11 | 1.6 ± .101 | 1.8 ± .106 | [1]n.b. | n.b. | n.b. | 1380 |
| Ab9 | 8.5 ± 1.491 | 7.8 ± 1.190 | [1]n.b. | n.b. | n.b. |  |
| Ab12 | 3.9 ± .137 | 1.9 ± .074 | [1]n.b. | n.b. | n.b. |  |
| Ab8 | 1.4 ± .222 | n.b. | [1]n.b. | n.b. | n.b. | 1603 |
| Ab13 | 4.3 ± .126 | n.b. | [1]n.b. | n.b. | n.b. |  |
| Ab14 | n.b. | 18.8 ± 1.343 | 2.1 ± .129 | n.b. | n.b. |  |
| Ab15 | 4.7 ± .706 | 11.0 ± .353 | 9.5 ± .074 | n.b. | n.b. |  |
| Ab-C5 | n.b. | <1E-12 | 0.9 ± .171 | 5.6 ± .179 | 3.0 ± .112 | 47 | n.b. = no binding detected at 200 nM Ab concentration
[1]n.b. = no binding detected at 333 nM Ab concentration Example 9: Blockade of Myostatin Activation Improves Muscle Performance The impact of Ab1 on muscle performance was investigated. A version of Ab1 with a murine constant region, called muAb1(SEQ ID NOs: 116-117), was used to avoid an immune response in immunocompetent animals. 9-week old C57BU/61 mice were acclimated for one week, then assigned to treatment groups with approximately equal body weights across all groups. The treatment or controls (IgG (20 mg/kg) and PBS) were administered I.P. via tuberculin syringe weekly. Data for IgG control was similar to that of PBS (data not shown). Following 4 weeks of treatment, animals had their plantarflexor function tested in vivo. Following this testing, the animal was sacrificed and extensor digitorum longus (EDL) function was tested in vitro.

muAb1-Heavy Chain constant region
(SEQ ID NO: 116)
ASTTPPSVYPLAPGSAAQTNSMVTLGCLVKGYFPEPVTVTWNSGLSLSSG

VHTFPALQSDLYTLSSSVTVPSSTWPSETVTCNVAHPASSTKVDKKIVPR

DCGCKPCICTVPEVSSVFIFPPKPKDVLTITLTPKVTCVVVDISKDDPEV

QFSWFVDDVEVHTAQTQPREEQFNSTFRSVSELPIMHQDWLNGKEFKCRV

NSAAFPAPIEKTISKTKGRPKAPQVYTIPPPKEQMAKDKVSLTCMITDFF

PEDITVEWQWNGQPAENYKNTQPIMDTDGSYFVYSKLNVQKSNWEAGNTF

TCSVLHEGLHNHHTEKSLSHSPG muAb1-Light Chain constant region
(SEQ ID NO: 117)
GQPKSSPSVTLFPPSSEELETNKATLVCTITDFYPGVVTVDWKVDGTPVT

QGMETTQPSKQSNNKYMASSYLTLTARAWERHSSYSCQVTHEGHTVEKSL

RADCS

Muscle performance was measured in vivo with a 305C muscle lever system (Aurora Scientific Inc., Aurora, CAN). Contractions were elicited by percutaneous electrical stimulation of the sciatic nerve. Optimal isometric twitch torque was determined by increasing the current with a minimum of 30 s between each contraction to avoid fatigue. A series of stimulations were then performed at increasing frequency of stimulation (0.2 ms pulse, 500 ms train duration): 1, 10, 20, 40, 60, 80, 100, 150 Hz, followed by a final stimulation at 1 Hz. Following the measurements, the foot was released and the pin removed and the mouse allowed to recover in a separate clean cage prior to returning to its living chamber.

Figure 37A:
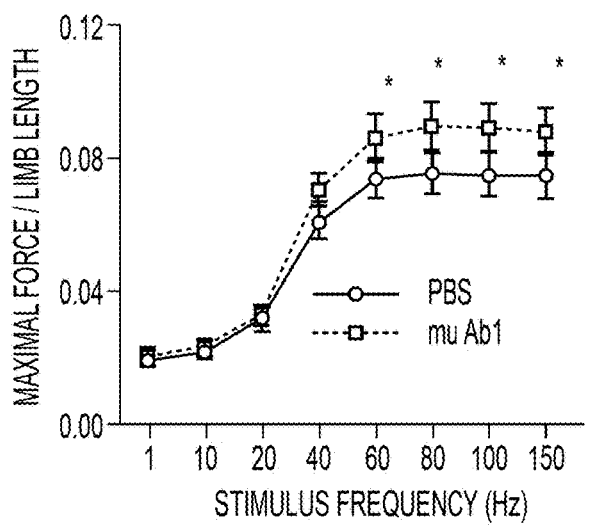
FIGS. 37A-37H shows administration of muAb1 in healthy animals enhances muscle function.
Figure 37B:
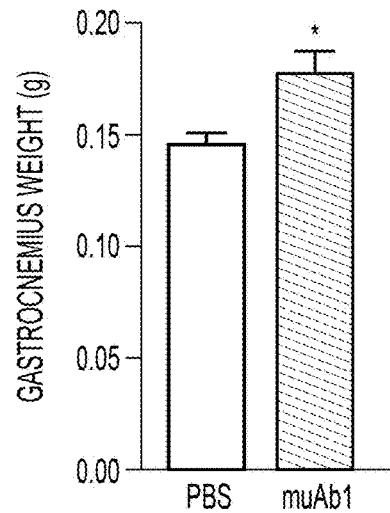
Figure 37C:
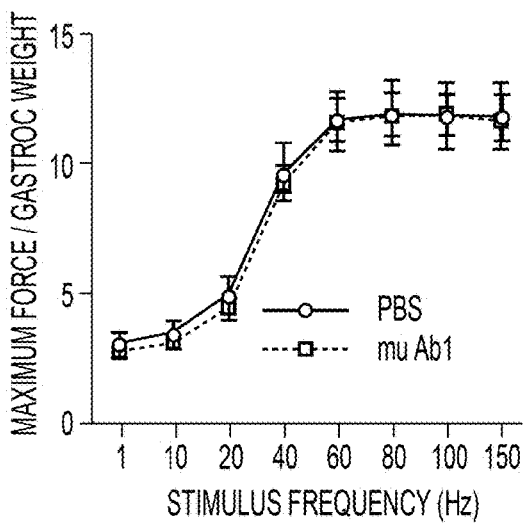
Figure 38C:
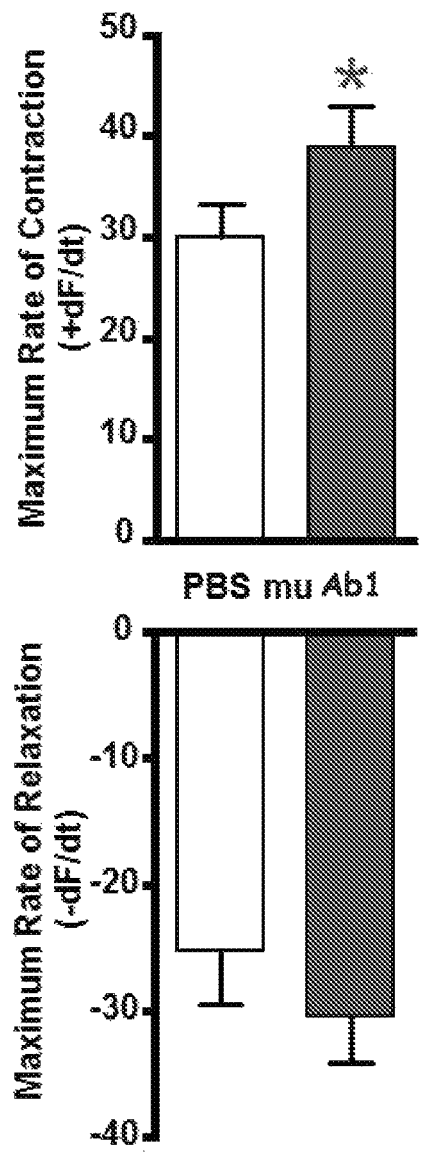

After four weeks of treatment nerve evoked function of the plantarflexor group (gastrocnemius, soleus and plantaris muscle group) was analyzed across its range of activation in vivo. In animals treated with muAb1 we observed ~19% increase isometric torque (normalized to limb length) at frequencies greater than 60 Hz (main effect p=0.003) (FIG. 37A). Accompanying this increased function, we identified a 31% increase in the maximal rate of contraction (p=0.025) (FIG. 38A) occurring independent of any change in the force-frequency response (FIG. 38B). Consistent with the anabolic effects of myostatin inhibition, we find that the increase in force was mirrored by a 22% increase in the gastrocnemius weight (p=0.009, FIG. 37B)). Therefore, when force is normalized to muscle weight, there are no differences between groups (FIG. 37C), suggesting that the hypertrophy induced by Ab1 did not adversely affect muscle quality, excitability, or neuromuscular junction.

To confirm the direct effects of myostatin blockade on the muscle, independent of the nerve, EDL muscle was isolated and force was measured in vitro. In vitro EDL muscle performance was measured in vitro with a 305C muscle lever system (Aurora Scientific Inc., Aurora, CAN) adapted with a horizontal perfusion bath. Briefly, the skin on the lower limb was degloved half length to the knee and the tibialis anterior muscle carefully dissected free from the underlying EDL. A silk suture (4-0) was tied to the distal tendon of the EDL and the tendon severed. The muscle was then carefully dissected free from the tibia and adjacent muscles, the proximal tendon visualized then severed. The muscle was placed in an ice-cold physiological buffered solution and a silk suture tied to the proximal tendon. The muscle was placed in the horizontal bath of the 305C muscle lever system and perfused with physiological buffer oxygenated with 95% $O_2$/5% $CO_2$ and kept at 37° C. The sutures were tied to a fixed post on one side, and the lever arm on the other. A series of 1 Hz and 100 Hz field stimulations (0.2 ms pulse, 100 ms duration) at 0.01 Hz frequency were delivered via platinum electrodes flanking the muscle to ensure that the sutures are tight and that the maximal developed force was stable. Once stable, a series of stimulations were performed at increasing frequency of stimulation (1 ms pulse, 250 ms train duration): 1, 10, 20, 40, 60, 80, 100, 150 Hz, followed by a final stimulation at 1 Hz.

Figure 37D:
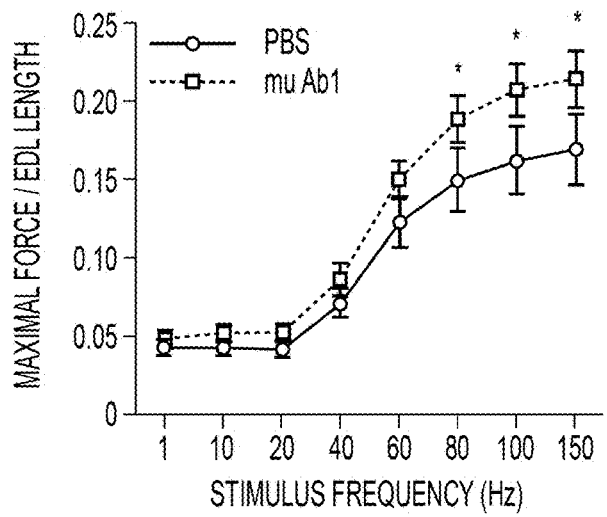
Figure 37E:
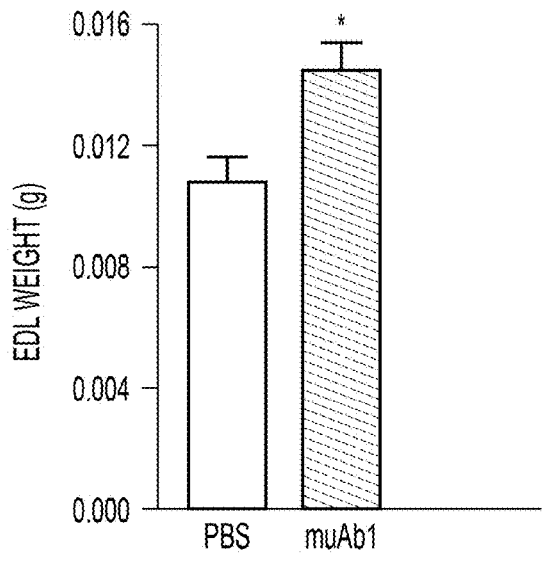
Figure 37F:
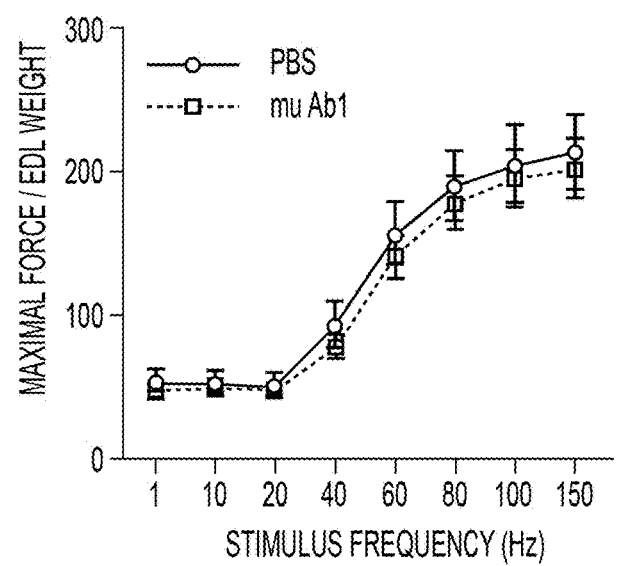
Figure 37G:
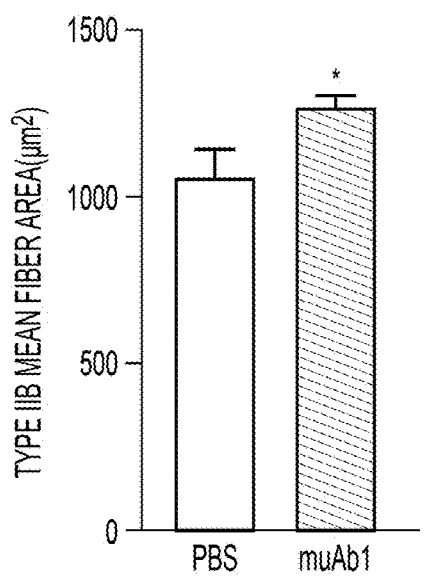
Figure 37H:
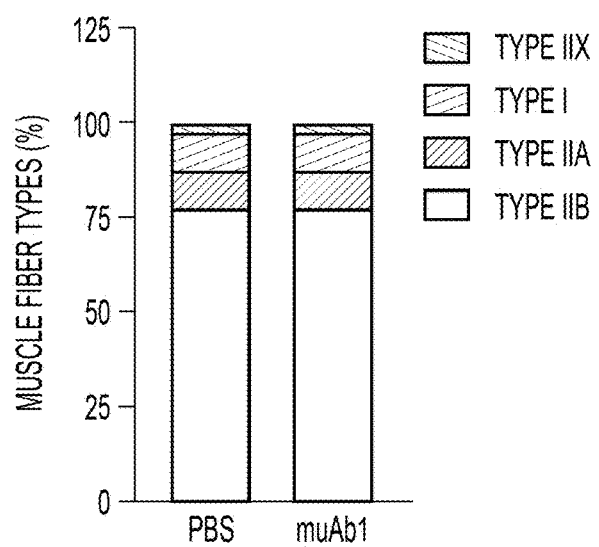
Figure 38D:
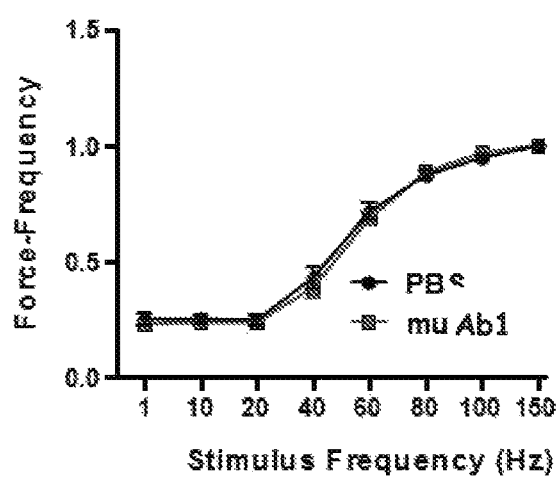

Treatment with muAb1 resulted in a 27% increase in maximal force at 150 hz (p=0.011, FIG. 37D) with no alteration in the rates of contraction and relaxation (FIG. 38C), nor any differences in force-frequency relationship (FIG. 38D). Again, myostatin blockade resulted in a 34% increase in the EDL weight (p=0.007, FIG. 37E), such that when force is normalized to muscle weight, there are no differences between groups (FIG. 37F). FIG. 37G shows the Type IIB mean fiber area of nuAB2 and PBS. FIG. 37H shows 4 muscle fiber types (%) in PBS and muAb samples.

Plantarflexor muscle group was frozen for histology and embedded in cryomatrix on a soft cork surface to enable easy sectioning. Briefly, frozen and embedded tissues were mounted in a cryotome and serially sectioned (10 µm thickness) perpendicular to the fiber axis. Multiple slices (5-10) were taken at different portions of the muscle. The slices were then fixed in ice-cold paraformaldehyde and kept at −80° C. until further use.

For cross-sectional area determination, fixed sections from the mid-belly of the muscle were stained with wheat germ agglutinin conjugated to a fluorophore to visualize cell membranes. Sections were digitized using fluorescent microscopy, cell boundaries were traced using predictive software, and cross-sectional area was determined via unbiased automated measurements. For muscle fiber type determination, histological slices were taken from the mid-belly of the soleus and the gastrocnemius muscle. The fixed tissue sections were then blocked using Tris-buffered saline supplemented with 4% bovine serum albumin, 0.01% Triton X-100 and 10 µg/ml Fab fragments for 1 h at room temperature. The slide was then washed with PBS and covered with a primary antibody against either MyHC-I, MyHC-IIa, or MyHC-IIb (1:20 dilution; Developmental Studies Hybridoma Database) and incubated overnight at 4° C. The slide was then washed with PBS and the appropriate secondary antibody added for 1 h at room temperature. The slide was washed again in PBS, covered in mounting solution, and a coverslip used to seal the tissue section for fluorescence microscopy measures. Fluorescently-labeled tissue sections were digitized using a fluorescent microscope (Nikon). Images were then analyzed for number of cells using standard counting software. Number of cells per volume were extrapolated from the section volume and the muscle weight.

H&E staining was performed according to Treat-NMD protocol MDC1a_M1.2.004. Briefly, muscle sections were fixed for 5 minutes in 4% paraformaldehyde, then rinsed for 1 minute in running tap water. Slides were immersed for 5 minutes in Mayer's hematoxylin solution followed by a 10 minute blueing period in warm running tap water. Red stain as achieved by a 10-minute incubation in 0.5% Eosin solution with 1% acetic acid, then rinsed 3 times for 1 minute in dd$H_2O$, then successive dehydration in 70%, 90%, 100% ethanol, and 100% xylene. Slides were mounted in xylene-based mounting media prior to imaging.

Figure 38E:
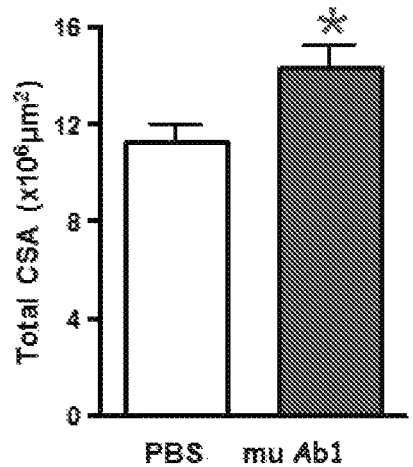
Figure 38F:
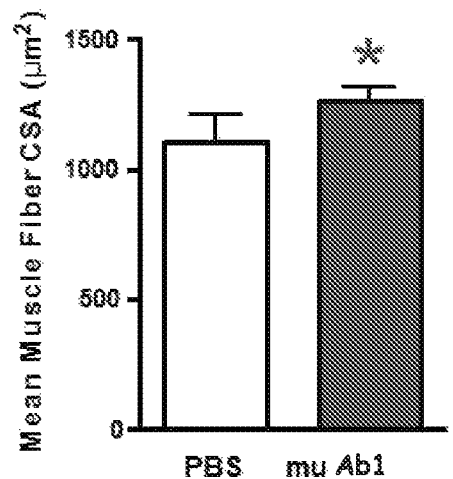
Figure 38G:
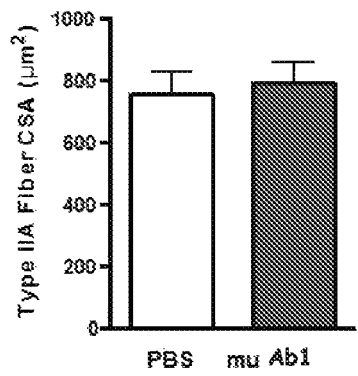
Figure 38H:
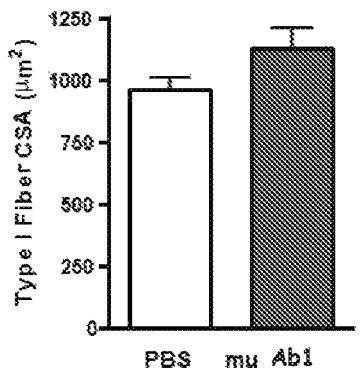
Figure 38I:
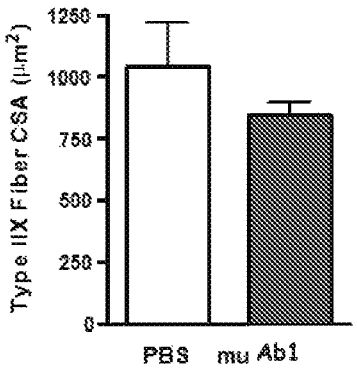

Histological evaluation of the plantarflexor muscle group revealed a 27% increase in total muscle cross sectional area (p=0.019, FIG. 38E), and a 14% increase in mean fiber cross sectional area (p=0.010, FIG. 38F) with muAb1 treatment. This increase was underpinned by 29% increase in Type IIB fiber cross-sectional area (p=0.009) (FIGS. 38G-38H) which was independent of any change relative distribution fiber types (FIG. 38I) or the CSA of the Type I, IIA, or IIx fibers (FIGS. 38G-38I).

Figure 44A:
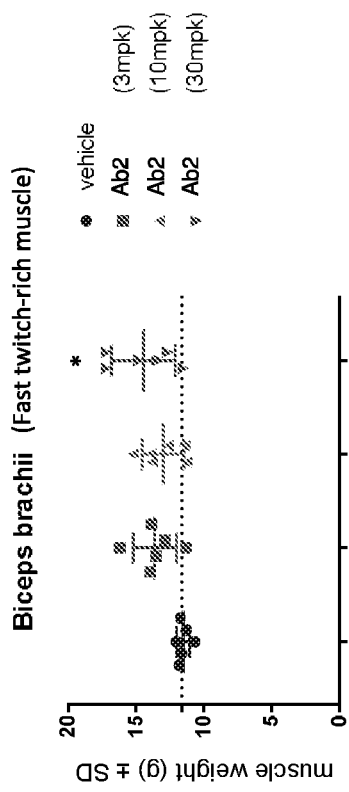
FIG. 44A shows the quadriceps (rectus femoris) weights of the different groups and FIG. 44B shows the gastrocnemius weights of the different groups.
Figure 44B:
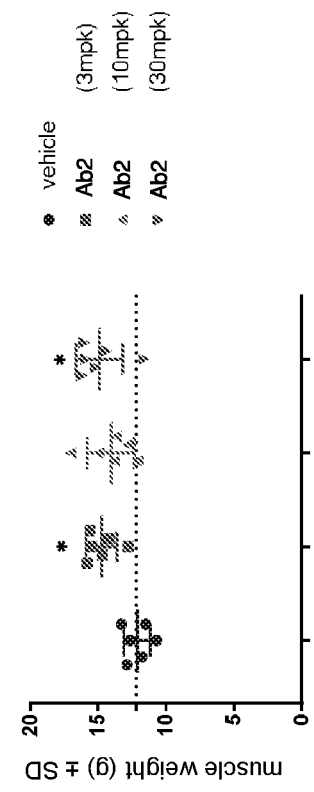

Example 10: Effects of Treatment with Ab2 on Lean Mass, Muscle Weight, and Serum Myostatin in Healthy Cynomolgus Monkeys Effects of treatment with Ab2 on change in lean mass were evaluated in healthy Cynomolgus monkeys (n=6 per treatment group). Healthy male Cynomolgus monkeys (avg age: 34 months at start of study) were dosed by intravenous injection once weekly for 8 weeks at three different dose levels of Ab2 (3 mg/kg, 10 mg/kg, and 30 mg/kg) with a 4-week recovery phase. Control animals were administered vehicle control (20 mM Citrate and 150 mM Sodium Chloride USP, pH 5.5). Lean mass was measured by Dual Energy X-Ray Absorptiometry (DEXA) at baseline and at intervals throughout the 12 week study (FIGS. 43A-43D). Treatment with Ab2 resulted in a 5-9% increase in the limb lean mass of Ab2-treated monkeys compared to vehicle control (FIGS. 43A-43D and FIG. 45). Effects of treatment with Ab2 on tissue weights from the biceps brachii and gastrocnemius muscles of healthy Cynomolgus monkeys were also measured at week 12 (FIGS. 44A-44B). Significant effects of Ab2 treatment were apparent in the weights of these muscles (FIGS. 44A-44B and FIG. 45). The gastrocnemius and biceps brachii muscles, which are rich in fast twitch fibers, were substantially larger by as much as 25% in Ab2-treated animals compared to the vehicle control (FIG. 45). Therefore, Ab2 treatment had a notable effect on muscle growth. Further, Ab2 treatment had a particularly robust effect on fast twitch-rich muscle fibers.

Figure 46A:
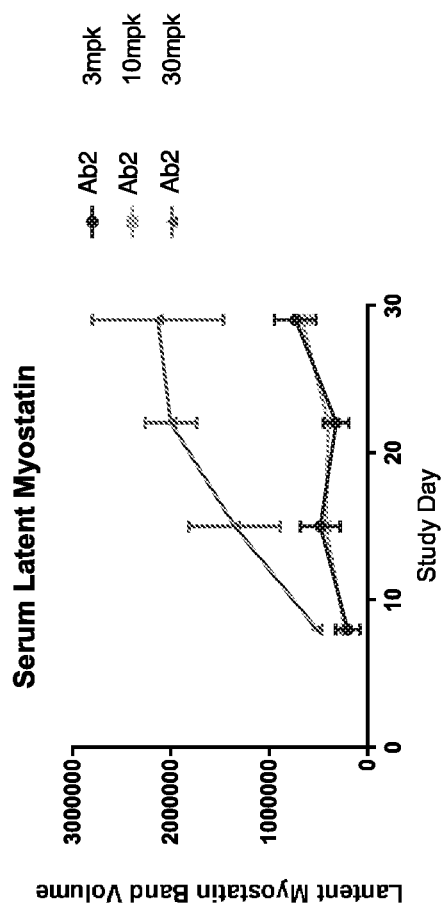
FIGS. 46A and 46B show latent myostatin levels in serum samples of Ab2-treated healthy Cynomolgus monkeys and in control animals measured using quantitative fluorescent western blotting. Healthy male Cynomolgus monkeys were dosed by intravenous injection once weekly for 8 weeks at three different doses, 3 mg/kg, 10 mg/kg, and 30 mg/kg, with a 4-week recovery phase. Control animals were administered vehicle control (20 mM Citrate and 150 mM Sodium Chloride USP, pH 5.5). Serum samples were collected over different study days and relative levels of latent myostatin in the serum samples were analyzed using quantitative fluorescent western blotting.
Figure 46B:
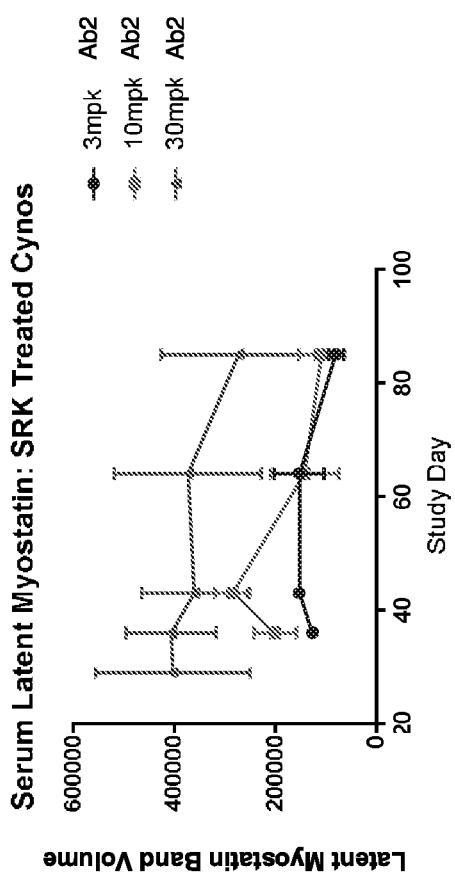

Throughout this study, serum samples for analysis of serum myostatin levels were collected on study days 2, 4, 8, 15, 22, 29, 36, 43, 64, and 85 as indicated in FIGS. 46A and 46B. Increase in myostatin levels in Ab2-treated animals peaked and plateaued between study days 15 and 29 and declined by study day 85 (FIGS. 46A-46B). Increase in latent myostatin levels in the serum was seen with all doses of Ab2 with greatest increase seen in animals treated with 30 mg/kg of Ab2 (FIGS. 46A-46B).

Example 11. Effect of Anti-Myostatin Antibody Treatment on Spinal Cord Injury Mice Spinal Cord Injury and Rest Article Treatment and Study Measures The effect of mu-Ab1 on spinal cord injury in mice was studied in a mouse severe contusion model. Adult female C57BL/6 mice (8 weeks old) were randomized to four test groups. Mice were anesthetized by intraperitoneal (i.p.) injection using a ketamine (100 mg/kg) and xylazine (10 mg/kg) cocktail, then subjected to a laminectomy between thoracic vertebrae T8 and T10 to expose the dorsal surface of the spinal cord. To induce spinal cord injury, the spinal cord at T9 was placed directly under the vertical shaft of the Infinite Horizon Impactor (IH-0400 impactor. Precision Systems Instrumentation, LLC, Virginia. USA), followed by slowly lowering of the shaft until the response peak on the force transducer reached the predetermined level (65 kDyne). The control group was subjected to laminectomy (only) at the T9 level (sham-operation). Immediately following injury animals were administered by i.p. injection with test articles—either vehicle (20 mM Citrate and 150 mM Sodium Chloride, pH 5.5). IgG (40 mg/Kg), or GDF8 (Mu-Ab1, 40 mg/Kg). Follow-up injection of test articles was administered in the same manner 1-week post-SCI. During the two-week study multiple physical and behavior measures were used to assess the effects of anti-myostatin pharmacotherapy. Physical measures included total body weight, muscle weight, total body composition (lean body mass (LBM), fat mass, and bone mineral density) and total metabolic energy expenditure determined using indirect calorimetry. Behavioral measures were also assessed including BMS motor score, rotarod test, and grip-strength test. Between-group differences were analyzed using one-way ANOVA, followed by Tukey post hoc comparison (Graph-Pad, Prism). Data are expressed as mean±SEM. A significance level of $p<0.05$ was accepted as different from control.

Results and Data Analysis

Body Mass, Muscle Mass, and Body Composition

Figure 47:
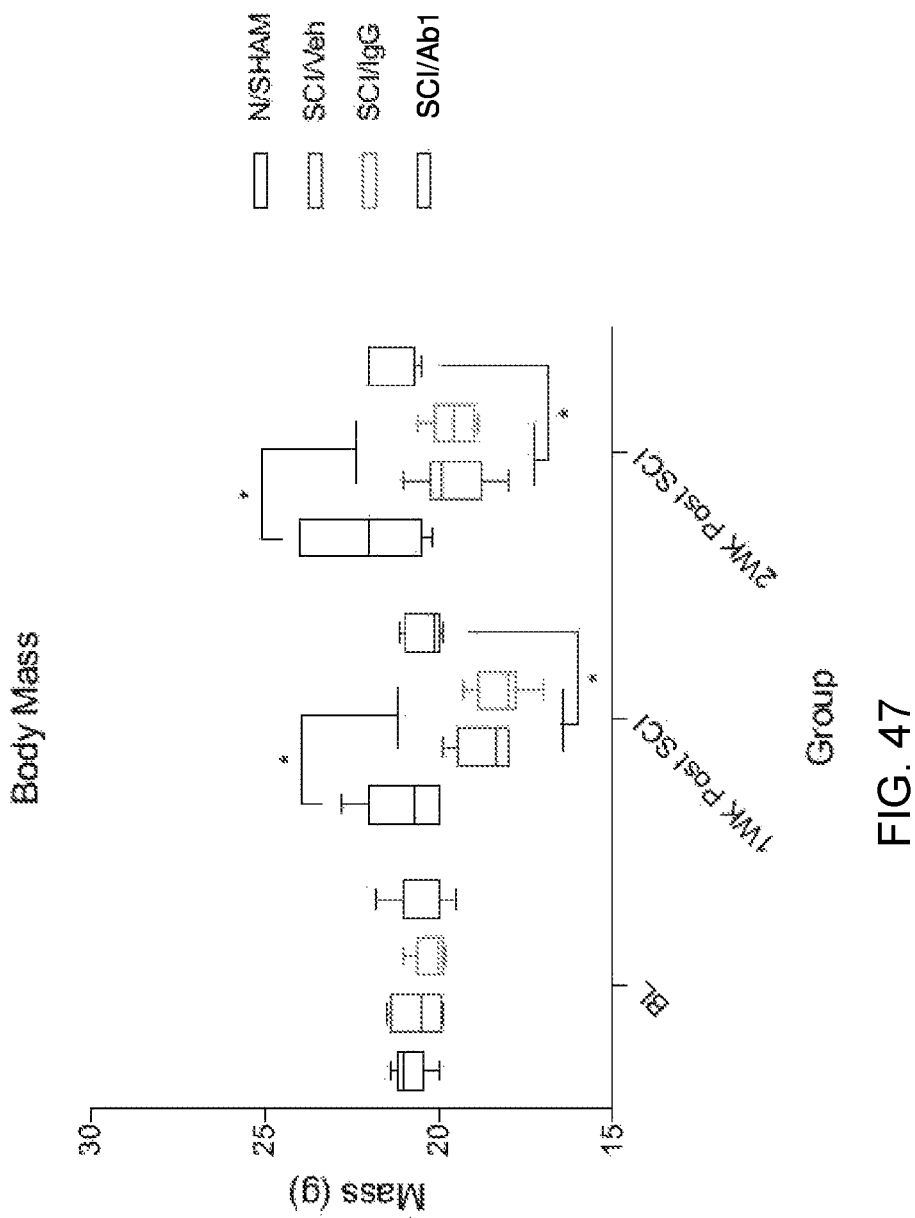
FIG. 47 depicts body mass in naïve mice, and sham, SCI-veh, SCI-IgG, SCI-Ab1 treatment groups at 1- and 2-weeks post-SCI. Asterisks * on the top reflect significant difference from sham; and asterisks * at the bottom of the bars reflect significant difference from SCI-Ab1.

Body mass was measured at the following time-points: 0 (Baseline: prior to survival surgery); 1-week post-surgery; and 2-weeks post-surgery (FIG. 47). There were no significant group differences in mass at baseline. 1-week following SCI (and treatment), there was a significant reduction in body mass in the SCI-veh (P<0.0001) and SCI-IgG (P<0.0001) groups, compared to sham control. There was no statistical difference in body mass between the sham control and SCI-GDF8 (Mu-Ab1) (P=0.2805) group, However, the SCI-GDF8 (Mu-Ab1) group mass was significantly greater than both SCI-veh (P=0.004) and SCI-IgG (P=0.0003) groups. 2-weeks post-SCI, body mass in SCI-veh (P=0.0011) and SCI-IgG (P=0.0009) remained significantly lower than sham-control. Body mass in the SCI-GDF8 (Mu-Ab1) group remained significantly greater than SCI-veh (P=0.0152) and SCI-IgG (P=0.0123) groups, but not different compared to sham control (P=0.585).

The data indicate that SCI induced a significant decrease in total body mass when compared to uninjured mice. GDF8 (Mu-Ab1) as a treatment significantly attenuated loss of body mass observed with SCI, such that group means between uninjured and GDF8 (Mu-Ab1) treated mice are qualitatively similar and statistically non-significant.

Figure 48:
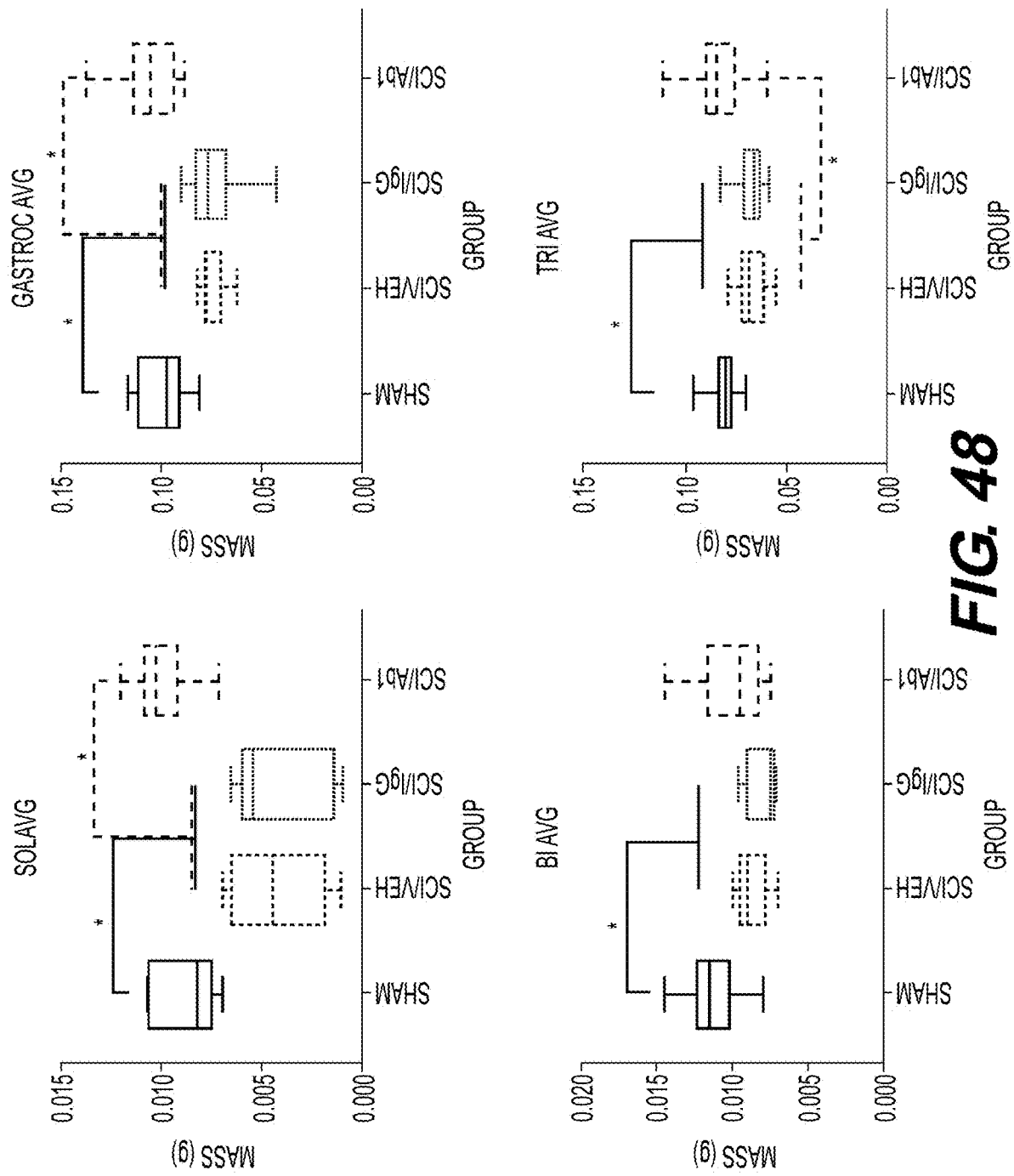
FIG. 48 depicts muscle wet weight (mass) in sham, SCI-veh, SCI-IgG, SCI-Ab1 treatment groups at 2-weeks post-SCI. Excised muscle includes sublesional soleus and gastrocnemius and supralesional biceps and triceps muscles.

At necropsy—2-weeks post-SCI—several muscle tissues (soleus, gastrocnemius, biceps and triceps) were extracted to evaluate the effect of SCI and treatment on wet weight (FIG. 48). The average weight of the soleus muscle was significantly less in the SCI-veh and SCI-IgG (both P's<0.0001) groups than the sham control. There was no statistical difference in soleus mass between the sham control and SCI-GDF8 (Mu-Ab1) (P=0.3129) group, however, the SCI-GDF8 (Mu-Ab1) group soleus mass was significantly greater than both SCI-veh and SCI-IgG (both P's<0.0001). Similarly, the average weight of the gastrocnemius muscle was significantly less in the SCI-veh and SCI-IgG (both P's<0.0001) than the sham control. There was no statistical difference in soleus mass between the sham control and SCI-GDF8 (Mu-Ab1) (P=0.3255) group, however the SCI-GDF8 (Mu-Ab1) group soleus mass was significantly greater than both SCI veh and SCI-IgG (both P's<0.0001).

The average mass of the biceps muscle was also significantly less in the SCI veh (P=0.045) and SCI-IgG (P=0.04) groups when compared to sham control. Group mean trends in biceps mass between the SCI-GDF8 (Mu-Ab1) group were greater than both SCI-veh and SCI-IgG groups. The average mass of the triceps muscle was also significantly less in the SCI-veh (P=0.007) and SCI-IgG group (P=0.0013) compared to sham control. The SCI-GDF8 (Mu-Ab1) group triceps mass was significantly greater than both SCI-veh and SCI-IgG (both P's<0.0001).

The data show that sublesional muscle mass—including the primarily oxidative soleus muscle, and the primarily glycolytic gastrocnemius muscle—was significantly reduced following SCI when compared to uninjured mice. GDF8 (Mu-Ab1) treatment surprisingly and significantly attenuated this muscle loss, where both soleus and gastrocnemius mean muscle mass was equal to the mass of uninjured mice, suggesting an effect across muscle phenotype. When examining supralesional muscle mass—including biceps and triceps muscles—there was also a significant reduction in mass with SCI compared to uninjured mice. This is likely due to an overall depression of physiological systems and global loss of mass with SCI (albeit a greater proportion of muscle mass loss is sublesional).

Figure 49:
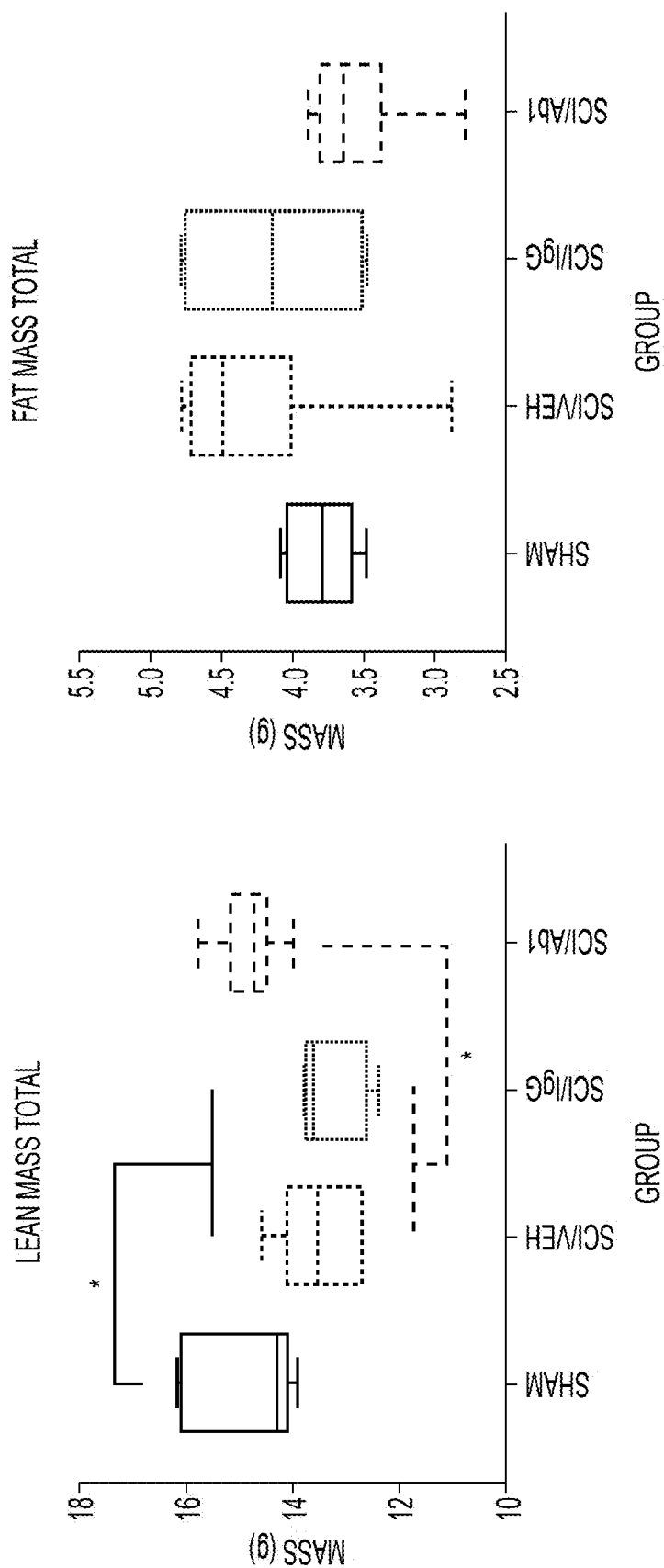
FIG. 49 depicts analysis of total fat-free (lean) and fat mass in sham, SCI-veh, SCI-IgG, and SCI-Ab1 treatment groups at 2-weeks post-SCI.
Figure 50:
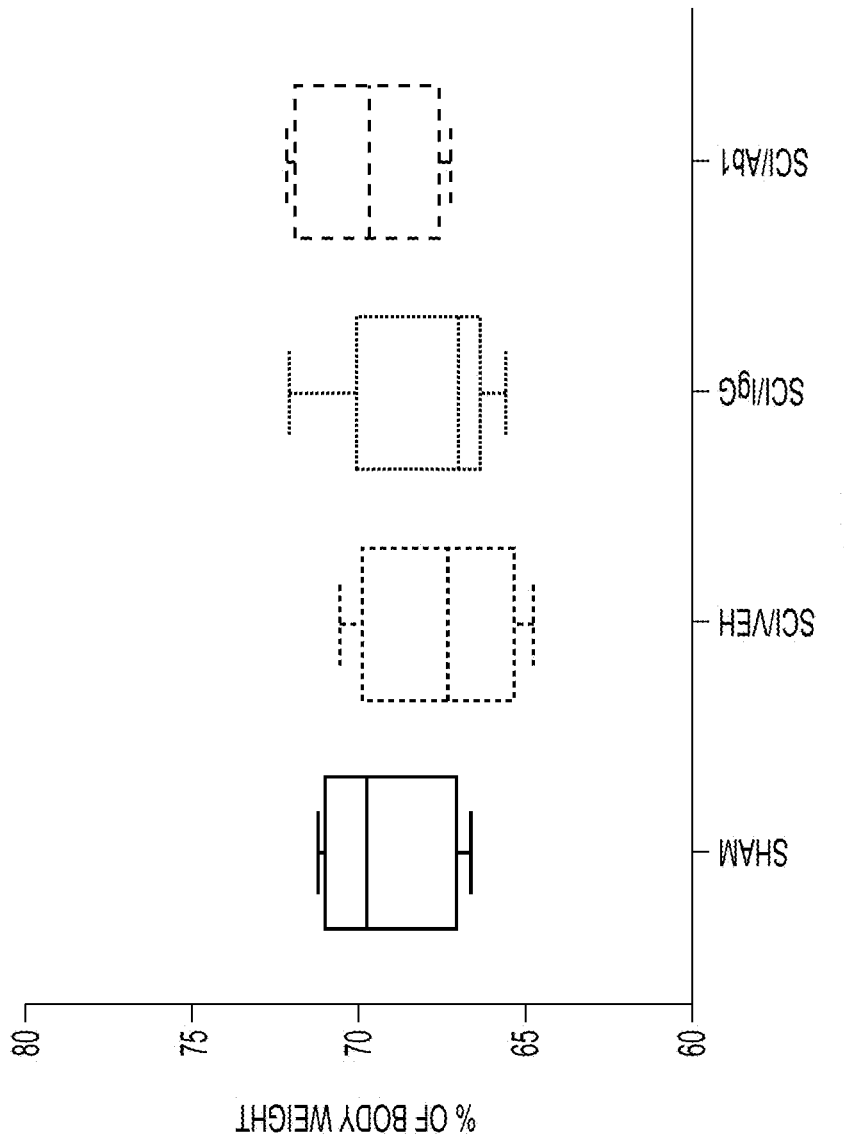
FIG. 50 depicts lean mass as a percentage of body mass in sham. SCI-veh, SCI-IgG, SCI-Ab1 treatment groups at 2-weeks post-SCI.

At 2-weeks post-SCI body composition (lean and fat mass) was assessed by dual-energy x-ray absorptiometry (DXA) densitometry (Lunar PIXImus™ densitometer (GE Medical-Lunar. Madison, WI)) in all experimental groups. Total body fat-free (lean) mass was significantly less in the SCI-veh (P=0.0124) and SCI-IgG (P=0.056) groups compared to sham control. The SCI-GDF8 (Mu-Ab1) group total fat-free (lean) mass was significantly greater than both the SCI-veh (P=0.0254) and SCI-IgG (P=0.0114) groups (FIG. 49), and group mean trends indicated greater fat mass in both the SCI-veh and SCI-IgG groups when compared to sham control (FIG. 49). The SCI-GDF8 (Mu-Ab1) group mean trend for whole body fat mass was also less than both the SCI-veh and SCI-IgG groups, and comparable to sham control. When examining the average fat-free (lean) mass as a percentage of body mass, there were no discernable differences between groups, suggesting that changes in body mass after SCI, and treatment effects of GDF8 (Mu-Ab1) were limited to changes in lean body mass (FIG. 50).

These data show that total—or whole body—fat free (lean) mass was significantly reduced following SCI compared to sham control. GDF8 (Mu-Ab1) treatment significantly attenuated this loss of fat-free (lean) mass after SCI, where mean fat-free (lean) mass was not different from uninjured mice, suggesting an effect on global lean tissue. Conversely, total fat mass after SCI appeared to increase compared to sham control, when examining group means. The reduction in sublesional fat-free (lean) mass, and the increase in adiposity (global and regional) is a well characterized feature of chronic SCI pathophysiology.

Metabolism and Total Energy Expenditure

Figure 51:
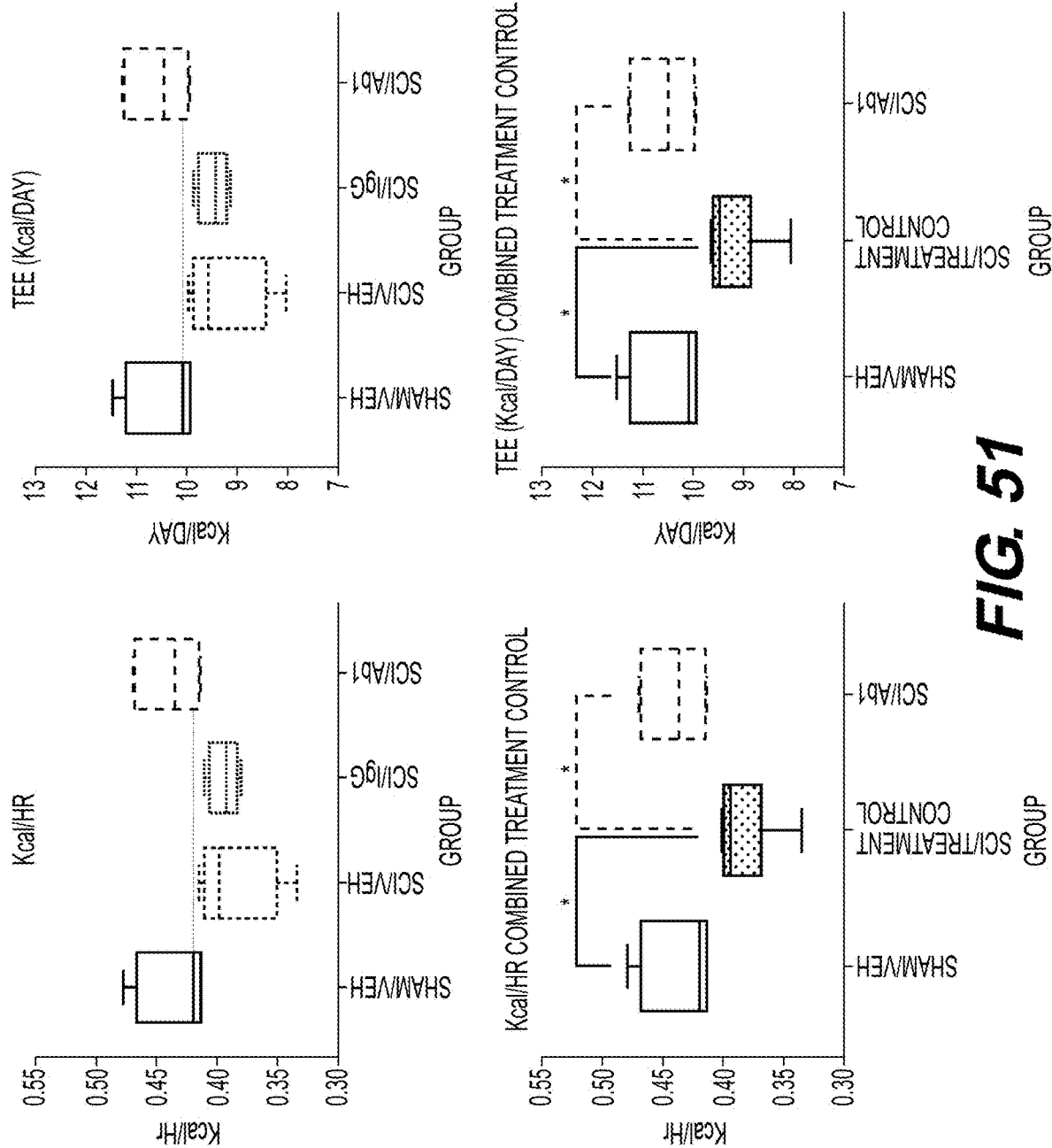
FIG. 51 depicts analysis of kcal/hr and TEE in sham, SCI-veh, SCI-IgG, and SCI-Ab1 treatment groups at 2-weeks post-SCI. In the lower graphs, the SCI/Treatment Control group represents the combined SCI/veh+SCI/IgG groups from the upper graphs.

Indirect calorimetry was performed on mice using a 12-chamber open-circuit Oxymax system of the Comprehensive Lab Animal Monitoring System (CLAMS; Columbus Instruments, Columbus, OH, USA). Mice were transferred to individual metabolic chambers for 3-days prior to (and including) the 2-week post-SCI analysis time-point. $VO_2$ and $VCO_2$ were measured continuously, and using indirect calorimetry, energy expenditure/hour (kcal/hr) and total energy expenditure/day (TEE) were calculated (FIG. 51). Group mean trends suggest a decrease in these measures in SCI-veh and SCI-IgG compared to sham control, and that the metabolic decrease in the SCI-veh group versus sham control approached statistical significant (P=0.075). Group means trended toward elevation in the SCI-GDF8 (Mu-Ab1) group when compared to the SCI-veh and SCI-IgG groups. Notably, the metabolic increase in the SCI-GDF8 (Mu-Ab1) compared to the SCI-veh approached statistically significant (P=0.0530), and the direction of the SCI-GDF8 group mean appeared slightly elevated compared to sham control. For additional analysis, the SCI groups not receiving the GDF8 (Mu-Ab1) treatment drug (SCI-veh+SCI-IgG) was collapsed to add group power to the SCI treatment control. In doing so, it was found that kcal/hr and TEE in the coalesced SCI-treatment control group was lower than the sham control (P=0.0159). There was no statistical difference in kcal/hr and TEE between the sham control and SCI-GDF8 (Mu-Ab1) (P=0.9764) group, however the SCI-GDF8 (Mu-Ab1) group kcal/hr and TEE was significantly greater than the coalesced SCI-treatment control (P=0.0106) group.

The results show that metabolism (as energy expenditure) was depressed following SCI, and that GDF8 (Mu-Ab1) treatment maintained resting metabolism at levels that approximate uninjured controls. These results further suggest that the biological effect of GDF8 (Mu-Ab1) on lean tissue, in particular muscle preserves levels of resting metabolism that are otherwise reduced following SCI.

Functional Measures

BMS Open Field Locomotor Test

The Basso Mouse Scale (BMS) open field locomotor test (using a 0 to 9 rating system) was used to assess recovery of hind-limb locomotor function following SCI, including (but not limited to) variables such as foot placement, weight support, and joint motion. Under blinded conditions, a team of two investigators evaluated the mice over a 4-minute time period at baseline, 1 day after SCI/sham, and weekly thereafter. The arena was divided into three zones (wall, inter and center) and mouse behavior was recorded over a 5-minute period using a high resolution, video camera. The total number of lines crossed, time spent in each zone, and stereotypical behaviors such as grooming and rearing were analyzed and expressed as number of events.

Figure 52:
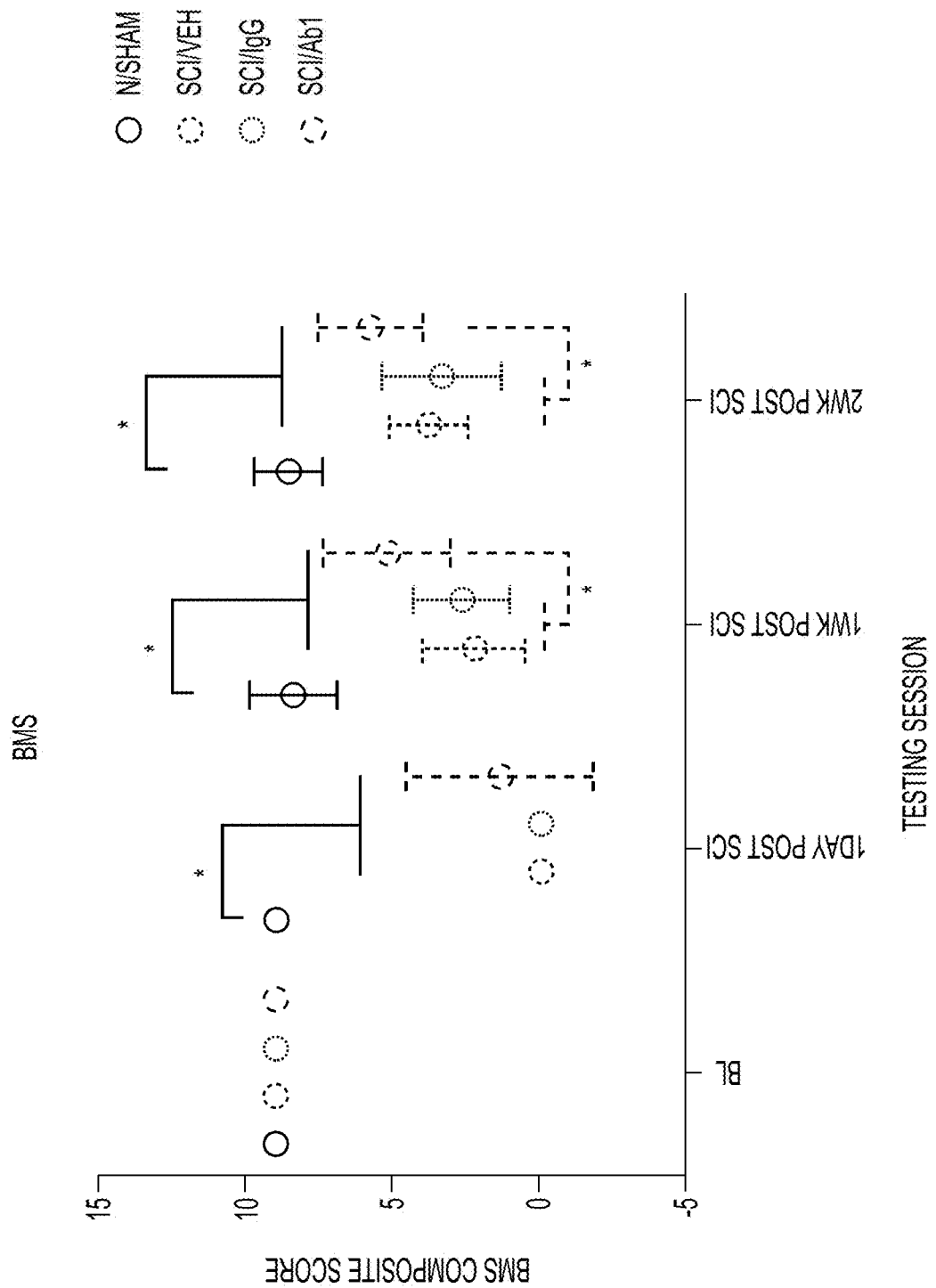
FIG. 52 depicts the BMS locomotor assessment in sham, SCI-veh, SCI-IgG, and SCI-Ab1 groups, at baseline (before survival surgery), 1-day, 1-week, and 2-weeks post-SCI. Statistical comparison at 1- and 2-weeks post-SCI reflect combined SCI-veh+SCI-IgG data.

There was a significant reduction in BMS composite score in the SCI-veh and SCI-IgG groups (both P's<0.0001) 1-day post-SCI (FIG. 52). Because of the uniformity at this timepoint in the SCI-veh and SCI-IgG groups, they were collapsed to provide additional study power at later time-points (SCI-treatment control). Also, at 1-day post-SCI, there was a significant reduction in BMS score in the SCI-GDF8 (Mu-Ab1) group (P<0.0001) compared to sham control. 1-week post-SCI, BMS scores remained significantly reduced in SCI-treatment control (P<0.0001) and SCI-GDF8 (Mu-Ab1) (P=0.0128) groups compared to sham control. However, the BMS score was significantly greater in the SCI-GDF8 (Mu-Ab1) (P=0.0148) group compared to the SCI-treatment control. Similarly, at 2-weeks post-SCI, BMS scores remained significantly reduced in both the SCI-treatment control (P<0.001) and SCI-GDF8 (Mu-Ab1) (P=0.0182) groups, but again, the SCI-GDF8 (Mu-Ab1) group had a significantly higher BMS score than the SCI treatment control (P=0.0143).

Rotarod Test

Motor coordination and balance were tested on the accelerating rotarod cylinder (Rotamex 4/8. Columbus Instruments). The procedure consisted of a 5-day pre-training (days 1 to 5) followed by the testing (1-week and 2-weeks post-SCI/sham). The cylinder rotated at increasing speed and constant acceleration (from 10 to 60 rpm over 10-minute period). The total time spent on the rod prior to fall was recorded and non-walking behaviors, such as passive clinging to the rod, were manually corrected. Each trial consisted of an average of 4 sessions.

Figure 53:
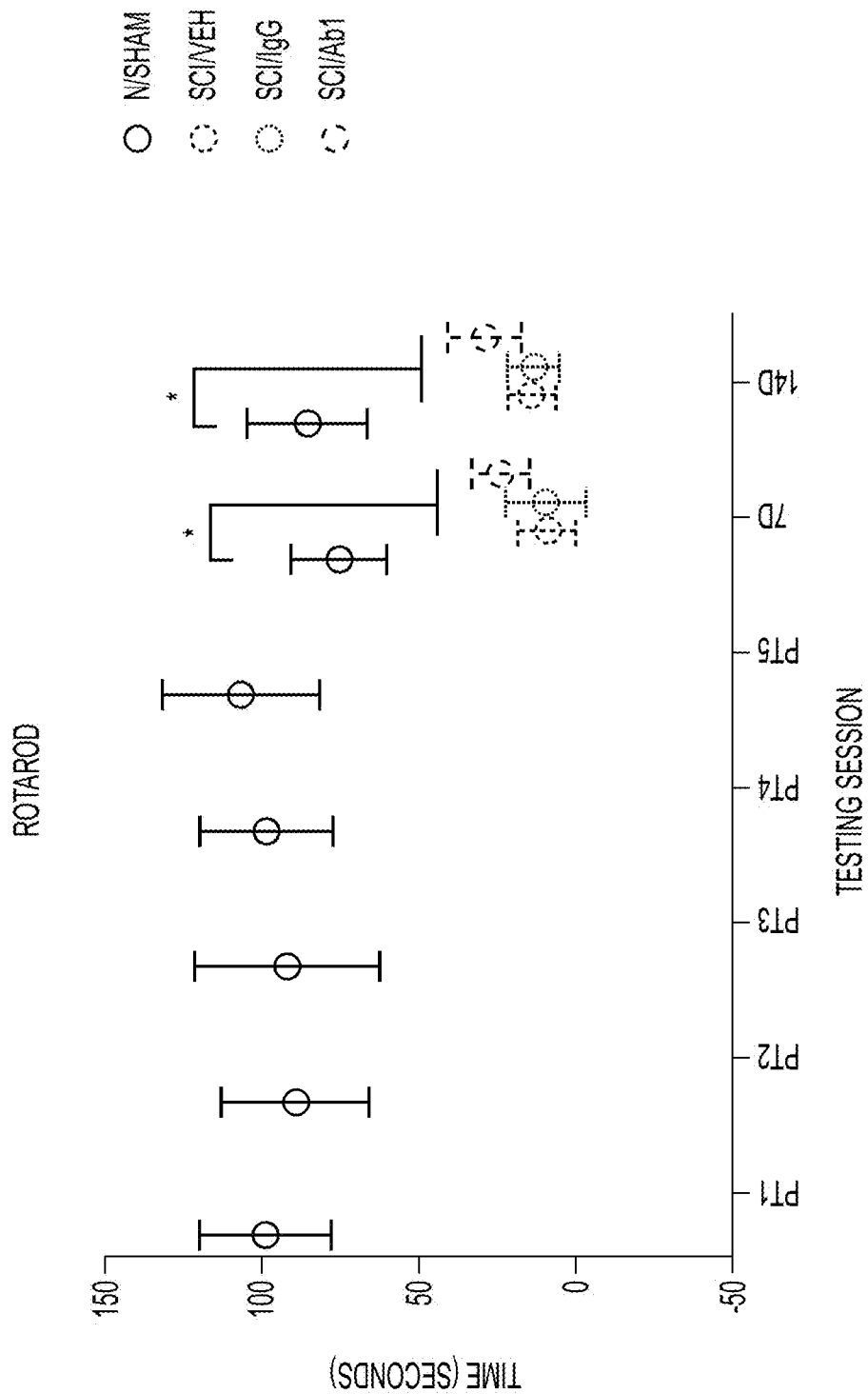
FIG. 53 depicts Rotarod time scores in sham, SCI-veh, SCI-IgG, and SCI-Ab1 groups, after pre-training (PT), 1-week, and 2-weeks post-SCI.

Using rotorod time trials as a proxy measure of motor coordination and balance this study showed that 1-week post SCI, there was a significant decrease in average rotarod time in the SCI-veh, SCI-IgG, and SCI-GDF8 groups (all P's<0.0001) compared to sham control (FIG. 53). The SCI-GDF8 (Mu-Ab1) group mean was greater than both the SCI-veh and SCI-IgG groups (P=0.118). Similarly, 2-weeks post SCI, a significant decrease persisted in average rotarod time in the SCI-veh. SCI-IgG, and SCI-GDF8 (Mu-Ab1) groups (all P's<0.0001) compared to sham control. Again, although there was no statistical difference between any of the SCI groups, the SCI-GDF8 (Mu-Ab1) group mean was greater than both the SCI-veh and SCI-IgG groups (P=0.1708).

Grip Strength Test

All animals from the sham and SCI groups underwent analysis of hindlimb peak force (muscle strength) using the grip-strength test. Hind-limb grip strength was assessed using a digital force gauge (Chatillon DFIS2, Ametek), which generates a measure of neuromuscular function as maximal muscle strength—with the unit of force measured in grams. The test consisted of a baseline assessment prior to surgery, followed by a test day at 1-week and 2-weeks post-surgery. Force values were the calculated average of 5-trials.

Figure 54:
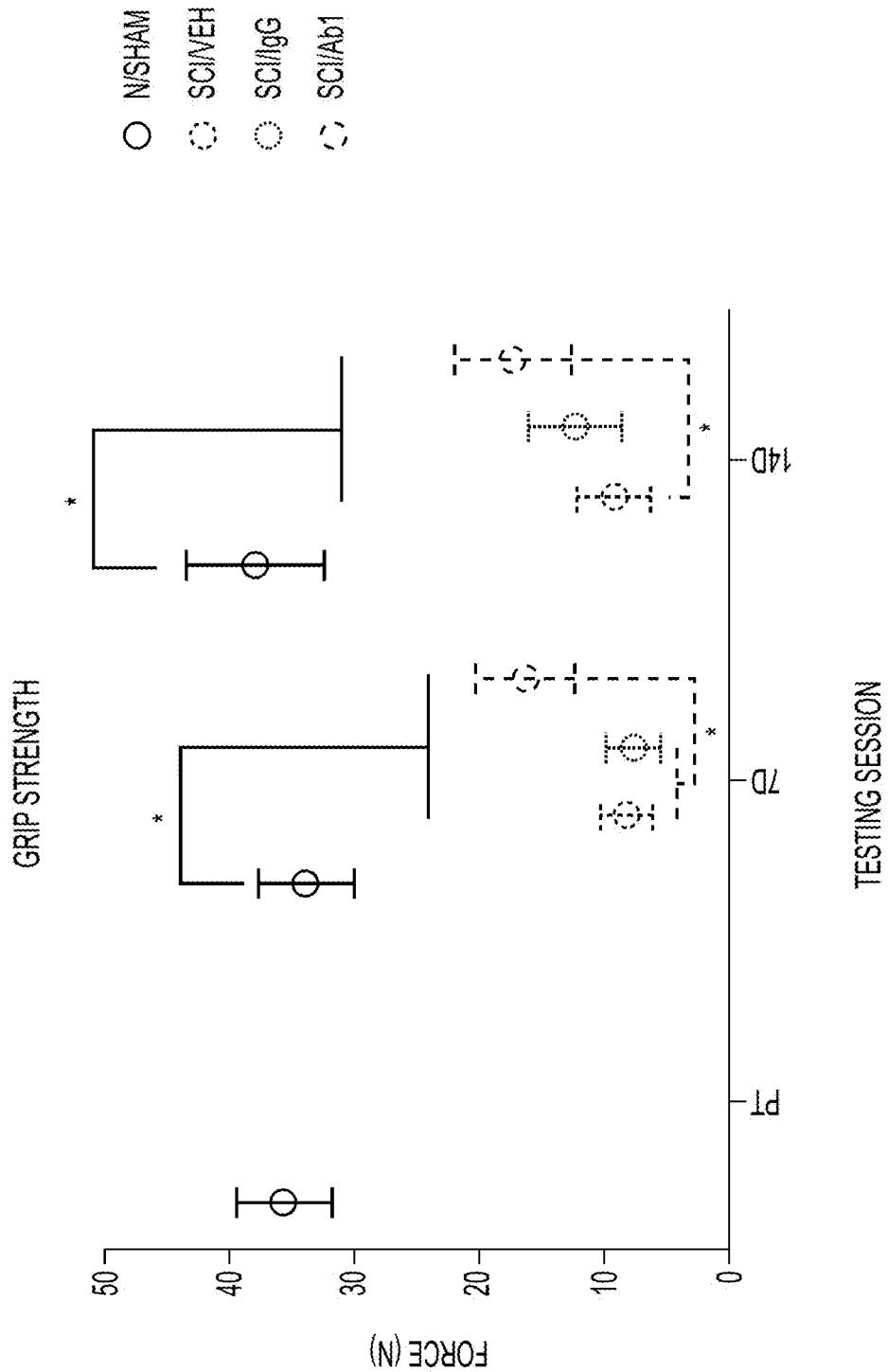
FIG. 54 depicts grip strength in sham, SCI-veh, SCI-IgG, and SCI-Ab1 groups, after pre-training (PT), 1-week, and 2-weeks post-SCI.
Figure 55:
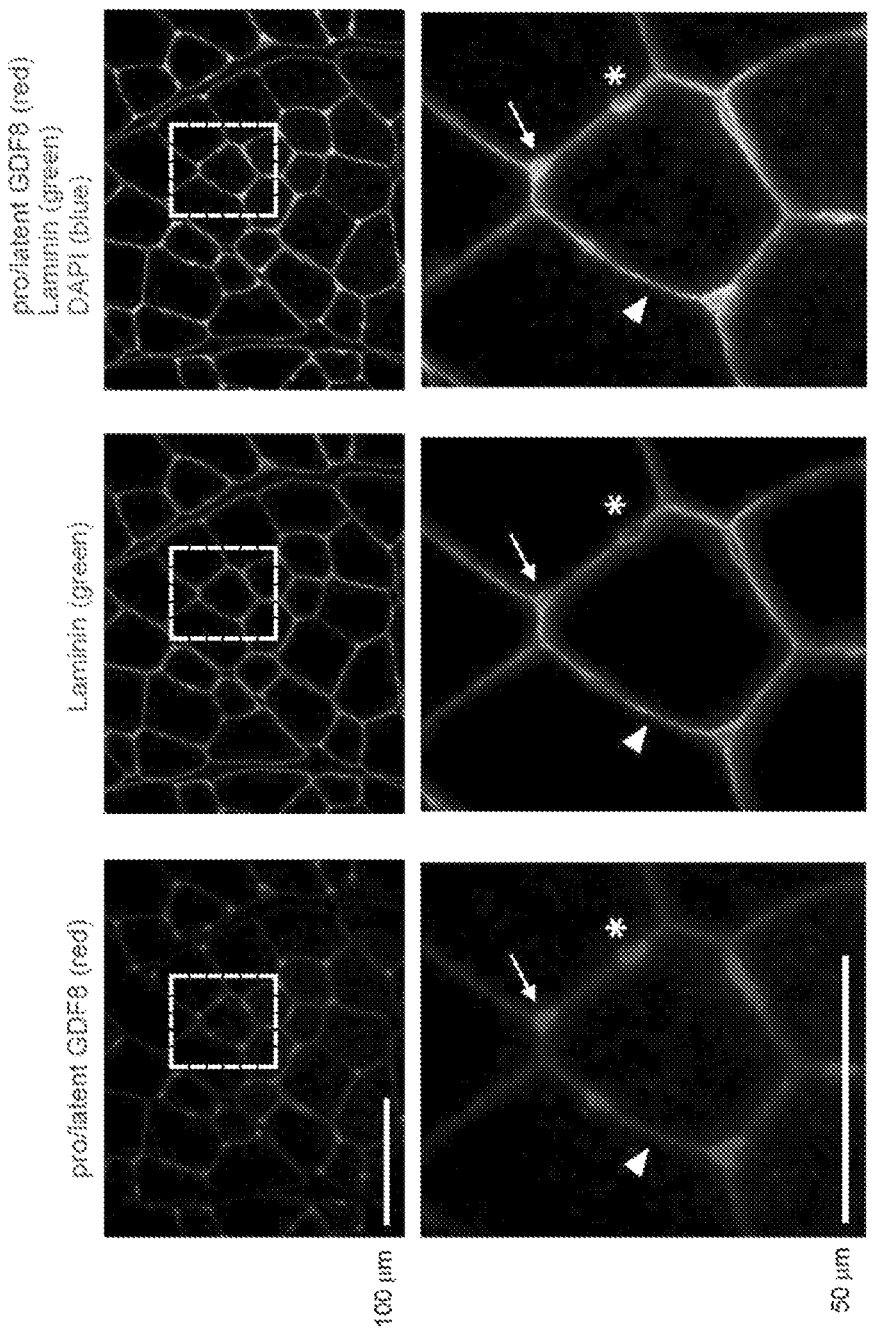
FIG. 55 depicts an immunofluorescence assay performed on cryosectioned tibialis anterior muscle from healthy mice using Ab2, and co-stained with laminin.

One week post-SCI, there was a significant decrease in grip strength in the SCI-veh, SCI-IgG, and SCI-GDF8 (Mu-Ab1) groups (all P's<0.0001) compared to sham control (FIG. 54). The SCI-GDF8 (Mu-Ab1) group grip strength was significantly greater than both the SCI-veh (P=0.0006) and SCI-IgG (P=0.0003), although the latter two groups were not different from each other. Two weeks post-SCI, there was a significant decrease in grip strength in the SCI-veh, SCI-IgG, and SCI-GDF8 (Mu-Ab1) groups (all P's<0.0001) compared to sham control. Grip strength for the SCI-GDF8 (Mu-Ab1) group was significantly greater than the SCI-veh group (P=0.0124), although not statistically different from the SCI-IgG group (however the group mean trended to greater strength; P=0.1856).

The results indicate that SCI causes a drastic reduction in hind-limb locomotor function (BMS), translating to marked reduction in motor coordination and balance (rotarod), as well as muscle strength (grip strength). GDF8 (Mu-Ab1) treatment prevented this change, as the composite BMS score for GDF8 was significantly greater than the other injury groups. Animals treated with GDF8(Mu-Ab1) also had higher motor coordination and balance as assessed by the rotarod time trials.

In conclusion, these data demonstrated a profound effect of GDF8 (Mu-Ab1) treatment on the anthropometric, physiological, and functional outcome measures of mice with SCI. SCI-induced reduction in body mass and sublesional muscle mass were attenuated with GDF8 (Mu-Ab1), and metabolic abnormalities associated with SCI—related to body composition and energy expenditure—were less pronounced following GDF8 (Mu-Ab1) treatment. Further, the effects of GDF8 (Mu-Ab1) treatment translate to locomotor and functional benefits when compared to the non-treated SCI condition.

Example 12: Intracellular Versus Secreted Pro-Myostatin

Methods

Immunofluorescence

Tibialis anterior (TA) muscles were fixed in ice cold 4% paraformaldehyde (EMS), PBS for 30 min, incubated overnight in 10% sucrose, PBS at 4° C., then incubated overnight in 20% sucrose, PBS. Muscles were then mounted on cork with tragacanth (Sigma) and frozen in liquid nitrogen cooled isopentane (Sigma) for cryosectioning. 10 µm sections of TA muscle were permeabilized with 0.1% Triton-X 100 (Sigma), PBS for 20 minutes, washed once with 0.05% Triton-X 100, PBS (PBS/T), and then incubated in Mouse IgG blocking reagent (Vector Lab) diluted at 1 drop per 1.5 mL PBS/T for 1 h. Sections were washed once with PBS/T and then incubated in 10% Normal Goat Serum (Sigma), 1% Blocking powder (Perkin Elmer), PBS/T (NGB) for 30 minutes at room temperature. Primary antibodies (Rabbit anti-laminin, 1:5000, Abcam; Ab10, 50 µg/mL; HuNeg, 50 µg/mL,) were diluted in NGB and applied to sections overnight at 4° C. Sections were washed 3 times with PBS/T, and then incubated in secondary antibodies (Alexa Fluor 488 conjugated Goat anti-Rabbit, 1:1000, Invitrogen; Alexa Fluor 594 conjugated Goat anti-Human IgG FCY, 1:500, Jackson ImmunoResearch) diluted in NGB for 1 h. Sections were then incubated in 350 nM DAPI (Thermo), PBS/T for 5 minutes, washed twice with PBS/T, and then mounted with Vectashield (Vector Laboratories). For recombinant protein absorption experiments, 50 µg/mL Ab10 was incubated overnight alone or with 10x molar excess of either rGDF8 or rGDF11 (both murine) in NGB, and then used as primary antibody.

Microscopy

Fluorescent images were captured with a Leica DM4 B equipped with 40x/0.80 Fluotar objective using Leica Application Suite X software. Images were then processed with Fiji (Schindelin, J.; Arganda-Carreras, 1. & Frise, E. et al. (2012), "Fiji: an open-source platform for biological-image analysis", Nature methods 9(7): 676-682, PMID 22743772).

Results

Previous data suggested that the majority of myostatin found in the muscle is stored as pro-myostatin. However, these methods cannot discriminate between intracellular and secreted stores of pro-myostatin. To address this, immunofluorescence was performed on cryosectioned TA muscle from healthy mice using antibody Ab10 that specifically detects pro- and latent myostatin.

Figure 39A:
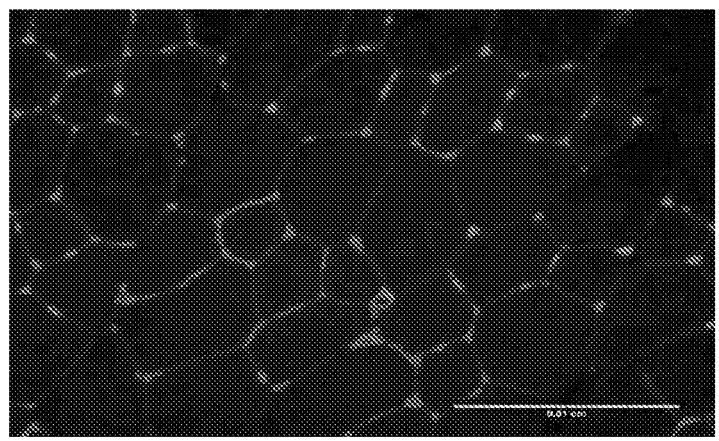
FIGS. 39A-39B show cross sections of tibilias anterior muscle probed with anti-pro/latent GDF8 antibody, Ab10 or non-specific targeting antibody, is shown in FIG. 39A, HuNeg is shown in FIG. 39B, and each of the figures are counterstained with DAPI. The scale bar is 0.01 cm.
Figure 39B:
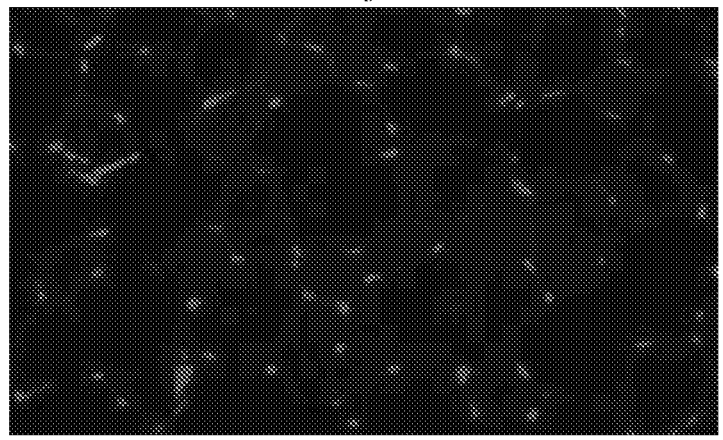

Control experiments to test specificity of anti-pro/latent GDF8 antibody, Ab10, are shown in FIGS. 39-40. FIGS. 39A-39B show cross sections of TA muscle probed with anti-pro/latent GDF8 antibody, Ab10, or a non-specific targeting antibody. Ab10 is shown in FIG. 39A, HuNeg is shown in FIG. 39B, and each of the figures are counterstained with DAPI. The scale bar is 0.01 cm. FIGS. 40A-40C show cross sections of TA muscle probed with anti-pro/latent GDF8 antibody, Ab10, that had been incubated in blocking buffer alone (FIG. 40A), incubated in blocking buffer with 10-fold molar excess a recombinant mouse GDF8 (FIG. 40B), or in blocking buffer with 10-fold molar excess of recombinant mouse GDF11 (FIG. 40C). FIGS. 40A-40C are counterstained with DAPI.

Co-staining of anti-pro/latent GDF8 antibody, Ab10, with laminin, an extracellular matrix marker, demonstrated that the majority of myostatin precursors detected in muscle are in the extracellular space with little signal detected intracellularly. FIGS. 41A-41C, and 55 show cross sections of TA muscle probed with anti-pro/latent GDF8 antibody, Ab10, and anti-laminin, and counterstained with DAPI. Pro/latent GDF8 and laminin colocalize in the interstitial space at muscle fiber vertices (arrow), between muscle fibers (arrow head), and around interstitial nuclei (asterisk). Thus, in healthy muscle, pro-myostatin lies dormant in a supracellular space, and Ab10 recognizes the major forms of myostatin found in muscle.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The invention claimed is:

1. A method for improving body composition in a subject in need thereof, the method comprising administering to the subject a pro/latent myostatin inhibitor in an amount effective to alter body composition, wherein the pro/latent myostatin inhibitor is an antibody or antigen-binding fragment thereof comprising:
   (a) a heavy chain amino acid sequence that is at least 95% identical to SEQ ID NO: 50 and a light chain amino acid sequence that is at least 95% identical to SEQ ID NO: 51;
   (b) a heavy chain variable region sequence that is at least 95% identical to SEQ ID NO: 73 and a light chain variable region sequence that is at least 95% identical to SEQ ID NO: 74; or
   (c) a heavy chain variable region sequence that is at least 95% identical to SEQ ID NO: 78 and a light chain variable region sequence that is at least 95% identical to SEQ ID NO: 79.

2. The method of claim 1, wherein the subject has a spinal cord injury (SCI), obesity, diabetes, diabetes associated with obesity, or Prader-Willi syndrome.

3. The method of claim 1, wherein the administration decreases a ratio of adipose-to-muscle tissue in the subject.

4. The method of claim 1, wherein the administration increases energy expenditure in the subject.

5. The method of claim 1, wherein the antibody or antigen-binding fragment thereof is administered in an amount sufficient to cause an increase in a level of circulating latent myostatin in the subject after the administration as compared to before the administration, wherein the level of circulating latent myostatin is measured in a serum sample from the subject.

6. The method of claim 1, wherein the antibody or antigen-binding fragment thereof is administered intravenously or subcutaneously.

7. The method of claim 1, wherein the subject is treated with one or more additional therapies.

8. The method of claim 1, wherein the antibody or antigen-binding fragment thereof is administered in an amount sufficient to cause two or more of the following in the subject:
   (a) an increase in the metabolic rate of the subject;
   (b) an increase in insulin sensitivity of the subject;
   (c) an increase in a level of brown adipose tissue in the subject;
   (d) an increase in a level of beige adipose tissue in the subject;
   (e) a decrease in a level of white adipose tissue in the subject;
   (f) a decrease in a level of visceral adipose tissue in the subject;
   (g) an increase in glucose uptake by a brown adipose tissue, a beige adipose tissue, or a muscle tissue in the subject;
   (h) a decrease in glucose uptake by a white adipose tissue or a liver tissue;
   (i) an increase in insulin dependent glycemic control in the subject; and/or
   (j) prevention of developing a metabolic dysregulation associated with muscle dysfunction in the subject.

* * * * *